US009923219B2

(12) United States Patent
Berlowitz et al.

(10) Patent No.: US 9,923,219 B2
(45) **Date of Patent: *Mar. 20, 2018**

(54) INTEGRATED OPERATION OF MOLTEN CARBONATE FUEL CELLS

(71) Applicants: Paul J. Berlowitz, Glen Gardner, NJ (US); Timothy Andrew Barckholtz, Whitehouse Station, NJ (US); Frank H. Hershkowitz, Basking Ridge, NJ (US)

(72) Inventors: Paul J. Berlowitz, Glen Gardner, NJ (US); Timothy Andrew Barckholtz, Whitehouse Station, NJ (US); Frank H. Hershkowitz, Basking Ridge, NJ (US)

(73) Assignee: EXXONMOBILE RESEARCH AND ENGINEERING COMPANY, Annandale, NJ (US)

( * ) Notice: Subject to any disclaimer, the term of this patent is extended or adjusted under 35 U.S.C. 154(b) by 786 days.

This patent is subject to a terminal disclaimer.

(21) Appl. No.: 14/207,697

(22) Filed: Mar. 13, 2014

(65) Prior Publication Data

US 2014/0272625 A1 Sep. 18, 2014

Related U.S. Application Data

(60) Provisional application No. 61/788,628, filed on Mar. 15, 2013, provisional application No. 61/787,587,
(Continued)

(51) Int. Cl.
*H01M 8/06* (2016.01)
*F02C 3/22* (2006.01)
(Continued)

(52) U.S. Cl.
CPC ................ *H01M 8/06* (2013.01); *C01B 3/16* (2013.01); *C01B 3/34* (2013.01); *C01B 3/48* (2013.01);
(Continued)

(58) Field of Classification Search
CPC .. H01M 8/249; H01M 8/0668; H01M 8/2475; H01M 8/04067; H01M 8/04007;
(Continued)

(56) References Cited

U.S. PATENT DOCUMENTS

| | | | |
|---|---|---|---|
| 3,615,839 | A | 10/1971 | Thompson et al. |
| 3,970,474 | A | 7/1976 | Anbar et al. |

(Continued)

FOREIGN PATENT DOCUMENTS

| | | | |
|---|---|---|---|
| CA | 2120858 | A1 | 10/1994 |
| CA | 23250702 | A1 | 4/2002 |

(Continued)

OTHER PUBLICATIONS

Desideri et al (MCFC-based CO2 capture system for small scale CHP plants. Internation Journal of Hydrogen Energy 37 (2012) 19295-19303.*

(Continued)

*Primary Examiner* — Stephen J Yanchuk
(74) *Attorney, Agent, or Firm* — Liza Negron

(57) ABSTRACT

In various aspects, systems and methods are provided for operating a molten carbonate fuel cell assembly at increased power density. This can be accomplished in part by performing an effective amount of an endothermic reaction within the fuel cell stack in an integrated manner. This can allow for increased power density while still maintaining a desired temperature differential within the fuel cell assembly.

19 Claims, 26 Drawing Sheets

Related U.S. Application Data filed on Mar. 15, 2013, provisional application No. 61/787,697, filed on Mar. 15, 2013, provisional application No. 61/787,879, filed on Mar. 15, 2013, provisional application No. 61/884,376, filed on Sep. 30, 2013, provisional application No. 61/884,545, filed on Sep. 30, 2013, provisional application No. 61/884,565, filed on Sep. 30, 2013, provisional application No. 61/884,586, filed on Sep. 30, 2013, provisional application No. 61/884,605, filed on Sep. 30, 2013, provisional application No. 61/884,635, filed on Sep. 30, 2013, provisional application No. 61/889,757, filed on Oct. 11, 2013.

(51) Int. Cl.

| | |
|---|---|
| ***H01M 8/04*** | (2016.01) |
| ***H01M 8/04089*** | (2016.01) |
| ***H01M 8/04746*** | (2016.01) |
| ***H01M 8/0612*** | (2016.01) |
| ***H01M 8/0637*** | (2016.01) |
| ***C21B 15/00*** | (2006.01) |
| ***C04B 7/36*** | (2006.01) |
| ***H01M 8/0668*** | (2016.01) |
| ***H01M 8/14*** | (2006.01) |
| ***H01M 8/0662*** | (2016.01) |
| ***H01M 8/04791*** | (2016.01) |
| ***H01M 8/04119*** | (2016.01) |
| ***C01B 3/50*** | (2006.01) |
| ***C07C 29/151*** | (2006.01) |
| ***C10G 2/00*** | (2006.01) |
| ***C07C 1/04*** | (2006.01) |
| ***C10K 3/04*** | (2006.01) |
| ***H01M 8/04111*** | (2016.01) |
| ***C01B 3/16*** | (2006.01) |
| ***C25B 3/02*** | (2006.01) |
| ***C01B 3/34*** | (2006.01) |
| ***C01B 3/48*** | (2006.01) |
| ***C07C 29/152*** | (2006.01) |
| ***F02C 6/18*** | (2006.01) |

(52) U.S. Cl.

CPC ................ *C01B 3/50* (2013.01); *C04B 7/367* (2013.01); *C07C 1/0485* (2013.01); *C07C 29/152* (2013.01); *C07C 29/1518* (2013.01); *C10G 2/32* (2013.01); *C10G 2/332* (2013.01); *C10G 2/34* (2013.01); *C10K 3/04* (2013.01); *C21B 15/00* (2013.01); *C25B 3/02* (2013.01); *F02C 3/22* (2013.01); *F02C 6/18* (2013.01); *H01M 8/04* (2013.01); *H01M 8/04097* (2013.01); *H01M 8/04111* (2013.01); *H01M 8/04156* (2013.01); *H01M 8/04761* (2013.01); *H01M 8/04805* (2013.01); *H01M 8/0612* (2013.01); *H01M 8/0618* (2013.01); *H01M 8/0625* (2013.01); *H01M 8/0631* (2013.01); *H01M 8/0637* (2013.01); *H01M 8/0662* (2013.01); *H01M 8/0668* (2013.01); *H01M 8/0687* (2013.01); *H01M 8/14* (2013.01); *H01M 8/141* (2013.01); *H01M 8/145* (2013.01); *C01B 2203/00* (2013.01); *C01B 2203/02* (2013.01); *C01B 2203/0205* (2013.01); *C01B 2203/0227* (2013.01); *C01B 2203/0233* (2013.01); *C01B 2203/0283* (2013.01); *C01B 2203/04* (2013.01); *C01B 2203/0405* (2013.01); *C01B 2203/046* (2013.01); *C01B 2203/0415* (2013.01); *C01B 2203/0475* (2013.01); *C01B 2203/0495* (2013.01); *C01B 2203/061* (2013.01); *C01B 2203/062* (2013.01); *C01B 2203/066* (2013.01); *C01B 2203/067* (2013.01); *C01B 2203/1205* (2013.01); *C01B 2203/1241* (2013.01); *C01B 2203/148* (2013.01); *C01B 2203/84* (2013.01); *C01B 2203/86* (2013.01); *C04B 2290/20* (2013.01); *C21B 2300/02* (2013.01); *H01M 2008/147* (2013.01); *H01M 2250/10* (2013.01); *H01M 2250/407* (2013.01); *H01M 2300/0051* (2013.01); *Y02B 90/14* (2013.01); *Y02E 20/14* (2013.01); *Y02E 20/16* (2013.01); *Y02E 20/185* (2013.01); *Y02E 50/18* (2013.01); *Y02E 60/50* (2013.01); *Y02E 60/526* (2013.01); *Y02E 60/563* (2013.01); *Y02E 60/566* (2013.01); *Y02P 10/132* (2015.11); *Y02P 20/129* (2015.11); *Y02P 20/13* (2015.11); *Y02P 30/30* (2015.11); *Y02P 70/56* (2015.11); *Y02T 10/16* (2013.01)

(58) Field of Classification Search

CPC .. H01M 8/145; C01B 3/50; C01B 2203/0233; C01B 2203/0283; C01B 2203/0475; C01B 2203/0495; C01B 2203/061; C01B 2203/062; C01B 2203/066; C01B 2203/067; C01B 2203/148; C01B 2203/84; C01B 2203/86; C01B 2203/0405; C01B 2203/0415; C01B 2203/043; C01B 2203/046; C07C 29/1518; C07C 1/0485; C04B 7/367; C04B 2290/20; C10K 3/04; C10G 2/32; C10G 2300/4043; F02C 3/22; Y02B 90/16; Y02B 60/526; Y02E 60/50; Y02P 10/132

See application file for complete search history.

(56) References Cited

U.S. PATENT DOCUMENTS

| | | | |
|---|---|---|---|
| 4,041,210 | A | 8/1977 | Van Dine |
| 4,160,663 | A | 7/1979 | Hseih |
| 4,772,634 | A | 9/1988 | Farooque |
| 4,810,595 | A | 3/1989 | Kahara et al. |
| 4,917,971 | A | 4/1990 | Farooque |
| 4,921,765 | A | 5/1990 | Geisbrecht et al. |
| 4,995,807 | A | 2/1991 | Rampley et al. |
| 5,039,579 | A | 8/1991 | Kinoshita |
| 5,071,719 | A | 12/1991 | Rostrup-Nielsen et al. |
| 5,079,103 | A | 1/1992 | Schramm |
| 5,082,752 | A | 1/1992 | Koga et al. |
| 5,084,362 | A | 1/1992 | Farooque |
| 5,134,043 | A | 7/1992 | Nakazawa |
| 5,169,717 | A | 12/1992 | Topsoe |
| 5,198,311 | A | 3/1993 | Nakazawa et al. |
| 5,208,113 | A | 5/1993 | Kinoshita |
| 5,232,793 | A | 8/1993 | Miyauchi et al. |
| 5,413,878 | A | 5/1995 | Williams et al. |
| 5,417,051 | A | 5/1995 | Ankersmit et al. |
| 5,380,600 | A | 6/1995 | Hansen et al. |
| 5,422,195 | A | 6/1995 | Bernard |
| 5,470,670 | A | 11/1995 | Yasumoto et al. |
| 5,541,014 | A | 7/1996 | Micheli et al. |
| 5,554,453 | A | 9/1996 | Steinfeld et al. |
| 5,616,430 | A | 4/1997 | Aoyama |
| 5,736,026 | A | 4/1998 | Patel et al. |
| 5,833,734 | A | 11/1998 | Cip et al. |
| 6,090,312 | A | 7/2000 | Ziaka et al. |
| 6,126,718 | A | 10/2000 | Sawa et al. |
| 6,162,556 | A | 12/2000 | Vollmar et al. |
| 6,267,799 | B1 | 7/2001 | Innes et al. |
| 6,322,916 | B1 | 11/2001 | Hemmes et al. |
| 6,365,290 | B1 | 4/2002 | Ghezel-Ayagh et al. |
| 6,383,251 | B1 | 5/2002 | Sherwood |

(56) References Cited

U.S. PATENT DOCUMENTS

| | | | |
|---|---|---|---|
| 6,524,356 | B2 | 2/2003 | Fournier et al. |
| 6,648,942 | B2 | 11/2003 | Hoffman et al. |
| 6,896,988 | B2 | 5/2005 | Wang et al. |
| 7,311,986 | B2 | 12/2007 | Hsu |
| 7,396,603 | B2 | 7/2008 | Farooque et al. |
| 7,563,527 | B2 | 7/2009 | Tanaka et al. |
| 7,862,938 | B2 | 1/2011 | Ghezel-Ayagh |
| 7,914,765 | B2 | 3/2011 | McLean et al. |
| 8,047,007 | B2 | 11/2011 | Zubrin et al. |
| 8,080,344 | B2 | 12/2011 | Skok et al. |
| 8,142,943 | B2 | 3/2012 | McElroy et al. |
| 8,349,504 | B1 | 1/2013 | Radovich |
| 8,562,903 | B2 | 10/2013 | Hayton et al. |
| 2002/0142208 | A1 | 10/2002 | Keefer et al. |
| 2003/0008183 | A1 | 1/2003 | Hsu |
| 2003/0143448 | A1 | 7/2003 | Keefer |
| 2004/0038089 | A1 | 2/2004 | Hoffman et al. |
| 2004/0202914 | A1 | 10/2004 | Sridhar et al. |
| 2005/0079395 | A1 | 4/2005 | Varatarajan et al. |
| 2005/0106429 | A1 | 5/2005 | Keefer |
| 2005/0112425 | A1 | 5/2005 | Hsu |
| 2005/0123810 | A1 | 6/2005 | Balan |
| 2005/0164051 | A1 | 7/2005 | Venkataraman et al. |
| 2005/0181247 | A1 | 8/2005 | Foger et al. |
| 2005/0271914 | A1 | 12/2005 | Farooque et al. |
| 2006/0127718 | A1 | 6/2006 | Kurashima et al. |
| 2006/0159967 | A1 | 7/2006 | Huijsmans et al. |
| 2006/0251940 | A1 | 11/2006 | Bamdjaier et al. |
| 2007/0017367 | A1 | 1/2007 | McElroy et al. |
| 2007/0072027 | A1 | 3/2007 | Sridhar et al. |
| 2007/0099038 | A1 | 5/2007 | Galloway |
| 2007/0184310 | A1 | 8/2007 | Kim et al. |
| 2007/0224467 | A1 | 9/2007 | Nervi et al. |
| 2007/0287046 | A1 | 12/2007 | Koda et al. |
| 2008/0057361 | A1 | 3/2008 | Moon et al. |
| 2008/0160358 | A1 | 7/2008 | Parodi et al. |
| 2009/0042070 | A1 | 2/2009 | Brown, Jr. et al. |
| 2009/0169452 | A1 | 7/2009 | Constantz et al. |
| 2009/0208784 | A1 | 8/2009 | Perry et al. |
| 2009/0317667 | A2 | 12/2009 | Nervi et al. |
| 2009/0317669 | A1 | 12/2009 | Hildebrandt et al. |
| 2010/0015486 | A1 | 1/2010 | Yoshiba |
| 2010/0077752 | A1* | 4/2010 | Papile .................... B01D 53/08 60/641.8 |
| 2010/0148410 | A1 | 6/2010 | Bleifuss et al. |
| 2010/0239924 | A1 | 9/2010 | McElroy et al. |
| 2011/0104577 | A1 | 5/2011 | Cui et al. |
| 2011/0111314 | A1* | 5/2011 | Cui ........................... C01B 3/38 429/417 |
| 2011/0111315 | A1 | 5/2011 | Cui et al. |
| 2011/0117460 | A1 | 5/2011 | Shin |
| 2011/0154951 | A1 | 6/2011 | Hiraoka |
| 2011/0167821 | A1 | 7/2011 | Baker et al. |
| 2011/0171544 | A1 | 7/2011 | Burmeister et al. |
| 2011/0223500 | A1 | 9/2011 | Uematsu et al. |
| 2011/0223501 | A1 | 9/2011 | Uematsu et al. |
| 2012/0028145 | A1 | 2/2012 | Boden et al. |
| 2012/0171588 | A1 | 7/2012 | Fan et al. |
| 2012/0214076 | A1 | 8/2012 | Hakala |
| 2012/0251898 | A1 | 10/2012 | Lehar et al. |
| 2012/0325053 | A1 | 12/2012 | Grossi |
| 2013/0014484 | A1 | 1/2013 | Caprile et al. |
| 2013/0081516 | A1 | 4/2013 | Simmons |
| 2013/0177824 | A1 | 7/2013 | Cui et al. |
| 2013/0209904 | A1 | 8/2013 | Liu et al. |

FOREIGN PATENT DOCUMENTS

| | | | |
|---|---|---|---|
| CN | 101098022 | A | 1/2008 |
| CN | 201902241 | U | 7/2011 |
| CN | 2694153 | A1 | 9/2011 |
| DE | 4005468 | A1 | 8/1991 |
| DE | 19515669 | A1 | 10/1996 |
| DE | 19545186 | A1 | 6/1997 |
| DE | 19941724 | A1 | 8/2000 |
| DE | 10016847 | A1 | 10/2001 |
| EP | 0170277 | A2 | 5/1986 |
| EP | 0473153 | A2 | 4/1992 |
| EP | 1926171 | A1 | 5/2008 |
| JP | 56069775 | A | 6/1981 |
| JP | H05163180 | A | 6/1993 |
| JP | 08096824 | A | 4/1996 |
| JP | 10172595 | A | 6/1999 |
| JP | 11191427 | A | 7/1999 |
| JP | 11312527 | A | 11/1999 |
| JP | 2002319248 | A | 10/2002 |
| JP | 2004014124 | A | 1/2004 |
| JP | 2004079495 | A | 3/2004 |
| JP | 2004186074 | A | 7/2004 |
| JP | 2006073316 | A | 3/2006 |
| JP | 2007287580 | A | 11/2007 |
| JP | 2008192425 | A | 8/2008 |
| JP | 2008287940 | A | 11/2008 |
| JP | 2009043487 | A | 2/2009 |
| JP | 2013045535 | A1 | 3/2013 |
| KR | 100651270 | B1 | 11/2006 |
| KR | 100827954 | B1 | 5/2008 |
| KR | 20090067426 | A | 6/2009 |
| KR | 20090124824 | A | 12/2009 |
| KR | 20110029963 | A | 3/2011 |
| KR | 20110032443 | A | 3/2011 |
| KR | 101032974 | B1 | 5/2011 |
| KR | 20110077775 | A | 7/2011 |
| KR | 20120050319 | A | 5/2012 |
| NL | 1008883 | C2 | 10/1999 |
| WO | 9733828 | A1 | 9/1997 |
| WO | 02070402 | A2 | 9/2002 |
| WO | 2002103833 | A1 | 12/2002 |
| WO | 2003063276 | A2 | 7/2003 |
| WO | 2004013924 | A2 | 2/2004 |
| WO | 2005001977 | A1 | 1/2005 |
| WO | 2008036169 | A2 | 3/2008 |
| WO | 02069430 | A2 | 9/2009 |
| WO | 2010044113 | A1 | 4/2010 |
| WO | 2010067223 | A1 | 6/2010 |
| WO | 2010125443 | A1 | 11/2010 |
| WO | 2010147885 | A1 | 12/2010 |
| WO | 2010147886 | A1 | 12/2010 |
| WO | 2011077224 | A1 | 6/2011 |
| WO | 2012091096 | A1 | 7/2012 |
| WO | 2012176176 | A1 | 12/2012 |
| WO | 2012176177 | A1 | 12/2012 |

OTHER PUBLICATIONS

Lee et al (Effect of carbon monoxide addition to the anode of a molten carbonate fuel cell. Journal of power sources. 125. 2004. 166-171).*

Cavallaro et al., "Syngas and electricity production by an integrated autothermal reforming/molten carbonate fuel cell system", Journal of Power Sources, Dec. 1, 1988 pp. 190-196, vol. 76, No. 2, Elsevier.

Appleby et al., "Current Technology of PAFC, MCFC and SOFC Systems: Status of Present Fuel Cell Power Plants", Electrochemical Hydrogen Technologies, Electrochemical Production and Combustion of Hydrogen, Jan. 1, 1990, pp. 425-495, Elsevier.

Appleby, "Fuel Cells and Hydrogen Fuel", International Journal of Hydrogen Energy, Feb. 1, 1994, pp. 175-180 vol. 19, No. 2, International Association for Hydrogen Energy, Pergamon Press Ltd., Great Britain.

Chiesa et al., "A Comparative Analysis of IGCCs with CO2 Sequestration", In: Proceedings of 4th International Conference on Greenhouse Gas Control Technologies, Interlaken, Switzerland Aug. 30, 1998-Sep. 2, 1998, pp. 107-112.

Amorelli et al., "An experimental investigation into the use of molten carbonate fuel cells to capture CO2 from gas turbine exhaust gases", 2nd annual conference on Carbon Seqquestration, May 5, 2003 to May 8, 2003, Hilton Alexandria Mark Center, Alexandria, VA.

(56) References Cited

OTHER PUBLICATIONS

Sugiura et al., "The carbon dioxide concentrator by using MCFC", Journal of Power Sources, May 25, 2003, pp. 218-227, vol. 118, No. 1-2, ScienceDirect, Elsevier.
Steynberg et al., eds., "Gas loop for POX reformers", Studies in Surface Science and Catalysis: Fischer Tropsch Technology, Jul. 28, 2004, vol. 152, p. 432, fig. 8, Elsevier B.V.
Verda et al., "Thermodynamic and economic optimization of a MCFC-based hybrid system for the combined production of electricity and hydrogen". International Journal of Hydrogen Energy, Jan. 1, 2010, vol. 35, No. 2, pp. 794-806, ScienceDirect, Elsevier.
Campanari et al., "CO2 capture from combined cycles integrated with Molten Carbonate Fuel Cells", International Journal of Greenhouse Gas Control, May 1, 2010, pp. 441-451, vol. 4, No. 3, Greenhouse Gas Control, ScienceDirect, Elsevier.
Kim et al., "Numerical studies of a separator for stack temperature control in a molten carbonate fuel cell", International Journal of Hydrogen Energy, Apr. 7, 2011, vol. 36, No. 14, pp. 8499-8507, ScienceDirect, Elsevier.
Pilatowski et al., "Thermodynamics of Fuel Cells", Cogeneration Fuel Cell-Sorption Air Conditioning Systems, Jun. 2, 2011, pp. 25-36, Springer.
Lowe et al., "Technology Assessment of Hydrogen Firing of Process Heaters", Energy Procedia, Jul. 1, 2011, pp. 1058-1065, vol. 4, ScienceDirect, Elsevier.
Appl, "Ammonia, 3. Production Plants", Ullmann's Encyclopedia of Industrial Chemistry, Oct. 15, 2011, vol. 3, Wiley-Verlag GmbH & Co., Weinheim.
Anonymous, "Lower and Higher Heating Values of Fuels", Hydrogen Data Resource Center: Hydrogen Calculator, Jan. 1, 2012, U.S. Dept. of Energy.
Giddey et al., "A comprehensive review of direct carbon fuel cell technology", Progress in Energy Combustion Science, Jan. 28, 2012, pp. 360-399, vol. 38, No. 3, Science Direct, Elsevier.
Anonymous, "Heat of Combustion", Wikipedia, the free Encyclopedia, Jun. 6, 2014.
International Search Report with Written Opinion from PCT/US2014/025173 dated Jun. 13, 2014.
International Search Report with Written Opinion from PCT/US2014/025214 dated Jul. 4, 2014.
International Search Report with Written Opinion from PCT/US2014/025228 dated Jul. 4, 2014.
International Search Report with Written Opinion from PCT/US2014/025237 dated Jul. 4, 2014.
International Search Report with Written Opinion from PCT/US2014/025181 dated Jul. 7, 2014.
International Search Report with Written Opinion from PCT/US2014/025186 dated Jul. 7, 2014.
International Search Report with Written Opinion from PCT/US2014/025189 dated Jul. 7, 2014.
International Search Report with Written Opinion from PCT/US2014/025240 dated Jul. 8, 2014.
International Search Report with Written Opinion from PCT/US2014/025216 dated Jul. 15, 2014.
International Search Report with Written Opinion from PCT/US2014/025223 dated Jul. 15, 2014.
International Search Report with Written Opinion from PCT/US2014/025192 dated Jul. 22, 2014.
International Search Report with Written Opinion from PCT/US2014/025208 dated Jul. 22, 2014.
International Search Report with Written Opinion from PCT/US2014/025195 dated Jul. 24, 2014.
International Search Report with Written Opinion from PCT/US2014/025180 dated Jul. 28, 2014.
International Search Report with Written Opinion from PCT/US2014/025175 dated Jul. 28, 2014.
International Search Report with Written Opinion from PCT/US2014/025185 dated Jul. 28, 2014.
International Search Report with Written Opinion from PCT/US2014/025212 dated Jul. 28, 2014.
International Search Report with Written Opinion from PCT/US2014/025179 dated Aug. 5, 2014.
International Search Report with Written Opinion from PCT/US2014/025229 dated Aug. 5, 2014.
Partial International Search Report from PCT/US2014/025188 dated Aug. 29, 2014.
Partial International Search Report from PCT/US2014/025219 dated Aug. 29, 2014.
International Search Report with Written Opinion from PCT/US2014/025203 dated Sep. 1, 2014.
Avidan, "Gasoline and Distillate Fuels from Methanol", Studies in Surface Science and Catalysis, 1988, vol. 36, pp. 307-323, Methane Conversion, Elsevier Science Publishers B.V., Amsterdam.
Keil, "Methanol-to-hydrocarbons: process technology" Microporous and Mesoporous Materials, 1999-06, vol. 29 (1-2), pp. 49-66, Elsevier.
Campanari, "Carbon Dioxide separation from high temperature fuel cell power plants", Journal of Power Sources, 2002, vol. 112, pp. 273-289, Science Direct, Elsevier.
Amorelli et al., "An experimental investigation into the use of molten carbonate fuel cells to capture CO2 from gas turbine exhaust gases", Energy, 2004, vol. 29, pp. 1279-1284, Science Direct, Elsevier.
Naqvi, "Dimethyl Ether as Fuel", SRI Consulting Report, Report No. 245A, Sep. 2005, Process Economics Program, Menlo Park, CA.
Greenhouse Gas Technology Center, "Test and Quality Assurance Plan: FuelCell Energy, Inc.—DFC 300A Molten Carbonate Fuel Cell Combined Heat and Power System" SRI/USEPA, Mar. 2007, pp. 1-42, Southern Research Institute, Morrisville, NC.
Abu-Zahra et al.,"CO2 capture from power plants Part I: A parametric study of the technical performance based on monoethanolamine", International Journal of Greenhouse Gas Control, 2007, vol. 1, pp. 37-46, ScienceDirect, Elsevier.
"Molten Carbonate Fuel Cell Technology", Fossil Energy Office of Communications, Jan. 11, 2011, U.S. Department of Energy.
Campanari et al., "Application of MCFCs for active CO2 capture within natural gas combine cycles" Energy Procedia, 2011, vol. 4, pp. 1235-1242, Science Direct, Elsevier.
Caprile, "Carbon capture: Energy wasting technologies or the MCFCs challenge?", International Journal of Hydrogen Energy, 2011, vol. 36, pp. 10269-10277, Science Direct, Elsevier.
Chiesa et al., "CO2 cryagenic separation from combined cycles integrated with molten carbonate fuel cells", International Journal of Hydrogen Energy, 2011, vol. 36, pp. 10355-10365, Science Direct, Elsevier.
Wesoff, "Will FuelCell Energy Be the First Profitable Company in the Industry?", Greentech Media, Dec. 15, 2011.
Manzolini et al., "CO2 Separation from Combined Cycles Using Molten Carbonate Fuel Cells," Journal of Fuel Cell Science and Technology, Feb. 2012, pp. 011018-1 to 011018-8, vol. 9, iss. 1, American Society of Mechanical Engineers.
Zhou et al., "Decrease of energy demand for bioethanol-based polygeneration system through case study," Applied Energy, Mar. 6, 2012, vol. 95, pp. 305-311, Elsevier.
Ghezel-Ayagh, "Electrochemical Membrane for CO2 Capture and Power Generation (No. DE-FE0007634)", presentation given at the 2012 NETL CO2 Capture Technology Meeting, Jul. 9, 2012, Pittsburgh, PA.
Desideri, U., et al., "MCFC-based CO2 capture system for small scale CHP plants," International Journal of Hydrogen Energy, Dec. 2012, pp. 19295-19303, vol. 37, iss. 24, SciVerse Science Direct, Elsevier.
Ghezel-Ayagh, "High Efficiency Direct FuelCell/Turbine® Power Plant", Project Fact Sheet for unit installed at the Billings Clinic in Billings, Montana, U.S. Department of Energy.
Office Action from related U.S. Appl. No. 14/315,419 dated Aug. 1, 2014.
Office Action from related U.S. Appl. No. 14/315,419 dated Jan. 27, 2015.
Office Action from related U.S. Appl. No. 14/315,439 dated Dec. 29, 2014.

(56) References Cited

OTHER PUBLICATIONS

Office Action from related U.S. Appl. No. 14/315,527 dated Jan. 9, 2015.
Office Action from related U.S. Appl. No. 14/315,479 dated Nov. 7, 2014.
International Search Report with Written Opinion from PCT/US2014/025188 dated Jan. 21, 2015.
International Search Report with Written Opinion from PCT/US2014/025219 dated Jan. 21, 2015.

* cited by examiner

| | Shifting Catalyst (Co-Based) | | Non-Shifting Catalyst (Fe-Based) | |
|---|---|---|---|---|
| | No CO2 Capture | w/ CO2 Capture | No CO2 Capture | w/ CO2 Capture |
| Fuel Utilization (%) | 35% | 35% | 35% | 35% |
| Steam to Carbon Ratio | 2.00 | 2.00 | 2.00 | 2.00 |
| Exhaust Gas Recycle (%) | N/A | N/A | N/A | N/A |
| Water Gas Shift Reactors | Reverse | Reverse | No | No |
| Internal Reforming (%) | 40% | 40% | 40% | 40% |
| MCFC CO2 Cathode Inlet Conc. (%) | 18.71% | 16.11% | 18.64% | 15.89% |
| MCFC CO2 Cathode Exhaust Conc. (%) | 5.2% | 1.3% | 5.2% | 1.1% |
| MCFC O2 Cathode Exhaust Conc. (%) | 7.0% | 7.5% | 6.8% | 7.3% |
| MCFC Voltage (V) | 0.65 | 0.65 | 0.65 | 0.65 |
| MCFC Current Density (A/m2) | 2918 | 2595 | 2915 | 2565 |
| MCFC Area (k-m2) | 77 | 87 | 77 | 88 |
| Anode steam penalty (MW) | 15.1 | 15.1 | 15.1 | 15.1 |
| Net MCFC Electrical Output (MW) | 132 | 132 | 132 | 132 |
| Net Steam Turbine Power (MW) | 17 | 16 | 40 | 39 |
| Total net power (MW) | 100 | 95 | 122 | 116 |
| Electrical efficiency (%) | 14.0% | 13.3% | 16.8% | 16.2% |
| Approximate Total Plant Efficiency (%) | 64.3% | 63.7% | 66.9% | 66.6% |
| Fischer Tropsch Liquids (bpd) | 5959 | 5948 | 5981 | 5981 |
| **Carbon Balance - Carbon as C1 (lbmol/hr)** | | | | |
| Inlet | | | | |
| Fresh Fuel to Duct Burner | 463 | 434 | 527 | 485 |
| Fresh Fuel to Anode | 6614 | 6614 | 6614 | 6614 |
| CO2 in Air to Duct Burner | 17 | 17 | 17 | 17 |
| Outlet | | | | |
| Stack Gas | 2575 | 599 | 2606 | 517 |
| FT Liquids | 4510 | 4501 | 4527 | 4527 |
| Sequestered | 0 | 1939 | 0 | 2048 |
| CO2 in Waste Water | 9 | 25 | 25 | 25 |

FIG. 9

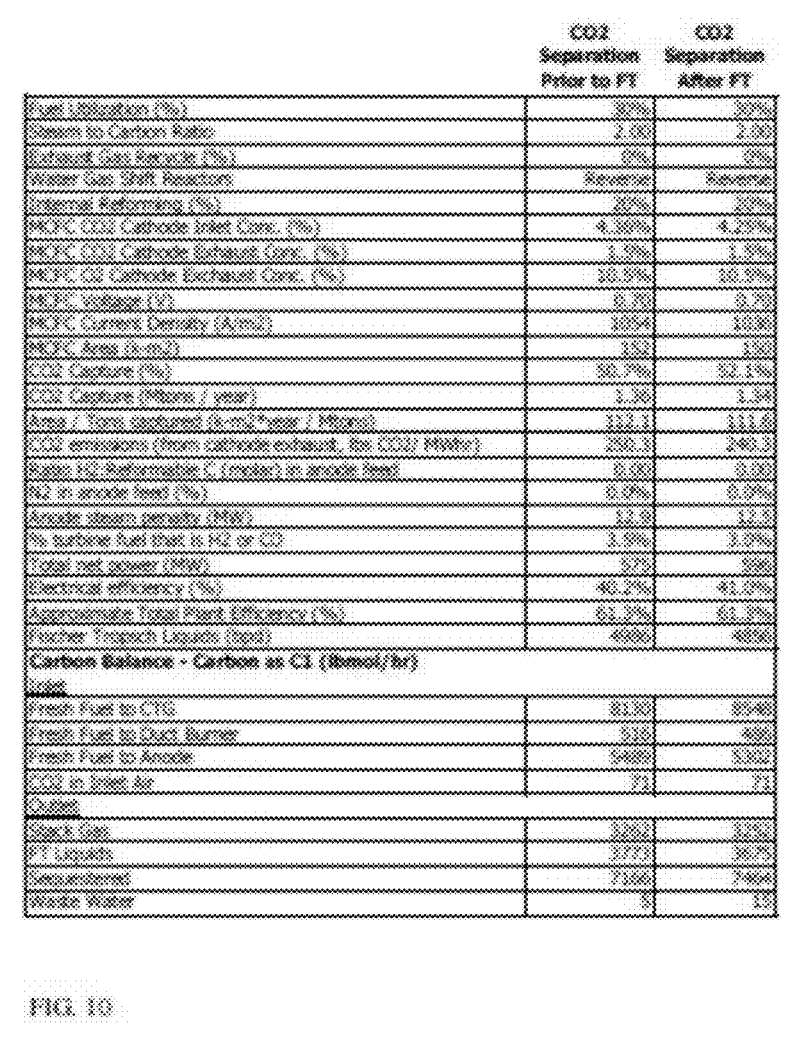

| | $CO_2$ Separation Prior to FT | $CO_2$ Separation After FT |
|---|---|---|
| Fuel Utilization (%) | 30% | 30% |
| Steam to Carbon Ratio | 2.00 | 2.00 |
| Exhaust Gas Recycle (%) | 0% | 0% |
| Water Gas Shift Reaction | Reverse | Reverse |
| Internal Reforming (%) | 30% | 30% |
| MCFC $CO_2$ Cathode Inlet Conc. (%) | 4.18% | 4.25% |
| MCFC $CO_2$ Cathode Exhaust Conc. (%) | 1.50% | 1.50% |
| MCFC $O_2$ Cathode Exhaust Conc. (%) | 10.5% | 10.5% |
| MCFC Voltage (V) | 0.70 | 0.70 |
| MCFC Current Density (A/m2) | 1054 | 1036 |
| MCFC Area (k m2) | 152 | 150 |
| $CO_2$ Capture (%) | 30.7% | 32.1% |
| $CO_2$ Capture (Mtons / year) | 1.36 | 1.34 |
| Area / Tons captured (k m2*year / Mtons) | 112.1 | 111.6 |
| $CO_2$ emissions (from cathode exhaust, lbs $CO_2$/ MWhr) | 250.3 | 249.1 |
| Ratio H2: Reformable C (molar) in anode feed | 0.00 | 0.00 |
| H2 in anode feed (%) | 0.0% | 0.0% |
| Anode steam penalty (MW) | 12.8 | 12.3 |
| % turbine fuel that is H2 or CO | 3.5% | 3.0% |
| Total net power (MW) | 975 | 980 |
| Electrical efficiency (%) | 40.2% | 41.0% |
| Approximate Total Plant Efficiency (%) | 61.3% | 61.3% |
| Fischer Tropsch Liquids (bpd) | 4800 | 4800 |
| **Carbon Balance - Carbon as C1 (lbmol/hr)** | | |
| Inlet | | |
| Fresh Fuel to CTG | 8130 | 8548 |
| Fresh Fuel to Duct Burner | 518 | 400 |
| Fresh Fuel to Anode | 5400 | 5,000 |
| $CO_2$ in Inlet Air | 71 | 71 |
| Outlet | | |
| Stack Gas | 3260 | 3260 |
| FT Liquids | 3771 | 3875 |
| Sequestered | 7100 | 7400 |
| Waste Water | 5 | 15 |

FIG. 10

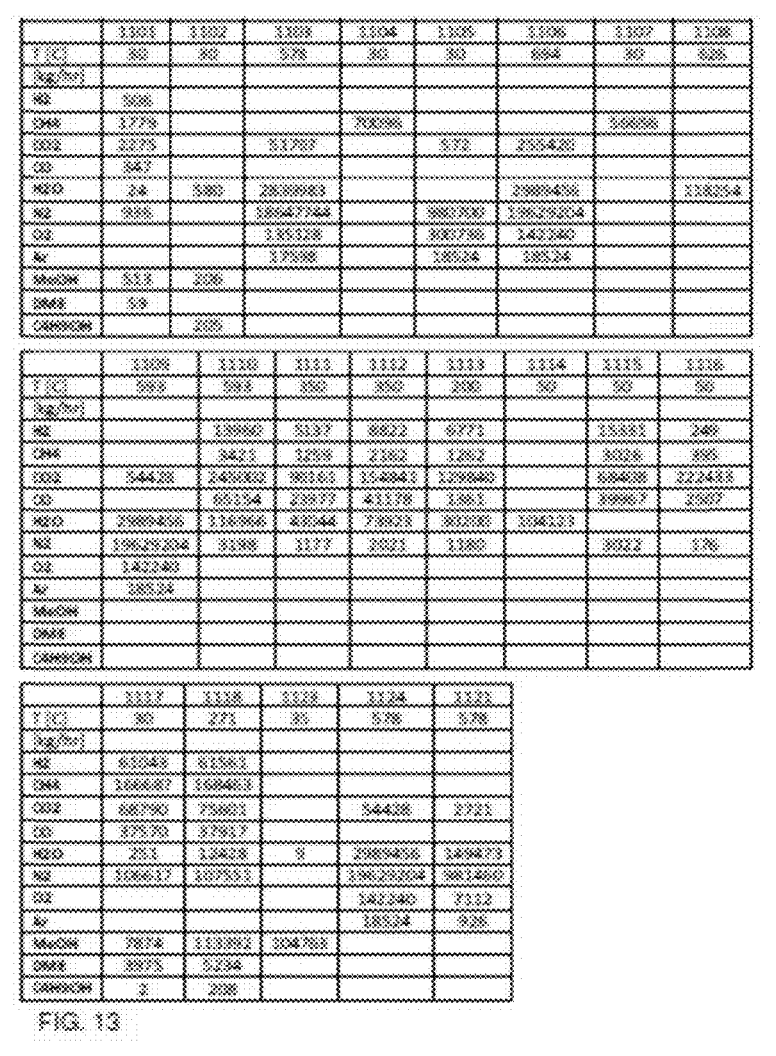

| | 1301 | 1302 | 1303 | 1304 | 1305 | 1306 | 1307 | 1308 |
|---|---|---|---|---|---|---|---|---|
| T (C) | 30 | 30 | 578 | 30 | 30 | 684 | 30 | 626 |
| [kg/hr] | | | | | | | | |
| H2 | 506 | | | | | | | |
| CH4 | 1779 | | | 29896 | | | 29896 | |
| CO2 | 2275 | | 51787 | | 572 | 235420 | | |
| CO | 567 | | | | | | | |
| H2O | 24 | 580 | 2889983 | | | 2889456 | | 118254 |
| N2 | 895 | | 16647744 | | 3887700 | 19629204 | | |
| O2 | | | 185128 | | 382790 | 142240 | | |
| Ar | | | 17508 | | 18524 | 18524 | | |
| MeOH | 513 | 226 | | | | | | |
| DME | 59 | | | | | | | |
| C2H5OH | | 235 | | | | | | |

| | 1309 | 1310 | 1311 | 1312 | 1313 | 1314 | 1315 | 1316 |
|---|---|---|---|---|---|---|---|---|
| T (C) | 593 | 593 | 350 | 350 | 298 | 30 | 30 | 30 |
| [kg/hr] | | | | | | | | |
| H2 | | 13860 | 5137 | 8822 | 6771 | | 15381 | 249 |
| CH4 | | 3421 | 1259 | 2182 | 1282 | | 3026 | 395 |
| CO2 | 54428 | 249883 | 98163 | 154941 | 129880 | | 68408 | 222433 |
| CO | | 48154 | 23877 | 41178 | 1461 | | 89867 | 2507 |
| H2O | 2889456 | 116966 | 48344 | 79835 | 36230 | 338131 | | |
| N2 | 19629204 | 3198 | 1177 | 2021 | 1180 | | 3022 | 176 |
| O2 | 142240 | | | | | | | |
| Ar | 18524 | | | | | | | |
| MeOH | | | | | | | | |
| DME | | | | | | | | |
| C2H5OH | | | | | | | | |

| | 1317 | 1318 | 1319 | 1320 | 1321 |
|---|---|---|---|---|---|
| T (C) | 30 | 271 | 35 | 578 | 578 |
| [kg/hr] | | | | | |
| H2 | 63049 | 61961 | | | |
| CH4 | 168687 | 168403 | | | |
| CO2 | 68790 | 75801 | | 54428 | 2721 |
| CO | 37570 | 37817 | | | |
| H2O | 251 | 13828 | 3 | 2889456 | 149873 |
| N2 | 186617 | 187351 | | 19629204 | 981460 |
| O2 | | | | 142240 | 7112 |
| Ar | | | | 18524 | 926 |
| MeOH | 7874 | 113092 | 104783 | | |
| DME | 3975 | 5234 | | | |
| C2H5OH | 3 | 236 | | | |

FIG. 13

| kg/hr | 1701 | 1702 | 1703 | 1704 | 1705 | 1706 | 1707 |
|---|---|---|---|---|---|---|---|
| $H_2$ | | | 10092 | 10092 | | 268 | 13164 |
| $CH_4$ | 41360 | | 1728 | 1728 | | 1712 | 16 |
| $CO_2$ | | | 167860 | 167860 | | 238876 | 2420 |
| CO | | | 49728 | 49728 | | 2940 | 28 |
| $H_2O$ | | 82768 | 81488 | 81488 | 1584 | 1856 | 16 |
| $N_2$ | | | | | | | |
| $O_2$ | | | | | | | |
| Ar | | | | | | | |

| kg/hr | 1708 | 1709 | 1710 | 1711 | 1712 | 1713 |
|---|---|---|---|---|---|---|
| $H_2$ | | | | | | |
| $CH_4$ | | | | | | |
| $CO_2$ | 165660 | | 168660 | 220 | 7744 | 29084 |
| CO | | | | | | |
| $H_2O$ | 105380 | 94816 | 10528 | | 2800 | 10528 |
| $N_2$ | 367444 | | 367444 | 397936 | 223448 | 765380 |
| $O_2$ | 7328 | | 7328 | 122016 | 21152 | 79584 |
| Ar | 6952 | | 6952 | 7524 | 3828 | 14476 |

FIG. 18

| | 1901 | 1902 | 1903 | 1904 | 1905 | 1906 | 1907 | 1908 | 1909 |
|---|---|---|---|---|---|---|---|---|---|
| T [C] | | 30 | 532 | 616 | 1200 | 700 | 631 | 523 | 30 |
| | | | | | | | | | |
| [kg/hr] | | | | | | | | | |
| CH4 | | 80510 | 23487 | 23487 | 23487 | 23432 | 23432 | 23432 | 90 |
| C2H6 | | | | | | | | | |
| C3H8 | | | | | | | | | |
| C4H10 | | | | | | | | | |
| H2O | 181310 | | 186188 | 198021 | 236809 | 275234 | 275234 | 275234 | 301233 |
| CO2 | | 0 | 363169 | 341590 | 262236 | 153914 | 153914 | 153914 | 8554 |
| H2 | | 0 | 13887 | 12879 | 8236 | | | | |
| CO | | 0 | 38178 | 31912 | 116418 | | | | |
| N2 | | | | | | | | | |
| O2 | | | | | | | | | |
| Ar | | | | | | | | | |
| | | | | | | | | | |

| | 1910 | 1911 | 1912 | 1913 | 1914 | 1915 | 1916 |
|---|---|---|---|---|---|---|---|
| T | 30 | 30 | 30 | 30 | 30 | 1210 | 536 |
| | | | | | | | |
| [kg/hr] | | | | | | | |
| CH4 | 23307 | 8768 | 14739 | | 1604 | | |
| C2H6 | | | | | | | |
| C3H8 | | | | | | | |
| C4H10 | | | | | | | |
| H2O | 8591 | 3236 | 5389 | | | 123183 | 123183 |
| CO2 | 414702 | 134684 | 260018 | | | 403899 | 403899 |
| H2 | | | | | | | |
| CO | | | | | | | |
| N2 | | | | 740742 | | 740742 | 740742 |
| O2 | | | | 224919 | | 15692 | 15692 |
| Ar | | | | | | | |

FIG. 20

| | 2101 | 2102 | 2103 | 2104 | 2105 | 2106 | 2107 | 2108 |
|---|---|---|---|---|---|---|---|---|
| T [C] | 30 | 10 | 150 | | | | 30 | |
| [kg/hr] | | | | | | | | |
| H2 | | | | | | | | 30847 |
| CH4 | 318461 | | | 126438 | | | | 5268 |
| CO2 | | | 530613 | | 530613 | | 112318 | 513066 |
| CO | | | | | | | | 152341 |
| H2O | | | 328946 | | 328946 | 252986 | 329078 | 249101 |
| N2 | | 3843305 | 3843249 | | 3843249 | | 3843352 | |
| O2 | | 1178302 | 410140 | | 410140 | | 257896 | |
| Ar | | 72396 | 72396 | | 72396 | | 72270 | |

| | 2109 | 2110 | 2111 | 2112 | 2113 | | | |
|---|---|---|---|---|---|---|---|---|
| T [C] | 653 | 653 | 592 | 592 | 145 | | | |
| [kg/hr] | | | | | | | | |
| H2 | 41707 | | 41707 | | | | | |
| CH4 | 5268 | | | | | | | |
| CO2 | 751989 | 751989 | | | | | | |
| CO | | | | | | | | |
| H2O | 162220 | | | | 162220 | | | |
| N2 | | | | 1012126 | | | | |
| O2 | | | | 310303 | | | | |
| Ar | | | | 19065 | | | | |

FIG. 22

| | 2301 | 2302 | 2303 | 2304 | 2305 | 2306 | 2307 | 2308 |
|---|---|---|---|---|---|---|---|---|
| T [C] | 30 | 10 | 150 | | | | 30 | |
| [kg/hr] | | | | | | | | |
| H2 | | | | | | | | |
| CH4 | 63040 | | | | | | 41299 | 0 |
| CO2 | | | 173360 | | | 173360 | | 173360 |
| CO | | | 0 | | | | | |
| H2O | | | 126080 | | | 126080 | | 126080 |
| N2 | | 442193 | 442193 | | | 442193 | | 442193 |
| O2 | | 135570 | 9490 | | | 9490 | | 9490 |
| Ar | | 8330 | 8330 | | | 8330 | | 8330 |

| | 2309 | 2310 | 2311 | 2312 | 2313 | 2314 | 2315 | 2317 | 2316 |
|---|---|---|---|---|---|---|---|---|---|
| T [C] | 652 | 652 | 592 | 592 | 145 | 30 | 30 | 30 | 10 |
| [kg/hr] | | | | | | | | | |
| H2 | | | 0 | 10076 | 13623 | | 13623 | | |
| CH4 | 41299 | | 0 | 1721 | 1721 | | | | |
| CO2 | | | 36487 | 167585 | 245624 | 245624 | | | |
| CO | | | 0 | 49662 | | | | | |
| H2O | | 83637 | 107488 | 81365 | 109743 | | | 109743 | |
| N2 | | | 1255367 | | 0 | | | | 330564 |
| O2 | | | 84237 | | 0 | | | | 101355 |
| Ar | | | 23606 | | | | | | 6227 |

FIG. 24

| Case | With H2 Turbine | Recycle to First Turbine | With H2 Turbine | Recycle to First Turbine | With H2 Turbine | Recycle to First Turbine |
|---|---|---|---|---|---|---|
| Fuel Utilization (%) | 75% | 75% | 80% | 80% | 30% | 30% |
| Steam to Carbon Ratio | 2.0 | 2.0 | 2.0 | 2.0 | 2.0 | 2.0 |
| Exhaust Gas Recycle (%) | 35% | 35% | 35% | 35% | 35% | 35% |
| Water Gas Shift Reactors | Yes | Yes | Yes | Yes | Yes | Yes |
| Internal Reforming (%) | 20% | 20% | 20% | 20% | 20% | 20% |
| MCFC CO2 Cathode Inlet Conc. (%) | 6.11% | 5.72% | 6.11% | 5.12% | 6.54% | 4.53% |
| MCFC CO2 Cathode Exhaust Conc. (%) | 1.5% | 1.5% | 1.5% | 1.5% | 1.5% | 1.5% |
| MCFC O2 Cathode Exhaust Conc. (%) | 5.9% | 6.2% | 5.9% | 6.6% | 4.7% | 6.5% |
| MCFC Voltage (V) | 0.70 | 0.70 | 0.70 | 0.70 | 0.70 | 0.70 |
| MCFC Current Density (A/m2) | 912 | 878 | 974 | 916 | 1197 | 1061 |
| MCFC Area (k-m2) | 184 | 175 | 172 | 148 | 154 | 105 |
| CO2 Capture (%) | 82.0% | 80.7% | 81.5% | 80.0% | 83.8% | 78.7% |
| CO2 Capture (Mtons / year) | 1.76 | 1.62 | 1.96 | 1.55 | 2.56 | 1.56 |
| Area / Tons captured (k-m2*year / Mtons) | 104.1 | 108.0 | 87.9 | 93.1 | 60.3 | 67.6 |
| CO2 emissions (from cathode exhaust, lbs CO2/ MWhr) | 153.2 | 147.8 | 144.0 | 160.2 | 113.3 | 183.3 |
| Ratio H2:Reformable C (molar) in anode feed | 0.00 | 0.00 | 0.00 | 0.00 | 0.00 | 0.00 |
| N2 in anode feed (%) | 0% | 0% | 0% | 0% | 0% | 0% |
| Anode steam penalty (MW) | 5.2 | 4.8 | 7.8 | 6.2 | 14.4 | 8.7 |
| % turbine fuel that is H2 or CO (LHV basis) | 0% / 100% * | 6.6% | 0% / 100% * | 16.4% | 0.0% / 95.4% * | 34.3% |
| Total net power (MW) | 580 | 610 | 624 | 571 | 791 | 502 |
| Electrical efficiency (%) | 51.9% | 57.7% | 50.0% | 55.4% | 48.2% | 48.7% |

* Formatted as Primary Gas Turbine / H2 Fired Gas Turbine

FIG. 26

INTEGRATED OPERATION OF MOLTEN CARBONATE FUEL CELLS

CROSS-REFERENCE TO RELATED APPLICATIONS

This application claims the benefit of U.S. Ser. Nos. 61/787,587, 61/787,697, 61/787,879, and 61/788,628, all filed on Mar. 15, 2013, each of which is incorporated by reference herein in its entirety. This application also claims the benefit of U.S. Ser. Nos. 61/884,376, 61/884,545, 61/884,565, 61/884,586, 61/884,605, and 61/884,635, all filed on Sep. 30, 2013, each of which is incorporated by reference herein in its entirety. This application further claims the benefit of U.S. Ser. No. 61/889,757, filed on Oct. 11, 2013, which is incorporated by reference herein in its entirety.

This application is related to 4 other co-pending, commonly assigned U.S. patent applications, filed on Mar. 5, 2014 as follows: Ser. No. 14/197,391; 14/197,430; 14/197,551; and Ser. No. 14/197,613. This application is also related to the following 21 co-pending, commonly assigned U.S. patent applications, filed on Mar. 13, 2014: Ser. Nos. 14/207,686; 14/207,686; 14/207,688; 14/207,687; 14/207,690; 14/207,696; 14/207,698; 14/207,704; 14/207,706; 14/207,691 14/207,693; 14/207,699; 14/207,700; 14/207,705; 14/207,708; 14/207,711; 14/207,714; 14/207,710; 14/207,712; 14/207,721; 14/207,726; 14/207,728. Each of these co-pending U.S. applications is hereby incorporated by reference herein in its entirety.

FIELD OF THE INVENTION

In various aspects, the invention is related to chemical production and/or power generation processes integrated using molten carbonate fuel cells.

BACKGROUND OF THE INVENTION

Molten carbonate fuel cells utilize hydrogen and/or other fuels to generate electricity. The hydrogen may be provided by reforming methane or other reformable fuels in a steam reformer that is upstream of the fuel cell or within the fuel cell. Reformable fuels can encompass hydrocarbonaceous materials that can be reacted with steam and/or oxygen at elevated temperature and/or pressure to produce a gaseous product that comprises hydrogen. Alternatively or additionally, fuel can be reformed in the anode cell in a molten carbonate fuel cell, which can be operated to create conditions that are suitable for reforming fuels in the anode. Alternately or additionally, the reforming can occur both externally and internally to the fuel cell.

Traditionally, molten carbonate fuel cells are operated to maximize electricity production per unit of fuel input, which may be referred to as the fuel cell's electrical efficiency. This maximization can be based on the fuel cell alone or in conjunction with another power generation system. In order to achieve increased electrical production and to manage the heat generation, fuel utilization within a fuel cell is typically maintained at 70% to 75%.

U.S. Published Patent Application 2011/0111315 describes a system and process for operating fuel cell systems with substantial hydrogen content in the anode inlet stream. The technology in the '315 publication is concerned with providing enough fuel in the anode inlet so that sufficient fuel remains for the oxidation reaction as the fuel approaches the anode exit. To ensure adequate fuel, the '315 publication provides fuel with a high concentration of $H_2$. The $H_2$ not utilized in the oxidation reaction is recycled to the anode for use in the next pass. On a single pass basis, the $H_2$ utilization may range from 10% to 30%. The '315 reference does not describe significant reforming within the anode, instead relying primarily on external reforming.

U.S. Published Patent Application 2005/0123810 describes a system and method for co-production of hydrogen and electrical energy. The co-production system comprises a fuel cell and a separation unit, which is configured to receive the anode exhaust stream and separate hydrogen. A portion of the anode exhaust is also recycled to the anode inlet. The operating ranges given in the '810 publication appear to be based on a solid oxide fuel cell. Molten carbonate fuel cells are described as an alternative.

U.S. Published Patent Application 2003/0008183 describes a system and method for co-production of hydrogen and electrical power. A fuel cell is mentioned as a general type of chemical converter for converting a hydrocarbon-type fuel to hydrogen. The fuel cell system also includes an external reformer and a high temperature fuel cell. An embodiment of the fuel cell system is described that has an electrical efficiency of about 45% and a chemical production rate of about 25% resulting in a system coproduction efficiency of about 70%. The '183 publication does not appear to describe the electrical efficiency of the fuel cell in isolation from the system.

U.S. Pat. No. 5,084,362 describes a system for integrating a fuel cell with a gasification system so that coal gas can be used as a fuel source for the anode of the fuel cell. Hydrogen generated by the fuel cell is used as an input for a gasifier that is used to generate methane from a coal gas (or other coal) input. The methane from the gasifier is then used as at least part of the input fuel to the fuel cell. Thus, at least a portion of the hydrogen generated by the fuel cell is indirectly recycled to the fuel cell anode inlet in the form of the methane generated by the gasifier.

An article in the Journal of Fuel Cell Science and Technology (G. Manzolini et. al., *J. Fuel Cell Sci. and Tech.*, Vol. 9, February 2012) describes a power generation system that combines a combustion power generator with molten carbonate fuel cells. Various arrangements of fuel cells and operating parameters are described. The combustion output from the combustion generator is used in part as the input for the cathode of the fuel cell. One goal of the simulations in the Manzolini article is to use the MCFC to separate $CO_2$ from the power generator's exhaust. The simulation described in the Manzolini article establishes a maximum outlet temperature of 660° C. and notes that the inlet temperature must be sufficiently cooler to account for the temperature increase across the fuel cell. The electrical efficiency (i.e. electricity generated/fuel input) for the MCFC fuel cell in a base model case is 50%. The electrical efficiency in a test model case, which is optimized for $CO_2$ sequestration, is also 50%.

An article by Desideri et al. (*Intl. J. of Hydrogen Energy*, Vol. 37, 2012) describes a method for modeling the performance of a power generation system using a fuel cell for $CO_2$ separation. Recirculation of anode exhaust to the anode inlet and the cathode exhaust to the cathode inlet are used to improve the performance of the fuel cell. The model parameters describe an MCFC electrical efficiency of 50.3%.

U.S. Pat. No. 5,169,717 describes a method for integrating a molten carbonate fuel cell with a system for production of ammonia. The integrated system uses a front end different from the molten carbonate fuel cell to process the input hydrogen and nitrogen streams for production of ammonia.

SUMMARY OF THE INVENTION

The operation of molten carbonate fuel cells can be integrated with a variety of processes for production of energy, production of hydrogen, syngas, or other fuels, and/or production of commercially useful compounds.

BRIEF DESCRIPTION OF THE FIGURES

FIGS. 9 and 10 show results from simulations of integrated MCFC and Fischer-Tropsch systems.

FIG. 13 shows process flow values from a calculation for an integrated MCFC and methanol synthesis process.

FIG. 18 shows process flows for an example of integration of molten carbonate fuel cells with a process for producing cement.

FIG. 20 shows process flows for an example of integration of molten carbonate fuel cells with a process for producing iron or steel.

FIG. 22 shows an example of process flows in a system for generating hydrogen and electrical power in a refinery setting.

FIG. 24 shows an example of process flows in a system for generating hydrogen and electrical power in a refinery setting.

FIG. 26 shows results of simulations of a system for generating electricity.

DETAILED DESCRIPTION OF THE EMBODIMENTS

Overview

Figure 1:
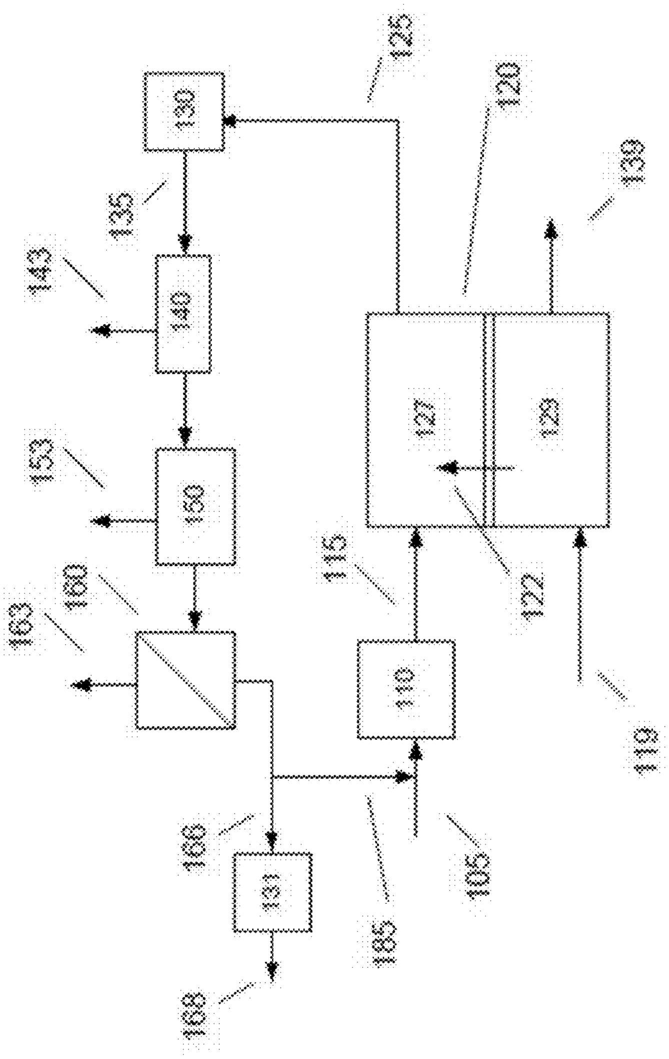
FIG. 1 schematically shows an example of a configuration for molten carbonate fuel cells and associated reforming and separation stages.

In various aspects, the operation of molten carbonate fuel cells can be integrated with a variety of chemical and/or materials production processes. The production processes can correspond to production of an output from the molten carbonate fuel cells, or the production process can consume or provide one or more fuel cell streams.

Integration with Fischer-Tropsch Synthesis

In various aspects, systems and methods are provided for producing high-quality products from Fischer-Tropsch synthesis based on reaction of syngas produced from a MCFC system. The systems and methods can optionally but sometimes preferably use a non-shifting Fischer-Tropsch catalyst, such as a cobalt-based catalyst, to produce largely saturated paraffins of high average molecular weight. This can sometimes be referred to as "low-temperature" Fischer-Tropsch synthesis. Alternatively, the systems and methods can optionally but sometimes preferably use a shifting Fischer-Tropsch catalyst, such as an iron-based catalyst. This can sometimes be referred to as "high-temperature" Fischer-Tropsch synthesis. While other catalyst systems and process conditions may be employed, typical commercial operations can utilize a catalyst based on either cobalt or iron. In some preferred aspects, the largely saturated paraffins typically formed in Fischer-Tropsch product streams can be processed into high-value products such as diesel fuel, jet fuel, and lubricants, and/or can be utilized as blending stocks for those products. In some aspects, the systems and methods can more efficiently produce these products while also producing substantial amounts of electrical power, for instance for the Fischer-Tropsch process and/or for export, while also making efficient use of the carbon input to the overall process. The system can provide high total efficiency in terms of the sum of the electrical and chemical outputs relative to the inputs. Additionally or alternately, the system can produce a $CO_2$ stream (or one or more $CO_2$ streams) suitable for carbon capture/sequestration.

Syngas can be utilized to make variety of products and components useful in the production of fuels, lubricants, chemicals, and/or specialties. One process for converting syngas to these products includes the Fischer-Tropsch process, in which syngas can be reacted over a catalyst at elevated temperature and pressure to produce long-chain hydrocarbons (or hydrocarbonaceous compounds) and oxygenates. The most common catalysts utilized can typically include iron-based catalysts (for so-called high-temperature-Fischer-Tropsch synthesis) and cobalt-based catalysts (for so-called low temperature-Fischer-Tropsch synthesis). Iron-based catalysts, along with other related catalysts, can also be referred to as shifting catalysts, as the water-gas shift reaction can tend to be readily equilibrated on these catalysts. Cobalt-containing catalysts and other related catalysts can be referred to as non-shifting, as they do not appear to substantially perform and/or catalyze the water-gas shift equilibration reaction at standard operating conditions.

Examples of suitable Fischer-Tropsch catalysts can generally include a supported or unsupported Group VIII, non-noble metal e.g., Fe, Ni, Ru, and/or Co, with or without a promoter e.g., ruthenium, rhenium, and/or zirconium. These Fischer-Tropsch processes can typically include fixed bed, fluid bed, and/or slurry hydrocarbon synthesis. In some aspects, a preferred Fischer-Tropsch process can be one that utilizes a non-shifting catalyst, such as based on cobalt and/or ruthenium, preferably comprising at least cobalt, and preferably a promoted cobalt, with the promoter comprising zirconium and/or rhenium, preferably being rhenium, although other promoter metals may also be used. The activities of these catalysts can be enhanced by the addition, optionally as part of a catalyst support, of a variety of metals, including copper, cerium, rhenium, manganese, platinum, iridium, rhodium, molybdenum, tungsten, ruthenium or zirconium. Such catalysts are well known, and a preferred catalyst is described in U.S. Pat. No. 4,568,663 as well as European Patent No. 0 266 898. The synthesis gas feed used in typical Fischer-Tropsch processes can comprise a mixture of $H_2$ and CO wherein $H_2$:CO are present in a ratio of at least about 1.7, preferably at least about 1.75, more preferably 1.75 to 2.5, such as at least about 2.1 and/or about 2.1 or less.

Fischer-Tropsch processes can be implemented in a variety of systems such as fixed bed, slurry bed, and multiple channel designs. In various aspects, Fischer-Tropsch processes can be employed in a wide variety of reactors, such as small reactors (e.g. 1+ barrel/day) or in very large reactors (e.g. 10,000-50,000 barrels/day or more). The product, typically a hydrocarbon wax, can be used as is and/or can be converted to other (e.g. liquid) components by a variety of well-known chemical processes.

Generally, the Fischer-Tropsch process can be operated in the temperature range of about 150° C. to about 32° C. (302° F.-626° F.) and at pressures ranging from about 100 kPaa to about 10 MPaa. Modifying the reaction conditions within the Fischer-Tropsch process can provide control over the yield and/or composition of the reaction products, including at least some control of the chain length of the reaction products. Typical reaction products can include alkanes (primary reaction product), as well as one or more of oxygenates, olefins, other hydrocarbonaceous compounds similar to hydrocarbons but which may contain one or more heteroatoms different from carbon and hydrogen, and various additional reaction by-products and/or unreacted feed components. These additional reaction products and feed components can include $H_2O$, unreacted syngas (CO and/or $H_2$), and $CO_2$, among other things. These additional reaction products and unreacted feed components can form a tail gas that can be separated from the primary reaction products of the Fischer-Tropsch process in gaseous form, as opposed to non-gaseous product, such as the more typical (desired) liquids and/or hydrocarbonaceous compounds generated by the process. When the goal of the Fischer-Tropsch process is synthesis of longer chain molecules, such as compounds suitable for use as a naphtha feed, a diesel feed, or other distillate boiling range molecules, some small (C1-C4) alkanes, olefins, oxygenates, and/or other hydrocarbonaceous compounds may be incorporated into the tail gas. The primary products from Fischer-Tropsch synthesis can be used directly, and/or can undergo further processing, as desired. For example, a Fischer-Tropsch synthesis process for forming distillate boiling range molecules can generate one or more product streams that can subsequently be dewaxed and/or hydrocracked in order to generate final products, e.g. with desired chain lengths, viscosities, and cold flow properties.

Integration of a Fischer-Tropsch process with molten carbonate fuel cells can allow for integration of process streams between the synthesis process and the fuel cell. The initial syngas input for the Fischer-Tropsch process can be generated by the reforming stage associated with the fuel cell. Additionally or alternately, the tail gas produced by the Fischer-Tropsch process can be recycled to provide a supplemental fuel stream for the anode of the fuel cell, and/or to provide a source of $CO_2$ for the fuel cell cathode. The MCFC/Fischer-Tropsch system can further additionally or alternately be integrated with the use of a gas turbine power plant and carbon capture, providing an overall plant producing larger amounts of electricity and liquid fuels.

In some aspects, the tail gas produced by a Fischer-Tropsch process can be used in an improved manner to provide at least a portion of the $CO_2$ for a cathode inlet stream. The tail gas from a Fischer-Tropsch synthesis reaction can generally be considered a relatively low value stream. The tail gas can include a substantial portion of $CO_2$, and can potentially include at least some fuel components such as CO, $H_2$, small alkanes, and/or small oxygenates. Due to the relatively low concentration of the fuel components and/or the relatively high concentration of the $CO_2$, the tail gas is generally not useful directly as a fuel. A separation can be performed to attempt to remove the fuel components from the tail gas, but such a separation can typically be inefficient relative to the amount of fuel derived from the separation.

Instead of attempting to separate the fuel components from the tail gas stream, in various aspects, a separation can be performed to separate a portion of the $CO_2$ from the tail gas stream. This can result in formation of a $CO_2$ stream and a remaining portion of the tail gas stream. This separation strategy can potentially provide several potential benefits. When the separation is done to isolate only a portion of the $CO_2$, the separation can preferably be used to form a relatively high purity $CO_2$ stream. Although the concentration of fuel in the remaining tail gas stream may be only moderately increased, the total volume of the tail gas stream can be reduced, making the remaining portion of the tail gas stream more suitable for use as at least a portion of a cathode inlet stream, or possibly using the remaining portion as the cathode inlet stream. Prior to use as a cathode inlet stream, the fuel in the remaining portion of the tail gas can be combusted to form $CO_2$ and $H_2O$, optionally while also heating the remaining portion of the tail gas to a desired cathode inlet temperature. It is noted that one option for controlling the temperature of the remaining portion of the tail gas stream after combustion can include controlling the amount of $CO_2$ removed during the separation. This type of separation strategy can allow the fuel in the tail gas to be used efficiently without having to perform a separation to isolate the fuel. Additionally, when only a partial separation is performed on the $CO_2$ in the tail gas, a relatively purer $CO_2$ stream can be generated. Such a relatively pure $CO_2$ stream can be suitable for sequestration or for other uses involving high purity $CO_2$.

In some aspects, integration of a Fischer-Tropsch process with a MCFC can enable a different type of process flow than a conventional process that utilizes, for example, a steam reformer or autothermal reformer. A typical syngas output from an autothermal reformer can have a $H_2$:CO ratio of less than about 2:1. As a result, to the degree that modification of the ratio of $H_2$ to CO is desired for a conventional process, the modification can typically correspond to increasing the amount of $H_2$ relative to the amount of CO, e.g., to about 2:1. By contrast, in various aspects the composition of the anode exhaust from a MCFC can have a $H_2$:CO ratio of at least about 2.5:1, such as at least about 3:1. In some aspects, it may be desirable to form a syngas with a ratio of $H_2$:CO of about 2:1, such as a ratio of at least about 1.7, or at least about 1.8, or at least about 1.9, and/or about 2.3 or less, or about 2.2 or less, or about 2.1 or less. In such aspects, in order to achieve the desired ratio, the amount of $H_2$ can be reduced relative to the amount of CO. This can be accomplished using a reverse water gas shift reaction, using a membrane to separate out a (high purity) $H_2$ stream, or by any other convenient method of modifying the ratio of $H_2$:CO.

Fischer-Tropsch synthesis can benefit from a number of features of a MCFC system. Typically, syngas produced by Fischer-Tropsch from methane can be made via steam-reforming, autothermal reforming, or partial oxidation involving the use of methane reacted with purified oxygen from air. Such systems can require substantial amounts of capital equipment (air separator) and must also utilize various steps for pre- and post-gas cleanup to produce a syngas of the correct $H_2$/CO ratio, which also needs to be free from undesirable impurities. This can be especially true of the more productive Co-catalyst-based (non-shifting) systems, which are sensitive to poisons such as sulfur. Fischer-Tropsch systems can require substantial heat management and/or heat exchange and can take place at relatively high temperatures.

The MCFC system, in the process of making electricity, can perform syngas production and can produce a clean syngas as a consequence of the large amount of catalyst located in the anode (typically Ni-based) which can tolerate and/or remove most Fischer-Tropsch poisons. As a result, gas processing, heat exchange, and/or cleanup can be at least partially performed in the MCFC. In addition, it can be relatively easy to achieve a desired $H_2$/CO ratio, as the anode effluent has sufficient amounts of all four water-gas shift components and can be adjusted simply by a combination of water and/or $CO_2$ removal and/or additional WGS (or reverse shift).

Fischer-Tropsch reactors can typically produce large amounts of steam, due to the exothermic nature of the reaction. Use of the steam productively can be difficult depending on the plant location. When coupled to an MCFC system that produces electricity, the system can offer a number of areas where heat integration can use the Fischer-Tropsch excess steam/heat. Potential integration examples can include heating reactants after removal of $CO_2$ (such as after cryogenic removal), heating incoming cathode oxidant (air) if it comes from a low temperature $CO_2$ source, and/or integration into a heat-recovery steam-generation system already present for combined cycle electrical generation from the MCFC.

Fischer-Tropsch processes can usually make a quantity of C1 to C4 hydrocarbons (possibly including C1 to C4 oxygenates) not readily incorporated into liquid products. Such C1 to C4 hydrocarbons and/or oxygenates can be recycled to the MCFC either directly or with a pre-reformer and can be used to make electrical power and/or to recycle syngas.

For installations where the use of $CO_2$ has additional value, the separation of $CO_2$ captured from the anode exhaust can provide additional opportunities for integration. Such $CO_2$ can be used, for example for secondary oil recover, for re-injection into the well, or in other processes that where it can be repurposed instead of being wasted in atmospheric exhaust, while enhancing the overall system.

The anode input for a combined Fischer-Tropsch Molten Carbonate Fuel Cell (FT-MCFC) system can comprise or be a fresh methane feed, another type of hydrocarbon or hydrocarbonaceous feed, a feed based on one or more recycle streams containing one or more of CO, $CO_2$, $H_2$, and light hydrocarbons from the Fischer-Tropsch reactor and/or from subsequent processing steps, or a combination thereof. Preferably, the anode feed can comprise or be natural gas and/or methane. The anode outlet from the MCFC system can be used directly, or more commonly can undergo a variety of processes to adjust the $H_2$/CO ratio and/or to reduce the water and $CO_2$ content, so as to be optimized for Fischer-Tropsch synthesis. Such adjustment processes may include separation, water-gas shift reaction, condensation, and absorption, and the like, as well as combinations thereof.

The cathode inlet can contain $CO_2$ and may be derived from a separate combustion process, if present (e.g. from a gas turbine and/or other $CO_2$ effluent). Additionally or alternately, the cathode inlet may additionally or alternately be generated at least in part by recycle of streams from the MCFC anode (after separation) and/or by recycle from the Fischer-Tropsch processes. Further additionally or alternately, the cathode inlet stream can contain $CO_2$ derived from the tail gas from the Fischer-Tropsch process. Still further additionally or alternately, the cathode inlet may be partly derived from combustion of fresh methane or hydrocarbon feed. The cathode effluent can typically be exhausted to the atmosphere, optionally but preferably after heat recovery to, for example, provide heat for other process streams and/or in combined cycle electrical production, though the cathode effluent could optionally but less preferably be sent for further treatment, if desired.

The MCFC fuel utilization conditions can be adjusted to provide a desired amount of electrical energy relative to syngas output. For applications where there are substantial electrical needs (for example, a small gas production alongside a very large off-shore crude oil platform), the FT-MCFC system may produce proportionally more electrical power. Operations based on large-scale conversion, where substantial infrastructure is present, can produce a variety of electrical/chemical mixtures and may vary the output based on local needs.

Figure 6:
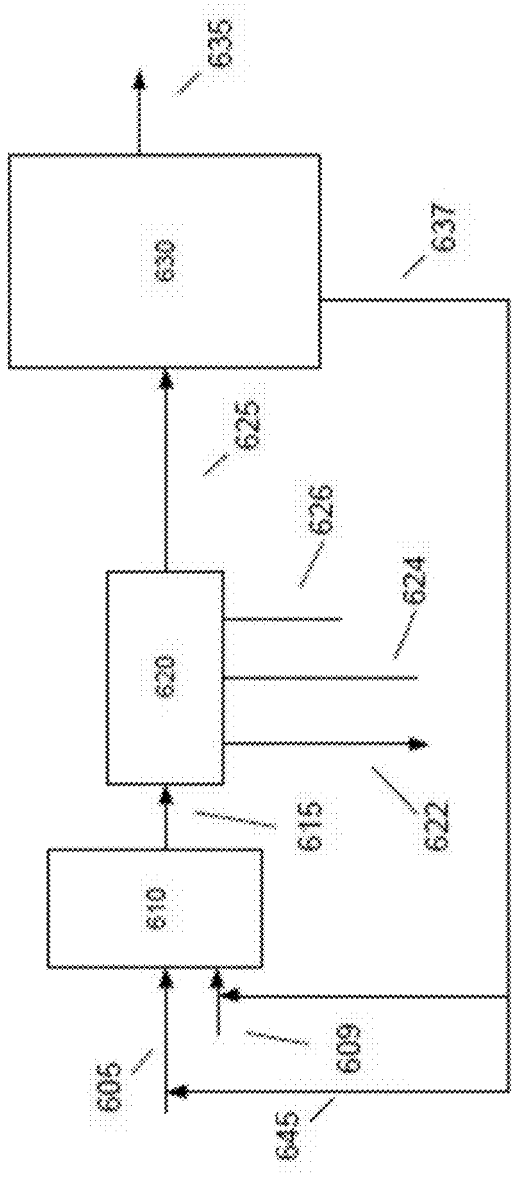
FIGS. 6-8 schematically show examples of configurations for integrating molten carbonate fuel cells with processes for generation of hydrocarbonaceous compounds.

FIG. 6 schematically shows an example of integration of molten carbonate fuel cells (such as an array of molten carbonate fuel cells) with a reaction system for performing Fischer-Tropsch synthesis. In FIG. 6, molten carbonate fuel cell 610 schematically represents one or more fuel cells (such as fuel cell stacks or a fuel cell array) along with associated reforming stages for the fuel cells. The fuel cell 610 can receive an anode input stream 605, such as a reformable fuel stream, and a $CO_2$-containing cathode input stream 609. The cathode output from fuel cell 610 is not shown in FIG. 6. The anode output 615 from fuel cell 610 can then, optionally but preferably, be passed through one or more separation stages 620, which can include $CO_2$, $H_2O$, and/or $H_2$ separation stages, and/or one or more water gas shift reaction stages, in any desired order, as described below and as further exemplified in FIGS. 1 and 2. Separation stages can produce one or more streams corresponding to a $CO_2$ output stream 622, $H_2O$ output stream 624, and/or $H_2$ output stream 626. The separation stages can also produce a syngas output 625 suitable for use as an input for Fischer-Tropsch reaction stage 630.

In the scheme shown in FIG. 6, the anode outlet can produce a syngas with relatively large amounts of water and $CO_2$, as well as exhibiting a $H_2$:CO ratio higher than the preferred 2:1 ratio. In a series of steps, the stream can be cooled to remove water, then passed through a $CO_2$ separation stage to remove most of the $CO_2$. The anode outlet stream and/or the resulting effluent can have a relatively high $H_2$:CO ratio (typically from about 2.5 to about 6:1, for example from about 3:1 to about 5:1) and enough $CO_2$ to provide reactant for the reverse water gas shift reaction. The anode outlet stream and/or the resulting effluent can then be heated to a relatively high temperature (typically from about 400° C. to about 550° C.) where $CO_2$ can react with $H_2$ to produce $CO+H_2O$. The resultant gas can exhibit a $H_2$:CO ratio closer to the conventional 2:1. This gas can then be fed into the Fischer-Tropsch reactor containing a non-shifting Fischer-Tropsch catalyst. As an alternative, from an energy management standpoint, it may be desirable to perform the reverse water gas shift reaction first, and then separate out $CO_2$ and $H_2O$ in a convenient order.

The Fischer-Tropsch reaction stage 630 can produce a Fischer-Tropsch product 635 that can be used directly or that can undergo further processing, such as additional hydroprocessing. Hydroprocessing of the Fischer-Tropsch wax, when desired, can typically be accomplished at elevated temperature and pressure in the presence of hydrogen to produce materials (such as at least one non-gaseous product) that can be useful products such as diesel blending stock and/or lube base stock. Fischer-Tropsch reaction stage 630 can additionally or alternately generate a tail gas 637 that can optionally be recycled for use as a recycled fuel 645, for instance for the anode and/or cathode portion of the fuel cell 610. In most cases, it can be preferable to recycle this stream at least to the cathode where the residual fuel components (CO, $H_2$, and light hydrocarbons) can be mixed and burned with oxidant (air) to reach an appropriate temperature for the cathode input. Optionally, the $CO_2$ output 622 from the separation stage(s) 620 can be used as at least a portion of the input (not shown) for the cathode of fuel cell 610, though this is generally not preferred.

In most embodiments, the syngas output from a MCFC system can be utilized as the source of syngas for a Fischer-Tropsch process. In the case of shifting FT catalysts (such as an Fe-based catalyst), the shifting catalyst can adjust the $H_2$/CO ratio, even if different than the conventional 2:1, via the water-gas shift reaction (or reverse water gas shift reaction) under reaction conditions to produce Fischer-Tropsch products. While a lower $H_2$:CO ratio can be desired in certain embodiments, individual systems could choose to adjust or not to adjust this ratio prior to exposure to a shifting catalyst. In some aspects, removal of $CO_2$ prior to introducing can be reduced or minimized when using a shifting catalyst. When using a Fischer-Tropsch synthesis catalyst based on cobalt (or another type of non-shifting catalyst), the synthesis catalyst typically does not have meaningful activity for performing the water gas shift reaction at Fischer-Tropsch reaction conditions. As a result, $CO_2$ present in a syngas stream exposed to a non-shifting Fischer-Tropsch catalyst can act mainly as a diluent, and therefore may not substantially interfere with the Fischer-Tropsch reaction, though it can tend to lower reactor productivity due to dilution. However, due to the non-shifting nature of the catalyst, the catalyst cannot easily adjust the ratio of $H_2$:CO of the syngas that enters the Fischer-Tropsch reactor.

Figure 7:
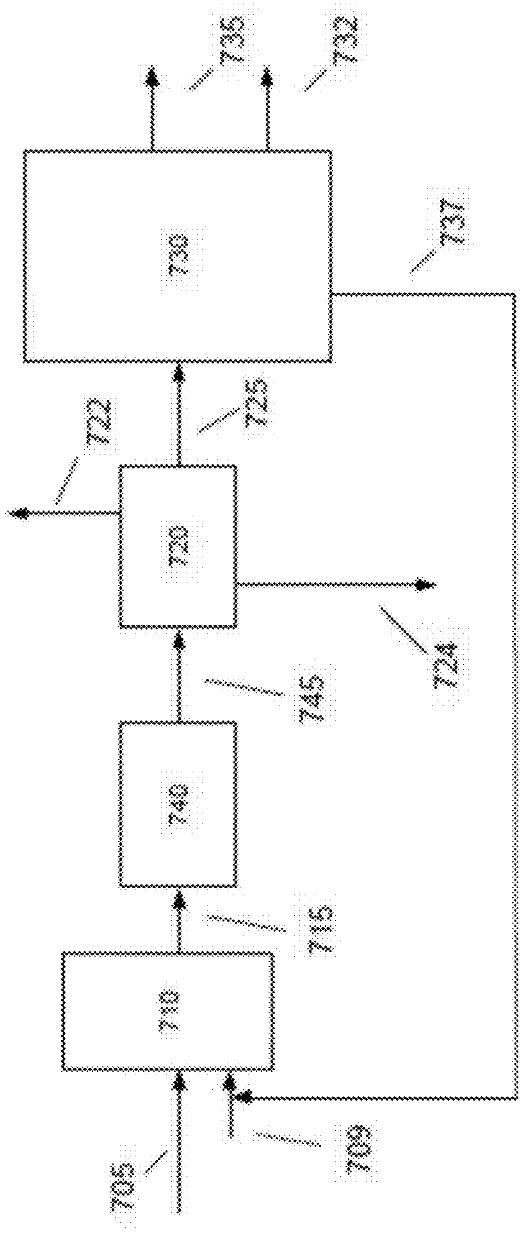

FIG. 7 schematically shows another example of integration of molten carbonate fuel cells (such as an array of molten carbonate fuel cells) with a reaction system for performing Fischer-Tropsch synthesis. The configuration shown in FIG. 7 can be suitable, for example, for use in a larger scale system. In FIG. 7, molten carbonate fuel cell 710 schematically represents one or more fuel cells (such as fuel cell stacks or a fuel cell array) along with associated reforming stages for the fuel cells. The fuel cell 710 can receive an anode input stream 705, such as a reformable fuel stream, and a $CO_2$-containing cathode input stream 709. The cathode input stream 709 can correspond to an exhaust gas from a combustion-powered turbine, to a recycle stream from another gas stream in the integrated Fischer-Tropsch/MCFC system, to a methane stream that has been combusted to generate heat, and/or to another convenient stream that can provide $CO_2$ at a desired temperature for the fuel cell. The cathode input stream 709 can typically include a portion of an oxygen-containing stream. The anode output 715 from fuel cell 710 can be initially passed through a reverse water gas shift stage 740 to modify the ratio of $H_2$:CO in the anode exhaust. The modified anode exhaust 745 can then be passed into one or more separation stages 720, which can include $CO_2$ and $H_2O$ separation stages. Separation stages can produce one or more streams corresponding to a $CO_2$ output stream 722 and/or an $H_2O$ output stream 724. Optionally but preferably, the output from the separation stage(s) for use in the Fischer-Tropsch process can have a $CO_2$ concentration that is less than half of a $CO_2$ concentration of the anode exhaust, a $H_2O$ concentration that is less than half of a $H_2O$ concentration of the anode exhaust, or a combination thereof. A compressor (not shown) can be used after some or all of the separation stages 720 to achieve a desired input pressure for the Fischer-Tropsch reaction process. Optionally, an $H_2$ output stream (not shown) could additionally or alternately be generated. The separation stages can typically produce a syngas output 725, which can be suitable for use as an input for Fischer-Tropsch reaction stage 730, such as a non-shifting Fischer-Tropsch synthesis catalyst. The Fischer-Tropsch reaction stage 730 can produce Fischer-Tropsch liquid products 735, lower boiling C2-C4 compounds 732, and a tail gas 737. The lower boiling C2-C4 compounds can be separated from the liquid products and then further isolated for use as products and/or raw materials for further reaction. Additionally or alternately, the C2-C4 compounds can be allowed to remain with the tail gas 737 and can be recycled, for example, to the cathode after combustion to provide heat and $CO_2$ for the fuel cell cathode.

Example of Integration Application—Distributed Processing

For some Fischer-Tropsch applications, such as those in isolated areas, a combined FT-MCFC system can have an advantage of being sized to provide at least a portion of the local electrical power to operate the system, and additionally or alternately to provide additional power for other facilities or a locality, while converting additional hydrocarbon inputs beyond this requirement into higher value products. The power provided can be a portion of the power or all of the necessary power for the system and/or a locality. Such installations could include isolated land-based gas sources, ship- and/or platform-mounted sea-based installations, or the like. Due to the ease of adjusting the size of the MCFC system, based on the size and number of fuel cell stacks or arrays, any conceivable scale from very small to world-scale installations can be integrated.

Fischer-Tropsch synthesis has traditionally been most practical when done at very large scale. This has been primarily due to the economies of scale of several of the core processes including air separation, reforming of methane to syngas (for example, by auto-thermal reforming, catalytic partial oxidation, or the like), and the hydrocarbon synthesis reactor. Conventionally, single process "trains" can produce greater than 10,000 barrels of product/day, and overall plant sizes from 30-150 thousands of barrels/day have been practiced commercially. For operations of this size, very large gas deposits were required, and this has limited the applications of the technology, at economically reasonable terms, to only a few gas reservoirs.

In contrast to such conventional large scale operations, in some aspects, a process and system are provided for using Fischer-Tropsch synthesis in an efficient system that can be applied advantageously to smaller gas deposits. The process and system can employ a MCFC to produce syngas to feed the Fischer-Tropsch reactor and need not necessarily include many of the complexities of a conventional large-scale plant. The MCFC system can be capable of producing at least a portion (and potentially all) of the electrical power for the various sub-systems, such as compressors and pumps, while producing a very high carbon conversion from syngas to liquid products. It can be used with either shifting or non-shifting catalysts in various configurations and can be suitable to either high- or low-temperature Fischer-Tropsch processes.

As noted above, examples of suitable Fischer-Tropsch catalysts can generally include a supported or unsupported Group VIII, non-noble metal e.g., Fe, Ni, Ru, and/or Co, with or without a promoter e.g., ruthenium, rhenium, and/or zirconium. These Fischer-Tropsch processes can be practiced using reactors such as fixed bed, fluid bed, and/or slurry hydrocarbon synthesis. Some Fischer-Tropsch processes can utilize a non-shifting catalyst, such as based on cobalt and/or ruthenium, preferably comprising at least cobalt, and preferably a promoted cobalt, with the promoter comprising or being zirconium and/or rhenium, preferably comprising or being rhenium. Such catalysts are well known, and a preferred catalyst is described in U.S. Pat. No. 4,568,663 as well as European Patent No. 0 266 898, both of which are hereby incorporated by reference for their description of such catalyst and its physico-chemical characteristics. The synthesis gas feed used in the Fischer-Tropsch process can comprise a mixture of $H_2$ and CO wherein $H_2$:CO are present in a ratio of at least about 1.7, preferably at least about 1.75, more preferably 1.75 to 2.5, such as at least about 2.1 and/or about 2.1 or less. For non-shifting catalysts, the syngas produced by the MCFC can typically start with a $H_2$:CO ratio well above 2:1, and additional processes can be used to "shift" the syngas mixture closer to the conventional $H_2$:CO ratio of about 2:1.

Alternately, a shifting catalyst (such as an Fe-based catalyst) can be used. While the product distribution and overall productivity of shifting catalysts can sometimes be considered inferior to non-shifting systems, shifting catalyst based systems can have the distinct advantage of being able to employ a wider range of syngas mixtures (having a wider range of $H_2$:CO ratios). Conventionally, shifting catalysts have been used primarily to accommodate coal-sourced syngas having a $H_2$:CO ratio typically from about 0.7 to about 1.5. In contrast, the syngas mixture employed herein can contain excess $H_2$, but also can contain a large percentage of $CO_2$. A system incorporating a shifting catalyst can advantageously "reverse-shift" these mixtures, reacting $H_2$ with $CO_2$ to produce additional CO for the Fischer-Tropsch reactor, in some embodiments without needing to pre-shift the reactants to approximately a 2:1 $H_2$:CO ratio.

In a distributed processing environment, a Fischer-Tropsch process can be operated in the temperature range of about 150° C. to about 33° C. (about 302° F. to about 626 F) and at pressures ranging from about 100 kPaa to about 10 MPaa (about 1 bara to about 100 bara). Modifying the reaction conditions of the Fischer-Tropsch process can provide control over the yield and composition of the reaction products, including at least some control of the chain length of the reaction products. Typical reaction products can include alkanes (primary reaction product), as well as one or more of oxygenates, olefins, other hydrocarbonaceous compounds similar to hydrocarbons but that may contain one or more heteroatoms different from carbon or hydrogen, and/or various additional reaction by-products and/or unreacted feed components. These additional reaction products and feed components, when present, can include one or more of $H_2O$, unreacted syngas (CO and/or $H_2$), $CO_2$, and $N_2$. These additional reaction products and unreacted feed components can additionally or alternately form a tail gas that can be separated from the primary reaction products of the Fischer-Tropsch process. When the goal of the Fischer-Tropsch process is synthesis of longer chain molecules, such as compounds suitable for use as a naphtha feed, a diesel feed, and/or other distillate boiling range molecules, some small (C1-C4) alkanes, olefins, oxygenates, and/or other hydrocarbonaceous compounds may be incorporated into the tail gas. The primary products from Fischer-Tropsch synthesis can be used directly, and/or can undergo further processing. For example, a Fischer-Tropsch synthesis process for forming distillate boiling range molecules can generate one or more product streams that can be subsequently dewaxed and/or hydrocracked in order to generate final products with desired chain lengths, viscosities, and cold flow properties.

Under typical operating conditions, representative gas compositions at the MCFC anode exhaust can have $H_2$:CO ratios that can range from about 2.5:1 to about 10:1 and that can, in most embodiments, fall in the range from about 3:1 to about 5:1. This anode exhaust composition can also contain significant amounts of both water and $CO_2$.

An integrated MCFC-FT system can allow for any one or more of several alternate configurations that may be used advantageously, avoiding processes typical of conventional Fischer-Tropsch. In an aspect with some similarities to a conventional configuration, the syngas from the anode exhaust can be shifted close to a 2:1 $H_2$:CO ratio (e.g., from about 2.5:1 to about 1.5:1, from about 1.7:1 to about 2.3:1, from about 1.9:1 to about 2.1:1, from about 2.1:1 to about 2.5:1, or from about 2.3:1 to about 1.9:1) and most (at least half) of the $CO_2$ and $H_2O$ can be removed. Alternately, in another configuration, the syngas from the anode exhaust can be used as is, without any change in composition, but with simple adjustment of temperature and pressure to the appropriate Fischer-Tropsch catalyst conditions. In still another configuration, the syngas from the anode exhaust can be used without being (water gas) shifted, but water can be condensed and largely removed, producing a syngas comprising $H_2$, CO, and $CO_2$, with small amounts (typically <5%) of other gasses. In yet another configuration, water can optionally be removed and then the syngas from the anode exhaust can be reacted in a water-gas shift reactor to "reverse" the shift process, thus converting more $CO_2$ to CO and rebalancing the $H_2$:CO ratio closer to about 2:1 (e.g., from about 2.5:1 to about 1.5:1, from about 1.7:1 to about 2.3:1, from about 1.9:1 to about 2.1:1, from about 2.1:1 to about 2.5:1, or from about 2.3:1 to about 1.9:1). In an alternate configuration, the shifting process can be followed by, or can precede, separation of some $CO_2$ to provide $CO_2$ for carbon capture and/or to reduce $CO_2$ dilution in the syngas from the anode exhaust.

In conventional Fischer-Tropsch processes, the tail gas containing unreacted syngas, along with methane and other C1-C4 gases, can represent unused reactants and low value products. For very large scale installations, these light gases may justify additional processing (e.g. cracking the C2 and C3 molecules to olefins for plastics, recovery of liquefied propane gas or butane, or the like). Unconverted syngas and methane can be recycled to the Fischer-Tropsch synthesis reactor, representing efficiency losses and loss of reactor throughput. In a distributed system environment, some or all lighter gases not converted to product liquids can be used more advantageously as feed for the anode of the fuel cell and/or can be used more advantageously to provide a source of $CO_2$ for the fuel cell cathode.

In one example of a process flow for a MCFC-FT system in a distributed environment, the anode exhaust from a MCFC can be used as the input to the Fischer-Tropsch reaction system after a reduced or minimized amount of processing. If the Fischer-Tropsch catalyst is a shifting catalyst, the anode exhaust can be compressed to a pressure suitable for the Fischer-Tropsch reaction. The compression process may coincidentally and/or purposefully result in some separation/removal of water. If the Fischer-Tropsch catalyst is a non-shifting catalyst, an additional reverse water gas shift reaction can be performed, typically prior to compression, to adjust the syngas $H_2$:CO ratio in the anode exhaust. Optionally, a hydrogen-permeable membrane, other gas-permeable membrane, or other separation technique could be used in addition to or in place of the reverse water gas shift reaction to separate out a (high purity) $H_2$ stream as part of adjusting the $H_2$:CO ratio in the anode exhaust. Otherwise, additional separations and/or modification of the anode exhaust can be avoided, allowing the anode exhaust to be used in the Fischer-Tropsch system with minimal processing. Because the anode exhaust can have a substantial content of $CO_2$, reducing or minimizing the number of separations and/or modifications prior to using a portion of the anode exhaust as the input for a Fischer-Tropsch process can result in having a Fischer-Tropsch input stream that also can contain a substantial content of $CO_2$. For example, the concentration (such as in volume percent) of $CO_2$ in the Fischer-Tropsch input stream can be at least about 60% of the concentration in the anode exhaust, or at least about 65%, or at least about 70%, or at least about 75%, or at least about 80%, or at least about 85%, or at least about 90%. Due to the $CO_2$ content of an anode exhaust from a MCFC, as well as the tendency for the Fischer-Tropsch system to independently generate a substantial amount of $CO_2$, there can be quite a considerable concentration of $CO_2$ in the Fischer-Tropsch product effluent. This $CO_2$ can be at least partially separated from the other products of the Fischer-Tropsch system for sequestration/capture, further processing, and/or use in one or more other processes.

Figure 8:
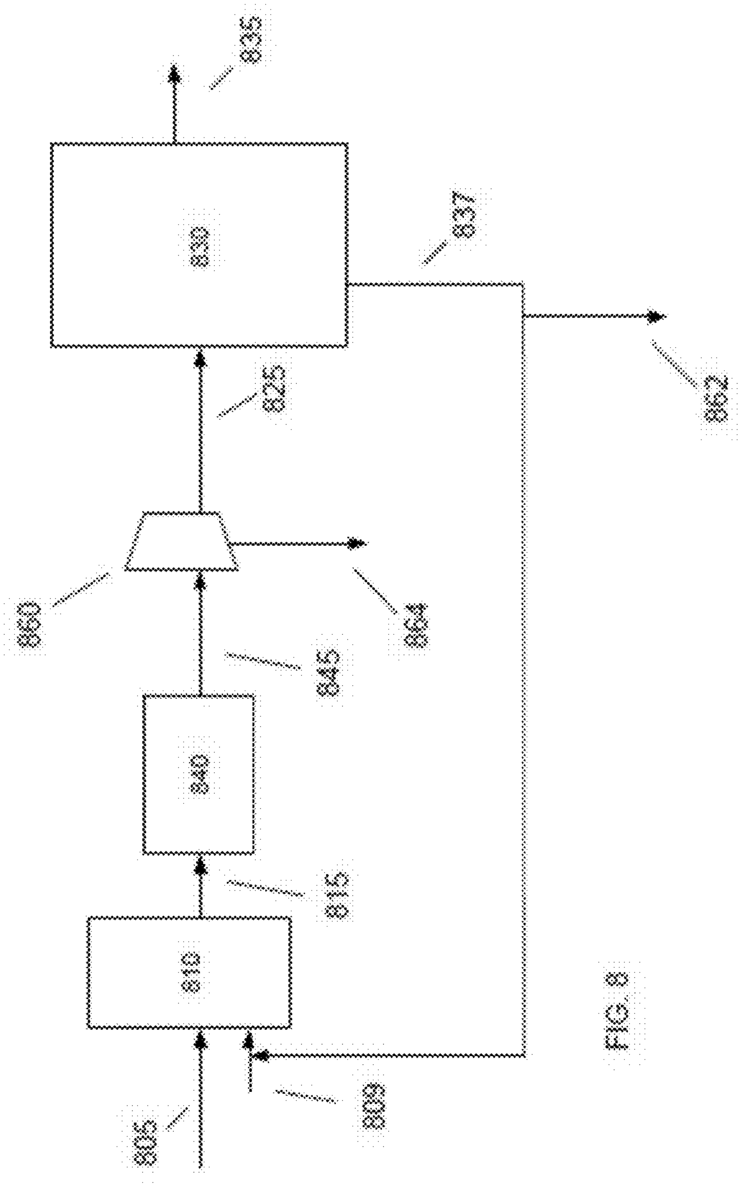

FIG. 8 schematically shows an example of integration of molten carbonate fuel cells (such as an array of molten carbonate fuel cells) with a reaction system for performing Fischer-Tropsch synthesis. The configuration in FIG. 8 can be suitable for use in a small scale or other distributed environment setting. In FIG. 8, molten carbonate fuel cell 810 schematically represents one or more fuel cells (such as fuel cell stacks or a fuel cell array) along with associated reforming stages for the fuel cells. The fuel cell 810 can receive an anode input stream 805, such as a reformable fuel stream, and a $CO_2$-containing cathode input stream 809. The anode output 815 can be passed through an optional reverse water gas shift stage 840. For example, if Fischer-Tropsch reaction stage 830 includes a shifting catalyst, the water gas shift stage 840 can be omitted. The optionally shifted anode exhaust 845 can then be passed into a compressor 860 to achieve a desired input pressure for the Fischer-Tropsch reaction stage 830. Optionally, a portion of the water present in the optionally shifted anode exhaust 845 can be removed 864, prior to, during, and/or after compression 860. The Fischer-Tropsch reaction stage 830 can produce a Fischer-Tropsch product 835 that can be used directly or that can undergo further processing, such as additional hydroprocessing. Fischer-Tropsch reaction stage 830 can also generate a tail gas 837 that can be recycled for use as a recycled fuel 845 for the cathode portion of the fuel cell 810. Prior to recycle, at least a portion 862 of the $CO_2$ present in the tail gas 837 can be separated from the tail gas. Alternatively, the separation of $CO_2$ can be performed prior to, during, and/or after the separation of Fischer-Tropsch product 835 from the tail gas 837.

Example 1—Integration of MCFC with Small Scale FT Processing System

This example describes operation of a small scale Fischer-Tropsch process integrated with operation of an MCFC to provide the syngas input for the Fischer-Tropsch process. The Fischer-Tropsch process in this example can generate about 6000 barrels per day of Fischer-Tropsch liquid products. The configuration for integrating the MCFC with the Fischer-Tropsch process in this example was a variation on the configuration shown in FIG. 8. Thus, in this example, a reduced or minimized amount of separations or modifications can be performed on the anode exhaust prior to introducing the anode exhaust to the Fischer-Tropsch process. In this example, simulation results are shown for both the case where $CO_2$ was separated from the Fischer-Tropsch tail gas for capture and the case where capture was not performed. In this example, the anode input comprised fresh methane, such as methane from a small local source. The cathode input in this example was based on use of combustion of the tail gas to form a cathode input, optionally after separation of $CO_2$ for sequester. However, the cathode input can be provided by any convenient source.

FIG. 9 shows results from simulations performed under several different sets of conditions. In FIG. 9, the first two columns show simulation results from use of a Co-based (non-shifting) catalyst for the Fischer-Tropsch reaction, while the third and fourth columns show results from use of a Fe-based (shifting) catalyst. For the Co-based catalyst, an additional "reverse" water gas shift was performed on the anode output stream to reduce the $H_2$:CO ratio to a value closer to the desired 2:1 ratio. This additional shift reaction was not performed on the anode output prior to introducing the portion of the anode output stream into the Fischer-Tropsch system when using the Fe-based catalyst. The first and third columns show simulation results from a system without $CO_2$ capture, while the second and fourth columns show simulation results from a system where $CO_2$ was separated from the Fischer-Tropsch tail gas for sequester. The amount of $CO_2$ removed was selected to be comparable for the second and fourth columns while still providing sufficient $CO_2$ in the cathode to maintain at least a ~1% $CO_2$ content in the cathode exhaust. In all of these simulations, the fuel utilization in the anode was about 35%. About 40% of the methane was reformed in the fuel cell, with the remainder of the methane being reformed in an earlier integrated reforming stage. The steam to carbon ratio in the anode feed was about 2. The row corresponding to power from a steam turbine represents additional power generated by heat recovery from the cathode exhaust.

Unlike a steam reformer, an MCFC can generate electrical power while also reforming fuel and assisting with separation of $CO_2$ from the cathode input stream. As a result, even for a small scale Fischer Tropsch system, the integrated MCFC-FT system can provide reasonable net efficiencies relative to the input carbon amounts. As shown in FIG. 9, relative to the net carbon input to the burner(s) for heating the system and the fuel cell anode, the total plant efficiency of production of Fischer-Tropsch liquids was between about 60% and about 70%, such as at least about 63%. The total plant efficiency represents an efficiency based on the combined electrical and chemical (Fischer-Tropsch liquid products) output of the plant relative to the total inputs.

Example 2—Integration of MCFC with a FT Processing System

This example describes operation of a Fischer-Tropsch process integrated with operation of an MCFC to provide the syngas input for the Fischer-Tropsch process. A combustion turbine was also integrated with this process via using the exhaust from the turbine as the input to the cathode of the MCFC. The configurations for integrating the MCFC with the Fischer-Tropsch process were variations on the configuration shown in FIG. 7. In this example, results are shown for a first configuration where $CO_2$ was separated from the anode exhaust prior to input to the Fischer-Tropsch process, and for a second configuration where $CO_2$ was instead separated from the Fischer-Tropsch tail gas. Both configurations used a non-shifting catalyst, so a reverse water gas shift was performed in both simulations to adjust the $H_2$:CO ratio. In this example, the anode input comprised fresh methane.

FIG. 10 shows results from the simulations that were performed. In the simulations shown in FIG. 10, a fuel utilization of about 30% was used for the fuel cells. The total efficiency in terms of combined electrical power generation and generation of Fischer-Tropsch products was about 61%, which was similar to the efficiency for the simulations from Example 1. However, about 40% of the total efficiency corresponded to electrical power generation in this example.

Integration with Production of Methanol Intermediate and Final Products

Methanol can typically be made from a syngas mixture, such as a mixture including CO, $H_2$, and optionally $CO_2$, at high pressure and temperature. Conventionally, the majority of methanol plants can utilize natural gas as a feedstock and can generate syngas by common processes like steam reforming, auto-thermal reforming, or partial oxidation. Most common configurations utilize a catalyst that can produce relatively low conversion per pass and can involve substantial recycle, along with production of various off-gasses and purge streams.

Integration of methanol synthesis with a molten carbonate fuel cell can allow for new configurations designed for higher efficiency and/or lower emissions. During methanol synthesis, carbon monoxide and hydrogen can react over a catalyst to produce methanol. Commercial methanol synthesis catalysts can be highly selective, with selectivities of greater than 99.8% possible under optimized reaction conditions. Typical reaction conditions can include pressures of about 5 MPa to about 10 MPa and temperatures of about 250° C. to about 300° C. With regard to the syngas input for methanol synthesis, the preferred ratio of $H_2$ to CO (about 2:1 $H_2$:CO) does not match the typical ratio generated by steam reforming. However, catalysts that facilitate methanol formation from syngas can sometimes additionally facilitate the water-gas shift reaction. As a result, the reaction scheme below shows that $CO_2$ can also be used to form methanol:

$$2H_2+CO=>CH_3OH$$

$$3H_2+CO_2=>CH_3OH+H_2O$$

For methanol synthesis reactions, the composition of the synthesis gas input can be characterized by the Module value M:

$$M=[H_2-CO_2]/[CO+CO_2]$$

Module values close to 2 can generally be suitable for production of methanol, such as values of M that are at least about 1.7, or at least about 1.8, or at least about 1.9, and/or less than about 2.3, or less than about 2.2, or less than about 2.1. As can be noted from the Module Value equation above, in addition to the ratio of $H_2$ to CO, the ratio of CO to $CO_2$ in the syngas can impact the reaction rate of the methanol synthesis reaction.

During operation, a molten carbonate fuel cell can transfer $CO_2$ from the cathode side of the fuel cell to the anode side as part of the internal reaction that allows for generation of electricity. Thus, a molten carbonate fuel cell can both provide additional power in the form of electrical energy as well as providing an anode exhaust that can be adjusted for use as a syngas input for methanol synthesis. The electrical power can typically be used for powering compressors, pumps, and/or other systems at high efficiency. In some aspects, the overall size of the MCFC system can be set to provide at least a portion of (or potentially all) necessary on-site power, or optionally additional power can be generated for the grid. The generation of power on-site can be more efficient due to reducing or minimizing transmission losses. Additionally or alternately, the electrical power can be readily provided as AC, DC, or a mixture of the two, optionally at a plurality of voltages and currents. This can reduce or potentially eliminate the need for inverters and/or other power electronics that can further lower electrical efficiency. Further additionally or alternately, the MCFC electrical power can be generated from input fuel materials from which $CO_2$ can be captured, as opposed to generation of power from disparate and off-site power sources. This power can be generated in a manner that can be integrated into both syngas production and the processing of various purge or off-gas streams.

The output stream from a MCFC anode can contain relatively high concentrations of $H_2$, $CO_2$ and water, with relatively lower concentrations of CO. Through a combination of separations, (reverse) water gas shift reactions, and/or other convenient mechanisms, the composition of the anode exhaust and/or a stream derived/withdrawn from the anode exhaust can be adjusted. The adjustment of the composition can include removing excess water and/or $CO_2$, adjusting the ratio of $H_2$:CO, adjusting the Module value M, or a combination thereof. For example, a typical MCFC anode output may have an $H_2$:CO ratio of about 4:1 when the overall fuel utilization is in the range from about 30% to about 50%. If the anode exhaust is passed through a stage to remove some of the $CO_2$ (for example, a simple cryogenic separation), the $CO_2$ concentration can be adjusted downwards until the "M" value is closer to about 2. As a benefit, this type of process can produce a purified $CO_2$ stream that can be used for other processes and/or removed to lower the plant's overall $CO_2$ emissions.

Various configurations and strategies can be used for integrating molten carbonate fuel cells with methanol synthesis. In one configuration, separations of $H_2O$ and/or $CO_2$ and/or water-gas shift reactions can be used to adjust the M value of the anode exhaust, and/or a portion of the anode exhaust such as a gas stream can be withdrawn from the anode exhaust, e.g., to get closer to the desired M value. Additionally or alternately, $H_2$ production by the fuel cell can be increased/maximized, such as by reducing fuel utilization, e.g., so that an additional $H_2$ stream can also be separated from the anode exhaust and/or from the withdrawn syngas stream.

In a typical methanol plant, a large percentage of the reactor exhaust can be recycled after recovery of methanol liquid, due to low conversion per pass. As with most configurations featuring high recycle amounts, buildup of inerts to the process (e.g. methane) can require significant purge streams that can be rich in non-reactive components. At best, conventional configurations may burn the purge streams for heat to integration, or more likely the purge streams can just be exhausted to the environment. It is noted that, in this type of conventional configuration, carbon not incorporated into the methanol can typically be exhausted to the environment, potentially resulting in high $CO_2$ emissions.

Figure 11:
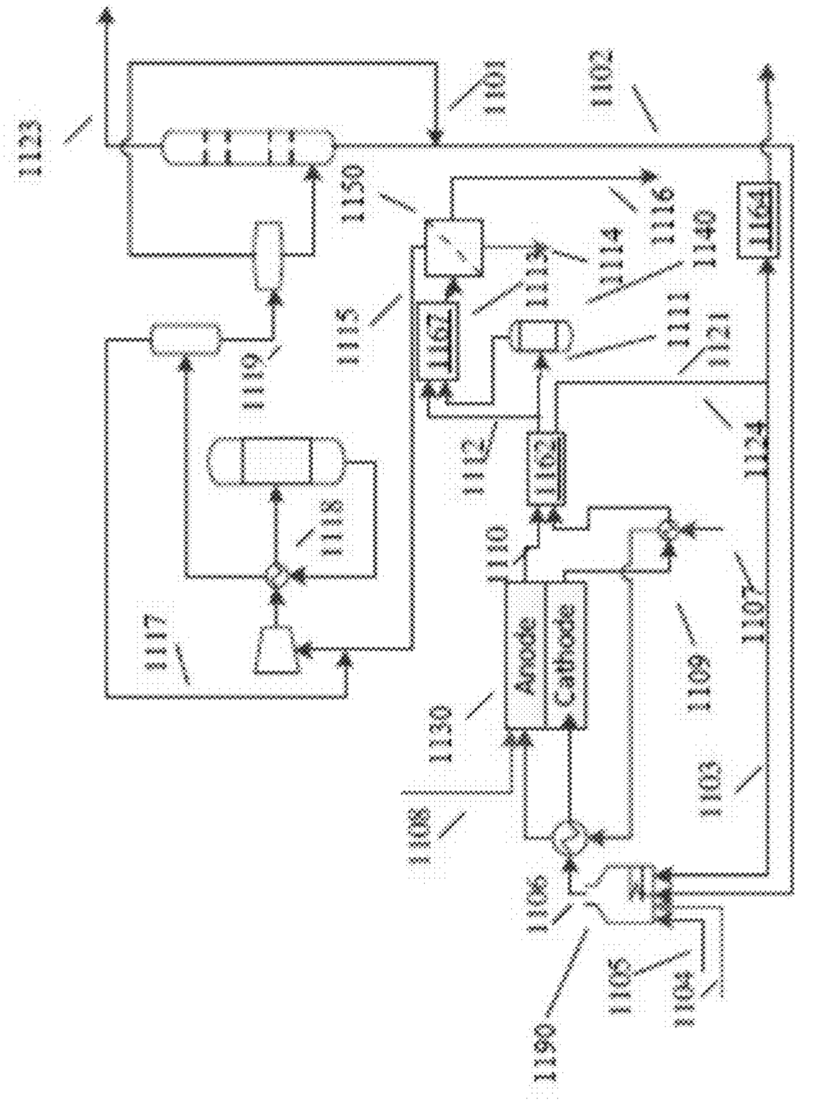
FIGS. 11 and 12 schematically show examples of configurations for integrating molten carbonate fuel cells with processes for synthesis of methanol.

FIG. 11 schematically shows an example of a configuration that can integrate an MCFC with a methanol synthesis process. The configuration shown in FIG. 11 can improve on one or more of the deficiencies of conventional systems. For example, in some configurations, the hot output from the MCFC can be fed to a heat recovery steam generation process (HRSG) to produce electricity, in addition to the electrical output from the MCFC. Additionally or alternately, the process of adjusting the M value of the syngas can result in a separated product rich in $CO_2$, which can be used for partial recycle to the fuel cell cathode and/or which can be purified into a separate increased-purity $CO_2$ product.

In some configurations, the output from the methanol synthesis reaction can be separated into a liquid alcohol product, a recycle syngas stream, and a vented purge. The vented purge can contain syngas components, fuel components (e.g. methane), and inerts. At least a portion of the vented purge can be used as anode and/or cathode feed components. For the liquid alcohol product, typically the collected liquid products can be put into a separation system such as a distillation column, where purified methanol can be withdrawn and a bottom product (e.g., comprised of higher alcohols) can be produced as a waste stream. In a conventional system, the vented purge and/or the waste stream can be used to raise steam for heating the syngas production. This use in a conventional system can be based in part on concerns about the potential buildup in inerts, if the stream(s) is(are) recycled to the methanol synthesis process. By contrast, in various aspects, any byproducts of the methanol synthesis process (such as the vented purge and/or the heavier alcohols, e.g., containing two or more carbons) can be used in the MCFC system to produce more syngas and/or as a carbon source (after combustion) to produce $CO_2$, e.g., for the cathode. Inerts introduced into the cathode that are not reformable (e.g. nitrogen) can be exhausted, while excess fuel molecules can converted into heat and into $CO_2$ that can be readily used within the cathode. As a result, integration of an MCFC with a methanol synthesis process can allow for improved integration of the secondary product streams from methanol synthesis, as the MCFC can avoid excessive buildup of inerts, while still allowing for use of fuel components, as well as allowing for separation of $CO_2$ into higher concentration output streams such as the anode exhaust.

Optionally but preferably, the integration of molten carbonate fuel cells with methanol synthesis can include integration with a turbine, such as a gas turbine. Because methanol synthesis can benefit from at least some $CO_2$ (as shown in the M value), having an external source of $CO_2$ for the cathode inlet of the fuel cell can provide additional benefits. Methanol synthesis can require high amounts of electrical power, at least a portion (or perhaps all) of which can be provided by the MCFC and/or the gas turbine. If electrical power is provided by the MCFC, at least a portion of the equipment (pumps and compressors) can run on DC power. Additionally or alternately, if a gas turbine is used, the gas turbine can allow for steam generation, and the steam from the turbine can be used as a driver for the compressors and methanol recycle. As an example for an integrated system, the input stream for the anode inlet can be generated by methane reforming (and/or by reforming of another reformable fuel). $CO_2$ for the cathode inlet can come from a co-located turbine, from $CO_2$ separation from the anode exhaust, and/or from another source. It is noted that providing $CO_2$ for the cathode inlet from a source such as a gas turbine, as opposed to recycling $CO_2$ from the anode exhaust, can avoid the need for a pressurize/decompress cycle. Further additionally or alternately, heat integration can be used so that low level heat from the methanol synthesis reactor can be used on the front end of the MCFC, e.g., for humidification.

Figure 12:
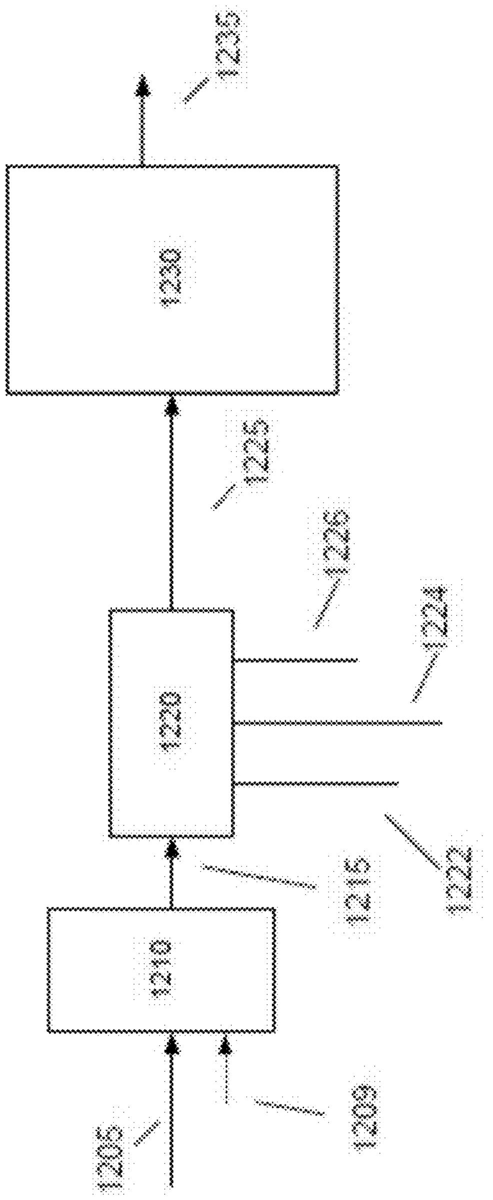

FIG. 12 schematically shows an example of integration of molten carbonate fuel cells (such as an array of molten carbonate fuel cells) with a reaction system for performing methanol synthesis. In FIG. 12, molten carbonate fuel cell 1210 schematically represents one or more fuel cells (such as fuel cell stacks or a fuel cell array) along with associated reforming stages for the fuel cells. The anode output 1215 from fuel cell 1210 can then be passed through one or more separation stages 1220, which can include $CO_2$, $H_2O$, and/or $H_2$ separation stages, as well as water gas shift reaction stages, in any desired order, as described below and as further exemplified in FIGS. 1 and 2. Separation stages can produce one or more streams corresponding to a $CO_2$ output stream 1222, $H_2O$ output stream 1224, and/or $H_2$ output stream 1226. It is noted that, in some aspects, the $CO_2$ output stream 1222 and $H_2$ output stream 1226 may not be present, due to adjustment of the fuel cell operating parameters to achieve a desired value of M in the syngas output. The separation stages can produce a syngas output 1225 suitable for use as an input for methanol synthesis stage 1230. The methanol synthesis stage 1230 can produce a methanol product 1235 that can be used directly and/or that can undergo further processing, such as use as a feed in a further process, such as a methanol-to-olefins and/or methanol-to-gasoline reaction system. Optionally, the $CO_2$ output 1222 from the separation stage(s) 1220 can be used as at least a portion of the input (not shown) for the cathode of fuel cell 1210.

As an example of producing and/or withdrawing a syngas stream from the anode exhaust, in an aspect, the effluent or exhaust from an anode can first be cooled and then pressurized to MeOH synthesis pressures, such as a pressure of about 700 psig (about 4.8 MPag) to about 1400 psig (about 9.7 MPag). Separation of the $CO_2$ in order to achieve a desired M value for the syngas stream, such as by cryogenic separation, can be easier at such pressures. Additionally or alternately, if the M ratio deviates from a desired value, the M value can be adjusted, e.g., by recycle (purge) of the excess syngas through the anode input loop. In some cases, $CO_2$ can build up in the recycle loop, and this can be recycled into the (cryogenic) separation loop as well.

FIG. 11 shows another example of an integrated system that includes a MCFC and a methanol synthesis process. In FIG. 11, the configuration can be suitable for, as an example, conversion of natural gas/methane to methanol with an integrated MCFC-catalytic reactor system. In this type of configuration, the MCFC can produce the intermediate syngas that can be fed to a catalytic reactor for methanol production. In a typical methanol form natural gas process, syngas can be generated by methane steam reforming in an autothermal reactor (ATR). The heat from the ATR can be recovered to produce electricity and steam for the rest of the process. Three commercial processes are documented in SRI Process Economics Program Report 49C on Methanol (See Apanel, George J., Methanol-Report No. 39C. SRI Consulting, March 2000). A two stage process from that report can be used as a representative example of a methanol synthesis process. This two stage process was used as the comparative basis for the simulations described herein.

FIG. 11 shows a diagram of the integrated process. Vent gases 1101 and heavy ($C_{2+}$) alcohol side products 1102 from the conversion reactors and a fraction of the cathode exhaust 1103 can be returned to the MCFC cathode feed burner 1190. Air 1104, methane 1105, vent gases 1101, alcohol side products 1102, and cathode exhaust 1103 can be combusted to produce a hot cathode feed 1106. By pre-heating the anode methane feed 1107, cathode feed 1106 can be cooled to the inlet operating temperature and then fed to the cathode. Anode (methane) feed 1107 and steam 1108 can be fed to the anode. The MCFC 1130 can produce a hot cathode exhaust 1109 depleted of $CO_2$ and a hot anode exhaust 1110, which can contain mostly $H_2/CO_2/C0$ and water. The MCFC 1130 can be run under a variety of conditions, including conditions with a reduced fuel utilization, such as a fuel utilization of about 50% or less. Cathode exhaust 1109 can be cooled by partially pre-heating anode methane and/or other fuel feed 1107 and then can be sent to a heat recovery steam generation system (HRSG) 1162 to recover more heat and/or to raise steam for the process. The cooled cathode exhaust 1124 can be split into stream 1103, which can be recycled to the cathode feed burner, and stream 1121 which can be emitted to the atmosphere and/or further treated, if desired (not shown). The remaining heat in 1121 can be recovered in a HRSG 1164. The anode exhaust 1110 can be sent to a HRSG, such as HRSG 1162. The cooled anode exhaust can be split or divided into streams 1111 and 1112, with stream 1111 being fed to a water-gas shift reactor 1140 to make shifted divided stream 1113. Shifted divided stream 1113 can be combined with the second divided stream 1112 and sent to a separator 1150, where it can be dehydrated 1114 and separated into a syngas stream 1115, with M=approximately 2, and remaining stream 1116, which can contain mostly $CO_2$. $CO_2$-containing stream 1116 can be compressed and sold for use and/or sent to a sequestration facility. The split between streams 1111 and 1112 can be determined such that syngas 1115 can have a desired M value for the methanol conversion reactor feed. Syngas 1115 can be combined with a reactor recycle stream 1117. The combined streams can be compressed, heated, and fed to the conversion reactor 1170 to make effluent 1118. Effluent 1118 can be, for example, flashed to recover the reactor recycle stream 1117 and a product stream 1119. Methanol 1123 can be recovered from product stream 1119, while also producing vent gases 1101 and heavy alcohol side products (containing 2 or more carbons) 1102 as byproducts.

The MCFC process can be sized to produce the necessary syngas feed for a methanol conversion reactor. In the calculations provided in this example, the MCFC was sized to produce syngas for a ~2500 tons per day (tpd) methanol conversion reactor, based on the representative process that was selected. Based on calculations performed using mass and heat balance considerations, the MCFC was calculated to produce about 176 MW. Additional details about the process flows are shown in FIG. 13, which shows the composition of the flows within the FIG. 11 configuration. The numbers at the head of each column correspond to the identifiers in FIG. 11. Part of the power generated by the MCFC can be used for syngas separation and compression, while the remainder can be used in other parts of the process and/or exported. Additionally, based on the calculations, the heat recovered from the MCFC anode and cathode effluent streams generated at least ~3146 tpd of high pressure steam, which was enough to meet steam and heating demands of the representative methanol synthesis process modeled in the calculations. It is noted that, for the calculation involving the MCFC, any utilities associated with autothermal reforming were not considered in determining if the MCFC could provide the inputs for the synthesis process. Under the assumption that separated $CO_2$-containing stream 1116 can be sold for use and/or sequestered, the integrated process shown in FIG. 11 can provide a method to produce methanol from natural gas (methane) with reduced $CO_2$ emissions, compared to a traditional process. Table B shows the amount of $CO_2$ that was calculated as being emitted from the selected literature comparative configuration, along with the reduced $CO_2$ emissions that were calculated based on the configuration in FIG. 11. For the base case calculation in Table A, it was assumed that the vent from the autothermal reformer and the exhaust from the natural gas boiler were the largest emission sources.

TABLE B

| | kg $CO_2$/kg MeOH produced |
|---|---|
| 2 stage process (base case) | 0.318 |
| MCFC + 2 stage process conversion reactor | 0.025 |

It is noted that some dimethyl ether (DME) and butanol ($C_4H_9OH$) can be generated during the methanol synthesis process. Dimethyl ether can be an example of a subsequent product that can be produced using methanol generated in a methanol synthesis process. More generally, methanol can be used to generate a variety of additional products, such as dimethyl ether, olefins, fuels such as naphtha and/or diesel, aromatics, and other industrially useful products, as well as combinations thereof. An MCFC can additionally or alternately be integrated into synthesis process where the output from a methanol synthesis plant is passed into an additional reaction system for production of another product. Such integration can include providing syngas inputs, providing electricity for the system, handling output streams of lower value, and/or separating out streams having increased concentration of $CO_2$, as described above for integration with a methanol synthesis process.

Integration with Production of Nitrogen-Containing Intermediate and Final Products Ammonia can typically be made from $H_2$ and $N_2$ via the Haber-Bosch process at elevated temperature and pressure. Conventionally, the inputs can be a) purified $H_2$, which can be made from a multi-step process that can typically require steam methane reforming, water gas shift, water removal, and trace carbon oxide conversion to methane via methanation; and b) purified $N_2$, which can typically be derived from air via pressure swing adsorption. The process can be complex and energy intensive, and the process equipment can benefit strongly from economies of scale. An ammonia synthesis process utilizing molten carbonate fuel cells can provide one or more advantages relative to a conventional process, including but not limited to additional power production, reduced complexity, and/or better scalability. Additionally or alternately, an ammonia synthesis process utilizing molten carbonate fuel cells can provide a mechanism to reduce $CO_2$ production and/or generate $CO_2$ for use in other processes.

In various aspects, the MCFC system can generate syngas as an output. The syngas can be largely free of any impurities such as sulfur that would need removal, and the syngas can provide a source of $H_2$ for the ammonia synthesis. The anode exhaust can first be reacted in a water-gas shift reactor to maximize the amount of $H_2$ relative to CO. Water-gas shift is a well-known reaction, and typically can be done at "high" temperatures (from about 300° C. to about 500° C.) and "low" temperatures (from about 100° C. to about 300° C.) with the higher temperature catalyst giving faster reaction rates, but with higher exit CO content, followed by the low temperature reactor to further shift the syngas to higher $H_2$ concentrations. Following this, the gas can undergo separation via one or more processes to purify the $H_2$. This can involve, for example, condensation of the water, removal of $CO_2$, purification of the $H_2$ and then a final methanation step at elevated pressure (typically about 15 barg to about 30 barg, or about 1.5 MPag to about 3 MPag) to ensure that as many carbon oxides as possible can be eliminated. In conventional ammonia processes, the water, $CO_2$, and methane streams generated during purification of the $H_2$ stream, as well as additional off-gases from the ammonia synthesis process, can represent waste streams of very low value. By contrast, in some aspects, the various "waste" gases can create streams that can be used in other parts of the MCFC—Ammonia system, while potentially generating still other streams that can be useful in further processes. Lastly, the $H_2$ stream can be compressed to ammonia synthesis conditions of about 60 barg (about 6 MPag) to about 180 barg (about 18 MPag). Typical ammonia processes can be performed at about 350° C. to about 500° C., such as at about 450° C. or less, and can result in low conversion per pass (typically less than about 20%) and a large recycle stream.

As an example of integration of molten carbonate fuel cells with ammonia synthesis, the fuel stream to the anode inlet can correspond to fresh sources of reformable fuel and/or $H_2$ along with (optionally but preferably) recycle off-gas from the ammonia synthesis process, which can contain $H_2$, $CH_4$ (or other reformable hydrocarbons), and/or CO. Ammonia processing, due to large recycle ratios and the presence of diluents (for example: the methane produced by methanation to remove all carbon oxides), can produce significant purge and waste streams. Most of these streams, as long as they do not contain reactive oxidants such as oxygen, can be compatible with the fuel cell anode inlet. The anode inlet can additionally or alternately comprise separation gases from hydrogen purification, as these gases can typically contain a mixture that comprises $H_2$, CO, $CO_2$, $H_2O$, and potentially other gases compatible with the anode. The anode exhaust can then be processed using a water gas shift reaction and $H_2$ separation to form a high purity $H_2$ stream. At least a portion of such an $H_2$ stream can then be used as an input for an ammonia synthesis process. Optionally, in addition to performing separations on the high purity $H_2$ stream, the $H_2$ stream can be passed through a methanator prior to use for ammonia synthesis. The goal of the one or more separations and/or purifications can be to increase the purity of the $H_2$ stream, so that at least a portion of an $H_2$ stream with increased purity can be used as an input for the ammonia synthesis.

For the cathode inlet stream, $CO_2$ and $O_2$ can be provided from any convenient source, such as a co-located external $CO_2$ source (for example, a gas-turbine and/or boiler exhaust stream), recycled $CO_2$ separated from the anode exhaust, recycled $CO_2$ and/or $O_2$ from the cathode exhaust, carbon containing streams separated as part of hydrogen purification, and/or $CO_2$ separated from an output of the ammonia synthesis plant. Typically, a mixture of these streams may be used advantageously, and any residual fuel value in the streams can be used, e.g., to provide heat to raise the cathode inlet stream temperature up to the MCFC inlet temperature. For example, fuel streams that are off-gasses from separation and/or the ammonia process can be mixed with sufficient oxidant (air) to combust substantially all the residual fuel components while also providing sufficient oxygen to react with $CO_2$ in the cathode to form carbonate ions. The cathode exhaust stream can have reduced concentrations of both $CO_2$ and $O_2$, as these gases can be reacted to form carbonate that can be transported into the anode stream. Because the MCFC can reduce the $CO_2$ and $O_2$ content of the cathode inlet stream, the cathode exhaust can have an enhanced nitrogen concentration on a dry basis in comparison to air. For systems that are designed to separate $CO_2$ effectively, the cathode exhaust may have $CO_2$ concentrations below about 10% or below about 5% or below about 1% on a dry basis. The oxygen content may additionally or alternately be below about 15% or below about 10% or below about 5% on a dry basis. The $N_2$ concentration can typically exceed about 80% or about 85% or can be greater than about 90% on a dry basis. After capture of the heating value of this stream (such as through steam generation for heat, heat exchange with other process streams, and/or additional electricity), the cathode exhaust can optionally but advantageously be used to form a high purity $N_2$ stream for use in the ammonia synthesis. Any of the typical separation methods for generating pure nitrogen can operate more efficiently on this stream. Optionally, one or more separation processes or purification processes can be performed on the $N_2$ stream in order to generate an $N_2$ stream of increased purity. At least a portion of the $N_2$ having increased purity can then optionally but advantageously be used as the input for ammonia synthesis. During operation, the fuel cell can be operated to match the needs of the ammonia synthesis, such as selected lower or greater amounts of electrical production relative to hydrogen (and/or syngas) production.

Relative to conventional systems (such as described in U.S. Pat. No. 5,169,717), the above integration method can reduce or eliminate the need for a separate front end system for generating the purified $H_2$ and $N_2$ input streams. For example, instead of having a dedicated steam reformer and subsequent cleanup stages, the MCFC can be operated to reform sufficient amounts of reformable fuel to provide purified $H_2$ while also generating electrical power. Typically this can be done by operating the fuel cell at lower fuel utilizations than typical. For example, the fuel utilization can be below about 70%, such as below about 60% or below about 50% or below about 40%. In conventional MCFC operations, fuel utilizations of about 70-80% can be typical, and the residual syngas produced by the anode can be used as fuel to heat incoming streams to the cathode and/or anode. In conventional operations, it can also be necessary to use the anode exhaust stream to provide $CO_2$ to the cathode after it is reacted with air. By contrast, in some aspects it is not necessary to use syngas from the anode exhaust for simple combustion and recycle. The ammonia synthesis process can provide a number of waste or purge streams which may be utilized, maximizing the amount of syngas available for ammonia synthesis. Similarly, as noted above, the cathode exhaust from the MCFC can provide a higher purity initial stream for forming the purified $N_2$ stream. Concentrating the generation of input streams for ammonia synthesis in the MCFC and associated separation stages can reduce the equipment footprint as well as providing improved heat integration for the various processes.

Urea is another large chemical product that can be made by the reaction of ammonia with $CO_2$. The basic process, developed in 1922, is also called the Bosch-Meiser urea process after its discoverers. The various urea processes can be characterized by the conditions under which urea formation takes place and the way in which unconverted reactants are further processed. The process can consist of two main equilibrium reactions, with incomplete conversion of the reactants. The net heat balance for the reactions can be exothermic. The first equilibrium reaction can be an exothermic reaction of liquid ammonia with dry ice (solid $CO_2$) to form ammonium carbamate ($H_2N$—$COONH_4$):

$$2NH_3+CO_2 \rightleftharpoons H_2N\text{—}COONH_4$$

The second equilibrium reaction can be an endothermic decomposition of ammonium carbamate into urea and water:

$$H_2N\text{—}COONH_4 \rightleftharpoons (NH_2)_2CO+H_2O$$

The urea process can use liquefied ammonia and $CO_2$ at high pressure as process inputs. In prior art processes, carbon dioxide is typically provided from an external resource where it must be compressed to high pressure. In contrast, the current process, as shown in FIG. 6, can produce a high pressure liquefied carbon dioxide stream suitable for reaction with the liquid ammonia product from the ammonia synthesis reaction.

In various aspects, urea production can be improved by providing one or more inputs (e.g., electric, heat, $CO_2$, $NH_3$, $H_2O$) and/or accepting one or more outputs (e.g., $H_2O$, heat) from the MCFC while eliminating the need for a large number of separate systems. Additionally, as with most equilibrium processes involving substantial product removal and recycle, purge or waste streams can be generated. These purge or waste streams can be the result of side reactions and impurity buildup within the recycle loop. In a typical stand-alone plant, these streams can often be of low value, and potentially can require further purification, with additional processes and equipment, for recycle. By contrast, in various aspects, the purge or waste streams can be used advantageously and in a much simpler fashion. The anode inlet can consume any reformable fuel and/or syngas composition. Streams diluted with materials that can be combusted, for example, nitrogen compounds such as ammonia, can be reacted with air to produce $N_2$, water and heat which can be utilized as part of the cathode inlet along with any streams containing residual $CO_2$, CO, and $H_2$. As the MCFC system can typically be operated at low pressure (below about 10 barg or about 1 MPag and often near-atmospheric conditions), there can be a reduced or minimized need to recompress any of the purge or waste streams, as these process streams can be sufficiently pressurized for MCFC use.

Additionally, the urea process can be integrated into a combined system with an ammonia synthesis process. This integrated approach can reduce and/or eliminate many processes from the conventional approach, which can require an ammonia plant (steam reformer, water gas shift, pressure swing adsorption to produce $H_2$+air separation plant) plus a separate supply of cold $CO_2$ (dry ice) typically made remotely and then transported to the plant. The current system can eliminate many of these processes and, as it can separate a $CO_2$ stream at high pressure, can provide the necessary reactants at advantageous conditions. Specifically, rather than transport $CO_2$ as dry ice for use at a remote urea plant, carbon dioxide can be provided from separation of a stream derived from the MCFC anode exhaust in liquefied form, and thus can easily be compressed to appropriate reaction pressures. This can avoid substantial energy inefficiencies in cooling, transport and recompression of the $CO_2$.

As described above, an MCFC can be integrated with an ammonia plant for ammonia production while reducing or minimizing the amount of additional equipment. Additionally or alternately, a separation can be performed on the anode exhaust from an MCFC system to provide a source of $CO_2$. This source of $CO_2$ can then be further separated and/or purified so that at least a portion of the $CO_2$ can be used for the urea synthesis process. For example, $CO_2$ separation can be performed using a process comprising cryogenic separation. This can reduce or eliminate the need for separate production and/or transport of cold $CO_2$. Further additionally or alternately, the MCFC system can provide electric power and/or can provide or consume heat by heat exchange with the MCFC inputs/output streams and/or by heat exchange with the separation systems.

Figure 16:
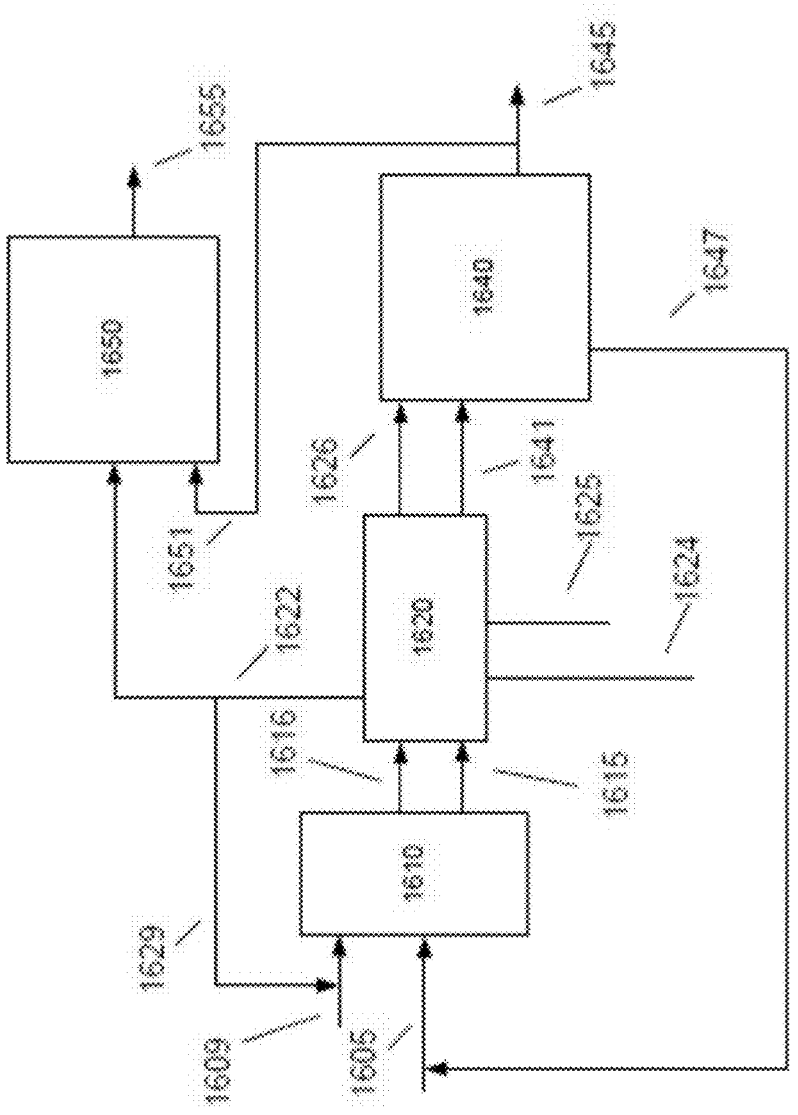
FIG. 16 schematically shows an examples of a configuration for integrating molten carbonate fuel cells with a process for synthesis of a nitrogen-containing compound.

FIG. 16 schematically shows an example of integration of molten carbonate fuel cells (such as an array of molten carbonate fuel cells) with a reaction system for performing ammonia synthesis and/or urea synthesis. In FIG. 16, molten carbonate fuel cell 1610 can schematically represent one or more fuel cells (such as fuel cell stacks or a fuel cell array) along with associated reforming stages for the fuel cells.

The fuel cell 1610 can receive an anode input stream 1605, such as a reformable fuel stream, and a $CO_2$-containing cathode input stream 1609. In FIG. 16, anode input stream 1605 can include an optional recycled portion of an off-gas 1647 produced by the ammonia synthesis process 1640. In FIG. 16, cathode input stream 1609 can include an optional recycled portion of $CO_2$ 1629 separated from the anode and/or cathode output of the fuel cell 1610 in separation stages 1620. The anode output 1615 from fuel cell 1610 can then be passed through one or more separation stages 1620, which can include $CO_2$, $H_2O$, and/or $H_2$ separation stages, optionally as well as water gas shift reaction stages, in any desired order, as described below and as further exemplified in FIGS. 1 and 2. Separation stages can produce one or more streams corresponding to a $CO_2$ output stream 1622, $H_2O$ output stream 1624, and a high purity $H_2$ output stream 1626. The separation stages can also produce an optional syngas output 1625. A cathode output 816 can be passed into one or more separation stages 1620. Typically, the separation stage(s) used for the cathode output can be different from the separation stage(s) for the anode output, but the resulting streams from the separation can optionally be combined, as shown in FIG. 16. For example, $CO_2$ can be separated from the cathode output 1616 and added to one or more $CO_2$ output streams 1622. The largest product separated from the cathode output 1616 can be a high purity $N_2$ stream 1641. The high purity $H_2$ output stream 626 and the high purity $N_2$ stream 1641 can be used as reactants for ammonia synthesis stage 1640 to generate an ammonia output stream 1645. Optionally, a portion of the ammonia output stream can be used as an input 1651 for urea production 1650, along with $CO_2$ stream(s) 622 from the separation stages 620, to generate a urea output 1655. Optionally, the input ammonia stream 1651 for urea production 1650 can be from a different source. Optionally, either the ammonia production stage 1640 or the urea production stage 1650 can be omitted from the configuration.

Integration with Production of Biofuels and Chemicals by Fermentation

Biofuels or biochemical can frequently be produced by a process of fermentation of carbohydrates derived from crops such as corn, sugar, or lignocellulosic materials like energy grasses. The most common example of this process includes ethanol manufacture, such as from corn. This process can typically require inputs of heat (for distillation), electricity (for general plant operations), and water (for processing raw materials, cleaning and other processes), and can produce—in addition to standard products—$CO_2$. $CO_2$ can be produced via the fermentation reaction in which sugar ($C_6H_{12}O_6$) can be converted to 2 $C_2H_5OH$ (ethanol)+2 $CO_2$. Fermentations to other products, such as butanol, higher alcohols, other oxygenates and the like, can produce similar products and can require similar inputs. The greenhouse gas emissions and overall economics of the plant can all be influenced by the efficiency in producing and/or providing these inputs and outputs. Other sources of carbohydrates or sugars can go through similar processes to yield desired bio-products and can result in some conversion of the original carbohydrates to sugar.

In various aspects, the combination of an MCFC system, such as an MCFC system using natural gas as a reformable fuel, with ethanol manufacture can provide a variety of advantages. This can be due in part to the fact that the MCFC system can provide essentially all the needed inputs while also consuming the $CO_2$ output from the ethanol plant. This can lower the greenhouse gas emissions, reduce water requirements, and/or increase overall efficiency.

The ethanol plant can use the electricity from the MCFC to power operations and the residual heat from the MCFC to provide heat to processes like distillation. The exact requirements of the plant (mix of heat to electric) can be managed by adjusting the overall fuel utilization of the MCFC plant, such as by producing extra hydrogen/syngas as the medium to provide more or less heat relative to electrical output. Alternately or in addition, the fuel sources to the MCFC can be adjusted to balance inputs and outputs for a given plant configuration and a given set of inputs, such as by using some of the fermentation product as anode feed, and/or by using heat and/or products from associated inputs, like non-fermentable biomass, as inputs. The electrochemical process can typically produce water by virtue of the reaction of carbonate ions with hydrogen; said water can be condensed from the anode outlet. Additional water may be produced in the production of excess syngas, e.g., via the water-gas shift reaction. The water can then be used as process water in the plant, as it can tend to be very pure and rather free from impurities. Example water uses include but are not limited to the dry milling process, where water can be added to corn that has been ground, and/or the wet milling process, where corn can be soaked in a solution of acid and water. The fermentation $CO_2$ output can be used as cathode input and, if needed, can be supplemented by recycle of anode outlet $CO_2$ and/or via burning of fresh fuel (methane and/or natural gas) to raise additional heat. As all the heat processes in an ethanol plant can typically be at relatively low temperature (e.g., distillation<100° C.), nearly all the waste heat of the MCFC system can be efficiently consumed.

A set of different configurations may be used for the MCFC inputs and outputs depending on specific plant configurations and feed stocks. For some configurations, the process can use the ethanol product, mixed with water, as the anode input fuel and can thus avoid, or reduce, the amount of natural gas required. Ethanol, made in fermentation, can be partially distilled, separated, or extracted, for instance to a molar ratio between about $1H_2O$:1 EtOH and about 4:1, such as from about 1.5:1 to about 3:1, or of about 2:1. This mixture can then be reformed with heat in and/or outside of the fuel cell to produce a mixture comprising hydrogen gas that can then be input to the anode. While the overall plant output of ethanol can be reduced, the amount of non-biologically based inputs can be reduced or eliminated from the process, resulting in lower life-cycle $CO_2$ emissions.

For some configurations, burning lignin sources such as corn stover, wood, and/or sugar bagasse could supplement and/or replace the input of traditional hydrocarbon fuels like methane. This can allow the plant to be self-sufficient in energy and can reduce the need to integrate into supply chains that could incur life cycle emissions debits. For these configurations, the lignin sources can produce heat, and, if partially oxidized to a gaseous mixture comprising syngas, the syngas can be used as input to the MCFC system. Lignin sources can be burned and used to provide some electricity (via steam production and steam turbine), while the exhaust gas from the process can provide the $CO_2$ input to the MCFC system.

For some configurations, the input $CO_2$ for the cathode inlet can be derived from separation of $CO_2$ from the anode output syngas mixture. This separation may occur before or after the stream can be used to produce heat for various processes (including additional power generation through steam production), and/or before or after the stream can be used to provide hydrogen to a process and/or to provide heat. Typically, this type of approach can be used where it may be desirable to capture the $CO_2$. For example, the anode outlet can be passed to a $CO_2$ separations stage where most of the $CO_2$ can be captured and where the residual syngas can then be used for heat, electrical, and/or chemical processes. The output from these processes can then be returned to the cathode along with potentially added methane and/or oxidant (air), to provide a cathode inlet with the proper temperature and gas composition.

Alternatively, for some configurations where $CO_2$ capture may not be desired, the $CO_2$ output from the fermentation system can be used as at least part of the (if not the entire) $CO_2$ source for the cathode when mixed with oxidant (air) and raised to the proper inlet temperature. For these configurations, the anode output may be used for heat, electrical, and/or chemical purposes, and the resulting final stream containing combusted syngas may be vented and/or partially returned as feed to the cathode inlet. Any one or a combination of these configurations may be desirable, depending on the plant configuration and requirements for $CO_2$ emissions. For example, some $CO_2$ from fermentation can be combined with residual syngas streams after use for various heat, electrical, and/or chemical processes, and the combined stream can be reacted with oxidant (air) to provide oxygen to the cathode and raise the temperature of the cathode inlet stream.

The anode outlet stream from the MCFC can be used for a variety of different processes. In one configuration, this stream can be used to provide heat for distillation and may involve combustion of the residual syngas in the anode outlet to raise additional heat for the distillation process. For this configuration, oxidant (air) can be added to the outlet stream, and the stream sensible heat and heat of combustion can typically be used to raise steam that can then be used to provide the energy for distillation. Optionally, the exhaust from this process, with or without the addition of the fermentation process, can be used as the cathode inlet before and/or after optional separation of some of the $CO_2$.

For some configurations, the anode outlet gas can be used as a source of hydrogen without further processing, after a shift reaction, and/or after separation of some $CO_2$ as a source of hydrogen. The hydrogen can be used for a variety of processes. These processes may include but are not limited to production of additional, largely carbon-free, electricity by combustion in a hydrogen turbine. Additionally or alternatively the hydrogen can be used for a chemical process such as treating other biofuel products. For example, lignocellulosic materials unsuited to fermentation (e.g. corn stover and/or sugar bagasse) can undergo a thermochemical process such a pyrolysis to produce an unstable, high oxygen product unsuited for use in fuels. A variety of processes may be used such as pyrolysis, fast pyrolysis, and/or hydropyrolysis, any/all of which may be accomplished with or without catalysts. Typically these products can contain residual oxygen that can reduce the products heating value and can often greatly reduce their stability in storage, transportation, and use. These types of products can advantageously be treated with hydrogen to produce a fuel compatible blend stock (pyrolysis oil) that can optionally be blended with the fermentation product to increase the overall production of biofuels.

Another use for hydrogen can be in the co-production of biodiesel materials. Typically, starch sources (for example, corn, sugar) can be used to make ethanol for use in gasoline fuels, while other crops heavy in “oils” (e.g., tri-acyl glycerides) such as soybeans or palms can be used to produce longer-chained molecules that may be suitable for diesel fuel and/or jet fuels, as is and/or after upgrading. Other renewable resources can contain even longer-chained molecules that may suitable for lubricants and/or heavier fuels such as bunker/marine fuels and/or home heating oils, as is and/or after upgrading. These materials can typically require some processing involving hydrogen, especially when the desired product can be largely oxygen free e.g., in the case of a hydro-treated vegetable oil instead of a fatty acid methyl ester (FAME) product). As biofuel products and crops may be largely co-located, the availability of hydrogen may aid in a variety of processing schemes.

In some aspects, a goal of the integrated MCFC and fermentation system can be to reduce or minimize the overall $CO_2$ production from the fermentation plant. In an example of such a system, biomass feed can enter a fermentation plant and undergo optional processes to prepare the material for fermentation (for example, grinding, water treatment). The electrical energy and water for the process can be at least partially (if not totally) provided for by the fuel cell outputs. The fermentation process can produce a biofuel plus secondary products (for example, distiller’s dry grains), and a gas stream comprising a relatively high amount of $CO_2$. A biofuel product from the fermentation plant mixed with an appropriate amount of water can be used as an anode input fuel to the MCFC. Depending on the aspect, the biofuel product can correspond to at least a portion of the fermentation product, at least a portion of a biogas or other fuel derived from a residual or secondary product of the fermentation, or a combination thereof. Syngas from the MCFC anode outlet can be combusted to provide at least some (if not all required) heat for all plant processes including distillation. The anode outlet product can be used before and/or after a $CO_2$ separation process. Alternatively, the anode outlet can be split, so that some of the anode outlet stream can be used to provide at least some heat for the fermentation plant processes, while a second stream can be used to provide heat for a different purpose, such as to preheat the cathode input stream. Some of the resulting $CO_2$ containing streams can be combined with air and used as a cathode inlet stream. The overall process can advantageously use no external energy source and could typically emit $CO_2$ only derived from biological processes. Alternatively, a $CO_2$ separation scheme can be added at any one or more of various points, such as after the anode and/or after all the $CO_2$ streams are combined. This stage can provide a substantially pure $CO_2$ output stream for sequestration and/or for some other use. In this configuration, the overall plant $CO_2$ emissions, from a life-cycle basis, can be negative (less than zero net $CO_2$ produced), as biologically derived $CO_2$ can be removed for sequestration with proportionally fewer (without any) external carbon-based fuel inputs.

Figure 15:
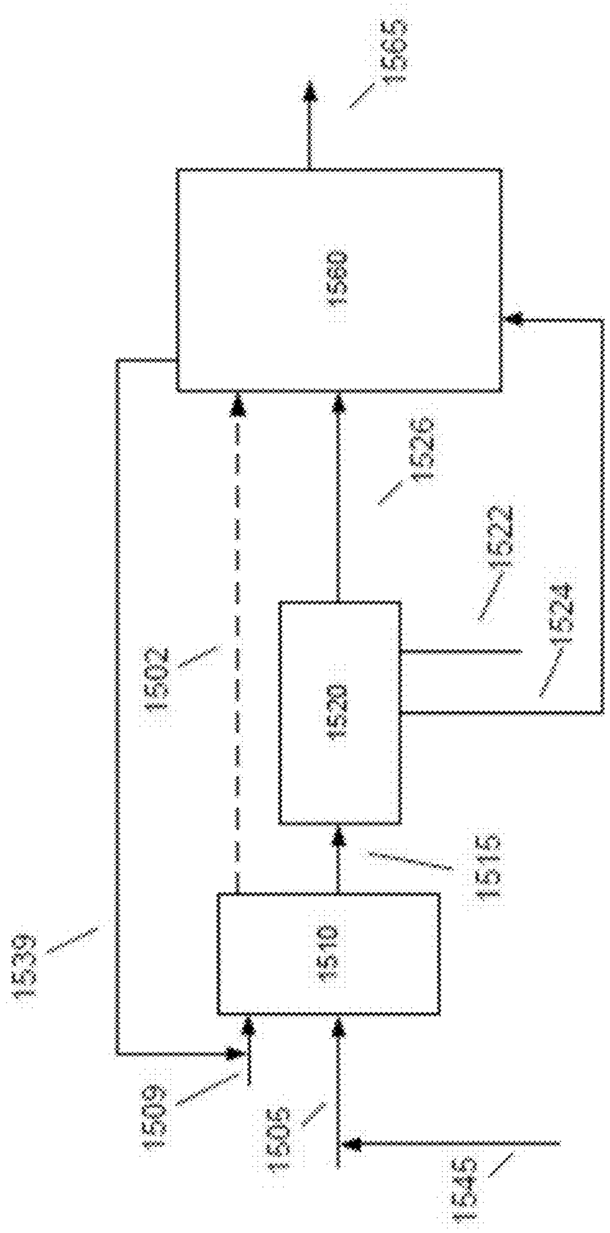

FIG. 15 schematically shows an example of integration of molten carbonate fuel cells (such as an array of molten carbonate fuel cells) with a reaction system for performing alcohol synthesis, such as ethanol synthesis. In FIG. 15, molten carbonate fuel cell 1510 schematically represents one or more fuel cells (such as fuel cell stacks or a fuel cell array) along with associated reforming stages for the fuel cells. The fuel cell 1510 can receive an anode input stream 1505, such as a reformable fuel stream, and a $CO_2$-containing cathode input stream 1509. Optionally, the anode input stream can include fuel from an additional source 1545, such as methane derived from lignin and/or corn stover by combustion and subsequent methanation. Optionally, the cathode input stream 1509 can include an additional $CO_2$-containing stream 1539 derived from the $CO_2$ generated during fermentation to make ethanol (or another fermentation product). The cathode output from fuel cell 1510 is not shown in FIG. 15. The anode output 1515 from fuel cell 1510 can then be passed through one or more separation stages 1520, which can include one or more of $CO_2$, $H_2O$, and/or $H_2$ separation stages, and/or one or more water gas shift reaction stages, in any desired order, e.g., as described below and as further exemplified in FIGS. 1 and 2. Separation stages can produce one or more streams corresponding to a $CO_2$ output stream 1522, $H_2O$ output stream 1524, and/or $H_2$ (and/or syngas) output stream 1526. The $H_2$ and/or syngas output stream (collectively 1526), when present, can be used, for example, to provide fuel for distillation of ethanol by ethanol processing plant 1560. $H_2O$ output stream 1524, when present, can provide water for the ethanol processing plant 1560. Additionally or alternately, the MCFC 1510 can generate electrical power 1502 used by ethanol processing plant 1560. Ethanol processing plant 1560 can generate an ethanol (and/or other alcohol) output 1565 that can preferably be at least partially distilled to enhance the alcohol concentration of the product. It is noted that the configuration in FIG. 15, or any of the other configurations described above, can be combined with any of the other alternate configurations such as the use of lignin sources or the co-production of other biofuels.

Example of Integrated MCFC and Fermentation System

This example demonstrates an integrated MCFC and cellulosic ethanol fermentation process to produce ethanol, hydrogen, and electricity with low $CO_2$ emissions. One focus of this example can be on the integration aspects with an MCFC system. The fermentation processes, such as for ethanol fermentation, can correspond to a conventional fermentation method. For purposes of providing an example, to the degree that details of an ethanol fermentation method were needed, a literature reference was used to provide a representative fermentation process. (See Humbird, et al, *Process Design and Economics for Biochemical Conversion of Lignocellulosic Biomass to Ethanol*, NREL. May 2011.) The base ethanol fermentation process described in this reference corresponds to a ~520 ton/day fermentation plant. However, any other convenient fermentation process could have been substituted into this example. In this example, ethanol can produced from fermentation of stover feedstock. The rejected biogas and biomass from the fermentation process can be burned to produce steam and power for the process, with some excess power being sold back to the grid. In this integrated MCFC-fermentation process, the MCFC can use a methane-steam mixture as the anode feed and mixture of $CO_2$ gases from the fermentation system as the cathode feed. The hot MCFC anode exhaust can be integrated with the steam system to produce enough low pressure steam to provide the distillation column heating demand. It is noted that this can also increase the steam rate through an existing steam turbine/HRSG system. The anode exhaust can be shifted and separated into $H_2$ and $CO_2$ product streams. The MCFC can produce at least enough power for the anode exhaust gas separation and compression of the gases to pipeline conditions.

Figure 14:
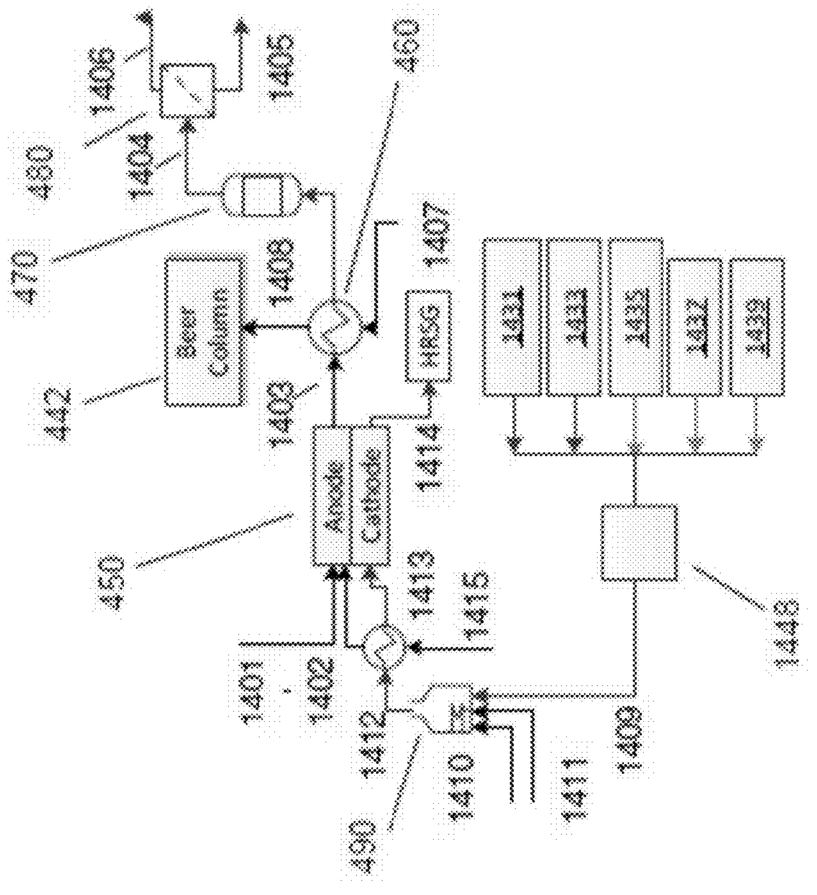
FIGS. 14-15 schematically show examples of configurations for integrating molten carbonate fuel cells with fermentation processes.

FIG. 14 shows an example of the MCFC portion of the configuration. In FIG. 14, steam 1401 and pre-heated methane 1402 can be fed to the anode of the MCFC 1450. The MCFC 1450 can produce a mixture 1403 of mostly $H_2$/CO/$CO_2$ at high temperature. Depending on the aspect, the MCFC can be operated at a low fuel utilization of about 25% to about 60%, such as a fuel utilization of at least about 30%, or at least about 40%, or about 50% or less, or about 40% or less. Additionally or alternately, the MCFC can be operated at a more conventional fuel utilization of about 70% or greater, but this can be less preferable, as the amount of potential $H_2$ that can be recovered from the anode exhaust would be reduced at higher fuel utilizations. Heat can be recovered from mixture 1403, for example, in heat exchanger 1460 to make low pressure steam 1408 from an input water stream 1407. Input water stream 1407 can be derived from any convenient source, such as water recovered from cathode outlet stream 1414 and/or anode outlet stream 1403. Low pressure steam can be used, for example, to provide heat for distillation, such as heat for beer column 1442 shown in FIG. 14. Cooled anode exhaust 1404 can be shifted to produce a mixture of mostly $H_2$/$CO_2$ in a water-gas shift reactor 1470. These gases can be separated in one or more separation stages 1480 into $H_2$ stream 1405 and $CO_2$ stream 1406. $H_2$ stream 1405 and $CO_2$ stream 1406 can be compressed and sold for use. Additionally or alternately, at least a portion of $CO_2$ stream can be directed to sequestration. In an alternate but less preferable configuration where low $CO_2$ emissions are not necessary, $CO_2$ stream 1406 could be emitted to the atmosphere. The cathode feed 1409 can be comprised of a mixture of off gas streams of the fermentation process. In the example shown in FIG. 14, cathode feed 1409 can made up of the vent scrubber off gas 1431 and biogas combustor off gas 1433, which can account for ~94% of the $CO_2$ emitted from the fermentation process. Additionally or alternately, cathode feed 1409 can include cellulose seed fermenter off gas 1435, cellulose fermenter off gas 1437, aerobic digester off gas 1439, and/or any other fermenter and/or digester off gases. The off gas (or off gasses) may pass through a gas cleanup system 1448 to pre-treat the cathode feed. The off gas mixture 1409 can be combined with fuel ($CH_4$) 1410 and oxidant (air) 1411 in a burner 1490 and combusted to heat the cathode feed to MCFC operating temperature. The additional heat in burner output 1412 can be used to pre-heat the methane anode feed 1402. The cathode exhaust 1414 can be sent to a HRSG to recover any heat and then emitted to the atmosphere and/or can be sent for further processing, if desired.

Table 2 shows an example of the amount of reduction in $CO_2$ emissions for a configuration similar to FIG. 14 in comparison with performing the same conventional fermentation process without using an integrated MCFC system. For the calculation shown in Table 2, it was assumed that all carbon used in the system corresponded to carbon originally derived from a biogenic source. As shown in Table 2, integration of a fermentation process with an MCFC system can have the potential to substantially reduce $CO_2$ emissions from ethanol fermentation. Instead of allowing the $CO_2$ generated by the fermentation process to escape to the atmosphere, using at least a portion of that $CO_2$ to form some or all of the cathode inlet stream can allow the majority of that $CO_2$ to be separated into the relatively pure anode outlet stream. The $CO_2$ can then be separated out from the anode outlet stream in an efficient manner (such as separating out at least about 90% of the $CO_2$, such as at least about 95%), resulting in sequestration of the $CO_2$. In particular, if the original source of carbon is considered, where carbon originally derived from a biogenic source may not count against the carbon input to the system, the net $CO_2$ emissions from the integrated system can actually be negative. This can reflect the fact that carbon originally consumed from the atmosphere by plant life (biogenic carbon) has been captured as $CO_2$ and sequestered in such a process, resulting in a net removal of carbon from the environment.

TABLE 2

Reduction in $CO_2$ emissions due to MCFC integration

| | EtOH Production [ton/day] | $H_2$ Production [ton/day] | $CO_2$ Emissions [kg $CO_2$/GJ] | $CO_2$ Emissions corrected for biogenic sources [kg $CO_2$/GJ] |
|---|---|---|---|---|
| Base case | 520 | 0 | 172 | 0 |
| Integrated Case | 520 | 265 | 25 | −147 |

Integration with Algae Growth and Processing

Algae farms (photosynthetic algae) that have been proposed for use in making biodiesel require several inputs: water, $CO_2$, sunlight, nutrients, primarily nitrogen, possibly heat. In an aspect, molten carbonate fuel cells can be integrated with the needs of an algae farm (and potentially other processes) to provide a more efficient overall process with reduced costs and reduced $CO_2$ emissions.

In an aspect, $CO_2$ produced by an MCFC can be used as a $CO_2$ source for the algae farm. Additionally or alternately, the inputs and outputs from an MCFC can be integrated with algae farms to do one or more of the following: 1) to use the water produced from the MCFC anode exhaust as make-up water for the algae; 2) to use the heat produced to heat the ponds during evenings/low temperature seasons; 3) to use the electricity produced by the MCFC to run circulation devices and other processes; 4) to use biomass offgas (e.g. an anaerobic digester) as the source of fuel/methane for the MCFC; 5) to use a different biomass after gasification (algae biomass, lignin) as the source of $H_2$/CO for the anode; 6) to use a $CO_2$ producing bioprocess (e.g. fermentation) as the $CO_2$ source for the cathode, to capture that $CO_2$ via separation in the anode and then to transfer that $CO_2$ to the algae after separation (e.g., to take CO produced from corn to ethanol, and to use it for algae growth to make other products); and 7) to use $H_2$ and/or $N_2$ produced by the MCFC to make nitrogen-containing compounds (e.g. $NH_3$, urea) for use as core nutrient to the algae production.

One benefit of the aspects described above can be that the MCFC process and subsequent separations can make very "clean" $CO_2$ substantially free of contaminants typical of exhaust streams such as power plant effluents or other $CO_2$ sources. The Integration benefits shown above can additionally or alternately allow for—depending on configuration—a large number of integrated pieces to fit together. For example, use of an MCFC can create a synergism between $CO_2$ producing processes and $CO_2$ consuming processes. In such synergistic processes, the MCFC can act as an intermediary that concentrates, separates, and uses the $CO_2$ in an efficient manner. The MCFC can further additionally or alternately be configured with a typical external $CO_2$ source (e.g. power plant, turbine), so that the MCFC can be used to a) concentrate, b) purify, and c) deliver the $CO_2$ to the algae growth environment in an easy to use form. This can be a notable improvement over just passing dilute $CO_2$ with contaminants to the algae.

Integration with Cement Manufacture

Concrete and steel are important infrastructure building materials that can account for the majority of mass, cost and carbon dioxide emissions in the building of major infrastructure projects. For example, concrete is currently responsible for about 5% of $CO_2$ emissions worldwide. Of the total emissions, the manufacture of cement, for example Portland cement, represents about 95% of the total emissions from the final product. The $CO_2$ can be primarily generated from two sources: the decomposition of calcium carbonate to calcium oxide and $CO_2$, and the heating of cement kilns to temperatures as high about 1800° C., which is typically done with coal as a fuel. Cement is made in hundreds of plants (about 150-200 in the US), typically near quarries where the constituent rock is found.

Manufacture of cement typically involves heating a mixture of materials to very high temperatures. The major constituents can include limestone ($CaCO_3$) along with one or more of silica (sand), iron ores, alumina (shale, bauxite, other ores), and/or other materials. The constituents can be crushed and mixed, after which they can be introduced into a kiln at very high temperatures, typically in air, and typically at temperatures of at least about 1400° C., such as at least about 1800° C., and sometime up to about 2000° C. or greater. Under these conditions a product, referred to as clinker, can be produced. Clinker can be a stable product typically ground in order to form a commercial cement. In this discussion, a clinker can be referred to as a cement product. The process to form the cement product can typically result in one significant chemical change: the decompositions of limestone to CaO and $CO_2$. The other ores, starting as oxides, typically do not change chemically. After some cooling, the cement product can typically be mixed with other components, such as gypsum, and optionally ground to achieve the final desired characteristics suitable for use in cement applications and/or concrete production.

In general, the MCFC can be used as a resource for management of $CO_2$ by using $CO_2$ from the cement manufacture process as an input for the cathode. The amount of $CO_2$ released by traditional cement manufacture can typically be at least about 50% from the decomposition of the $CaCO_3$ and about 50% or less due to heating based on combustion of carbon-containing fuels, with the amounts potentially varying depending on the characteristics of an individual manufacturing operation. Additionally or alternately, concrete and cement manufacture can require electricity and mechanical energy for the overall process. When typically co-located, or closely located with local resources, such as quarries for production of minerals, transport, grinding, a variety of mechanical processes associated with the cement production process can consume a large amount of electricity. These energy needs can be met at least in part by electricity generated by an MCFC integrated with the cement plant. Further additionally or alternately, separation steps performed on the anode exhaust can produce water, and this water can be used to mitigate and/or satisfy the water needs of the typical cement plant. Optionally, the MCFC can be operated at low fuel utilization to provide hydrogen as a fuel, which can still further additionally or alternately remove or mitigate $CO_2$ emissions due to fuel combustion.

In an aspect, an MCFC system can be integrated with a cement production plant to use cement effluent as a $CO_2$ source while also using the MCFC heat and electricity to power the production plant. This first configuration can consume the main source of $CO_2$ and can also mitigate some of the secondary sources of $CO_2$ due to heat and electrical demand. The net result can be a lower carbon emissions cement manufacture process with the possibility of carbon capture.

In an additional or alternate configuration, an MCFC system can be heat integrated with a cement manufacturing operation so that a reduced amount of additional fuel or even no additional fuel may be needed to preheat one or more of the MCFC inlet streams, such as all of the MCFC inlet streams. For example, the cathode inlet, which may comprise some $CO_2$ containing effluent from the kiln plus additional (cold) oxidant (air) to provide sufficient oxygen, can be preheated fully to typical cathode inlet temperatures of about 500° C. to about 700° C. by heat exchange with kiln outputs. Additionally or alternately, the heat for the kiln, typically provided by burning coal, can instead be partially or completely provided by burning anode exhaust effluent from the MCFC system, which, when derived from a less carbon-intensive source than coal, can reduce overall $CO_2$ emissions.

In another additional or alternate configuration, the MCFC system can be configured to avoid a substantial majority of overall plant carbon emissions. In this configuration, the MCFC system anode outlet, a stream typically containing $CO_2$, CO, $H_2$, and water, can undergo a series of processes designed to separate $CO_2$ for sequestration/capture, to remove water in that same or in a different separation process, and/or to "shift" the water-gas shift gases to produce a stream highly enriched in hydrogen. This hydrogen stream can then be used as the heating input (when combusted) for the kiln, yielding reduced or minimized carbon emissions. Optionally, any off-gasses containing fuel value can be recycled to the anode (for example, a CO containing off-gas). Further additionally or alternately, water from the anode exhaust can be used to off-set any water used in the grinding, mixing, or other cement processes that might be drawn from local sources. The electricity needed for at least a portion of or the entire cement, concrete, and/or quarry operations, and/or for at least a portion of the operations, can be provided by the MCFC on-site. This can reduce or minimize transmission losses as well as reducing corresponding $CO_2$ emissions from the fuels used to provide electricity via the electrical grid. The overall process can then exhibit "life-cycle" $CO_2$ emissions that can be substantially reduced, when compared to conventional mining and manufacturing operations, while operating at higher overall thermal efficiency.

In these configurations, the fuel for the inlet to the anode can typically be provided by a source of natural gas, methane, and/or other light hydrocarbons, optionally along with off-gasses and/or other waste streams containing some light fuel components and/or along with water-gas shift components. The fuel to the anode may contain other inert gases, such as nitrogen, in acceptable amounts, but preferably does not contain substantial amounts of oxygen, such as no intentionally added oxygen. The anode inlet may additionally or alternately include and/or be derived from other hydrocarbonaceous materials, including coal, if these materials are first converted to a reformable fuel. At least a portion of the heat (perhaps even all the heat) required for these conversions, and optionally for preheating the anode inlet, can advantageously provided by heat exchange from contact with kiln exhaust gases or products. The heat exchange can be direct, and/or can be indirect through a heat transfer medium such as steam. Water (steam) for such heat exchange processes, and/or water used in other processes related to cement manufacture, can be provided at least in part using water produced by the anode chemical and electrochemical reactions after separation from the anode exhaust stream.

The cathode inlet stream can be derived at least in part from the kiln exhaust that can be rich in $CO_2$. This stream may contain dust, dirt, minerals, and/or other solid substances not suitable for introduction into a MCFC. Such unsuitable substances can be removed with, for example, filters. Additionally or alternately, typically cement plants can contain systems to reduce, minimize, and/or substantially eliminate particulate emissions from the kiln, and similar systems can be employed in a system that is integrated with a MCFC. The kiln exhaust and/or cathode inlet stream containing at least a portion of kiln exhaust may contain some residual gases not harmful to the cathode. Examples of such residual gases can include nitrogen, oxygen, and/or other air components, as well as optional minor amounts of impurity pollutants such as nitrogen oxides, when present at acceptable concentrations (for example, such as less than about 100 vppm, or less than about 50 vppm, or less than about 25 vppm, depending on the impurity pollutant(s)). The cathode can additionally or alternately require the use of fresh air to obtain a sufficient oxygen concentration. Preferably, the oxygen concentration at the cathode outlet can be at least about the $CO_2$ concentration at the cathode outlet, but oxygen concentrations of at least about half the $CO_2$ concentration can also be acceptable. Optionally, the oxygen concentration at the cathode inlet can be at least about the $CO_2$ concentration at the cathode inlet. In many MCFC systems it can be necessary to burn some fuel to heat the cathode inlet stream. However, for the configurations described above, heat exchange with the kiln gaseous exhaust and/or solid product can provide at least a portion of the heat, or substantially all of the heat, required to heat one or more of the cathode inlet streams. This can reduce, minimize, or possibly eliminate the need for combustion of fuel to provide additional heat for the cathode inlet streams.

The anode outlet stream, in most traditional power-producing MCFC systems, can typically be partially or fully recycled to the cathode to provide $CO_2$ and heat. In these configurations according to the invention, this anode exhaust is not required for those purposes, instead optionally but preferably being used for another purpose, such as to provide heat for the kiln. Advantageously, the MCFC can be operated at reduced fuel utilization such that the anode exhaust, when used either with or without shift and/or separation steps, can provide at least a portion (or all) of the heat necessary to raise the kiln to the operating temperature. Advantageously, the conditions can additionally or alternately be chosen such that the total electrical power output can be sufficient for at least a portion (or all) of the local power needs, which may include the direct cement manufacture as well as associated concrete, quarry and other operations. The MCFC systems can be designed such that, by varying the fuel utilization, the system can meet both requirements and can respond to variability in those requirements through adjusting fuel utilization, cell voltage and current, and/or other parameters.

The cathode exhaust stream, typically comprising a reduced $CO_2$ and $O_2$ concentration relative to the cathode inlet stream, along with inert (air) components such as nitrogen, can typically be exhausted to the atmosphere, but alternately can be first exposed to one or more post-treatments before doing so.

Figure 17:
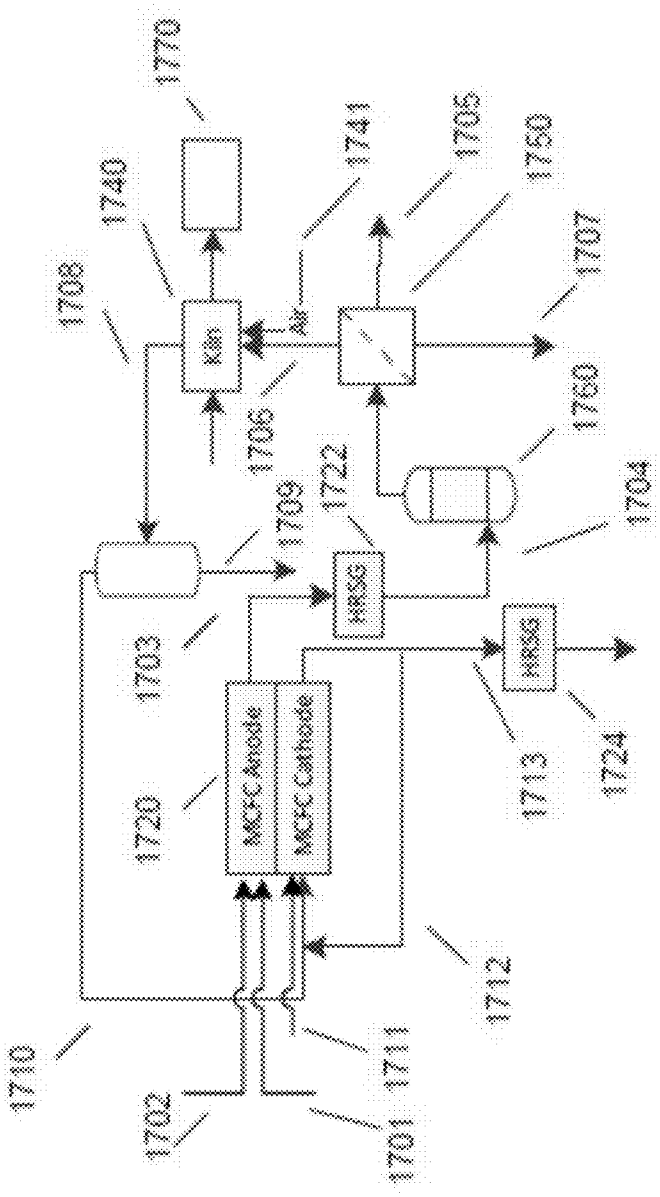
FIG. 17 schematically shows an example of integration of molten carbonate fuel cells with a process for producing cement.

FIG. 17 shows an example of an MCFC system integrated in a cement manufacturing plant to produce low $CO_2$ emissions cement. The two largest $CO_2$ sources of a cement plant are typically from the combustion of fossil fuels for heat in the kiln, such as a rotary kiln, and the decomposition of $CaCO_3$ to CaO in the kiln. In the configuration shown in FIG. 17, the integrated process can instead combust $H_2$ produced from the MCFC in the kiln. The decomposition $CO_2$ off gas can additionally or alternately be used as the cathode feed.

In the configuration shown in FIG. 17, gas flows of methane 1701 and steam 1702 can be fed to the anode of MCFC 1720. The anode exhaust 1703, which can comprise a mixture of $H_2$, CO, $CO_2$, and $H_2O$, can be cooled in a heat recovery steam generator (HRSG) 1722 and shifted in a water gas shift reactor (not shown), producing a mixture of mostly $H_2$ and $CO_2$ 1704. Stream 1704 can, in this case, be dehydrated 1760 and separated 1750 into $H_2$-containing stream 1706 and $CO_2$-containing stream 1707. Stream 1707 can be compressed (and sold for use, shipped for use remotely, etc.) and/or can be sent to a sequestration facility. Stream 1706 can be used as fuel for the open flame (along with oxidant/air 1741) in the rotary kiln 1740. The "clinker" product formed in kiln 1740 can be passed into clinker cooler 1770. Various types of heat exchange can be performed with the kiln 1740, the clinker product, and/or the clinker cooler 1770 to provide heat for other processes in the system. In the kiln 1740, as $CaCO_3$ decomposes, $CO_2$ can be released. The $CO_2$ can combine with the flame exhaust gases and exit the top of the kiln 1740 as a kiln off gas 1708. The kiln off gas 1708 can be cleaned and/or dehydrated 1730 to form a water and/or impurities stream 1709 and a $CO_2$-containing stream 1710 that can be returned to the front of the cathode of MCFC 1720. Stream 1710 can be mixed with air 1711 and optionally part of the cathode exhaust 1712 to help meet the $CO_2$ feed demand to the cathode. The cathode exhaust, depleted in $CO_2$, can be split, with a fraction optionally recycled 1712 and another fraction sent to a HRSG 1724 and emitted to the atmosphere 1713 (if not sent for further processing, not shown).

As an example of the heating requirements and $CO_2$ production from a rotary kiln, values were taken from *Energy and Emissions from the Cement Industry*. (Choate, William T. *Energy and Emissions Reduction Opportunities for the Cement Industry*. U.S. Department of Energy, December 2003.) Based on these representative values, calculations were performed for an example of an integrated process sized to process ~300 tonnes/hour of clinker in the rotary kiln. Flow values based on mass and energy balance calculations for a configuration similar to FIG. 17 are shown in the tables in FIG. 18. In FIG. 18, the number at the top of each column indicates the corresponding element from the configuration in FIG. 17. The calculations can be used to show that the large amount of heat in the clinker cooler 1770 shown in FIG. 17 can be used to pre-heat all the MCFC inlet streams to operating temperatures. In addition to $H_2$ fuel for the kiln, the MCFC can also produce ~176 MW of power that can be used in the other energy intensive processes, like grinding of the raw material for the kiln feed. Table A shows a summary of the additional electric power generation and reduced $CO_2$ emissions that were calculated based on the calculations shown in FIG. 18. As shown in Table A, the calculations for a configuration similar to FIG. 17 using representative values for the rotary kiln show that integration of a MCFC with a cement process can provide additional electrical power while reducing $CO_2$ emissions by about 90%.

TABLE A

Power Generation and $CO_2$ Emissions during Cement Processing

| | Power Generation [MW] | CO2 Emissions [kg CO2/tonne Clinker] |
|---|---|---|
| Fossil fuel fired kiln | 0 | 976.5 |
| MCFC + kiln | 172 | 96.9 |

As noted above, about half of the $CO_2$ emissions from a typical cement process are due to combustion of fuels to provide heat for a kiln. Such combustion processes usually use air to provide a source of oxygen, resulting in off gasses from combustion that are relatively dilute in $CO_2$ concentration due in part to the large amount of $N_2$ present in air. The conventional alternative for separating $CO_2$ from a stream containing dilute $CO_2$ (such as 10 vol % $CO_2$ or less) is to use an amine wash, such as an amine wash based on monoethanolamine. For comparison purposes, a typical expected energy cost for using an amine wash based on monoethanolamine (MEA) to capture $CO_2$ from dilute $CO_2$ streams (such as streams with approximately 10 vol % or less $CO_2$) was estimated to be about 3 GJ/ton $CO_2$. Based on this expected energy cost, using an amine wash to capture $CO_2$ instead of using a MCFC could eliminate the additional electrical energy generated by the MCFC while also incurring a substantial energy cost.

Integration with Iron or Steel Manufacture

In various aspects, processes are provided that integrate the production of iron and/or steel with the use of an MCFC system. Iron can be produced from the reduction of iron oxides present in iron ore. The reaction can require high temperatures, such as up to 2000° C., more typically from about 800° C. to about 1600° C., and a reductant that can remove tightly bound oxygen from iron oxide that can be used in the blast furnace to produce iron metal. The most widely used method involves the processing of coal to produce coke and subsequently to produce a blast furnace gas comprising CO as the primary chemical reductant. The process can typically also require a substantial amount of heat, and frequently significant amounts of electricity used both in the basic process itself, and in subsequent steelmaking processing. The electrical requirements may include typical plant needs for operating pumps, valves and other machinery as well as large, direct electrical inputs such as for direct-reduction iron processing, electric furnace steelmaking, and similar processes. Substantial amounts of water can be needed in steelmaking beyond the water simply used for cooling, as water can be used to process coal, directly remove scale from steel, for steam generation, hydraulics and other systems.

In a conventional iron production process, the furnace gas can comprise a significant amount of CO, as well as some amounts of $H_2$, $H_2O$, $N_2$, optionally but typically sulfur (such as $H_2S$), and optionally but typically one or more other various gases derived from coal. As iron can be an effective water-gas shift catalyst, the four water-gas shift molecules (CO, $CO_2$, $H_2O$, $H_2$) can typically be at or near equilibrium in the process. CO can react with iron oxides to produce $CO_2$ and reduced iron, while incorporating some carbon into the reduced iron. This carbon can then be partially removed, for instance by controlled oxidation, to the desired level for making various grades of iron and steel products. The role of the coal and coke in a conventional iron production process can be two-fold. First, the coal or coke can provide the reductant for conversion of iron oxides to iron. Second, coal or coke can be combusted to provide heat to maintain the very high furnace temperatures. The process can typically take place at or near atmospheric pressures. In a conventional process, effluent blast furnace gas still can typically contain some amounts of combustible materials that can then be burned for additional heat.

Disadvantages of conventional processes can include the production of large quantities of $CO_2$ for every ton of iron or steel produced. In addition to the coal and coke used in a process, a flux (typically a carbonate such as $CaCO_3$ or mixture of carbonates and other materials) can be decomposed in the process releasing additional $CO_2$. To capture or reduce the amount of $CO_2$ emanating from the furnace can require separation of $CO_2$ from the various exhaust systems which can be difficult, and which can involve a number of collection, concentration and clean-up steps.

In various aspects, integrating operation of molten carbonate fuel cells with processes for iron and/or steel production can provide process improvements including but not limited to increased efficiency, reduction of carbon emissions per ton of product produced, and/or simplified capture of the carbon emissions as an integrated part of the system. The number of separate processes and the complexity of the overall production system can be reduced while providing flexibility in fuel feed stock and the various chemical, heat, and electrical outputs needed to power the processes.

In additional or alternate aspects, the combined MCFC and iron production system can allow for efficient collection of carbon with simpler systems while providing flexibility in heating. Additionally or alternately, the combined MCFC and iron production system can incorporate direct production of electricity that can be utilized as part of the entire electrical input to the plant. As the electricity is produced on-site, transmission losses can be reduced or minimized and potential losses produced when converting AC to DC power can additionally or alternately be avoided. Furthermore, the carbon in the fuel utilized to produce electricity can be incorporated into the same carbon capture systems used for capture of carbon dioxide from the blast furnace exhaust (or exhaust from another type of furnace used for iron or steel production). The proposed system can be designed for variable production of reductant (CO), heat, and electrical output, allowing it to be adapted to a broad range of iron and steelmaking processes and technologies using the same core components.

In an aspect, an MCFC system can be used to form an anode exhaust stream containing excess $H_2$ and/or CO (syngas). The excess syngas from the MCFC anode exhaust can be withdrawn and used to perform iron or steel production while reducing, minimizing, or eliminating the use of coke. The anode exhaust from the MCFC can be exhausted at a pressure of about 500 kPag or less, such as about 400 kPag or less, or about 250 kPag or less. For example, one can take syngas produced or withdrawn from the anode exhaust, separate at least a portion of the $H_2$ from the CO, fire the furnace with the $H_2$, perform the reduction of iron with the CO, and then consume the resulting $CO_2$ from the iron production process in the MCFC and capture it, leading to a substantial reduction in $CO_2$ emissions from the process. In such aspects, the MCFC can act as both a management system for carbon oxides (source of CO, sink of $CO_2$) and as a source of supplemental inputs to the iron or steel production process, such as by providing $H_2$ for heating, heat exchange with input and exhaust streams for efficiency, carbon capture, and/or clean process water creation. It is noted that various steel processes can additionally or alternately use electrical energy that can be provided by the MCFC system. For example, steel production can involve the use of arc furnaces, and direct reduction of iron can be done with electrical current. In various aspects, the furnaces used in an integrated system including an MCFC can be electrically heated or heated by other indirect methods that can generally allow combustion of the syngas in the furnace to be avoided.

As an example of integration of molten carbonate fuel cells in a reaction system for producing iron or steel, the reductant gas to a blast furnace can be provided by first introducing methane or other reformable fuel into an MCFC anode where the MCFC can be used to produce both electricity (such as for use by the plant) and syngas from the anode output. The MCFC system can preferably be sized such that the amount of syngas produced can be sufficient to provide all or substantially all of the CO reductant needed for the iron or steel making process. Optionally, a portion of the CO for the iron or steel making process can additionally or alternately be introduced as part of the iron ore or other iron oxide feed to the furnace. Depending on the types of processes involved, which may require larger amounts of electricity (for example, in a direct reduction steel making process) or smaller amounts of electricity, electricity may be returned to grid or drawn from the grid, to balance the energy inputs from the plant. Alternatively, the MCFC can be sized so that it can produce both all the electrical energy and reductant needed, with the MCFC being operated at a fuel utilization that balances the two main outputs to suit the plant requirements. The flexibility of the system can allow for adjusting this ratio (by adjusting fuel utilization, voltage, and/or input/output temperatures, among other variables) to adapt to changing processes or process conditions within a given plant.

Optionally but preferably, an MCFC system integrated with iron or steel production can be operated at low fuel utilization, to increase the amount of syngas available to be produced/withdrawn from the anode exhaust. While this may not be necessary, as most MCFC operations can typically produce an anode effluent comprising syngas, it can sometimes be preferable to maximize the production of anode syngas. For example, the fuel utilization can be at least about 25%, such as at least about 30%, or at least about 35%, or at least about 40%. Additionally or alternately, the fuel utilization can be about 60% or less, such as about 55% or less, or about 50% or less, or about 45% or less, or about 40% or less. Use of a low fuel utilization value can allow for an increased content of $H_2$ and CO in the anode output. The anode output can then be used as a source of reducing gas for the blast furnace. If desired, the fuel utilization can be adjusted so that the syngas output can be in balance with the electrical requirements of the overall plant. This can potentially avoid the need for separate grid-power and can provide energy self-sufficiency to the plant with only a single fuel source feeding a single power production system; the MCFC in such a situation could provide both the electrical and chemical constituents needed for plant operations. Alternatively, the plant may utilize a separate electrical generation system such as a turbine in conjunction with an MCFC system, such that some electrical power can be produced by both systems, and so that the MCFC system can be optimized for syngas production. The size, available fuel sources, intrinsic electrical demand and other factors may result in any of these combinations being an (the most) efficient and/or economically advantageous arrangement.

In various aspects, the fuel input for an MCFC in an integrated iron or steel production system can preferentially comprise or be methane or natural gas, but can indeed be any hydrocarbonaceous material compatible with an MCFC. For hydrocarbonaceous materials that cannot be directly reformed within the MCFC (e.g. C2-C5 light gases), a pre-reformer can be employed to convert the input fuel to methane plus a syngas mixture. In such situations, preferably the anode input gas can contain a large or predominant percentage of a reformable gas and may contain amounts of syngas constituents and inerts. The anode input can preferably have impurities such as sulfur removed, which may be accomplished by conventional systems, and which can vary depending on the source and purity of the input fuel. Input fuels such as coal and/or other solid fuels can be used, if first converted to mixtures comprising reformable fuels from which impurities are removed. Inputs to the cathode can be derived primarily from iron reduction process exhaust and may contain other streams containing one or more of $CO_2$, $H_2O$, $O_2$, and inerts. Air/oxygen containing streams may be added to provide sufficient oxygen for the cathode and can typically require oxygen amounts in the overall cathode exhaust to be in excess of the total $CO_2$ amounts.

Syngas effluent from the anode outlet can be sent to a separation process where $CO_2$ and possibly some water can be removed from the stream. The separation system can be designed to remove enough $H_2O$ and $CO_2$ to produce a syngas composition that, when equilibrated in the iron reduction process conditions in the blast furnace, can have an appropriate amount of CO relative to other gas components. As opposed to conventional processes, the CO produced can be largely free from impurities such as sulfur, simplifying the need for pollutant control systems around the overall iron or steel-making plant which would normally be required when utilizing coal and/or coke. After the consumption of CO in the iron reduction process, $CO_2$ can be produced in the effluent from the process. This $CO_2$-enriched effluent stream can then be used as the input to the MCFC cathode, after appropriate heat exchange if desired. This can typically involve steam generation, which can then feed secondary electricity production from a steam turbine. For example, the effluent gas may contain combustible materials which can then be burned to produce further heat by the addition of air or oxygen. The heat produced can be used in various plant processes, but the $CO_2$ produced by the combustion can remain in the flue gas, which, when subsequently introduced into the cathode, can be concentrated/captured effectively by the MCFC system.

Separate combustion of fuel for heating the MCFC system can be reduced or minimized in any of the above systems, as sufficient waste heat for heat exchange should typically be available from the iron or steel production processes. Preferably, lower fuel utilization can be employed, as operating under such conditions can produce higher CO production per fuel cell array employed and greater carbon capture per MCFC array employed. The blast furnace off gas can additionally or alternately be heat integrated with the MCFC inlet/outlet. A portion of the blast furnace off gas can be used as at least a portion (or potentially all) of the cathode feed, while the remainder of the blast furnace off gas can be emitted to the atmosphere and/or compressed for $CO_2$ sequestration in a low $CO_2$ emissions iron or steel production scheme.

In another embodiment, the $H_2$ and CO can be separated after production by the anode, and the $H_2$ can optionally but preferably be used to provide carbon-free heating for the various plant processes, while the CO can optionally but preferably be used in the iron reduction. This can allow for fewer $CO_2$ sources within the overall plant and may simplify $CO_2$ collection for introduction as cathode feed gas.

An advantage of the MCFC system over conventional carbon capture systems, such as amine capture, can include a lack of criticality for the $CO_2$ separation system to capture a relatively high percentage (e.g. at least about 90% or at least about 95%, by volume) of the $CO_2$ from the anode. As opposed to conventional capture technologies, any carbon (as CO or $CO_2$) not captured can be converted to $CO_2$, recycled from the iron reduction process to the cathode inlet, and then (typically) mostly converted to carbonate ions to be transported across the MCFC membrane to the anode, where they can undergo the $CO_2$ separation process. The only $CO_2$ emission from the system in such a configuration can come from the cathode exhaust. The overall $CO_2$ capture efficiency of the plant can be adjusted based on the ratio of the cathode out $CO_2$ concentration relative to the cathode input $CO_2$ concentration, which can be easily varied, such as by adjusting the number of operation stages of the MCFC arrays and/or by adjusting the number of MCFC cells to increase the available fuel cell area.

Figure 19:
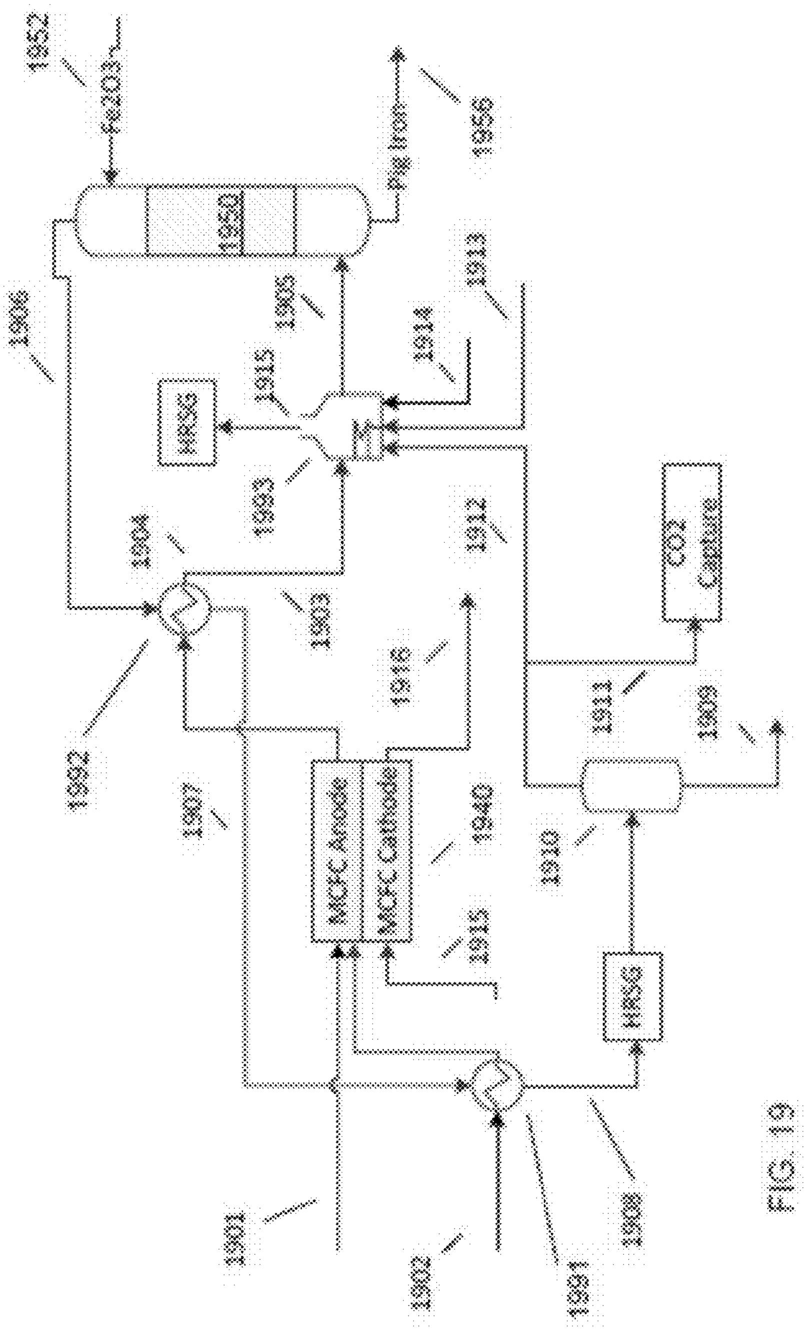
FIG. 19 schematically shows an example of integration of molten carbonate fuel cells with a process for producing iron or steel.

FIG. 19 shows an example of a configuration suitable for operating molten carbonate fuel cells (MCFCs) in conjunction with an iron reduction process. The FIG. 19 configuration can be suitable for reducing iron oxides, such as $Fe_2O_3$ and/or other iron oxides found in various types of iron ore, to pig iron (about 95% Fe). In FIG. 19, steam 1901 and pre-heated methane 1902 can be fed to the anode of the MCFC 1940. Optionally but preferably, the methane 1902 can be pre-heated via a heat exchanger 1991 by recovering heat from stream 1907 derived from the blast furnace off gas. The MCFC 1940, such as an MCFC operating at about 30% fuel utilization, can produce reducing gases (e.g., CO and $H_2$) in the anode exhaust 1903 that can be sent to the blast furnace. Anode exhaust 1903 can optionally but preferably be heated, e.g., by recovering some of the heat from the blast furnace off gas 1906 in heat exchanger 1992. The heated anode exhaust 1904 can be heated to the blast furnace inlet gas temperature (for example about 1200° C.) in pre-heater 1993, resulting in an inlet gas stream 1905. Conventional methods can be used for introduction 1952 of solid particles of iron oxides into the top of the blast furnace 1950. Optionally, the input flow 1952 of particles of iron oxides can be introduced along with a flux agent, such as $CaCO_3$, that can assist with formation of a slag that can be readily separated from the iron product. The input flow 1952 of particles of iron oxides can flow through the blast furnace 1950 counter current to the reducing gas 1905, which can enter the blast furnace 1950 at a location typically more toward the bottom. Reduced Fe can leave the furnace as a bottoms flow 1956, while a furnace off gas comprising $CO_2$ and $H_2O$ can leave the furnace as 1906. Furnace off gas 1906 can be integrated with the process to heat the anode exhaust 1903 in heat exchanger 1992 and/or pre-heat anode input flow 1902 in heat exchanger 1991. These heat recovery processes can result in a cooled furnace off gas stream 1908. Optionally, further heat can be removed from furnace off gas stream 1908 using a heat recovery steam generator (HRSG). Water can be condensed from the cooled off gas stream 1908 in condenser 1994, producing process water 1909 and a gas 1910 with a relatively high concentration of $CO_2$. Gas 1910 can optionally also contain some methane. A fraction of gas stream 1910 can be split off as a feed stream 1912 to a burner and can be burned using an oxidizing source (air) 1913 and a fuel (methane) 1914 to produce enough $CO_2$ at an appropriate temperature for the cathode feed 1915. The remainder of gas 1910 can be sent 1911 to a $CO_2$ separator/compression system, for instance to produce pipeline quality $CO_2$ for use and/or sequestration or alternately to be emitted to the atmosphere. Some heat from burning streams 1912, 1913, and 1914 can additionally or alternately be used to heat stream 1904. A heat recovery steam generator (HRSG) can be used to remove any additional heat in 1915 before it is sent to the cathode and to generate steam for the downstream steel manufacturing processes. The MCFC can remove a convenient or desired portion of the $CO_2$, for example, at least about 50% or at least about 70% of the $CO_2$ in 1915, giving a reduced $CO_2$ exhaust stream 1916. Exhaust stream 1916 can be emitted to the atmosphere and/or recycled back as part of cathode input stream 1915.

Example of Configuration for Integration of MCFC with Blast Furnace

This example demonstrates an integrated MCFC system with an iron blast furnace, which reduced $Fe_2O_3$ to pig iron (95% Fe). The reaction system configuration for this example was similar to the configuration shown in FIG. 19. In this example, the MCFC system was operated at 30% fuel utilization with a methane-steam feed to the anode to produce reducing gas for the blast furnace. The blast furnace off gas was heat integrated with the MCFC inlet/outlet and a fraction of it can be used as the cathode feed, while the remainder can be emitted to the atmosphere or compressed for $CO_2$ sequestration in a low $CO_2$ emissions iron/steel production scheme.

The integrated MCFC process was sized to produce enough reducing gas to operate the blast furnace of a ~2.8 Mton/year steel plant. In addition to generating the reducing gas feed for the blast furnace based on the anode exhaust, the MCFC also produced about 233 MW of power which could be used to power other parts of the steel plant, to power separation and compression of $CO_2$ for pipeline transport (such as $CO_2$ stream 1911 as shown in FIG. 19), and/or to be sold back to the grid. FIG. 20 shows representative values for the flow composition at various locations in a system having a configuration similar to the configuration shown in FIG. 19. For convenience, the stream designations shown in FIG. 19 were also used to designate the streams in FIG. 20. It is noted that the composition of anode output stream 1903 was based on a fuel utilization in the anode of about 30%. The changes in the relative composition of streams 1904 and 1905 were due to equilibration via the water gas shift reaction. It is noted that the composition of blast furnace off gas 1906 was based on simulated consumption of ~100% of the reducing gas in the blast furnace, while no methane was consumed in the furnace. In a real system, it is likely that an excess of reducing gas would be used to provide process stability. Additionally, it is likely that a small amount of methane would be consumed in the blast furnace via reaction with previously reduced iron, potentially leading to introduction of minor additional carbon into the iron as well as production of additional $H_2$. However, this idealized calculation of the composition of blast furnace off gas 1906 provides representative values for the energy content and composition.

It is noted that a conventional configuration for a similarly sized steel plant was reported in a journal article by Arasto et al. (Title: Post-combustion capture of $CO_2$ at an integrated steel mill—Part I: Technical concept analysis; Antti Arastoa, Eemeli Tsuparia, Janne Kärkia, Erkki Pisilä, Lotta Sorsamäkia, International Journal of Greenhouse Gas Control, 16, (2013) p. 271-277). The configuration in Arasto et al. produced 135 MW with an HRSG-turbine system that recovered heat from the traditional coal burners and blast furnace. This was enough power to operate the ~2.8 Mton/year steel plant, provide electricity to a local community, and export some to the gird. By contrast, by using an MCFC for power generation on the methane feed, as opposed to generating power from the excess heat of the steel plant, the MCFC in this example generated about 233 MW of power. Compared to the conventional steel plant configuration reported in Arasto et al., the integrated MCFC-blast furnace system can produce more power, and can also reduce the $CO_2$ emissions by at least 65%.

Integration of MCFC with Refinery Hydrogen Use and "Carbon-Free" Hydrogen

Hydrogen can be used within the refinery for a variety of processes. Most refineries both generate hydrogen in some processes (for example, gasoline reforming to produce aromatics) and use hydrogen for other processes (for example, sulfur removal from gasoline and diesel blending streams). Additionally, refineries can have a large number of boilers, furnaces and/or other systems for heating reactors that require energy. These heating and/or energy generation systems generally do not utilize hydrogen, because hydrogen can typically be more valuable than other fuel sources, and because most refineries are, on an overall basis, net importers of hydrogen. Generally, hydrogen import can be done by building on-site, and/or by accessing nearby/pipeline sources of hydrogen to bring the overall refinery into balance.

Since most refinery processes typically take place at elevated temperature and usually require heat provided by boilers of various sorts (as well as process steam), refineries generally contain large numbers of heating systems. This can result in a large number of point sources of $CO_2$ that can vary widely in size. Some, like cat cracking, can produce large amounts of $CO_2$, while others can produce modest amounts. Each of these point sources of $CO_2$ can contribute to the overall refinery $CO_2$ production. As most integrated refineries are typically about 70-95% thermally efficient on an overall basis at converting crude oil to products, typically about 5-30% of the carbon entering the refinery in crude oil or other inputs can be exhausted (to the air) as $CO_2$. Reduction of these emissions can improve refinery greenhouse gas emissions per unit of product produced.

In various aspects, integration of an MCFC system with a refinery hydrogen supply can reduce, minimize, or eliminate hydrogen constraints on the overall refinery operation. Additionally or alternately, the MCFC system can use, as inputs, any of a wide variety of off-gasses and/or other streams, as long as they can be converted to "clean" light gasses and syngas mixtures. It is noted that the light gas and/or syngas mixtures can be used without much restriction on the amount of inerts (e.g., $N_2$, $CO_2$, and the like, and combinations thereof) present. This "input integration" can additionally or alternately be a feature in streamlining overall efficiency in refinery operation. More generally, an MCFC system can provide a single integrated solution for up to four (or potentially more) aspects of refinery operation: production of heat for process units, production of hydrogen as a reactant, collection and sequestration of carbon, and efficient utilization of off-gases and purge streams from various processes.

In some aspects, $H_2$ can be used as the fuel in burners in a refinery to reduce, minimize, or eliminate $CO_2$ emission point sources. A centralized supply of $H_2$ for both purposes can simplify overall refinery operations by reducing the number and type of fuels and reactants—only one material can be distributed for these purposes. For example, hydrogen can be used at a variety of temperatures and pressures. An MCFC system can produce hydrogen from the anode exhaust stream after (optional) separation of water and $CO_2$, and further (optional) purification through any conventional method, such as pressure-swing adsorption. Once purified to typical refinery requirements, such as a purity (on a dry basis) of at least about 80 vol % $H_2$, or at least about 90 vol %, or at least 95 vol % or at least 98 vol %, a hydrogen-containing stream can be pressurized to an appropriate pressure for process use and piped/transported to any process. The hydrogen-containing stream may be split into multiple streams where lower purity and/or lower pressure streams can be sent to some processes or burners, while higher purity and/or higher pressure streams can be sent to other processes.

The integrated system can additionally or alternately, but typically advantageously, produce electricity. The electrical production may be used to at least partially power MCFC-related systems, such as separation systems or compressors, as well as to power at least a portion (such as up to all) of the refinery electrical demand. This electricity can be produced at relatively high efficiency with little or no transmission losses. Additionally, some or all of the electricity can optionally be direct current (DC) electricity, for instance where DC power could be preferred for the operation of some systems without the normal losses in transformers/inverters. In some aspects, an MCFC system can be sized so that at least a portion (or all) of the power needed by the refinery can be provided, or even so that excess power can be provided. Additionally or alternately, the MCFC system can be sized to a desired $H_2$/heat load and/or to the electrical load. Furthermore, the system can be operated over a range of conditions, allowing for variable amounts of both electrical and hydrogen demand.

At least a portion of the refinery processes that produce $CO_2$ can be collected and used as some or all of the gasses for the cathode inlet, such as a majority of the $CO_2$ production processes or all of the $CO_2$ production processes. If necessary, these gases can be mixed with air or other oxygen containing streams to comprise a gas mixture with both $CO_2$ and oxygen appropriate for the cathode inlet. Fuel constituents present in these streams can typically be burned with excess oxygen/air to provide preheating of the cathode inlet. The $CO_2$ concentration of the overall cathode inlet can vary widely, and can typically be at least about 4 vol %, such as at least about 6 vol %, at least about 8 vol %, or at least about 10 vol %. If the collected streams do not contain sufficient $CO_2$ concentrations for MCFC operations (or even if so), then $CO_2$ produced in the separation of the anode exhaust and/or from one or more off-gas or purge streams from the separation process can be recycled to the cathode inlet. Heating for the cathode inlet streams may come from combustion of off-gases in these streams, heat exchange, and/or addition of combustible fuel components. For example, in some aspects the MCFC system can use high carbon materials, like coke or petcoke, and/or other "bottoms" from petroleum processes, to provide heat for inlet streams where the combustion products from those materials can be used as a $CO_2$ source for the cathode.

Additionally or alternately, at least a portion of the $CO_2$ for the cathode inlet stream can be provided by a combustion turbine, such as a turbine that can use methane/natural gas as a fuel. In this type of configuration, $CO_2$ generated by processes such as catalytic cracking may not be mitigated, but $CO_2$ generated by heaters, boilers, and/or other burners can be reduced or minimized by using $H_2$ generated by the MCFC.

The anode outlet stream can contain a large concentration of carbon dioxide as well as other syngas components. Typically, $CO_2$ can be removed from this stream efficiently to produce a $CO_2$ product that can be used for a variety of other processes. As a significant fraction of the carbon dioxide produced from the refinery can exit from an MCFC anode, collection of $CO_2$ can be efficient and greatly simplified. The collection of $CO_2$ as a single point source can then be used for other operations (e.g., EOR if near oil fields, re-injection to gas wells) and/or can be captured/sequestered. The removal of a majority of the entire $CO_2$ load, such as at least about 70%, or at least about 80%, for both $H_2$ production and electricity use, can substantially lower the greenhouse gas impact of refinery operations and can improve overall refinery efficiency (conversion of crude to products) by adding a high-efficiency source of electricity, hydrogen, and heat within a single process.

In aspects where an MCFC system is integrated with the hydrogen delivery system in a refinery, the anode input for the MCFC system can be selected from a large variety of materials available from various refinery processes, such as light gasses pre-reformed to reduce C2+; methane; gasified heavy materials like gasified coke or bitumen; syngas; and/or any other hydrocarbonaceous material that can be cleaned of sulfur and other harmful impurities; as well as combinations thereof. Thus, the MCFC system, with proper pre-cleanup, can act as a "disposal" for all sorts of inputs which might otherwise not have an efficient or effective use in the refinery. Instead of eventually being exhausted to the atmosphere, optionally after being burned as a fuel, a predominant amount of the carbon in these "waste", "purge", or other undesirable streams can be effectively concentrated/captured as separated $CO_2$ by the system. The cathode input can be or comprise any refinery stream containing $CO_2$ off-gasses plus any recycle from the anode exhaust or burned fresh methane that might be used for heat exchange. Most refineries have a wide variety of processes operating at various temperatures, so appropriate refinery processes can be selected for some heat integration to manage, for example, clean-up cooling and heating. The cathode exhaust can generally be exhausted to the atmosphere. The anode exhaust can be used as is, optionally after separation of some components, and/or can undergo both separation and water-gas shift to produce a stream that is nearly all $H_2$. The high $H_2$ content stream can be purified to a desired level for various reactive processes, while combustion $H_2$ can contain greater levels of residual CO, $CO_2$, and so forth, as combustion of such a stream can still result in reduced emissions of carbon oxides relative to combustion of a hydrocarbonaceous fuel. $CO_2$ separated from the anode to exhaust can optionally be recycled, for example, for use as an input to the cathode. Additionally or alternately, feeds to the anode can include those with large $CO_2$ impurities such as natural gas with a large $CO_2$ content. For normal refinery operations this type of stream could increase the $CO_2$ emissions from the refinery when used for either heat or hydrogen generation. When fed to the anode of an MCFC system, however, the separation stage(s) can effectively remove this additional $CO_2$ as part of removal of other $CO_2$ in the anode exhaust.

An additional difficulty in capturing carbon from the disparate $CO_2$ sources in a refinery can be the low concentration of the $CO_2$ often present in the refinery streams. In general, the energy required for separation of the $CO_2$ from the gas stream is highly dependent on the concentration of $CO_2$ in the stream. For processes that generate gas streams with low $CO_2$ concentrations, such as $CO_2$ concentrations of about 10 vol % or less, substantial energy can be required to separate $CO_2$ from a stream to form a high purity $CO_2$ stream. By contrast, in some aspects, a feature of an MCFC containing system can be that $CO_2$ can be transferred from a relatively low concentration stream (such as a cathode inlet stream) to a relatively high concentration stream (such as an anode exhaust). This can reduce the energy requirements for forming a high purity $CO_2$ gas stream. As a result, an MCFC can provide substantial energy savings when attempting to form, for example, a $CO_2$-containing stream for sequestration.

Output electricity generated by the MCFC directly can typically be as DC power, but can be configured to produce any convenient mix of DC and/or AC power at a variety of current and voltage settings. Typically, a power plant/input electrical for a refinery can be a common high voltage AC current (e.g. ~960V). Due to the way molten carbonate fuel cells are constructed, one can produce essentially any DC current/voltage and, with inversion, a variety of AC voltages. DC, produced locally, should not suffer transmission losses typical of long-distance power lines and should not require inverters, at considerable cost and some efficiency loss. This can provide some flexibility in designing compressors, pumps, and other components and/or can eliminate a number of grid and/or local electrical inefficiencies.

In addition to use within a refinery, hydrogen can be more generally useful for a wide variety of products and processes, as it produces only water vapor on combustion. However, most conventional approaches to making hydrogen require large emissions of carbon. For example, production of hydrogen from steam reforming of methane can typically produce $CO_2$ (from the carbon in the methane) and waste heat. Production of hydrogen from electrolysis can require electricity that can typically be derived from a mixture of fossil fuel production to the electrical grid. These production systems can all result in effluent exhausts comprising $CO_2$. The effluents, if carbon capture is required, would typically entail separate carbon capture systems at those various sources, without any convenient integration into wider refinery operations. Typically, these sources can actually be outside of the refinery gates, allowing for little or no synergistic production/consumption of the various chemical, electrical, and heat inputs and outputs.

Additionally or alternately, MCFC containing systems according to the invention can provide the means to separate $CO_2$ efficiently from the process as an integral part of the separation and hydrogen purification steps. The $CO_2$ can then be captured, and/or used for other useful processes. This can occur at high overall system efficiency—far higher than conventional means of producing net hydrogen export, especially at small scale and under variable load.

The use of a MCFC system for hydrogen production for use in subsequent processes that may generate electrical power or heat can allow for relatively low-emission production at relatively high efficiency and with low (minimum) carbon emissions. The MCFC system can dynamically respond to varying needs for hydrogen by adjusting the ratio of chemical energy production to electrical energy production and can be ideal for uses where loads and demands may not be approximately constant—varying from pure electrical production with no excess hydrogen to high hydrogen production. Furthermore, the integrated MCFC system can be scaled over a wider range of applications with relatively high efficiency than larger scale systems such as methane steam reformers.

The MCFC-hydrogen production system can have an advantage that repurposing the hydrogen for fuel value can produce lower net $CO_2$ emissions than conventional systems without carbon capture and can produce far lower emissions with use of the inherent system $CO_2$ separation. This can be valuable in a variety of applications. Hydrogen can be produced for fuel cell vehicles that can use low temperature/low pressure hydrogen. The amount of hydrogen and electricity can be varied depending on overall demand maintaining overall high system efficiency. Hydrogen for export into boilers and/or other combined heat and power systems can allow for the constant production of electricity, e.g., in stand-alone generation, along with a variable amount of carbon-free heat via the production of hydrogen with subsequent combustion in heater/boiler and similar systems. For example, an installation could produce primarily electricity in the summer for air conditioning systems while switching to a mix of primarily chemical energy in the winter for heating operations. Other applications can include systems designed to provide on-site hydrogen such as in laboratories and other technical and manufacturing facilities where some hydrogen can be beneficial along with a need for electrical energy.

In aspects involving hydrogen production and/or electrical power generation, the anode inlet can be fed by fresh methane, another suitable hydrocarbon fuel, and/or the combination of fresh fuel and recycled CO and/or $H_2$ from the various processes. The anode outlet stream comprising $H_2$ and/or CO can provide the components to produce hydrogen. This can typically be done through some combination of reaction, separation, and purification steps. An example would be a first stage employing water-gas shift to shift as much CO as possible to $H_2$ by the reaction $H_2O+CO=H_2+CO_2$, followed by a second (and subsequent) stage(s) that remove $H_2O$ and $CO_2$ from the $H_2$, and provide a suitable purity product. Such stages can include PSA, cryogenic separation, membranes, and other known separation methods, either individually or in combination. The off-gasses from these steps can be recycled and/or used to provide heat for inlet streams. The separated $CO_2$ can be used as a recycle stream and/or can be captured and/or used for other processes. The cathode inlet can be composed of recycled $CO_2$ from the overall process and/or $CO_2$ produced by the combustion of fresh (or recycled) fuel used to provide heat to the inlet streams. The cathode effluent can typically be exhausted to the atmosphere, optionally but preferably after heat recovery to, for example, provide heat for other process streams and/or in combined cycled electrical production, though the cathode effluent could optionally but less preferably be sent for further treatment, if desired.

MCFC systems integrated into carbon-free heat and power applications can be used over a range of operating conditions ranging from fuel utilizations with lower hydrogen make (e.g., 60-70%) to lower fuel utilizations (e.g., 20-30%) for high hydrogen production. The exact operational range of an individual application may vary widely both by application and over time. The ability to adapt to this operational range can be a desirable advantage. The number of separation stages and/or the purity achieved can depend on the ultimate application. Simple production of hydrogen for low-emissions heat can be tolerant to modest impurities in the hydrogen, as even a few percent $CO_2$ and/or CO could still result in very low overall emissions. High purification applications such as fuel cell vehicles and/or hydrogen for laboratories may require multiple steps (e.g. cryogenic separation followed by PSA) to achieve purity specifications.

As an example of providing hydrogen to multiple refinery processes, an MCFC can be operated to generate electricity and an anode exhaust that contains $H_2$, $CO_2$, and $H_2O$. One or more separations can be used to separate $CO_2$ and/or $H_2O$ from the anode exhaust (or alternatively from a gas stream derived from the anode exhaust). This can result in a first gas stream having an increased volume percent of $H_2$ relative to the anode exhaust. A separation can then be performed on the first gas stream to form a second gas stream with an even higher volume percentage of $H_2$ than the first gas stream. The remaining portion of the first gas stream can then be compressed to a first pressure for use in a process with less stringent requirements for hydrogen, while the second gas stream can be compressed to a second (higher) pressure for use in a process requiring a higher pressure and/or higher purity hydrogen input.

Example—Integration of MCFC with Refinery Hydrogen Supply

In the following example, calculations were performed for a configuration where an MCFC system was used as a source of hydrogen for supplying various burners, boilers, and/or other units that use combustion of a fuel as a source of energy. While the following examples focus on supplying hydrogen to combustion reactions, the hydrogen generated by the MCFC could additionally or alternately be used to supply one or more processes (such as a plurality of processes) where hydrogen can be used for a purpose other than combustion. For example, the hydrogen generated by the MCFC could be used in one or more hydroprocessing reactors within a refinery.

In the following example, the $CO_2$ for the cathode was calculated based on using an external source of $CO_2$. This choice was made for convenience in demonstrating the energy benefits of using an MCFC for reducing $CO_2$ emissions in comparison with attempting to capture $CO_2$ via another method, such as using conventional amine washes for each potential point source of carbon. For comparison purposes, a typical expected energy cost for using an amine wash based on using monoethanolamine (MEA) to capture $CO_2$ from relatively dilute $CO_2$ streams (such as streams with approximately 10 vol % or less $CO_2$) was approximated to be about 3 GJ/ton $CO_2$. A substantial portion of this energy cost can be avoided by using an MCFC to concentrate $CO_2$ in an anode exhaust stream. It is noted that, in embodiments where $CO_2$ is collected from various point sources within a refinery for use as part of the cathode input, some additional energy cost may be required to deliver the $CO_2$ streams to the MCFC. However, those costs can be at least approximately or roughly offset (if not exceeded) by the additional energy inefficiencies required for a conventional configuration where a separate amine wash would need to incur similar costs for delivery of $CO_2$ to a central amine wash, and/or by the additional energy inefficiencies that would be incurred by having a separate amine wash for each point source of $CO_2$.

The following configuration examples provide two alternatives for operating an MCFC to provide hydrogen for consumption in a refinery. In the calculations for the first configuration, a gas turbine was used to generate electricity and to provide a source of $CO_2$ for the cathode input. In the calculations for the second configuration, additional methane was burned to provide the heat and $CO_2$ for operating the fuel cell. In both configurations, the anode exhaust was processed in one or more separation stages to separate $CO_2$ (such as for sequestration) from $H_2$ (used for fuel in the refinery).

In these examples, calculations were performed for supplying the heat requirements of a typical refinery that can process about 500 kbd of crude oil. A refinery with a refining capacity of about 500 kbd can use about 118 Mscf/d (or roughly $3.34\times10^6$ $m^3$ per day) of natural gas to the heating system, which can produce roughly 118 Mscf/d of $CO_2$ emissions from combustion, if no capture/sequestration mechanism is used. The following examples integrate a MCFC process with a refinery gas fired heater system in a roughly 500 kbd system to provide distributed heating with low $CO_2$ emissions.

Figure 21:
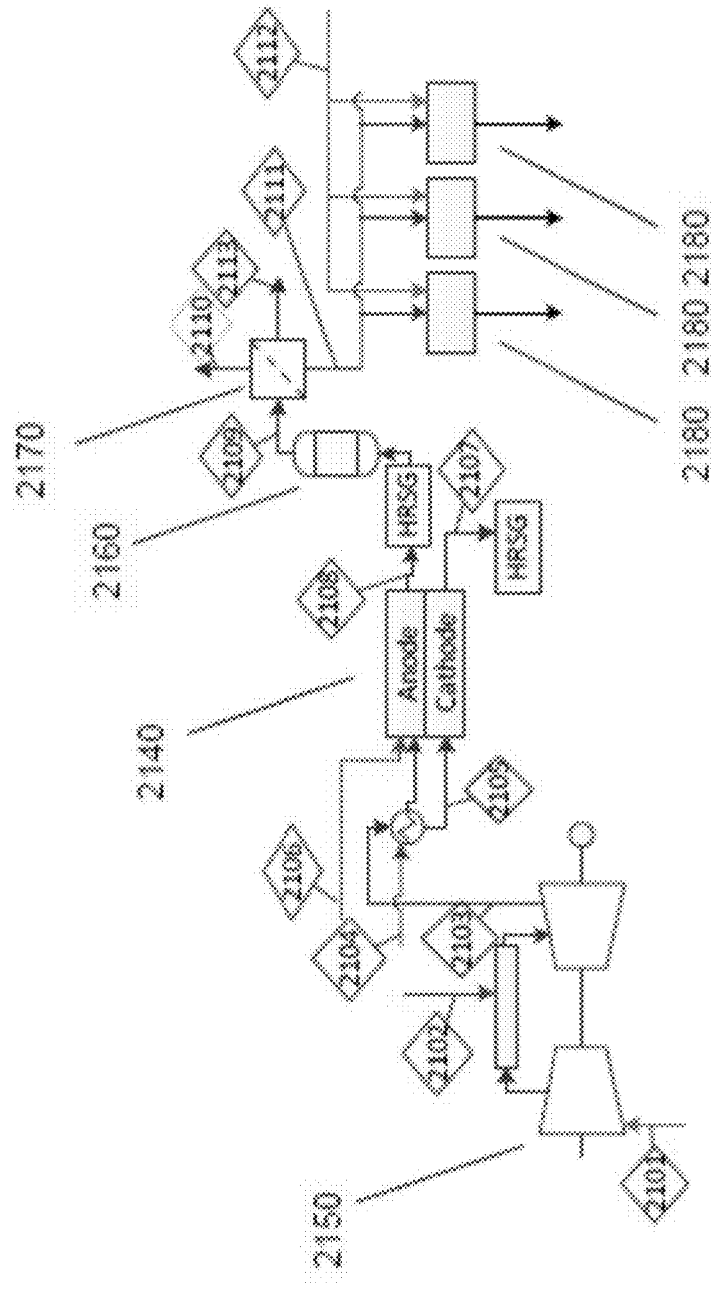
FIG. 21 schematically shows an example of a system for generating hydrogen and electrical power in a refinery setting.

FIG. 21 schematically shows an example of a system for integrated processing with a combustion gas turbine, MCFC system, and refinery wide fired heaters that burn $H_2$. The system in FIG. 21 is configured such that the turbine can generate the $CO_2$ feed required in the cathode to produce enough $H_2$ in the MCFC system to run the refinery heating system. Air 2101 and methane 2102 were fed to a combustion gas turbine 2150 and burned to produce a hot cathode feed 2103. The excess heat in hot cathode feed 2103 was used to pre-heat the anode methane feed 2104, which can then be fed 2105 to the cathode of MCFC 2140. Anode methane feed 2104 and steam 2106 were fed to the anode of MCFC 2140. The MCFC can produce a low $CO_2$ content cathode exhaust 2107 at high temperature. Depending on the aspect, the MCFC can be operated at a low fuel utilization (e.g., of about 25% to about 60%, such as a fuel utilization of at least about 30%, or at least about 40%, or about 50% or less, or about 40% or less). Additionally or alternately, the MCFC can be operated at a more conventional fuel utilization (e.g., of about 70% or greater, though conventional fuel utilization can typically be between 70% and 75%), but this can be less preferable, as the amount of potential $H_2$ that capable of being recovered from the anode exhaust can be reduced. Heat can be recovered from cathode exhaust 2107 in a HRSG (Heat Recovery Steam Generation system) before the cathode exhaust is emitted to the atmosphere (or further processed). The anode exhaust 2108 can be cooled in a HRSG and/or can be shifted in a water gas shift reaction stage 2160. The shifted gas 2109, mostly $H_2$ and $CO_2$, can go through a separation unit 2170 to produce a $CO_2$ stream 2110 and a $H_2$ stream 2111. The $CO_2$ stream 2110 can be compressed and sold for use and/or sequestered. $H_2$ stream 2111 can be distributed to the refinery heaters as the heating fuel. Each sub-stream of $H_2$ stream 2111 can be burned with oxidant (air) 2112 in burners 2180 that can be located at one or more locations in the refinery to provide heat with substantially no $CO_2$ emissions. For a configuration similar to FIG. 21, FIG. 22 shows representative values for the flow volumes within the configuration.

Figure 23:
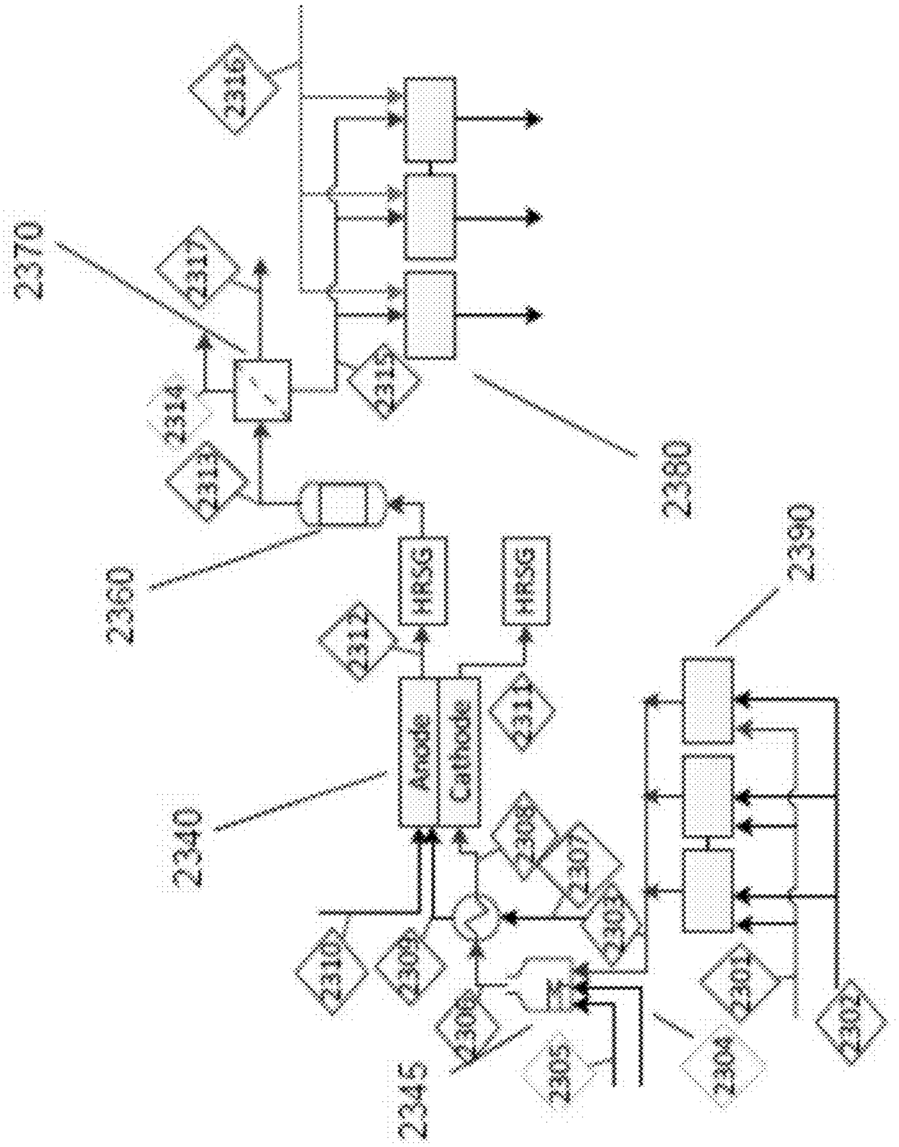
FIG. 23 schematically shows an example of a system for generating hydrogen and electrical power in a refinery setting.

FIG. 23 schematically shows another example of a system for integrated processing with an MCFC system and a refinery fired heaters with methane and hydrogen burners. This system was configured such that the methane burners can generate the $CO_2$ feed required in the cathode to produce enough $H_2$ in the MCFC system to run the remaining hydrogen burners. Methane 2301 and oxidant (air) 2302 can be distributed to the methane burners 2390. The off-gas 2303 can be collected from the methane burners and sent to a feed pre-heater 2345. Methane 2304, oxidant (air) 2305, and off-gas 2303 can be burned in pre-heater 2345 to produce a hot cathode feed 2306. The excess heat in 2306 can be used to pre-heat the anode (methane) feed 2307 and fed to the cathode at 2308. The pre-heated methane 2309 and steam 2310 were fed to the anode. The MCFC 2350 can produce a low $CO_2$ content cathode exhaust 2311 at relatively high temperature. Heat can be recovered from cathode exhaust 2311 in a HRSG, e.g., before it is emitted to the atmosphere or sent for further treatment (not shown). The anode exhaust 2312 can be cooled in a HRSG and shifted in 2360. The shifted gas 2313, mostly $H_2$ and $CO_2$, can go through a separation unit 2370 to produce a $CO_2$ stream 2314 and a $H_2$ stream 2315. $H_2$ stream 2315 can be distributed to the hydrogen burners 2380. Each sub-stream can be burned with oxidant (air) 2316 in burners 2380 that can be located at one or more locations in the refinery to provide heat with substantially no $CO_2$ emissions. For a configuration similar to FIG. 23, FIG. 24 shows representative values for the flow volumes within the configuration.

Based on configurations similar to FIGS. 21 and 23, and based on process flow similar to FIGS. 22 and 24, the relative net power production was calculated for sequestering carbon for a refinery integrated with an MCFC. This was compared with a calculation for the net power production for a conventional refinery system where amine wash systems were used for carbon capture for each point source. As noted above, it has been determined that using a representative amine wash (e.g., with MEA) to capture $CO_2$ from a typical dilute refinery stream (such as streams containing about 2 vol % to about 8 vol % $CO_2$) can require about 3 GJ/ton $CO_2$. Table 2 shows the comparison for the inventive configurations similar to FIGS. 21 and 23 (which can result in $CO_2$ streams such as stream 2110 or stream 2314) relative to a conventional amine wash method. For the comparison in Table 2, the % $CO_2$ emission reduction represents the percentage of carbon that passes through the anode of the MCFC. Based on the calculated values shown in Table 2, use of an MCFC to provide $H_2$ for refinery burners and to centrally separate $CO_2$ can result in additional available power being generated. This can notably be in contrast to the substantial power requirements for separating $CO_2$ using a conventional configuration.

TABLE 2

Carbon Capture and Net Power Generation

| | Configuration 1 | Configuration 2 |
|---|---|---|
| % CO2 emissions reduction | 55.98% | 86% |
| Net power with MCFC power [MW] | 110 | 36 |
| Net power with MEA capture [MW] | −115 | −180 |

Low Temperature Combustion Exhaust Sources Integrated with MCFC Systems

Low temperature combustion exhaust sources can comprise any stream containing $CO_2$ and $O_2$ (or possibly just $CO_2$ with addition of air) that requires cooling before use in a fuel cell. Generally this can be a direct result of having some pollutants (e.g. sulfur, metals) that would poison the Ni catalyst on the cathode. For these purposes, small amounts of NOx or SOx are typically not considered a poison for the cathode Ni catalyst. For combustion exhaust sources containing elevated levels of pollutants, the original combustion effluent needs to be cooled to a temperature where the impurities can be removed, then reheated via heat exchange, e.g., with cathode effluent, to the MCFC operational temperature.

Examples of low temperature combustion exhaust sources can include coal-fired combustion sources, like coal power plants and lignin fired combustion such as from wood and other biomass combustion. Other "dirty" fuels might include heavy fuels derived from petroleum like bunker fuel or other heavy marine fuels where there are enough impurities to need clean-up.

The combined system can offer the ability to do multiple operations more cleanly than would otherwise be possible. For example, lignin (e.g. from cellulosic ethanol production) can be burned to make $CO_2$, heat exchanged so that it is cool enough to remove impurities, and then the $CO_2$ stream can be combined with the $CO_2$ off-gas from fermentation as the cathode inlet. This $CO_2$ then produces (along with methane in the anode) the electrical power to power the plant's operations, and the residual heat to power other reactors which, for biofuels, would be at lower temperature. Residual $CO_2$ can be separated/captured, which then improves the overall emissions from the plant. For a ship-board system using heavy fuel oil, the core electrical power for the ship can be provided along with heat and by default, a much cleaner total exhaust (even though the $CO_2$ would be emitted). For coal combustion the benefits can be based on the potential for reduction of $CO_2$ emissions, although the ability to produce excess syngas for this (and other cases) can also be used as a combustion aid in the prime combustion of the "dirty" material. In such aspects, the $H_2$ or $H_2/CO$ used as a combustion aid can improve the combustion characteristics of a lower quality fuel, allowing for cleaner/more efficient burning in the first place. Additionally, the excess syngas as $H_2$ can be used in clean-up operations for the material up front (e.g. hydrodesulfurization) providing the necessary ingredient without actually building any additional equipment.

The cathode input can be the combustion source after cooling, contaminant removal, and reheating via heat exchange. Some of the up-front clean-up of the material to be combusted may be done via hydrogen treatment where the $H_2$ is derived from the MCFC. The cathode input can be supplemented with either fresh methane burned at lean conditions or, if more O2 is needed, air. The cathode output can be exhausted to the atmosphere. The anode input can be methane, natural gas, or another reformable fuel, but could also be augmented by partially gasified material (gasified biomass or coal), and pre-reformed light hydrocarbons if present. The $H_2$ in the anode exhaust can be separated and/or recycled.

Integration with a Hydrogen Turbine

In some aspects, an objective in producing low-carbon power can be to increase or maximize the total power output while maintaining high $CO_2$ capture efficiency and/or while efficiently utilizing existing systems. In a conventional system, a gas turbine can be connected to a MCFC system such that the gas turbine produces an exhaust stream comprising $CO_2$ that serves as a component of the cathode inlet providing heat and $CO_2$ to the cathode. For this configuration, as is known in the literature, $CO_2$ can be captured by conventional means and the MCFC system can be operated at relatively high fuel utilizations (typically above 70% to about 80%, or about 75%) to maintain heat balance within the MCFC under ordinary operating conditions.

The efficient utilization of the MCFC can be improved by lowering the fuel utilization to process excess fuel, for example methane, and produce excess syngas as an exhaust. This exhaust/effluent can undergo various separations to yield a syngas stream that can be useful for a variety of chemical and industrial purposes. However, where syngas is not useful as a feed stock, and/or for cases where electrical power generation can be a primary goal, generation of a syngas stream may not provide additional low-carbon power.

In various aspects, systems and methods are provided for producing an increased or maximized amount of electrical power from a fixed MCFC system while optionally but preferably providing for consistent high carbon capture. In some aspects, such a system can be provided by combining the use of a conventional gas turbine as the $CO_2$ source for the MCFC cathode, a low fuel utilization for production of high amounts of syngas, and a combination of separation and/or conversion systems that can allow for increased production of hydrogen derived from the MCFC anode exhaust. This hydrogen stream derived from the anode exhaust can then be introduced into a second hydrogen turbine where additional power can be generated with reduced or minimized emissions of $CO_2$. Because the second turbine can be powered by the hydrogen-containing stream derived from the anode exhaust, the amount of additional $CO_2$ generated in order to power the second turbine can be limited to, for example, carbon oxide(s) and carbon fuel residual components in the hydrogen-containing stream. Additionally or alternatively, the hydrogen from the anode exhaust can be used to generate electricity in other manners, such as by combusting the hydrogen to raise steam, which can then be used to generate electricity. Further additionally or alternately, a portion of the hydrogen derived from the anode exhaust can be used as an input for the first (conventional) turbine. This can be beneficial, for example, if the carbon-containing fuel for the first turbine has an elevated content of inerts, such as $CO_2$ and/or $N_2$.

In addition to use within a refinery, hydrogen can more generally be useful for a wide variety of products and processes, as it produces only water vapor on combustion. However, most conventional approaches to making hydrogen can require large emissions of carbon. For example, production of hydrogen from steam reforming of methane can produce $CO_2$ (from the carbon in the methane) and waste heat. Production of hydrogen from electrolysis can require electricity, which is typically generated for the electrical grid based on combustion of a mixture of fossil fuels. These production systems can all typically result in effluent exhausts comprising $CO_2$.

Applications such as fuel cell vehicles can require low-temperature fuel cells which utilize high purity hydrogen. While the vehicle does not produce much carbon emissions, the production of the hydrogen for the vehicle can be inefficient, not easily adapted to smaller-scale, and can produce significant carbon emissions.

In some additional or alternative aspects, the systems and methods herein can facilitate separation of $CO_2$ efficiently from the process as an integral part of the separation and hydrogen purification steps. The $CO_2$ can then be captured and/or used for other useful processes. This can occur at high overall system efficiency, as compared to conventional means of producing net hydrogen production/export, especially at small scale and under variable load.

The use of a MCFC system for hydrogen production for use in subsequent processes that may generate electrical power and/or heat can allow for low-emission energy production at high efficiency and with reduced or minimized carbon emissions. The MCFC system can dynamically respond to varying needs for hydrogen by adjusting the ratio of chemical energy production to electrical energy production and can be suitable for uses where loads and demands may not be constant—varying from heightened electrical production with little or no excess hydrogen to heightened hydrogen production. Additionally, the integrated system can be scaled over a wider range of applications with high efficiency, as compared with larger scale systems such as methane steam reformers. This could allow, for example, for co-production of hydrogen for other uses, such as a fuel cell vehicle system, and for variable electrical power or simply to vary electrical power output.

For example, in some operating configurations, the base gas turbine (such as a turbine powered by combustion of a carbon-containing fuel) can be run at constant high-efficiency conditions with the MCFC system run under variable fuel utilizations to yield different electrical and hydrogen production values, which can control the electrical output from the entire system. The amount of hydrogen and electricity can be varied depending on overall demand while maintaining overall high system efficiency. Hydrogen for export into boilers and/or other combined heat and power systems can allow for the constant production of electricity, e.g., in stand-alone generation, along with a variable amount of carbon-free heat via the production of hydrogen with subsequent combustion in heater/boiler and/or similar systems. For example, an installation could produce primarily electricity in the summer for air conditioning systems while switching to a mix of primarily chemical energy in the winter for heating operations. During high electrical demand, increased hydrogen can be sent to the hydrogen turbine for maximized electrical production. Other applications can include systems designed to provide on-site hydrogen such as in laboratories and other technical and manufacturing facilities, where some hydrogen can be needed along with a need for electrical energy.

In aspects involving hydrogen production and/or electrical power generation, the anode inlet can be fed by fresh methane, another suitable hydrocarbon fuel, and/or the combination of fresh fuel and recycled CO and/or $H_2$ from the various processes. The anode outlet stream comprising $H_2$ and/or CO can provide the components to produce hydrogen. This is typically done through some combination of reaction, separation, and purification steps. An example can be a first stage employing water-gas shift to shift as much as possible (nearly all) of the CO to $H_2$ by the reaction $H_2O+CO=H_2+CO_2$, followed by a second (and potentially subsequent) stage(s) that can remove $H_2O$ and/or $CO_2$ from the $H_2$, and can provide a suitable purity product. Such stages can include PSA, cryogenic separation, membranes, and/or other known separation methods, either individually or in combination. The off-gasses from these steps can be recycled and/or can be used to provide heat for inlet streams. The separated $CO_2$ can be used as a recycle stream and/or can be captured and optionally used for other processes. The cathode inlet can be composed of recycled $CO_2$ from the overall process and/or of $CO_2$ produced by the combustion of fresh (or recycled) fuel used to provide heat to the inlet streams. In some preferred aspects, the cathode inlet can include at least a portion of a combustion exhaust from a first conventional combustion turbine. The cathode effluent can typically be exhausted to the atmosphere, optionally but preferably after heat recovery to, for example, provide heat for other process streams and/or in combined cycle electrical production, though the cathode effluent could optionally but less preferably be sent for further treatment, if desired.

MCFC systems integrated into carbon-free heat and power applications can be used over a range of operating conditions comprising high (e.g., from about 60% to about 70%) fuel utilization with low hydrogen make to low fuel utilizations (e.g., from about 20% to about 60%) with increased hydrogen production. Examples of low fuel utilizations can include at least about 20%, such as at least about 30%, and/or about 60% or less, such as about 50% or less. The exact operational range of an individual application can vary widely both by application and over time. The ability to adapt to this operational range can be a desirable advantage. The number of separation stages and the purity achieved can depend on the ultimate application. Simple production of hydrogen for low-emissions heat can be tolerant to modest impurities in the hydrogen, as even a few percent $CO_2$ and/or CO in emitted streams could still result in very low overall carbon emissions. High purification applications such as fuel cell vehicles and/or hydrogen for laboratories can require multiple steps (e.g. cryogenic separation, followed by PSA) to achieve purity specifications.

In other configurations, the MCFC can be operated under lower fuel utilizations with the excess anode outlet fuel used to provide heat and/or power. In both cases, an advantage can be that the "base load" power output of the fixed gas turbine and MCFC systems can remain approximately constant, while a small sub-section of the overall process, the hydrogen turbine, can be used for variable load. The combination of variable fuel utilization and variable hydrogen turbine feed can allow the overall plant to meet a large variety of needs for heat, electricity, and/or hydrogen demand, while operating the major subsystems of the plant at fairly consistent operating conditions.

Figure 25:
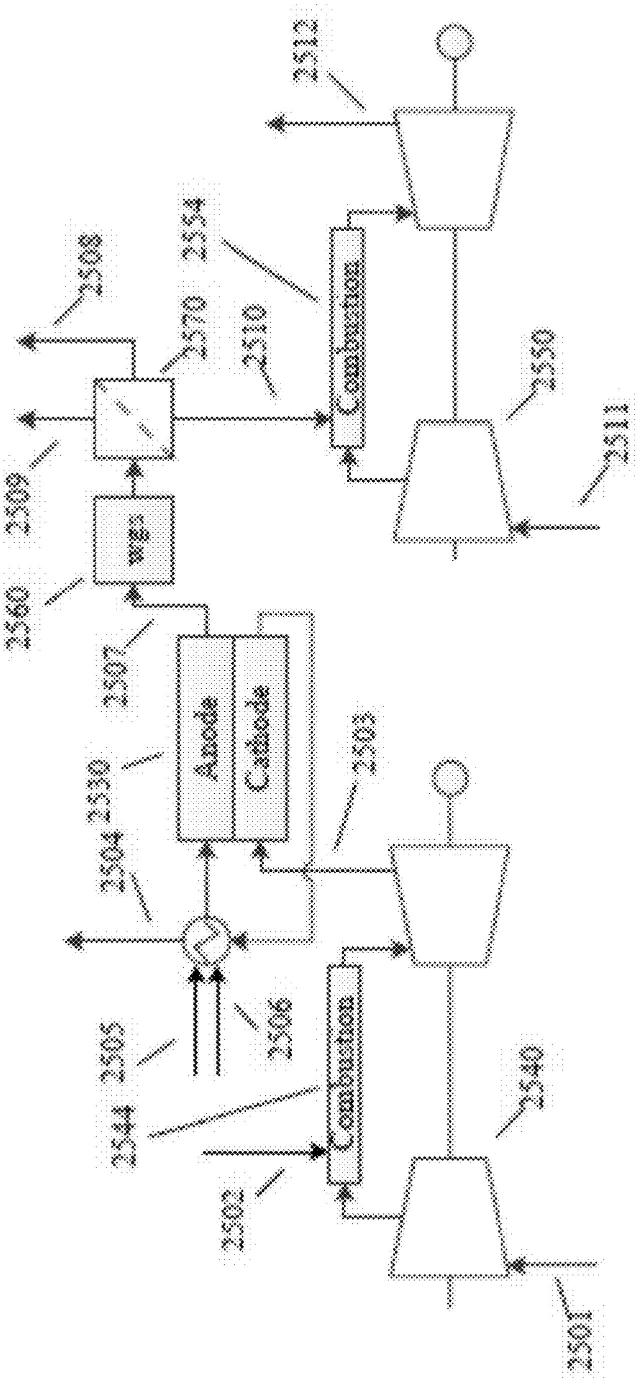
FIG. 25 schematically shows an example of a configuration for generating electricity.

FIG. 25 shows an example flow sheet of an integrated power generation MCFC process that can produce low $CO_2$ emissions power from a convenient carbon-containing fuel, such as natural gas and/or methane. In this scheme a natural gas fired turbine 2540 can combust oxidant (air) 2501 and methane/natural gas 2502 to generate power and exhaust gas stream 2503. Exhaust 2503 can be fed into a cathode of MCFC 2530. The anode of MCFC 2530 can be fed additional fuel (methane/natural gas) 2505 and steam 2506. Through an electrochemical reaction, the MCFC 2530 can generate power, can produce a $CO_2$ depleted cathode exhaust 2504, and can produce an anode exhaust 2507 that contains $H_2/CO_2/CO$. Heat can be recovered from cathode exhaust 2504, and then cathode exhaust 2504 can be emitted to the atmosphere and/or subject to further treatment, if desired. Anode exhaust 2507 can be shifted in a water gas shift reactor 2560 to increase the $H_2$ concentration. The shift reactor effluent can undergo separations 2570 to remove water 2508, recover $CO_2$ 2509, and form a separated stream 2510 containing $H_2$. $CO_2$-containing stream 2509 can be compressed to pipeline conditions and can then be sold for use, used for a different process, and/or sequestered. The separated stream 2510 can be combined with oxidant (air) 2511 and sent to a hydrogen turbine 2550 to generate additional power. The exhaust 2512 from the hydrogen turbine 2550 can be mostly water and $N_2$ and can be emitted to the atmosphere and/or subject to further treatment, if desired.

As an example, simulations were performed using a configuration similar to the system shown in FIG. 25. Comparative simulations were also performed for systems where a hydrogen turbine was not included. In the comparative simulations, fuel (comprising hydrogen) from the anode exhaust was instead recycled to the combustion zone for the conventional turbine. It is noted that the size of the conventional turbine was held constant in the simulations, so recycle of fuel from the anode exhaust resulted in a reduction in the amount of fresh natural gas delivered to the conventional turbine.

The results from the simulations are shown in FIG. 26. The results in FIG. 26 appeared to show that, at conventional fuel utilizations, such as a fuel utilization of ~75%, use of a second hydrogen turbine may not be as beneficial. At a fuel utilization of ~75%, the results appeared to show that using the second hydrogen turbine can reduce the overall efficiency of generation of electrical power while also reducing the net power produced.

For a fuel utilization of about 50%, the simulation results in FIG. 26 appeared to show the benefits of operating with a second hydrogen turbine. The overall efficiency of the system with the second hydrogen turbine still appeared to be lower, as the overall efficiency was about 50% versus the ~55% that was simulated for the comparative example. However, the simulations appeared to show that operating at about 50% fuel utilization resulted in a larger amount of power produced (about 624 MW) than any of the comparative examples, while also appearing to have lower emissions of $CO_2$ per MWhr (about 144 lbs/MWhr) relative to any of the comparative examples. The simulations at a fuel utilization of about 30% appeared to show even greater benefits of producing large hydrogen volumes by operating at lower fuel utilization. The simulations appeared to show significantly increased power production (about 790 MW) while also significantly reducing the amount of $CO_2$ emissions (about 113 lbs/MWhr). The combination of increased power and reduced $CO_2$ emissions appeared to be achieved in the simulations in part due to the increased amount of $CO_2$ captured (about 1.92 Mtons/yr at about 50% fuel utilization, about 2.56 Mtons/year at about 30% fuel utilization). As a result, the simulations appeared to show that use of a hydrogen turbine, in combination with a fuel utilization of about 60% or less, such as about 50% or less, can provide unexpectedly low $CO_2$ emissions per unit of energy generated while providing increased electrical energy production.

Additional Fuel Cell Operation Strategies

As an addition, complement, and/or alternative to the fuel cell operating strategies described herein, a molten carbonate fuel cell can be operated so that the amount of reforming can be selected relative to the amount of oxidation in order to achieve a desired thermal ratio for the fuel cell. As used herein, the "thermal ratio" is defined as the heat produced by exothermic reactions in a fuel cell assembly divided by the endothermic heat demand of reforming reactions occurring within the fuel cell assembly. Expressed mathematically, the thermal ratio (TH)=$Q_{EX}/Q_{EN}$, where $Q_{EX}$ is the sum of heat produced by exothermic reactions and $Q_{EN}$ is the sum of heat consumed by the endothermic reactions occurring within the fuel cell. Note that the heat produced by the exothermic reactions corresponds to any heat due to reforming reactions, water gas shift reactions, and the electrochemical reactions in the cell. The heat generated by the electrochemical reactions can be calculated based on the ideal electrochemical potential of the fuel cell reaction across the electrolyte minus the actual output voltage of the fuel cell. For example, the ideal electrochemical potential of the reaction in a MCFC is believed to be about 1.04V based on the net reaction that occurs in the cell. During operation of the MCFC, the cell will typically have an output voltage less than 1.04 V due to various losses. For example, a common output/operating voltage can be about 0.7 V. The heat generated is equal to the electrochemical potential of the cell (i.e. ~1.04V) minus the operating voltage. For example, the heat produced by the electrochemical reactions in the cell is ~0.34 V when the output voltage of ~0.7V. Thus, in this scenario, the electrochemical reactions would produce ~0.7 V of electricity and ~0.34 V of heat energy. In such an example, the ~0.7 V of electrical energy is not included as part of $Q_{EX}$. In other words, heat energy is not electrical energy.

In various aspects, a thermal ratio can be determined for any convenient fuel cell structure, such as a fuel cell stack, an individual fuel cell within a fuel cell stack, a fuel cell stack with an integrated reforming stage, a fuel cell stack with an integrated endothermic reaction stage, or a combination thereof. The thermal ratio may also be calculated for different units within a fuel cell stack, such as an assembly of fuel cells or fuel cell stacks. For example, the thermal ratio may be calculated for a single anode within a single fuel cell, an anode section within a fuel cell stack, or an anode section within a fuel cell stack along with integrated reforming stages and/or integrated endothermic reaction stage elements in sufficiently close proximity to the anode section to be integrated from a heat integration standpoint. As used herein, "an anode section" comprises anodes within a fuel cell stack that share a common inlet or outlet manifold.

In various aspects of the invention, the operation of the fuel cells can be characterized based on a thermal ratio. Where fuel cells are operated to have a desired thermal ratio, a molten carbonate fuel cell can be operated to have a thermal ratio of about 1.5 or less, for example about 1.3 or less, or about 1.15 or less, or about 1.0 or less, or about 0.95 or less, or about 0.90 or less, or about 0.85 or less, or about 0.80 or less, or about 0.75 or less. Additionally or alternately, the thermal ratio can be at least about 0.25, or at least about 0.35, or at least about 0.45, or at least about 0.50. Additionally or alternately, in some aspects the fuel cell can be operated to have a temperature rise between anode input and anode output of about 40° C. or less, such as about 20° C. or less, or about 10° C. or less. Further additionally or alternately, the fuel cell can be operated to have an anode outlet temperature that is from about 10° C. lower to about 10° C. higher than the temperature of the anode inlet. Still further additionally or alternately, the fuel cell can be operated to have an anode inlet temperature that is greater than the anode outlet temperature, such as at least about 5° C. greater, or at least about 10° C. greater, or at least about 20° C. greater, or at least about 25° C. greater. Yet still further additionally or alternately, the fuel cell can be operated to have an anode inlet temperature that is greater than the anode outlet temperature by about 100° C. or less, such as by about 80° C. or less, or about 60° C. or less, or about 50° C. or less, or about 40° C. or less, or about 30° C. or less, or about 20° C. or less.

As an addition, complement, and/or alternative to the fuel cell operating strategies described herein, a molten carbonate fuel cell (such as a fuel cell assembly) can be operated with increased production of syngas (or hydrogen) while also reducing or minimizing the amount of $CO_2$ exiting the fuel cell in the cathode exhaust stream. Syngas can be a valuable input for a variety of processes. In addition to having fuel value, syngas can be used as a raw material for forming other higher value products, such as by using syngas as an input for Fischer-Tropsch synthesis and/or methanol synthesis processes. One option for making syngas can be to reform a hydrocarbon or hydrocarbon-like fuel, such as methane or natural gas. For many types of industrial processes, a syngas having a ratio of $H_2$ to CO of close to 2:1 (or even lower) can often be desirable. A water gas shift reaction can be used to reduce the $H_2$ to CO ratio in a syngas if additional $CO_2$ is available, such as is produced in the anodes.

One way of characterizing the overall benefit provided by integrating syngas generation with use of molten carbonate fuel cells can be based on a ratio of the net amount of syngas that exits the fuel cells in the anode exhaust relative to the amount of $CO_2$ that exits the fuel cells in the cathode exhaust. This characterization measures the effectiveness of producing power with low emissions and high efficiency (both electrical and chemical). In this description, the net amount of syngas in an anode exhaust is defined as the combined number of moles of $H_2$ and number of moles of CO present in the anode exhaust, offset by the amount of $H_2$ and CO present in the anode inlet. Because the ratio is based on the net amount of syngas in the anode exhaust, simply passing excess $H_2$ into the anode does not change the value of the ratio. However, $H_2$ and/or CO generated due to reforming in the anode and/or in an internal reforming stage associated with the anode can lead to higher values of the ratio. Hydrogen oxidized in the anode can lower the ratio. It is noted that the water gas shift reaction can exchange $H_2$ for CO, so the combined moles of $H_2$ and CO represents the total potential syngas in the anode exhaust, regardless of the eventual desired ratio of $H_2$ to CO in a syngas. The syngas content of the anode exhaust ($H_2$+CO) can then be compared with the $CO_2$ content of the cathode exhaust. This can provide a type of efficiency value that can also account for the amount of carbon capture. This can equivalently be expressed as an equation as $$\text{Ratio of net syngas in anode exhaust to cathode } CO_2=\text{net moles of } (H_2+CO)_{ANODE}/\text{moles of } (CO_2)_{CATHODE}$$

In various aspects, the ratio of net moles of syngas in the anode exhaust to the moles of $CO_2$ in the cathode exhaust can be at least about 2.0, such as at least about 3.0, or at least about 4.0, or at least about 5.0. In some aspects, the ratio of net syngas in the anode exhaust to the amount of $CO_2$ in the cathode exhaust can be still higher, such as at least about 10.0, or at least about 15.0, or at least about 20.0. Ratio values of about 40.0 or less, such as about 30.0 or less, or about 20.0 or less, can additionally or alternately be achieved. In aspects where the amount of $CO_2$ at the cathode inlet is about 6.0 volume % or less, such as about 5.0 volume % or less, ratio values of at least about 1.5 may be sufficient/realistic. Such molar ratio values of net syngas in the anode exhaust to the amount of $CO_2$ in the cathode exhaust can be greater than the values for conventionally operated fuel cells.

As an addition, complement, and/or alternative to the fuel cell operating strategies described herein, a molten carbonate fuel cell (such as a fuel cell assembly) can be operated at a reduced fuel utilization value, such as a fuel utilization of about 50% or less, while also having a high $CO_2$ utilization value, such as at least about 60%.

In this type of configuration, the molten carbonate fuel cell can be effective for carbon capture, as the $CO_2$ utilization can advantageously be sufficiently high. Rather than attempting to maximize electrical efficiency, in this type of configuration the total efficiency of the fuel cell can be improved or increased based on the combined electrical and chemical efficiency. The chemical efficiency can be based on withdrawal of a hydrogen and/or syngas stream from the anode exhaust as an output for use in other processes. Even though the electrical efficiency may be reduced relative to some conventional configurations, making use of the chemical energy output in the anode exhaust can allow for a desirable total efficiency for the fuel cell.

In various aspects, the fuel utilization in the fuel cell anode can be about 50% or less, such as about 40% or less, or about 30% or less, or about 25% or less, or about 20% or less. In various aspects, in order to generate at least some electric power, the fuel utilization in the fuel cell can be at least about 5%, such as at least about 10%, or at least about 15%, or at least about 20%, or at least about 25%, or at least about 30%. Additionally or alternatively, the $CO_2$ utilization can be at least about 60%, such as at least about 65%, or at least about 70%, or at least about 75%.

As an addition, complement, and/or alternative to the fuel cell operating strategies described herein, a molten carbonate fuel cell can be operated at conditions that increase or maximize syngas production, possibly at the detriment of electricity production and electrical efficiency. Instead of selecting the operating conditions of a fuel cell to improve or maximize the electrical efficiency of the fuel cell, operating conditions, possibly including an amount of reformable fuel passed into the anode, can be established to increase the chemical energy output of the fuel cell. These operating conditions can result in a lower electrical efficiency of the fuel cell. Despite the reduced electrical efficiency, optionally, but preferably, the operating conditions can lead to an increase in the total efficiency of the fuel cell, which is based on the combined electrical efficiency and chemical efficiency of the fuel cell. By increasing the ratio of reformable fuel introduced into the anode to the fuel that is actually electrochemically oxidized at the anode, the chemical energy content in the anode output can be increased.

In some aspects, the reformable hydrogen content of reformable fuel in the input stream delivered to the anode and/or to a reforming stage associated with the anode can be at least about 50% greater than the net amount of hydrogen reacted at the anode, such as at least about 75% greater or at least about 100% greater. Additionally or alternately, the reformable hydrogen content of fuel in the input stream delivered to the anode and/or to a reforming stage associated with the anode can be at least about 50% greater than the net amount of hydrogen reacted at the anode, such as at least about 75% greater or at least about 100% greater. In various aspects, a ratio of the reformable hydrogen content of the reformable fuel in the fuel stream relative to an amount of hydrogen reacted in the anode can be at least about 1.5:1, or at least about 2.0:1, or at least about 2.5:1, or at least about 3.0:1. Additionally or alternately, the ratio of reformable hydrogen content of the reformable fuel in the fuel stream relative to the amount of hydrogen reacted in the anode can be about 20:1 or less, such as about 15:1 or less or about 10:1 or less. In one aspect, it is contemplated that less than 100% of the reformable hydrogen content in the anode inlet stream can be converted to hydrogen. For example, at least about 80% of the reformable hydrogen content in an anode inlet stream can be converted to hydrogen in the anode and/or in an associated reforming stage(s), such as at least about 85%, or at least about 90%. Additionally or alternately, the amount of reformable fuel delivered to the anode can be characterized based on the Lower Heating Value (LHV) of the reformable fuel relative to the LHV of the hydrogen oxidized in the anode. This can be referred to as a reformable fuel surplus ratio. In various aspects, the reformable fuel surplus ratio can be at least about 2.0, such as at least about 2.5, or at least about 3.0, or at least about 4.0. Additionally or alternately, the reformable fuel surplus ratio can be about 25.0 or less, such as about 20.0 or less, or about 15.0 or less, or about 10.0 or less.

As an addition, complement, and/or alternative to the fuel cell operating strategies described herein, a molten carbonate fuel cell (such as a fuel cell assembly) can also be operated at conditions that can improve or optimize the combined electrical efficiency and chemical efficiency of the fuel cell. Instead of selecting conventional conditions for maximizing the electrical efficiency of a fuel cell, the operating conditions can allow for output of excess synthesis gas and/or hydrogen in the anode exhaust of the fuel cell. The synthesis gas and/or hydrogen can then be used in a variety of applications, including chemical synthesis processes and collection of hydrogen for use as a "clean" fuel. In aspects of the invention, electrical efficiency can be reduced to achieve a high overall efficiency, which includes a chemical efficiency based on the chemical energy value of syngas and/or hydrogen produced relative to the energy value of the fuel input for the fuel cell.

In some aspects, the operation of the fuel cells can be characterized based on electrical efficiency. Where fuel cells are operated to have a low electrical efficiency (EE), a molten carbonate fuel cell can be operated to have an electrical efficiency of about 40% or less, for example, about 35% EE or less, about 30% EE or less, about 25% EE or less, or about 20% EE or less, about 15% EE or less, or about 10% EE or less. Additionally or alternately, the EE can be at least about 5%, or at least about 10%, or at least about 15%, or at least about 20%. Further additionally or alternately, the operation of the fuel cells can be characterized based on total fuel cell efficiency (TFCE), such as a combined electrical efficiency and chemical efficiency of the fuel cell(s). Where fuel cells are operated to have a high total fuel cell efficiency, a molten carbonate fuel cell can be operated to have a TFCE (and/or combined electrical efficiency and chemical efficiency) of about 55% or more, for example, about 60% or more, or about 65% or more, or about 70% or more, or about 75% or more, or about 80% or more, or about 85% or more. It is noted that for a total fuel cell efficiency and/or combined electrical efficiency and chemical efficiency, any additional electricity generated from use of excess heat generated by the fuel cell can be excluded from the efficiency calculation.

In various aspects of the invention, the operation of the fuel cells can be characterized based on a desired electrical efficiency of about 40% or less and a desired total fuel cell efficiency of about 55% or more. Where fuel cells are operated to have a desired electrical efficiency and a desired total fuel cell efficiency, a molten carbonate fuel cell can be operated to have an electrical efficiency of about 40% or less with a TFCE of about 55% or more, for example, about 35% EE or less with about a TFCE of 60% or more, about 30% EE or less with about a TFCE of about 65% or more, about 25% EE or less with about a 70% TFCE or more, or about 20% EE or less with about a TFCE of 75% or more, about 15% EE or less with about a TFCE of 80% or more, or about 10% EE or less with about a TFCE of about 85% or more.

As an addition, complement, and/or alternative to the fuel cell operating strategies described herein, a molten carbonate fuel cell (such as a fuel cell assembly) can be operated at conditions that can provide increased power density. The power density of a fuel cell corresponds to the actual operating voltage $V_A$ multiplied by the current density I. For a molten carbonate fuel cell operating at a voltage $V_A$, the fuel cell also can tend to generate waste heat, the waste heat defined as $(V_0-V_A)$*I based on the differential between $V_A$ and the ideal voltage $V_0$ for a fuel cell providing current density I. A portion of this waste heat can be consumed by reforming of a reformable fuel within the anode of the fuel cell. The remaining portion of this waste heat can be absorbed by the surrounding fuel cell structures and gas flows, resulting in a temperature differential across the fuel cell. Under conventional operating conditions, the power density of a fuel cell can be limited based on the amount of waste heat that the fuel cell can tolerate without compromising the integrity of the fuel cell.

In various aspects, the amount of waste heat that a fuel cell can tolerate can be increased by performing an effective amount of an endothermic reaction within the fuel cell. One example of an endothermic reaction includes steam reforming of a reformable fuel within a fuel cell anode and/or in an associated reforming stage, such as an integrated reforming stage in a fuel cell stack. By providing additional reformable fuel to the anode of the fuel cell (or to an integrated/associated reforming stage), additional reforming can be performed so that additional waste heat can be consumed. This can reduce the amount of temperature differential across the fuel cell, thus allowing the fuel cell to operate under an operating condition with an increased amount of waste heat. The loss of electrical efficiency can be offset by the creation of an additional product stream, such as syngas and/or $H_2$, that can be used for various purposes including additional electricity generation further expanding the power range of the system.

In various aspects, the amount of waste heat generated by a fuel cell, $(V_0-V_A)$*I as defined above, can be at least about 30 mW/cm$^2$, such as at least about 40 mW/cm$^2$, or at least about 50 mW/cm$^2$, or at least about 60 mW/cm$^2$, or at least about 70 mW/cm$^2$, or at least about 80 mW/cm$^2$, or at least about 100 mW/cm$^2$, or at least about 120 mW/cm$^2$, or at least about 140 mW/cm$^2$, or at least about 160 mW/cm$^2$, or at least about 180 mW/cm$^2$. Additionally or alternately, the amount of waste heat generated by a fuel cell can be less than about 250 mW/cm$^2$, such as less than about 200 mW/cm$^2$, or less than about 180 mW/cm$^2$, or less than about 165 mW/cm$^2$, or less than about 150 mW/cm$^2$.

Although the amount of waste heat being generated can be relatively high, such waste heat may not necessarily represent operating a fuel cell with poor efficiency. Instead, the waste heat can be generated due to operating a fuel cell at an increased power density. Part of improving the power density of a fuel cell can include operating the fuel cell at a sufficiently high current density. In various aspects, the current density generated by the fuel cell can be at least about 150 mA/cm$^2$, such as at least about 160 mA/cm$^2$, or at least about 170 mA/cm$^2$, or at least about 180 mA/cm$^2$, or at least about 190 mA/cm$^2$, or at least about 200 mA/cm$^2$, or at least about 225 mA/cm$^2$, or at least about 250 mA/cm$^2$. Additionally or alternately, the current density generated by the fuel cell can be about 500 mA/cm$^2$ or less, such as 450 mA/cm$^2$, or less, or 400 mA/cm$^2$, or less or 350 mA/cm$^2$, or less or 300 mA/cm$^2$ or less.

In various aspects, to allow a fuel cell to be operated with increased power generation and increased generation of waste heat, an effective amount of an endothermic reaction (such as a reforming reaction) can be performed. Alternatively, other endothermic reactions unrelated to anode operations can be used to utilize the waste heat by interspersing "plates" or stages into the fuel cell array that are in thermal communication but not fluid communication. The effective amount of the endothermic reaction can be performed in an associated reforming stage, an integrated reforming stage, an integrated stack element for performing an endothermic reaction, or a combination thereof. The effective amount of the endothermic reaction can correspond to an amount sufficient to reduce the temperature rise from the fuel cell inlet to the fuel cell outlet to about 100° C. or less, such as about 90° C. or less, or about 80° C. or less, or about 70° C. or less, or about 60° C. or less, or about 50° C. or less, or about 40° C. or less, or about 30° C. or less. Additionally or alternately, the effective amount of the endothermic reaction can correspond to an amount sufficient to cause a temperature decrease from the fuel cell inlet to the fuel cell outlet of about 100° C. or less, such as about 90° C. or less, or about 80° C. or less, or about 70° C. or less, or about 60° C. or less, or about 50° C. or less, or about 40° C. or less, or about 30° C. or less, or about 20° C. or less, or about 10° C. or less. A temperature decrease from the fuel cell inlet to the fuel cell outlet can occur when the effective amount of the endothermic reaction exceeds the waste heat generated. Additionally or alternately, this can correspond to having the endothermic reaction(s) (such as a combination of reforming and another endothermic reaction) consume at least about 40% of the waste heat generated by the fuel cell, such as consuming at least about 50% of the waste heat, or at least about 60% of the waste heat, or at least about 75% of the waste heat. Further additionally or alternately, the endothermic reaction(s) can consume about 95% of the waste heat or less, such as about 90% of the waste heat or less, or about 85% of the waste heat or less.

As an addition, complement, and/or alternative to the fuel cell operating strategies described herein, a molten carbonate fuel cell (such as a fuel cell assembly) can be operated at conditions corresponding to a decreased operating voltage and a low fuel utilization. In various aspects, the fuel cell can be operated at a voltage $V_A$ of less than about 0.7 Volts, for example less than about 0.68 V, less than about 0.67 V, less than about 0.66 V, or about 0.65 V or less. Additionally or alternatively, the fuel cell can be operated at a voltage $V_A$ of at least about 0.60, for example at least about 0.61, at least about 0.62, or at least about 0.63. In so doing, energy that would otherwise leave the fuel cell as electrical energy at high voltage can remain within the cell as heat as the voltage is lowered. This additional heat can allow for increased endothermic reactions to occur, for example increasing the $CH_4$ conversion to syngas.

Definitions

Syngas: In this description, syngas is defined as mixture of $H_2$ and CO in any ratio. Optionally, $H_2O$ and/or $CO_2$ may be present in the syngas. Optionally, inert compounds (such as nitrogen) and residual reformable fuel compounds may be present in the syngas. If components other than $H_2$ and CO are present in the syngas, the combined volume percentage of $H_2$ and CO in the syngas can be at least 25 vol % relative to the total volume of the syngas, such as at least 40 vol %, or at least 50 vol %, or at least 60 vol %. Additionally or alternately, the combined volume percentage of $H_2$ and CO in the syngas can be 100 vol % or less, such as 95 vol % or less or 90 vol % or less.

Reformable fuel: A reformable fuel is defined as a fuel that contains carbon-hydrogen bonds that can be reformed to generate $H_2$. Hydrocarbons are examples of reformable fuels, as are other hydrocarbonaceous compounds such as alcohols. Although CO and $H_2O$ can participate in a water gas shift reaction to form hydrogen, CO is not considered a reformable fuel under this definition.

Reformable hydrogen content: The reformable hydrogen content of a fuel is defined as the number of $H_2$ molecules that can be derived from a fuel by reforming the fuel and then driving the water gas shift reaction to completion to maximize $H_2$ production. It is noted that $H_2$ by definition has a reformable hydrogen content of 1, although $H_2$ itself is not defined as a reformable fuel herein. Similarly, CO has a reformable hydrogen content of 1. Although CO is not strictly reformable, driving the water gas shift reaction to completion will result in exchange of a CO for an $H_2$. As examples of reformable hydrogen content for reformable fuels, the reformable hydrogen content of methane is $4H_2$ molecules while the reformable hydrogen content of ethane is $7H_2$ molecules. More generally, if a fuel has the composition CxHyOz, then the reformable hydrogen content of the fuel at 100% reforming and water-gas shift is $n(H_2\ \text{max reforming})=2x+y/2-z$. Based on this definition, fuel utilization within a cell can then be expressed as $n(H_2\ \text{ox})/n(H_2\ \text{max reforming})$. Of course, the reformable hydrogen content of a mixture of components can be determined based on the reformable hydrogen content of the individual components. The reformable hydrogen content of compounds that contain other heteroatoms, such as oxygen, sulfur or nitrogen, can also be calculated in a similar manner.

Oxidation Reaction: In this discussion, the oxidation reaction within the anode of a fuel cell is defined as the reaction corresponding to oxidation of $H_2$ by reaction with $CO_3^{2-}$ to form $H_2O$ and $CO_2$. It is noted that the reforming reaction within the anode, where a compound containing a carbon-hydrogen bond is converted into $H_2$ and CO or $CO_2$, is excluded from this definition of the oxidation reaction in the anode. The water-gas shift reaction is similarly outside of this definition of the oxidation reaction. It is further noted that references to a combustion reaction are defined as references to reactions where $H_2$ or a compound containing carbon-hydrogen bond(s) are reacted with $O_2$ to form $H_2O$ and carbon oxides in a non-electrochemical burner, such as the combustion zone of a combustion-powered generator.

Aspects of the invention can adjust anode fuel parameters to achieve a desired operating range for the fuel cell. Anode fuel parameters can be characterized directly, and/or in relation to other fuel cell processes in the form of one or more ratios. For example, the anode fuel parameters can be controlled to achieve one or more ratios including a fuel utilization, a fuel cell heating value utilization, a fuel surplus ratio, a reformable fuel surplus ratio, a reformable hydrogen content fuel ratio, and combinations thereof.

Fuel utilization: Fuel utilization is an option for characterizing operation of the anode based on the amount of oxidized fuel relative to the reformable hydrogen content of an input stream can be used to define a fuel utilization for a fuel cell. In this discussion, "fuel utilization" is defined as the ratio of the amount of hydrogen oxidized in the anode for production of electricity (as described above) versus the reformable hydrogen content of the anode input (including any associated reforming stages).

Reformable hydrogen content has been defined above as the number of $H_2$ molecules that can be derived from a fuel by reforming the fuel and then driving the water gas shift reaction to completion to maximize $H_2$ production. For example, each methane introduced into an anode and exposed to steam reforming conditions results in generation of the equivalent of $4H_2$ molecules at max production. (Depending on the reforming and/or anode conditions, the reforming product can correspond to a non-water gas shifted product, where one or more of the $H_2$ molecules is present instead in the form of a CO molecule.) Thus, methane is defined as having a reformable hydrogen content of $4H_2$ molecules. As another example, under this definition ethane has a reformable hydrogen content of $7H_2$ molecules.

The utilization of fuel in the anode can also be characterized by defining a heating value utilization based on a ratio of the Lower Heating Value of hydrogen oxidized in the anode due to the fuel cell anode reaction relative to the Lower Heating Value of all fuel delivered to the anode and/or a reforming stage associated with the anode. The "fuel cell heating value utilization" as used herein can be computed using the flow rates and Lower Heating Value (LHV) of the fuel components entering and leaving the fuel cell anode. As such, fuel cell heating value utilization can be computed as (LHV(anode_in)−LHV(anode_out))/LHV (anode_in), where LHV(anode_in) and LHV(anode_out) refer to the LHV of the fuel components (such as $H_2$, $CH_4$, and/or CO) in the anode inlet and outlet streams or flows, respectively. In this definition, the LHV of a stream or flow may be computed as a sum of values for each fuel component in the input and/or output stream. The contribution of each fuel component to the sum can correspond to the fuel component's flow rate (e.g., mol/hr) multiplied by the fuel component's LHV (e.g., joules/mol).

Lower Heating Value: The lower heating value is defined as the enthalpy of combustion of a fuel component to vapor phase, fully oxidized products (i.e., vapor phase $CO_2$ and $H_2O$ product). For example, any $CO_2$ present in an anode input stream does not contribute to the fuel content of the anode input, since $CO_2$ is already fully oxidized. For this definition, the amount of oxidation occurring in the anode due to the anode fuel cell reaction is defined as oxidation of $H_2$ in the anode as part of the electrochemical reaction in the anode, as defined above.

It is noted that, for the special case where the only fuel in the anode input flow is $H_2$, the only reaction involving a fuel component that can take place in the anode represents the conversion of $H_2$ into $H_2O$. In this special case, the fuel utilization simplifies to ($H_2$-rate-in minus $H_2$-rate-out)/$H_2$-rate-in. In such a case, $H_2$ would be the only fuel component, and so the $H_2$ LHV would cancel out of the equation. In the more general case, the anode feed may contain, for example, $CH_4$, $H_2$, and CO in various amounts. Because these species can typically be present in different amounts in the anode outlet, the summation as described above can be needed to determine the fuel utilization.

Alternatively or in addition to fuel utilization, the utilization for other reactants in the fuel cell can be characterized. For example, the operation of a fuel cell can additionally or alternately be characterized with regard to "$CO_2$ utilization" and/or "oxidant" utilization. The values for $CO_2$ utilization and/or oxidant utilization can be specified in a similar manner.

Fuel surplus ratio: Still another way to characterize the reactions in a molten carbonate fuel cell is by defining a utilization based on a ratio of the Lower Heating Value of all fuel delivered to the anode and/or a reforming stage associated with the anode relative to the Lower Heating Value of hydrogen oxidized in the anode due to the fuel cell anode reaction. This quantity will be referred to as a fuel surplus ratio. As such the fuel surplus ratio can be computed as (LHV (anode_in)/(LHV(anode_in)−LHV(anode_out)) where LHV(anode_in) and LHV(anode_out) refer to the LHV of the fuel components (such as $H_2$, $CH_4$, and/or CO) in the anode inlet and outlet streams or flows, respectively. In various aspects of the invention, a molten carbonate fuel cell can be operated to have a fuel surplus ratio of at least about 1.0, such as at least about 1.5, or at least about 2.0, or at least about 2.5, or at least about 3.0, or at least about 4.0. Additionally or alternately, the fuel surplus ratio can be about 25.0 or less.

It is noted that not all of the reformable fuel in the input stream for the anode may be reformed. Preferably, at least about 90% of the reformable fuel in the input stream to the anode (and/or into an associated reforming stage) can be reformed prior to exiting the anode, such as at least about 95% or at least about 98%. In some alternative aspects, the amount of reformable fuel that is reformed can be from about 75% to about 90%, such as at least about 80%.

The above definition for fuel surplus ratio provides a method for characterizing the amount of reforming occurring within the anode and/or reforming stage(s) associated with a fuel cell relative to the amount of fuel consumed in the fuel cell anode for generation of electric power.

Optionally, the fuel surplus ratio can be modified to account for situations where fuel is recycled from the anode output to the anode input. When fuel (such as $H_2$, CO, and/or unreformed or partially reformed hydrocarbons) is recycled from anode output to anode input, such recycled fuel components do not represent a surplus amount of reformable or reformed fuel that can be used for other purposes. Instead, such recycled fuel components merely indicate a desire to reduce fuel utilization in a fuel cell.

Reformable fuel surplus ratio: Calculating a reformable fuel surplus ratio is one option to account for such recycled fuel components is to narrow the definition of surplus fuel, so that only the LHV of reformable fuels is included in the input stream to the anode. As used herein the "reformable fuel surplus ratio" is defined as the Lower Heating Value of reformable fuel delivered to the anode and/or a reforming stage associated with the anode relative to the Lower Heating Value of hydrogen oxidized in the anode due to the fuel cell anode reaction. Under the definition for reformable fuel surplus ratio, the LHV of any $H_2$ or CO in the anode input is excluded. Such an LHV of reformable fuel can still be measured by characterizing the actual composition entering a fuel cell anode, so no distinction between recycled components and fresh components needs to be made. Although some non-reformed or partially reformed fuel may also be recycled, in most aspects the majority of the fuel recycled to the anode can correspond to reformed products such as $H_2$ or CO. Expressed mathematically, the reformable fuel surplus ratio ($R_{RFS}$)=$LHV_{RF}$/$LHV_{OH}$, where $LHV_{RF}$ is the Lower Heating Value (LHV) of the reformable fuel and $LHV_{OH}$ is the Lower Heating Value (LHV) of the hydrogen oxidized in the anode. The LHV of the hydrogen oxidized in the anode may be calculated by subtracting the LHV of the anode outlet stream from the LHV of the anode inlet stream (e.g., LHV(anode_in)−LHV(anode_out)). In various aspects of the invention, a molten carbonate fuel cell can be operated to have a reformable fuel surplus ratio of at least about 0.25, such as at least about 0.5, or at least about 1.0, or at least about 1.5, or at least about 2.0, or at least about 2.5, or at least about 3.0, or at least about 4.0. Additionally or alternately, the reformable fuel surplus ratio can be about 25.0 or less. It is noted that this narrower definition based on the amount of reformable fuel delivered to the anode relative to the amount of oxidation in the anode can distinguish between two types of fuel cell operation methods that have low fuel utilization. Some fuel cells achieve low fuel utilization by recycling a substantial portion of the anode output back to the anode input. This recycle can allow any hydrogen in the anode input to be used again as an input to the anode. This can reduce the amount of reforming, as even though the fuel utilization is low for a single pass through the fuel cell, at least a portion of the unused fuel is recycled for use in a later pass. Thus, fuel cells with a wide variety of fuel utilization values may have the same ratio of reformable fuel delivered to the anode reforming stage(s) versus hydrogen oxidized in the anode reaction. In order to change the ratio of reformable fuel delivered to the anode reforming stages relative to the amount of oxidation in the anode, either an anode feed with a native content of non-reformable fuel needs to be identified, or unused fuel in the anode output needs to be withdrawn for other uses, or both.

Reformable hydrogen surplus ratio: Still another option for characterizing the operation of a fuel cell is based on a "reformable hydrogen surplus ratio." The reformable fuel surplus ratio defined above is defined based on the lower heating value of reformable fuel components. The reformable hydrogen surplus ratio is defined as the reformable hydrogen content of reformable fuel delivered to the anode and/or a reforming stage associated with the anode relative to the hydrogen reacted in the anode due to the fuel cell anode reaction. As such, the "reformable hydrogen surplus ratio" can be computed as (RFC(reformable_anode_in)/(RFC(reformable_anode_in)−RFC(anode_out)), where RFC(reformable_anode_in) refers to the reformable hydrogen content of reformable fuels in the anode inlet streams or flows, while RFC (anode_out) refers to the reformable hydrogen content of the fuel components (such as $H_2$, $CH_4$, and/or CO) in the anode inlet and outlet streams or flows. The RFC can be expressed in moles/s, moles/hr, or similar. An example of a method for operating a fuel cell with a large ratio of reformable fuel delivered to the anode reforming stage(s) versus amount of oxidation in the anode can be a method where excess reforming is performed in order to balance the generation and consumption of heat in the fuel cell. Reforming a reformable fuel to form $H_2$ and CO is an endothermic process. This endothermic reaction can be countered by the generation of electrical current in the fuel cell, which can also produce excess heat corresponding (roughly) to the difference between the amount of heat generated by the anode oxidation reaction and the carbonate formation reaction and the energy that exits the fuel cell in the form of electric current. The excess heat per mole of hydrogen involved in the anode oxidation reaction/carbonate formation reaction can be greater than the heat absorbed to generate a mole of hydrogen by reforming. As a result, a fuel cell operated under conventional conditions can exhibit a temperature increase from inlet to outlet. Instead of this type of conventional operation, the amount of fuel reformed in the reforming stages associated with the anode can be increased. For example, additional fuel can be reformed so that the heat generated by the exothermic fuel cell reactions can be (roughly) balanced by the heat consumed in reforming, or even the heat consumed by reforming can be beyond the excess heat generated by the fuel oxidation, resulting in a temperature drop across the fuel cell. This can result in a substantial excess of hydrogen relative to the amount needed for electrical power generation. As one example, a feed to the anode inlet of a fuel cell or an associated reforming stage can be substantially composed of reformable fuel, such as a substantially pure methane feed. During conventional operation for electric power generation using such a fuel, a molten carbonate fuel cell can be operated with a fuel utilization of about 75%. This means that about 75% (or ¾) of the fuel content delivered to the anode is used to form hydrogen that is then reacted in the anode with carbonate ions to form $H_2O$ and $CO_2$. In conventional operation, the remaining about 25% of the fuel content can be reformed to $H_2$ within the fuel cell (or can pass through the fuel cell unreacted for any CO or $H_2$ in the fuel), and then combusted outside of the fuel cell to form $H_2O$ and $CO_2$ to provide heat for the cathode inlet to the fuel cell. The reformable hydrogen surplus ratio in this situation can be 4/(4−1)=4/3.

Electrical efficiency: As used herein, the term "electrical efficiency" ("EE") is defined as the electrochemical power produced by the fuel cell divided by the rate of Lower Heating Value ("LHV") of fuel input to the fuel cell. The fuel inputs to the fuel cell includes both fuel delivered to the anode as well as any fuel used to maintain the temperature of the fuel cell, such as fuel delivered to a burner associated with a fuel cell. In this description, the power produced by the fuel may be described in terms of LHV(el) fuel rate.

Electrochemical power: As used herein, the term "electrochemical power" or LHV(el) is the power generated by the circuit connecting the cathode to the anode in the fuel cell and the transfer of carbonate ions across the fuel cell's electrolyte. Electrochemical power excludes power produced or consumed by equipment upstream or downstream from the fuel cell. For example, electricity produced from heat in a fuel cell exhaust stream is not considered part of the electrochemical power. Similarly, power generated by a gas turbine or other equipment upstream of the fuel cell is not part of the electrochemical power generated. The "electrochemical power" does not take electrical power consumed during operation of the fuel cell into account, or any loss incurred by conversion of the direct current to alternating current. In other words, electrical power used to supply the fuel cell operation or otherwise operate the fuel cell is not subtracted from the direct current power produced by the fuel cell. As used herein, the power density is the current density multiplied by voltage. As used herein, the total fuel cell power is the power density multiplied by the fuel cell area.

Fuel inputs: As used herein, the term "anode fuel input," designated as LHV(anode_in), is the amount of fuel within the anode inlet stream. The term "fuel input", designated as LHV(in), is the total amount of fuel delivered to the fuel cell, including both the amount of fuel within the anode inlet stream and the amount of fuel used to maintain the temperature of the fuel cell. The fuel may include both reformable and nonreformable fuels, based on the definition of a reformable fuel provided herein. Fuel input is not the same as fuel utilization.

Total fuel cell efficiency: As used herein, the term "total fuel cell efficiency" ("TFCE") is defined as: the electrochemical power generated by the fuel cell, plus the rate of LHV of syngas produced by the fuel cell, divided by the rate of LHV of fuel input to the anode. In other words, TFCE=(LHV(el)+LHV(sg net))/LHV(anode_in), where LHV(anode_in) refers to rate at which the LHV of the fuel components (such as $H_2$, $CH_4$, and/or CO) delivered to the anode and LHV(sg net) refers to a rate at which syngas ($H_2$, CO) is produced in the anode, which is the difference between syngas input to the anode and syngas output from the anode. LHV(el) describes the electrochemical power generation of the fuel cell. The total fuel cell efficiency excludes heat generated by the fuel cell that is put to beneficial use outside of the fuel cell. In operation, heat generated by the fuel cell may be put to beneficial use by downstream equipment. For example, the heat may be used to generate additional electricity or to heat water. These uses, when they occur apart from the fuel cell, are not part of the total fuel cell efficiency, as the term is used in this application. The total fuel cell efficiency is for the fuel cell operation only, and does not include power production, or consumption, upstream, or downstream, of the fuel cell.

Chemical efficiency: As used herein, the term "chemical efficiency", is defined as the lower heating value of $H_2$ and CO in the anode exhaust of the fuel cell, or LHV(sg out), divided by the fuel input, or LHV(in).

Neither the electrical efficiency nor the total system efficiency takes the efficiency of upstream or downstream processes into consideration. For example, it may be advantageous to use turbine exhaust as a source of $CO_2$ for the fuel cell cathode. In this arrangement, the efficiency of the turbine is not considered as part of the electrical efficiency or the total fuel cell efficiency calculation. Similarly, outputs from the fuel cell may be recycled as inputs to the fuel cell. A recycle loop is not considered when calculating electrical efficiency or the total fuel cell efficiency in single pass mode.

Syngas produced: As used herein, the term "syngas produced" is the difference between syngas input to the anode and syngas output from the anode. Syngas may be used as an input, or fuel, for the anode, at least in part. For example, a system may include an anode recycle loop that returns syngas from the anode exhaust to the anode inlet where it is supplemented with natural gas or other suitable fuel. Syngas produced LHV (sg net)=(LHV(sg out)−LHV(sg in)), where LHV(sg in) and LHV(sg out) refer to the LHV of the syngas in the anode inlet and syngas in the anode outlet streams or flows, respectively. It is noted that at least a portion of the syngas produced by the reforming reactions within an anode can typically be utilized in the anode to produce electricity. The hydrogen utilized to produce electricity is not included in the definition of "syngas produced" because it does not exit the anode. As used herein, the term "syngas ratio" is the LHV of the net syngas produced divided by the LHV of the fuel input to the anode or LHV (sg net)/LHV(anode in). Molar flow rates of syngas and fuel can be used instead of LHV to express a molar-based syngas ratio and a molar-based syngas produced.

Steam to carbon ratio (S/C): As used herein, the steam to carbon ratio (S/C) is the molar ratio of steam in a flow to reformable carbon in the flow. Carbon in the form of CO and $CO_2$ are not included as reformable carbon in this definition. The steam to carbon ratio can be measured and/or controlled at different points in the system. For example, the composition of an anode inlet stream can be manipulated to achieve a S/C that is suitable for reforming in the anode. The S/C can be given as the molar flow rate of $H_2O$ divided by the product of the molar flow rate of fuel multiplied by the number of carbon atoms in the fuel, e.g. one for methane. Thus, $S/C=f_{H2O}/(f_{CH4}\times\#C)$, where $f_{H2O}$ is the molar flow rate of water, where $f_{CH4}$ is the molar flow rate of methane (or other fuel) and #C is the number of carbons in the fuel.

EGR ratio: Aspects of the invention can use a turbine in partnership with a fuel cell. The combined fuel cell and turbine system may include exhaust gas recycle ("EGR"). In an EGR system, at least a portion of the exhaust gas generated by the turbine can be sent to a heat recovery generator. Another portion of the exhaust gas can be sent to the fuel cell. The EGR ratio describes the amount of exhaust gas routed to the fuel cell versus the total exhaust gas routed to either the fuel cell or heat recovery generator. As used herein, the "EGR ratio" is the flow rate for the fuel cell bound portion of the exhaust gas divided by the combined flow rate for the fuel cell bound portion and the recovery bound portion, which is sent to the heat recovery generator.

In various aspects of the invention, a molten carbonate fuel cell (MCFC) can be used to facilitate separation of $CO_2$ from a $CO_2$-containing stream while also generating additional electrical power. The $CO_2$ separation can be further enhanced by taking advantage of synergies with the combustion-based power generator that can provide at least a portion of the input feed to the cathode portion of the fuel cell.

Fuel Cell and Fuel Cell Components: In this discussion, a fuel cell can correspond to a single cell, with an anode and a cathode separated by an electrolyte. The anode and cathode can receive input gas flows to facilitate the respective anode and cathode reactions for transporting charge across the electrolyte and generating electricity. A fuel cell stack can represent a plurality of cells in an integrated unit. Although a fuel cell stack can include multiple fuel cells, the fuel cells can typically be connected in parallel and can function (approximately) as if they collectively represented a single fuel cell of a larger size. When an input flow is delivered to the anode or cathode of a fuel cell stack, the fuel stack can include flow channels for dividing the input flow between each of the cells in the stack and flow channels for combining the output flows from the individual cells. In this discussion, a fuel cell array can be used to refer to a plurality of fuel cells (such as a plurality of fuel cell stacks) that are arranged in series, in parallel, or in any other convenient manner (e.g., in a combination of series and parallel). A fuel cell array can include one or more stages of fuel cells and/or fuel cell stacks, where the anode/cathode output from a first stage may serve as the anode/cathode input for a second stage. It is noted that the anodes in a fuel cell array do not have to be connected in the same way as the cathodes in the array. For convenience, the input to the first anode stage of a fuel cell array may be referred to as the anode input for the array, and the input to the first cathode stage of the fuel cell array may be referred to as the cathode input to the array. Similarly, the output from the final anode/cathode stage may be referred to as the anode/cathode output from the array.

It should be understood that reference to use of a fuel cell herein typically denotes a "fuel cell stack" composed of individual fuel cells, and more generally refers to use of one or more fuel cell stacks in fluid communication. Individual fuel cell elements (plates) can typically be "stacked" together in a rectangular array called a "fuel cell stack". This fuel cell stack can typically take a feed stream and distribute reactants among all of the individual fuel cell elements and can then collect the products from each of these elements. When viewed as a unit, the fuel cell stack in operation can be taken as a whole even though composed of many (often tens or hundreds) of individual fuel cell elements. These individual fuel cell elements can typically have similar voltages (as the reactant and product concentrations are similar), and the total power output can result from the summation of all of the electrical currents in all of the cell elements, when the elements are electrically connected in series. Stacks can also be arranged in a series arrangement to produce high voltages. A parallel arrangement can boost the current. If a sufficiently large volume fuel cell stack is available to process a given exhaust flow, the systems and methods described herein can be used with a single molten carbonate fuel cell stack. In other aspects of the invention, a plurality of fuel cell stacks may be desirable or needed for a variety of reasons.

For the purposes of this invention, unless otherwise specified, the term "fuel cell" should be understood to also refer to and/or is defined as including a reference to a fuel cell stack composed of set of one or more individual fuel cell elements for which there is a single input and output, as that is the manner in which fuel cells are typically employed in practice. Similarly, the term fuel cells (plural), unless otherwise specified, should be understood to also refer to and/or is defined as including a plurality of separate fuel cell stacks.

In other words, all references within this document, unless specifically noted, can refer interchangeably to the operation of a fuel cell stack as a "fuel cell". For example, the volume of exhaust generated by a commercial scale a) combustion generator may be too large for processing by a fuel cell (i.e., a single stack) of conventional size. In order to process the full exhaust, a plurality of fuel cells (i.e., two or more separate fuel cells or fuel cell stacks) can be arranged in parallel, so that each fuel cell can process (roughly) an equal portion of the combustion exhaust. Although multiple fuel cells can be used, each fuel cell can typically be operated in a generally similar manner, given its (roughly) equal portion of the combustion exhaust.

"Internal reforming" and "external reforming": A fuel cell or fuel cell stack may include one or more internal reforming sections. As used herein, the term "internal reforming" refers to fuel reforming occurring within the body of a fuel cell, a fuel cell stack, or otherwise within a fuel cell assembly. External reforming, which is often used in conjunction with a fuel cell, occurs in a separate piece of equipment that is located outside of the fuel cell stack. In other words, the body of the external reformer is not in direct physical contact with the body of a fuel cell or fuel cell stack. In a typical set up, the output from the external reformer can be fed to the anode inlet of a fuel cell. Unless otherwise noted specifically, the reforming described within this application is internal reforming.

Internal reforming may occur within a fuel cell anode. Internal reforming can additionally or alternately occur within an internal reforming element integrated within a fuel cell assembly. The integrated reforming element may be located between fuel cell elements within a fuel cell stack. In other words, one of the trays in the stack can be a reforming section instead of a fuel cell element. In one aspect, the flow arrangement within a fuel cell stack directs fuel to the internal reforming elements and then into the anode portion of the fuel cells. Thus, from a flow perspective, the internal reforming elements and fuel cell elements can be arranged in series within the fuel cell stack. As used herein, the term "anode reforming" is fuel reforming that occurs within an anode. As used herein, the term "internal reforming" is reforming that occurs within an integrated reforming element and not in an anode section.

In some aspects, a reforming stage that is internal to a fuel cell assembly can be considered to be associated with the anode(s) in the fuel cell assembly. In some alternative aspects, for a reforming stage in a fuel cell stack that can be associated with an anode (such as associated with multiple anodes), a flow path can be available so that the output flow from the reforming stage is passed into at least one anode. This can correspond to having an initial section of a fuel cell plate not in contact with the electrolyte and instead can serve just as a reforming catalyst. Another option for an associated reforming stage can be to have a separate integrated reforming stage as one of the elements in a fuel cell stack, where the output from the integrated reforming stage can be returned to the input side of one or more of the fuel cells in the fuel cell stack.

From a heat integration standpoint, a characteristic height in a fuel cell stack can be the height of an individual fuel cell stack element. It is noted that the separate reforming stage and/or a separate endothermic reaction stage could have a different height in the stack than a fuel cell. In such a scenario, the height of a fuel cell element can be used as the characteristic height. In some aspects, an integrated endothermic reaction stage can be defined as a stage that is heat integrated with one or more fuel cells, so that the integrated endothermic reaction stage can use the heat from the fuel cells as a heat source for the endothermic reaction. Such an integrated endothermic reaction stage can be defined as being positioned less than 5 times the height of a stack element from any fuel cells providing heat to the integrated stage. For example, an integrated endothermic reaction stage (such as a reforming stage) can be positioned less than 5 times the height of a stack element from any fuel cells that are heat integrated, such as less than 3 times the height of a stack element. In this discussion, an integrated reforming stage and/or integrated endothermic reaction stage that represent an adjacent stack element to a fuel cell element can be defined as being about one stack element height or less away from the adjacent fuel cell element.

In some aspects, a separate reforming stage that is heat integrated with a fuel cell element can correspond to a reforming stage associated with the fuel cell element. In such aspects, an integrated fuel cell element can provide at least a portion of the heat to the associated reforming stage, and the associated reforming stage can provide at least a portion of the reforming stage output to the integrated fuel cell as a fuel stream.

In other aspects, a separate reforming stage can be integrated with a fuel cell for heat transfer without being associated with the fuel cell. In this type of situation, the separate reforming stage can receive heat from the fuel cell, but the decision can be made not to use the output of the reforming stage as an input to the fuel cell. Instead, the decision can be made to use the output of such a reforming stage for another purpose, such as directly adding the output to the anode exhaust stream, and/or for forming a separate output stream from the fuel cell assembly.

More generally, a separate stack element in a fuel cell stack can be used to perform any convenient type of endothermic reaction that can take advantage of the waste heat provided by integrated fuel cell stack elements. Instead of plates suitable for performing a reforming reaction on a hydrocarbon fuel stream, a separate stack element can have plates suitable for catalyzing another type of endothermic reaction. A manifold or other arrangement of inlet conduits in the fuel cell stack can be used to provide an appropriate input flow to each stack element. A similar manifold or other arrangement of outlet conduits can additionally or alternately be used to withdraw the output flows from each stack element. Optionally, the output flows from a endothermic reaction stage in a stack can be withdrawn from the fuel cell stack without having the output flow pass through a fuel cell anode. In such an optional aspect, the products of the exothermic reaction can therefore exit from the fuel cell stack without passing through a fuel cell anode. Examples of other types of endothermic reactions that can be performed in stack elements in a fuel cell stack can include, without limitation, ethanol dehydration to form ethylene and ethane cracking.

Recycle: As defined herein, recycle of a portion of a fuel cell output (such as an anode exhaust or a stream separated or withdrawn from an anode exhaust) to a fuel cell inlet can correspond to a direct or indirect recycle stream. A direct recycle of a stream to a fuel cell inlet is defined as recycle of the stream without passing through an intermediate process, while an indirect recycle involves recycle after passing a stream through one or more intermediate processes. For example, if the anode exhaust is passed through a $CO_2$ separation stage prior to recycle, this is considered an indirect recycle of the anode exhaust. If a portion of the anode exhaust, such as an $H_2$ stream withdrawn from the anode exhaust, is passed into a gasifier for converting coal into a fuel suitable for introduction into the fuel cell, then that is also considered an indirect recycle.

Anode Inputs and Outputs

In various aspects of the invention, the MCFC array can be fed by a fuel received at the anode inlet that comprises, for example, both hydrogen and a hydrocarbon such as methane (or alternatively a hydrocarbonaceous or hydrocarbon-like compound that may contain heteroatoms different from C and H). Most of the methane (or other hydrocarbonaceous or hydrocarbon-like compound) fed to the anode can typically be fresh methane. In this description, a fresh fuel such as fresh methane refers to a fuel that is not recycled from another fuel cell process. For example, methane recycled from the anode outlet stream back to the anode inlet may not be considered "fresh" methane, and can instead be described as reclaimed methane. The fuel source used can be shared with other components, such as a turbine that uses a portion of the fuel source to provide a $CO_2$-containing stream for the cathode input. The fuel source input can include water in a proportion to the fuel appropriate for reforming the hydrocarbon (or hydrocarbon-like) compound in the reforming section that generates hydrogen. For example, if methane is the fuel input for reforming to generate $H_2$, the molar ratio of water to fuel can be from about one to one to about ten to one, such as at least about two to one. A ratio of four to one or greater is typical for external reforming, but lower values can be typical for internal reforming. To the degree that $H_2$ is a portion of the fuel source, in some optional aspects no additional water may be needed in the fuel, as the oxidation of $H_2$ at the anode can tend to produce $H_2O$ that can be used for reforming the fuel. The fuel source can also optionally contain components incidental to the fuel source (e.g., a natural gas feed can contain some content of $CO_2$ as an additional component). For example, a natural gas feed can contain $CO_2$, $N_2$, and/or other inert (noble) gases as additional components. Optionally, in some aspects the fuel source may also contain CO, such as CO from a recycled portion of the anode exhaust. An additional or alternate potential source for CO in the fuel into a fuel cell assembly can be CO generated by steam reforming of a hydrocarbon fuel performed on the fuel prior to entering the fuel cell assembly.

More generally, a variety of types of fuel streams may be suitable for use as an input stream for the anode of a molten carbonate fuel cell. Some fuel streams can correspond to streams containing hydrocarbons and/or hydrocarbon-like compounds that may also include heteroatoms different from C and H. In this discussion, unless otherwise specified, a reference to a fuel stream containing hydrocarbons for an MCFC anode is defined to include fuel streams containing such hydrocarbon-like compounds. Examples of hydrocarbon (including hydrocarbon-like) fuel streams include natural gas, streams containing C1-C4 carbon compounds (such as methane or ethane), and streams containing heavier C5+ hydrocarbons (including hydrocarbon-like compounds), as well as combinations thereof. Still other additional or alternate examples of potential fuel streams for use in an anode input can include biogas-type streams, such as methane produced from natural (biological) decomposition of organic material.

In some aspects, a molten carbonate fuel cell can be used to process an input fuel stream, such as a natural gas and/or hydrocarbon stream, with a low energy content due to the presence of diluent compounds. For example, some sources of methane and/or natural gas are sources that can include substantial amounts of either $CO_2$ or other inert molecules, such as nitrogen, argon, or helium. Due to the presence of elevated amounts of $CO_2$ and/or inerts, the energy content of a fuel stream based on the source can be reduced. Using a low energy content fuel for a combustion reaction (such as for powering a combustion-powered turbine) can pose difficulties. However, a molten carbonate fuel cell can generate power based on a low energy content fuel source with a reduced or minimal impact on the efficiency of the fuel cell. The presence of additional gas volume can require additional heat for raising the temperature of the fuel to the temperature for reforming and/or the anode reaction. Additionally, due to the equilibrium nature of the water gas shift reaction within a fuel cell anode, the presence of additional $CO_2$ can have an impact on the relative amounts of $H_2$ and CO present in the anode output. However, the inert compounds otherwise can have only a minimal direct impact on the reforming and anode reactions. The amount of $CO_2$ and/or inert compounds in a fuel stream for a molten carbonate fuel cell, when present, can be at least about 1 vol %, such as at least about 2 vol %, or at least about 5 vol %, or at least about 10 vol %, or at least about 15 vol %, or at least about 20 vol %, or at least about 25 vol %, or at least about 30 vol %, or at least about 35 vol %, or at least about 40 vol %, or at least about 45 vol %, or at least about 50 vol %, or at least about 75 vol %. Additionally or alternately, the amount of $CO_2$ and/or inert compounds in a fuel stream for a molten carbonate fuel cell can be about 90 vol % or less, such as about 75 vol % or less, or about 60 vol % or less, or about 50 vol % or less, or about 40 vol % or less, or about 35 vol % or less.

Yet other examples of potential sources for an anode input stream can correspond to refinery and/or other industrial process output streams. For example, coking is a common process in many refineries for converting heavier compounds to lower boiling ranges. Coking typically produces an off-gas containing a variety of compounds that are gases at room temperature, including CO and various C1-C4 hydrocarbons. This off-gas can be used as at least a portion of an anode input stream. Other refinery off-gas streams can additionally or alternately be suitable for inclusion in an anode input stream, such as light ends (C1-C4) generated during cracking or other refinery processes. Still other suitable refinery streams can additionally or alternately include refinery streams containing CO or $CO_2$ that also contain $H_2$ and/or reformable fuel compounds.

Still other potential sources for an anode input can additionally or alternately include streams with increased water content. For example, an ethanol output stream from an ethanol plant (or another type of fermentation process) can include a substantial portion of $H_2O$ prior to final distillation. Such $H_2O$ can typically cause only minimal impact on the operation of a fuel cell. Thus, a fermentation mixture of alcohol (or other fermentation product) and water can be used as at least a portion of an anode input stream.

Biogas, or digester gas, is another additional or alternate potential source for an anode input. Biogas may primarily comprise methane and $CO_2$ and is typically produced by the breakdown or digestion of organic matter. Anaerobic bacteria may be used to digest the organic matter and produce the biogas. Impurities, such as sulfur-containing compounds, may be removed from the biogas prior to use as an anode input.

The output stream from an MCFC anode can include $H_2O$, $CO_2$, CO, and $H_2$. Optionally, the anode output stream could also have unreacted fuel (such as $H_2$ or $CH_4$) or inert compounds in the feed as additional output components. Instead of using this output stream as a fuel source to provide heat for a reforming reaction or as a combustion fuel for heating the cell, one or more separations can be performed on the anode output stream to separate the $CO_2$ from the components with potential value as inputs to another process, such as $H_2$ or CO. The $H_2$ and/or CO can be used as a syngas for chemical synthesis, as a source of hydrogen for chemical reaction, and/or as a fuel with reduced greenhouse gas emissions.

In various aspects, the composition of the output stream from the anode can be impacted by several factors. Factors that can influence the anode output composition can include the composition of the input stream to the anode, the amount of current generated by the fuel cell, and/or the temperature at the exit of the anode. The temperature of at the anode exit can be relevant due to the equilibrium nature of the water gas shift reaction. In a typical anode, at least one of the plates forming the wall of the anode can be suitable for catalyzing the water gas shift reaction. As a result, if a) the composition of the anode input stream is known, b) the extent of reforming of reformable fuel in the anode input stream is known, and c) the amount of carbonate transported from the cathode to anode (corresponding to the amount of electrical current generated) is known, the composition of the anode output can be determined based on the equilibrium constant for the water gas shift reaction.

$$K_{eq}=[CO_2][H_2]/[CO][H_2O]$$

In the above equation, $K_{eq}$ is the equilibrium constant for the reaction at a given temperature and pressure, and [X] is the partial pressure of component X. Based on the water gas shift reaction, it can be noted that an increased $CO_2$ concentration in the anode input can tend to result in additional CO formation (at the expense of $H_2$) while an increased $H_2O$ concentration can tend to result in additional $H_2$ formation (at the expense of CO).

To determine the composition at the anode output, the composition of the anode input can be used as a starting point. This composition can then be modified to reflect the extent of reforming of any reformable fuels that can occur within the anode. Such reforming can reduce the hydrocarbon content of the anode input in exchange for increased hydrogen and $CO_2$. Next, based on the amount of electrical current generated, the amount of $H_2$ in the anode input can be reduced in exchange for additional $H_2O$ and $CO_2$. This composition can then be adjusted based on the equilibrium constant for the water gas shift reaction to determine the exit concentrations for $H_2$, CO, $CO_2$, and $H_2O$.

Table 1 shows the anode exhaust composition at different fuel utilizations for a typical type of fuel. The anode exhaust composition can reflect the combined result of the anode reforming reaction, water gas shift reaction, and the anode oxidation reaction. The output composition values in Table 1 were calculated by assuming an anode input composition with an about 2 to 1 ratio of steam ($H_2O$) to carbon (reformable fuel). The reformable fuel was assumed to be methane, which was assumed to be 100% reformed to hydrogen. The initial $CO_2$ and $H_2$ concentrations in the anode input were assumed to be negligible, while the input $N_2$ concentration was about 0.5%. The fuel utilization $U_f$ (as defined herein) was allowed to vary from about 35% to about 70% as shown in the table. The exit temperature for the fuel cell anode was assumed to be about 650° C. for purposes of determining the correct value for the equilibrium constant.

TABLE 1

| | | Anode Exhaust Composition | | | | | | | |
|---|---|---|---|---|---|---|---|---|---|
| Uf | % | 35% | 40% | 45% | 50% | 55% | 60% | 65% | 70% |
| | | Anode Exhaust Composition | | | | | | | |
| $H_2O$ | %, wet | 32.5% | 34.1% | 35.5% | 36.7% | 37.8% | 38.9% | 39.8% | 40.5% |
| $CO_2$ | %, wet | 26.7% | 29.4% | 32.0% | 34.5% | 36.9% | 39.3% | 41.5% | 43.8% |
| $H_2$ | %, wet | 29.4% | 26.0% | 22.9% | 20.0% | 17.3% | 14.8% | 12.5% | 10.4% |
| CO | %, wet | 10.8% | 10.0% | 9.2% | 8.4% | 7.5% | 6.7% | 5.8% | 4.9% |
| $N_2$ | %, wet | 0.5% | 0.5% | 0.5% | 0.4% | 0.4% | 0.4% | 0.4% | 0.4% |
| $CO_2$ | %, dry | 39.6% | 44.6% | 49.6% | 54.5% | 59.4% | 64.2% | 69.0% | 73.7% |
| $H_2$ | %, dry | 43.6% | 39.4% | 35.4% | 31.5% | 27.8% | 24.2% | 20.7% | 17.5% |
| CO | %, dry | 16.1% | 15.2% | 14.3% | 13.2% | 12.1% | 10.9% | 9.7% | 8.2% |
| $N_2$ | %, dry | 0.7% | 0.7% | 0.7% | 0.7% | 0.7% | 0.7% | 0.7% | 0.7% |
| $H_2/CO$ | | 2.7 | 2.6 | 2.5 | 2.4 | 2.3 | 2.2 | 2.1 | 2.1 |
| $(H_2 - CO_2)/(CO + CO_2)$ | | 0.07 | −0.09 | −0.22 | −0.34 | −0.44 | −0.53 | −0.61 | −0.69 |

Table 1 shows anode output compositions for a particular set of conditions and anode input composition. More generally, in various aspects the anode output can include about 10 vol % to about 50 vol % $H_2O$. The amount of $H_2O$ can vary greatly, as $H_2O$ in the anode can be produced by the anode oxidation reaction. If an excess of $H_2O$ beyond what is needed for reforming is introduced into the anode, the excess $H_2O$ can typically pass through largely unreacted, with the exception of $H_2O$ consumed (or generated) due to fuel reforming and the water gas shift reaction. The $CO_2$ concentration in the anode output can also vary widely, such as from about 20 vol % to about 50 vol % $CO_2$. The amount of $CO_2$ can be influenced by both the amount of electrical current generated as well as the amount of $CO_2$ in the anode input flow. The amount of $H_2$ in the anode output can additionally or alternately be from about 10 vol % $H_2$ to about 50 vol % $H_2$, depending on the fuel utilization in the anode. At the anode output, the amount of CO can be from about 5 vol % to about 20 vol %. It is noted that the amount of CO relative to the amount of $H_2$ in the anode output for a given fuel cell can be determined in part by the equilibrium constant for the water gas shift reaction at the temperature and pressure present in the fuel cell. The anode output can further additionally or alternately include 5 vol % or less of various other components, such as $N_2$, $CH_4$ (or other unreacted carbon-containing fuels), and/or other components.

Optionally, one or more water gas shift reaction stages can be included after the anode output to convert CO and $H_2O$ in the anode output into $CO_2$ and $H_2$, if desired. The amount of $H_2$ present in the anode output can be increased, for example, by using a water gas shift reactor at lower temperature to convert $H_2O$ and CO present in the anode output into $H_2$ and $CO_2$. Alternatively, the temperature can be raised and the water-gas shift reaction can be reversed, producing more CO and $H_2O$ from $H_2$ and $CO_2$. Water is an expected output of the reaction occurring at the anode, so the anode output can typically have an excess of $H_2O$ relative to the amount of CO present in the anode output. Alternatively, $H_2O$ can be added to the stream after the anode exit but before the water gas shift reaction. CO can be present in the anode output due to incomplete carbon conversion during reforming and/or due to the equilibrium balancing reactions between $H_2O$, CO, $H_2$, and $CO_2$ (i.e., the water-gas shift equilibrium) under either reforming conditions or the conditions present during the anode reaction. A water gas shift reactor can be operated under conditions to drive the equilibrium further in the direction of forming $CO_2$ and $H_2$ at the expense of CO and $H_2O$. Higher temperatures can tend to favor the formation of CO and $H_2O$. Thus, one option for operating the water gas shift reactor can be to expose the anode output stream to a suitable catalyst, such as a catalyst including iron oxide, zinc oxide, copper on zinc oxide, or the like, at a suitable temperature, e.g., between about 190° C. to about 210° C. Optionally, the water-gas shift reactor can include two stages for reducing the CO concentration in an anode output stream, with a first higher temperature stage operated at a temperature from at least about 300° C. to about 375° C. and a second lower temperature stage operated at a temperature of about 225° C. or less, such as from about 180° C. to about 210° C. In addition to increasing the amount of $H_2$ present in the anode output, the water-gas shift reaction can additionally or alternately increase the amount of $CO_2$ at the expense of CO. This can exchange difficult-to-remove carbon monoxide (CO) for carbon dioxide, which can be more readily removed by condensation (e.g., cryogenic removal), chemical reaction (such as amine removal), and/or other $CO_2$ removal methods. Additionally or alternately, it may be desirable to increase the CO content present in the anode exhaust in order to achieve a desired ratio of $H_2$ to CO.

After passing through the optional water gas shift reaction stage, the anode output can be passed through one or more separation stages for removal of water and/or $CO_2$ from the anode output stream. For example, one or more $CO_2$ output streams can be formed by performing $CO_2$ separation on the anode output using one or more methods individually or in combination. Such methods can be used to generate $CO_2$ output stream(s) having a $CO_2$ content of 90 vol % or greater, such as at least 95% vol % $CO_2$, or at least 98 vol % $CO_2$. Such methods can recover about at least about 70% of the $CO_2$ content of the anode output, such as at least about 80% of the $CO_2$ content of the anode output, or at least about 90%. Alternatively, in some aspects it may be desirable to recover only a portion of the $CO_2$ within an anode output stream, with the recovered portion of $CO_2$ being about 33% to about 90% of the $CO_2$ in the anode output, such as at least about 40%, or at least about 50%. For example, it may be desirable to retain some $CO_2$ in the anode output flow so that a desired composition can be achieved in a subsequent water gas shift stage. Suitable separation methods may comprise use of a physical solvent (e.g., Selexol™ or Rectisol™); amines or other bases (e.g., MEA or MDEA); refrigeration (e.g., cryogenic separation); pressure swing adsorption; vacuum swing adsorption; and combinations thereof. A cryogenic $CO_2$ separator can be an example of a suitable separator. As the anode output is cooled, the majority of the water in the anode output can be separated out as a condensed (liquid) phase. Further cooling and/or pressurizing of the water-depleted anode output flow can then separate high purity $CO_2$, as the other remaining components in the anode output flow (such as $H_2$, $N_2$, $CH_4$) do not tend to readily form condensed phases. A cryogenic $CO_2$ separator can recover between about 33% and about 90% of the $CO_2$ present in a flow, depending on the operating conditions.

Removal of water from the anode exhaust to form one or more water output streams can also be beneficial, whether prior to, during, or after performing $CO_2$ separation. The amount of water in the anode output can vary depending on operating conditions selected. For example, the steam-to-carbon ratio established at the anode inlet can affect the water content in the anode exhaust, with high steam-to-carbon ratios typically resulting in a large amount of water that can pass through the anode unreacted and/or reacted only due to the water gas shift equilibrium in the anode. Depending on the aspect, the water content in the anode exhaust can correspond to up to about 30% or more of the volume in the anode exhaust. Additionally or alternately, the water content can be about 80% or less of the volume of the anode exhaust. While such water can be removed by compression and/or cooling with resulting condensation, the removal of this water can require extra compressor power and/or heat exchange surface area and excessive cooling water. One beneficial way to remove a portion of this excess water can be based on use of an adsorbent bed that can capture the humidity from the moist anode effluent and can then be 'regenerated' using dry anode feed gas, in order to provide additional water for the anode feed. HVAC-style (heating, ventilation, and air conditioning) adsorption wheels design can be applicable, because anode exhaust and inlet can be similar in pressure, and minor leakage from one stream to the other can have minimal impact on the overall process. In embodiments where $CO_2$ removal is performed using a cryogenic process, removal of water prior to or during $CO_2$ removal may be desirable, including removal by triethyleneglycol (TEG) system and/or desiccants. By contrast, if an amine wash is used for $CO_2$ removal, water can be removed from the anode exhaust downstream from the $CO_2$ removal stage.

Alternately or in addition to a $CO_2$ output stream and/or a water output stream, the anode output can be used to form one or more product streams containing a desired chemical or fuel product. Such a product stream or streams can correspond to a syngas stream, a hydrogen stream, or both syngas product and hydrogen product streams. For example, a hydrogen product stream containing at least about 70 vol % $H_2$, such as at least about 90 vol % $H_2$ or at least about 95 vol % $H_2$, can be formed. Additionally or alternately, a syngas stream containing at least about 70 vol % of $H_2$ and CO combined, such as at least about 90 vol % of $H_2$ and CO can be formed. The one or more product streams can have a gas volume corresponding to at least about 75% of the combined $H_2$ and CO gas volumes in the anode output, such as at least about 85% or at least about 90% of the combined $H_2$ and CO gas volumes. It is noted that the relative amounts of $H_2$ and CO in the products streams may differ from the $H_2$ to CO ratio in the anode output based on use of water gas shift reaction stages to convert between the products.

In some aspects, it can be desirable to remove or separate a portion of the $H_2$ present in the anode output. For example, in some aspects the $H_2$ to CO ratio in the anode exhaust can be at least about 3.0:1. By contrast, processes that make use of syngas, such as Fischer-Tropsch synthesis, may consume $H_2$ and CO in a different ratio, such as a ratio that is closer to 2:1. One alternative can be to use a water gas shift reaction to modify the content of the anode output to have an $H_2$ to CO ratio closer to a desired syngas composition.

Another alternative can be to use a membrane separation to remove a portion of the $H_2$ present in the anode output to achieve a desired ratio of $H_2$ and CO, or still alternately to use a combination of membrane separation and water gas shift reactions. One advantage of using a membrane separation to remove only a portion of the $H_2$ in the anode output can be that the desired separation can be performed under relatively mild conditions. Since one goal can be to produce a retentate that still has a substantial $H_2$ content, a permeate of high purity hydrogen can be generated by membrane separation without requiring severe conditions. For example, rather than having a pressure on the permeate side of the membrane of about 100 kPaa or less (such as ambient pressure), the permeate side can be at an elevated pressure relative to ambient while still having sufficient driving force to perform the membrane separation. Additionally or alternately, a sweep gas such as methane can be used to provide a driving force for the membrane separation. This can reduce the purity of the $H_2$ permeate stream, but may be advantageous, depending on the desired use for the permeate stream.

In various aspects of the invention, at least a portion of the anode exhaust stream (preferably after separation of $CO_2$ and/or $H_2O$) can be used as a feed for a process external to the fuel cell and associated reforming stages. In various aspects, the anode exhaust can have a ratio of $H_2$ to CO of about 1.5:1 to about 10:1, such as at least about 3.0:1, or at least about 4.0:1, or at least about 5.0:1. A syngas stream can be generated or withdrawn from the anode exhaust. The anode exhaust gas, optionally after separation of $CO_2$ and/or $H_2O$, and optionally after performing a water gas shift reaction and/or a membrane separation to remove excess hydrogen, can correspond to a stream containing substantial portions of $H_2$ and/or CO. For a stream with a relatively low content of CO, such as a stream where the ratio of $H_2$ to CO is at least about 3:1, the anode exhaust can be suitable for use as an $H_2$ feed. Examples of processes that could benefit from an $H_2$ feed can include, but are not limited to, refinery processes, an ammonia synthesis plant, or a turbine in a (different) power generation system, or combinations thereof. Depending on the application, still lower $CO_2$ contents can be desirable. For a stream with an $H_2$-to-CO ratio of less than about 2.2 to 1 and greater than about 1.9 to 1, the stream can be suitable for use as a syngas feed. Examples of processes that could benefit from a syngas feed can include, but are not limited to, a gas-to-liquids plant (such as a plant using a Fischer-Tropsch process with a non-shifting catalyst) and/or a methanol synthesis plant. The amount of the anode exhaust used as a feed for an external process can be any convenient amount. Optionally, when a portion of the anode exhaust is used as a feed for an external process, a second portion of the anode exhaust can be recycled to the anode input and/or recycled to the combustion zone for a combustion-powered generator.

The input streams useful for different types of Fischer-Tropsch synthesis processes can provide an example of the different types of product streams that may be desirable to generate from the anode output. For a Fischer-Tropsch synthesis reaction system that uses a shifting catalyst, such as an iron-based catalyst, the desired input stream to the reaction system can include $CO_2$ in addition to $H_2$ and CO. If a sufficient amount of $CO_2$ is not present in the input stream, a Fischer-Tropsch catalyst with water gas shift activity can consume CO in order to generate additional $CO_2$, resulting in a syngas that can be deficient in CO. For integration of such a Fischer-Tropsch process with an MCFC fuel cell, the separation stages for the anode output can be operated to retain a desired amount of $CO_2$ (and optionally $H_2O$) in the syngas product. By contrast, for a Fischer-Tropsch catalyst based on a non-shifting catalyst, any $CO_2$ present in a product stream could serve as an inert component in the Fischer-Tropsch reaction system.

In an aspect where the membrane is swept with a sweep gas such as a methane sweep gas, the methane sweep gas can correspond to a methane stream used as the anode fuel or in a different low pressure process, such as a boiler, furnace, gas turbine, or other fuel-consuming device. In such an aspect, low levels of $CO_2$ permeation across the membrane can have minimal consequence. Such $CO_2$ that may permeate across the membrane can have a minimal impact on the reactions within the anode, and such $CO_2$ can remain contained in the anode product. Therefore, the $CO_2$ (if any) lost across the membrane due to permeation does not need to be transferred again across the MCFC electrolyte. This can significantly reduce the separation selectivity requirement for the hydrogen permeation membrane. This can allow, for example, use of a higher-permeability membrane having a lower selectivity, which can enable use of a lower pressure and/or reduced membrane surface area. In such an aspect of the invention, the volume of the sweep gas can be a large multiple of the volume of hydrogen in the anode exhaust, which can allow the effective hydrogen concentration on the permeate side to be maintained close to zero. The hydrogen thus separated can be incorporated into the turbine-fed methane where it can enhance the turbine combustion characteristics, as described above.

It is noted that excess $H_2$ produced in the anode can represent a fuel where the greenhouse gases have already been separated. Any $CO_2$ in the anode output can be readily separated from the anode output, such as by using an amine wash, a cryogenic $CO_2$ separator, and/or a pressure or vacuum swing absorption process. Several of the components of the anode output ($H_2$, CO, $CH_4$) are not easily removed, while $CO_2$ and $H_2O$ can usually be readily removed. Depending on the embodiment, at least about 90 vol % of the $CO_2$ in the anode output can be separated out to form a relatively high purity $CO_2$ output stream. Thus, any $CO_2$ generated in the anode can be efficiently separated out to form a high purity $CO_2$ output stream. After separation, the remaining portion of the anode output can correspond primarily to components with chemical and/or fuel value, as well as reduced amounts of $CO_2$ and/or $H_2O$, Since a substantial portion of the $CO_2$ generated by the original fuel (prior to reforming) can have been separated out, the amount of $CO_2$ generated by subsequent burning of the remaining portion of the anode output can be reduced. In particular, to the degree that the fuel in the remaining portion of the anode output is $H_2$, no additional greenhouse gases can typically be formed by burning of this fuel.

The anode exhaust can be subjected to a variety of gas processing options, including water-gas shift and separation of the components from each other. Two general anode processing schemes are shown in FIGS. 1 and 2.

Figure 2:
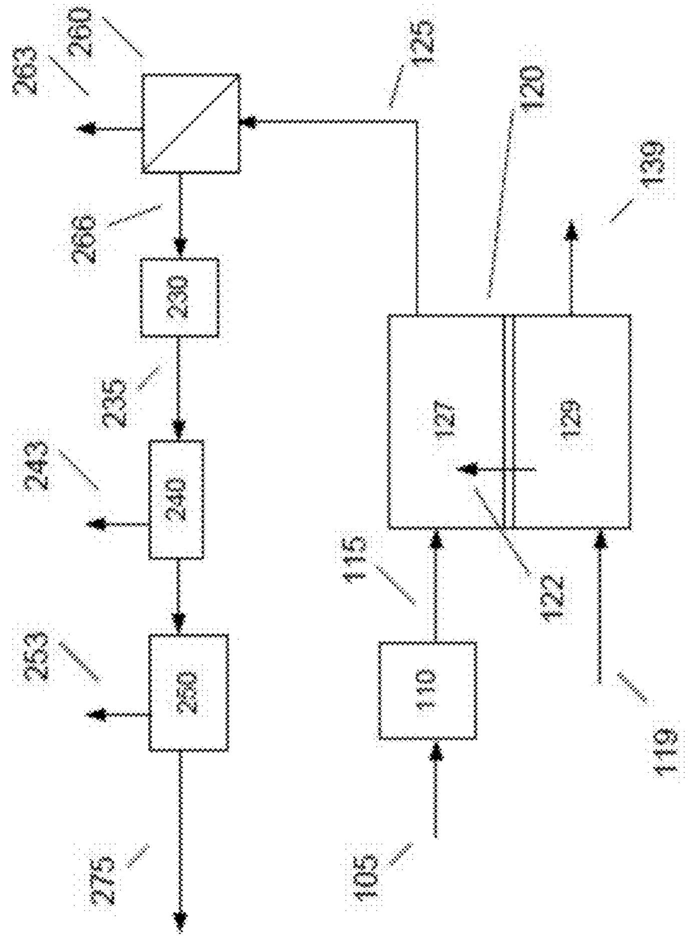
FIG. 2 schematically shows another example of a configuration for molten carbonate fuel cells and associated reforming and separation stages.

FIG. 1 schematically shows an example of a reaction system for operating a fuel cell array of molten carbonate fuel cells in conjunction with a chemical synthesis process. In FIG. 1, a fuel stream 105 is provided to a reforming stage (or stages) 110 associated with the anode 127 of a fuel cell 120, such as a fuel cell that is part of a fuel cell stack in a fuel cell array. The reforming stage 110 associated with fuel cell 120 can be internal to a fuel cell assembly. In some optional aspects, an external reforming stage (not shown) can also be used to reform a portion of the reformable fuel in an input stream prior to passing the input stream into a fuel cell assembly. Fuel stream 105 can preferably include a reformable fuel, such as methane, other hydrocarbons, and/or other hydrocarbon-like compounds such as organic compounds containing carbon-hydrogen bonds. Fuel stream 105 can also optionally contain $H_2$ and/or CO, such as $H_2$ and/or CO provided by optional anode recycle stream 185. It is noted that anode recycle stream 185 is optional, and that in many aspects no recycle stream is provided from the anode exhaust 125 back to anode 127, either directly or indirectly via combination with fuel stream 105 or reformed fuel stream 115. After reforming, the reformed fuel stream 115 can be passed into anode 127 of fuel cell 120. A $CO_2$ and $O_2$-containing stream 119 can also be passed into cathode 129. A flow of carbonate ions 122, $CO_3^{2-}$, from the cathode portion 129 of the fuel cell can provide the remaining reactant needed for the anode fuel cell reactions. Based on the reactions in the anode 127, the resulting anode exhaust 125 can include $H_2O$, $CO_2$, one or more components corresponding to incompletely reacted fuel ($H_2$, CO, $CH_4$, or other components corresponding to a reformable fuel), and optionally one or more additional nonreactive components, such as $N_2$ and/or other contaminants that are part of fuel stream 105. The anode exhaust 125 can then be passed into one or more separation stages. For example, a $CO_2$ removal stage 140 can correspond to a cryogenic $CO_2$ removal system, an amine wash stage for removal of acid gases such as $CO_2$, or another suitable type of $CO_2$ separation stage for separating a $CO_2$ output stream 143 from the anode exhaust. Optionally, the anode exhaust can first be passed through a water gas shift reactor 130 to convert any CO present in the anode exhaust (along with some $H_2O$) into $CO_2$ and $H_2$ in an optionally water gas shifted anode exhaust 135. Depending on the nature of the $CO_2$ removal stage, a water condensation or removal stage 150 may be desirable to remove a water output stream 153 from the anode exhaust. Though shown in FIG. 1 after the $CO_2$ separation stage 140, it may optionally be located before the $CO_2$ separation stage 140 instead. Additionally, an optional membrane separation stage 160 for separation of $H_2$ can be used to generate a high purity permeate stream 163 of $H_2$. The resulting retentate stream 166 can then be used as an input to a chemical synthesis process. Stream 166 could additionally or alternately be shifted in a second water-gas shift reactor 131 to adjust the $H_2$, CO, and $CO_2$ content to a different ratio, producing an output stream 168 for further use in a chemical synthesis process. In FIG. 1, anode recycle stream 185 is shown as being withdrawn from the retentate stream 166, but the anode recycle stream 185 could additionally or alternately be withdrawn from other convenient locations in or between the various separation stages. The separation stages and shift reactor(s) could additionally or alternately be configured in different orders, and/or in a parallel configuration. Finally, a stream with a reduced content of $CO_2$ 139 can be generated as an output from cathode 129. For the sake of simplicity, various stages of compression and heat addition/removal that might be useful in the process, as well as steam addition or removal, are not shown.

As noted above, the various types of separations performed on the anode exhaust can be performed in any convenient order. FIG. 2 shows an example of an alternative order for performing separations on an anode exhaust. In FIG. 2, anode exhaust 125 can be initially passed into separation stage 260 for removing a portion 263 of the hydrogen content from the anode exhaust 125. This can allow, for example, reduction of the $H_2$ content of the anode exhaust to provide a retentate 266 with a ratio of $H_2$ to CO closer to 2:1. The ratio of $H_2$ to CO can then be further adjusted to achieve a desired value in a water gas shift stage 230. The water gas shifted output 235 can then pass through $CO_2$ separation stage 240 and water removal stage 250 to produce an output stream 275 suitable for use as an input to a desired chemical synthesis process. Optionally, output stream 275 could be exposed to an additional water gas shift stage (not shown). A portion of output stream 275 can optionally be recycled (not shown) to the anode input. Of course, still other combinations and sequencing of separation stages can be used to generate a stream based on the anode output that has a desired composition. For the sake of simplicity, various stages of compression and heat addition/removal that might be useful in the process, as well as steam addition or removal, are not shown.

Cathode Inputs and Outputs

Conventionally, a molten carbonate fuel cell can be operated based on drawing a desired load while consuming some portion of the fuel in the fuel stream delivered to the anode. The voltage of the fuel cell can then be determined by the load, fuel input to the anode, air and $CO_2$ provided to the cathode, and the internal resistances of the fuel cell. The $CO_2$ to the cathode can be conventionally provided in part by using the anode exhaust as at least a part of the cathode input stream. By contrast, the present invention can use separate/different sources for the anode input and cathode input. By removing any direct link between the composition of the anode input flow and the cathode input flow, additional options become available for operating the fuel cell, such as to generate excess synthesis gas, to improve capture of carbon dioxide, and/or to improve the total efficiency (electrical plus chemical power) of the fuel cell, among others.

In a molten carbonate fuel cell, the transport of carbonate ions across the electrolyte in the fuel cell can provide a method for transporting $CO_2$ from a first flow path to a second flow path, where the transport method can allow transport from a lower concentration (the cathode) to a higher concentration (the anode), which can thus facilitate capture of $CO_2$. Part of the selectivity of the fuel cell for $CO_2$ separation can be based on the electrochemical reactions allowing the cell to generate electrical power. For nonreactive species (such as $N_2$) that effectively do not participate in the electrochemical reactions within the fuel cell, there can be an insignificant amount of reaction and transport from cathode to anode. By contrast, the potential (voltage) difference between the cathode and anode can provide a strong driving force for transport of carbonate ions across the fuel cell. As a result, the transport of carbonate ions in the molten carbonate fuel cell can allow $CO_2$ to be transported from the cathode (lower $CO_2$ concentration) to the anode (higher $CO_2$ concentration) with relatively high selectivity. However, a challenge in using molten carbonate fuel cells for carbon dioxide removal can be that the fuel cells have limited ability to remove carbon dioxide from relatively dilute cathode feeds. The voltage and/or power generated by a carbonate fuel cell can start to drop rapidly as the $CO_2$ concentration falls below about 2.0 vol %. As the $CO_2$ concentration drops further, e.g., to below about 1.0 vol %, at some point the voltage across the fuel cell can become low enough that little or no further transport of carbonate may occur and the fuel cell ceases to function. Thus, at least some $CO_2$ is likely to be present in the exhaust gas from the cathode stage of a fuel cell under commercially viable operating conditions.

The amount of carbon dioxide delivered to the fuel cell cathode(s) can be determined based on the $CO_2$ content of a source for the cathode inlet. One example of a suitable $CO_2$-containing stream for use as a cathode input flow can be an output or exhaust flow from a combustion source.

Examples of combustion sources include, but are not limited to, sources based on combustion of natural gas, combustion of coal, and/or combustion of other hydrocarbon-type fuels (including biologically derived fuels). Additional or alternate sources can include other types of boilers, fired heaters, furnaces, and/or other types of devices that burn carbon-containing fuels in order to heat another substance (such as water or air). To a first approximation, the $CO_2$ content of the output flow from a combustion source can be a minor portion of the flow. Even for a higher $CO_2$ content exhaust flow, such as the output from a coal-fired combustion source, the $CO_2$ content from most commercial coal-fired power plants can be about 15 vol % or less. More generally, the $CO_2$ content of an output or exhaust flow from a combustion source can be at least about 1.5 vol %, or at least about 1.6 vol %, or at least about 1.7 vol %, or at least about 1.8 vol %, or at least about 1.9 vol %, or at least greater 2 vol %, or at least about 4 vol %, or at least about 5 vol %, or at least about 6 vol %, or at least about 8 vol %. Additionally or alternately, the $CO_2$ content of an output or exhaust flow from a combustion source can be about 20 vol % or less, such as about 15 vol % or less, or about 12 vol % or less, or about 10 vol % or less, or about 9 vol % or less, or about 8 vol % or less, or about 7 vol % or less, or about 6.5 vol % or less, or about 6 vol % or less, or about 5.5 vol % or less, or about 5 vol % or less, or about 4.5 vol % or less. The concentrations given above are on a dry basis. It is noted that the lower $CO_2$ content values can be present in the exhaust from some natural gas or methane combustion sources, such as generators that are part of a power generation system that may or may not include an exhaust gas recycle loop.

Other potential sources for a cathode input stream can additionally or alternately include sources of bio-produced $CO_2$. This can include, for example, $CO_2$ generated during processing of bio-derived compounds, such as $CO_2$ generated during ethanol production. An additional or alternate example can include $CO_2$ generated by combustion of a bio-produced fuel, such as combustion of lignocellulose. Still other additional or alternate potential $CO_2$ sources can correspond to output or exhaust streams from various industrial processes, such as $CO_2$-containing streams generated by plants for manufacture of steel, cement, and/or paper.

Yet another additional or alternate potential source of $CO_2$ can be $CO_2$-containing streams from a fuel cell. The $CO_2$-containing stream from a fuel cell can correspond to a cathode output stream from a different fuel cell, an anode output stream from a different fuel cell, a recycle stream from the cathode output to the cathode input of a fuel cell, and/or a recycle stream from an anode output to a cathode input of a fuel cell. For example, an MCFC operated in standalone mode under conventional conditions can generate a cathode exhaust with a $CO_2$ concentration of at least about 5 vol %. Such a $CO_2$-containing cathode exhaust could be used as a cathode input for an MCFC operated according to an aspect of the invention. More generally, other types of fuel cells that generate a $CO_2$ output from the cathode exhaust can additionally or alternately be used, as well as other types of $CO_2$-containing streams not generated by a "combustion" reaction and/or by a combustion-powered generator. Optionally but preferably, a $CO_2$-containing stream from another fuel cell can be from another molten carbonate fuel cell. For example, for molten carbonate fuel cells connected in series with respect to the cathodes, the output from the cathode for a first molten carbonate fuel cell can be used as the input to the cathode for a second molten carbonate fuel cell.

For various types of $CO_2$-containing streams from sources other than combustion sources, the $CO_2$ content of the stream can vary widely. The $CO_2$ content of an input stream to a cathode can contain at least about 2 vol % of $CO_2$, such as at least about 4 vol %, or at least about 5 vol %, or at least about 6 vol %, or at least about 8 vol %. Additionally or alternately, the $CO_2$ content of an input stream to a cathode can be about 30 vol % or less, such as about 25 vol % or less, or about 20 vol % or less, or about 15 vol % or less, or about 10 vol % or less, or about 8 vol % or less, or about 6 vol % or less, or about 4 vol % or less. For some still higher $CO_2$ content streams, the $CO_2$ content can be greater than about 30 vol %, such as a stream substantially composed of $CO_2$ with only incidental amounts of other compounds. As an example, a gas-fired turbine without exhaust gas recycle can produce an exhaust stream with a $CO_2$ content of approximately 4.2 vol %. With EGR, a gas-fired turbine can produce an exhaust stream with a $CO_2$ content of about 6-8 vol %. Stoichiometric combustion of methane can produce an exhaust stream with a $CO_2$ content of about 11 vol %. Combustion of coal can produce an exhaust stream with a $CO_2$ content of about 15-20 vol %. Fired heaters using refinery off-gas can produce an exhaust stream with a $CO_2$ content of about 12-15 vol %. A gas turbine operated on a low BTU gas without any EGR can produce an exhaust stream with a $CO_2$ content of ~12 vol %.

In addition to $CO_2$, a cathode input stream must include $O_2$ to provide the components necessary for the cathode reaction. Some cathode input streams can be based on having air as a component. For example, a combustion exhaust stream can be formed by combusting a hydrocarbon fuel in the presence of air. Such a combustion exhaust stream, or another type of cathode input stream having an oxygen content based on inclusion of air, can have an oxygen content of about 20 vol % or less, such as about 15 vol % or less, or about 10 vol % or less. Additionally or alternately, the oxygen content of the cathode input stream can be at least about 4 vol %, such as at least about 6 vol %, or at least about 8 vol %. More generally, a cathode input stream can have a suitable content of oxygen for performing the cathode reaction. In some aspects, this can correspond to an oxygen content of about 5 vol % to about 15 vol %, such as from about 7 vol % to about 9 vol %. For many types of cathode input streams, the combined amount of $CO_2$ and $O_2$ can correspond to less than about 21 vol % of the input stream, such as less than about 15 vol % of the stream or less than about 10 vol % of the stream. An air stream containing oxygen can be combined with a $CO_2$ source that has low oxygen content. For example, the exhaust stream generated by burning coal may include a low oxygen content that can be mixed with air to form a cathode inlet stream.

In addition to $CO_2$ and $O_2$, a cathode input stream can also be composed of inert/non-reactive species such as $N_2$, $H_2O$, and other typical oxidant (air) components. For example, for a cathode input derived from an exhaust from a combustion reaction, if air is used as part of the oxidant source for the combustion reaction, the exhaust gas can include typical components of air such as $N_2$, $H_2O$, and other compounds in minor amounts that are present in air. Depending on the nature of the fuel source for the combustion reaction, additional species present after combustion based on the fuel source may include one or more of $H_2O$, oxides of nitrogen (NOx) and/or sulfur (SOx), and other compounds either present in the fuel and/or that are partial or complete combustion products of compounds present in the fuel, such as CO. These species may be present in amounts that do not poison the cathode catalyst surfaces though they may reduce the overall cathode activity. Such reductions in performance may be acceptable, or species that interact with the cathode catalyst may be reduced to acceptable levels by known pollutant removal technologies.

The amount of $O_2$ present in a cathode input stream (such as an input cathode stream based on a combustion exhaust) can advantageously be sufficient to provide the oxygen needed for the cathode reaction in the fuel cell. Thus, the volume percentage of $O_2$ can advantageously be at least 0.5 times the amount of $CO_2$ in the exhaust. Optionally, as necessary, additional air can be added to the cathode input to provide sufficient oxidant for the cathode reaction. When some form of air is used as the oxidant, the amount of $N_2$ in the cathode exhaust can be at least about 78 vol %, e.g., at least about 88 vol %, and/or about 95 vol % or less. In some aspects, the cathode input stream can additionally or alternately contain compounds that are generally viewed as contaminants, such as $H_2S$ or $NH_3$. In other aspects, the cathode input stream can be cleaned to reduce or minimize the content of such contaminants.

In addition to the reaction to form carbonate ions for transport across the electrolyte, the conditions in the cathode can also be suitable for conversion of nitrogen oxides into nitrate and/or nitrate ions. Hereinafter, only nitrate ions will be referred to for convenience. The resulting nitrate ions can also be transported across the electrolyte for reaction in the anode. NOx concentrations in a cathode input stream can typically be on the order of ppm, so this nitrate transport reaction can have a minimal impact on the amount of carbonate transported across the electrolyte. However, this method of NOx removal can be beneficial for cathode input streams based on combustion exhausts from gas turbines, as this can provide a mechanism for reducing NOx emissions. The conditions in the cathode can additionally or alternately be suitable for conversion of unburned hydrocarbons (in combination with $O_2$ in the cathode input stream) to typical combustion products, such as $CO_2$ and $H_2O$.

A suitable temperature for operation of an MCFC can be between about 450° C. and about 750° C., such as at least about 500° C., e.g., with an inlet temperature of about 550° C. and an outlet temperature of about 625° C. Prior to entering the cathode, heat can be added to or removed from the combustion exhaust, if desired, e.g., to provide heat for other processes, such as reforming the fuel input for the anode. For example, if the source for the cathode input stream is a combustion exhaust stream, the combustion exhaust stream may have a temperature greater than a desired temperature for the cathode inlet. In such an aspect, heat can be removed from the combustion exhaust prior to use as the cathode input stream. Alternatively, the combustion exhaust could be at very low temperature, for example after a wet gas scrubber on a coal-fired boiler, in which case the combustion exhaust can be below about 100° C. Alternatively, the combustion exhaust could be from the exhaust of a gas turbine operated in combined cycle mode, in which the gas can be cooled by raising steam to run a steam turbine for additional power generation. In this case, the gas can be below about 50° C. Heat can be added to a combustion exhaust that is cooler than desired.

Fuel Cell Arrangement

In various aspects, a configuration option for a fuel cell (such as a fuel cell array containing multiple fuel cell stacks) can be to divide the $CO_2$-containing stream between a plurality of fuel cells. Some types of sources for $CO_2$-containing streams can generate large volumetric flow rates relative to the capacity of an individual fuel cell. For example, the $CO_2$-containing output stream from an industrial combustion source can typically correspond to a large flow volume relative to desirable operating conditions for a single MCFC of reasonable size. Instead of processing the entire flow in a single MCFC, the flow can be divided amongst a plurality of MCFC units, usually at least some of which can be in parallel, so that the flow rate in each unit can be within a desired flow range.

A second configuration option can be to utilize fuel cells in series to successively remove $CO_2$ from a flow stream. Regardless of the number of initial fuel cells to which a $CO_2$-containing stream can be distributed to in parallel, each initial fuel cell can be followed by one or more additional cells in series to further remove additional $CO_2$. If the desired amount of $CO_2$ in the cathode output is sufficiently low, attempting to remove $CO_2$ from a cathode input stream down to the desired level in a single fuel cell or fuel cell stage could lead to a low and/or unpredictable voltage output for the fuel cell. Rather than attempting to remove $CO_2$ to the desired level in a single fuel cell or fuel cell stage, $CO_2$ can be removed in successive cells until a desired level can be achieved. For example, each cell in a series of fuel cells can be used to remove some percentage (e.g., about 50%) of the $CO_2$ present in a fuel stream. In such an example, if three fuel cells are used in series, the $CO_2$ concentration can be reduced (e.g., to about 15% or less of the original amount present, which can correspond to reducing the $CO_2$ concentration from about 6% to about 1% or less over the course of three fuel cells in series).

In another configuration, the operating conditions can be selected in early fuel stages in series to provide a desired output voltage while the array of stages can be selected to achieve a desired level of carbon separation. As an example, an array of fuel cells can be used with three fuel cells in series. The first two fuel cells in series can be used to remove $CO_2$ while maintaining a desired output voltage. The final fuel cell can then be operated to remove $CO_2$ to a desired concentration but at a lower voltage.

In still another configuration, there can be separate connectivity for the anodes and cathodes in a fuel cell array. For example, if the fuel cell array includes fuel cathodes connected in series, the corresponding anodes can be connected in any convenient manner, not necessarily matching up with the same arrangement as their corresponding cathodes, for example. This can include, for instance, connecting the anodes in parallel, so that each anode receives the same type of fuel feed, and/or connecting the anodes in a reverse series, so that the highest fuel concentration in the anodes can correspond to those cathodes having the lowest $CO_2$ concentration.

In yet another configuration, the amount of fuel delivered to one or more anode stages and/or the amount of $CO_2$ delivered to one or more cathode stages can be controlled in order to improve the performance of the fuel cell array. For example, a fuel cell array can have a plurality of cathode stages connected in series. In an array that includes three cathode stages in series, this can mean that the output from a first cathode stage can correspond to the input for a second cathode stage, and the output from the second cathode stage can correspond to the input for a third cathode stage. In this type of configuration, the $CO_2$ concentration can decrease with each successive cathode stage. To compensate for this reduced $CO_2$ concentration, additional hydrogen and/or methane can be delivered to the anode stages corresponding to the later cathode stages. The additional hydrogen and/or methane in the anodes corresponding to the later cathode stages can at least partially offset the loss of voltage and/or current caused by the reduced $CO_2$ concentration, which can increase the voltage and thus net power produced by the fuel cell. In another example, the cathodes in a fuel cell array can be connected partially in series and partially in parallel. In this type of example, instead of passing the entire combustion output into the cathodes in the first cathode stage, at least a portion of the combustion exhaust can be passed into a later cathode stage. This can provide an increased $CO_2$ content in a later cathode stage. Still other options for using variable feeds to either anode stages or cathode stages can be used if desired.

The cathode of a fuel cell can correspond to a plurality of cathodes from an array of fuel cells, as previously described. In some aspects, a fuel cell array can be operated to improve or maximize the amount of carbon transferred from the cathode to the anode. In such aspects, for the cathode output from the final cathode(s) in an array sequence (typically at least including a series arrangement, or else the final cathode (s) and the initial cathode(s) would be the same), the output composition can include about 2.0 vol % or less of $CO_2$ (e.g., about 1.5 vol % or less or about 1.2 vol % or less) and/or at least about 0.5 vol % of $CO_2$, or at least about 1.0 vol %, or at least about 1.2 vol % or at least about 1.5 vol %. Due to this limitation, the net efficiency of $CO_2$ removal when using molten carbonate fuel cells can be dependent on the amount of $CO_2$ in the cathode input. For cathode input streams with $CO_2$ contents of greater than about 6 vol %, such as at least about 8%, the limitation on the amount of $CO_2$ that can be removed is not severe. However, for a combustion reaction using natural gas as a fuel and with excess air, as is typically found in a gas turbine, the amount of $CO_2$ in the combustion exhaust may only correspond to a $CO_2$ concentration at the cathode input of less than about 5 vol %. Use of exhaust gas recycle can allow the amount of $CO_2$ at the cathode input to be increased to at least about 5 vol %, e.g., at least about 6 vol %. If EGR is increased when using natural gas as a fuel to produce a $CO_2$ concentration beyond about 6 vol %, then the flammability in the combustor can be decreased and the gas turbine may become unstable. However, when $H_2$ is added to the fuel, the flammability window can be significantly increased, allowing the amount of exhaust gas recycle to be increased further, so that concentrations of $CO_2$ at the cathode input of at least about 7.5 vol % or at least about 8 vol % can be achieved. As an example, based on a removal limit of about 1.5 vol % at the cathode exhaust, increasing the $CO_2$ content at the cathode input from about 5.5 vol % to about 7.5 vol % can correspond to a ~10% increase in the amount of $CO_2$ that can be captured using a fuel cell and transported to the anode loop for eventual $CO_2$ separation. The amount of $O_2$ in the cathode output can additionally or alternately be reduced, typically in an amount proportional to the amount of $CO_2$ removed, which can result in small corresponding increases in the amount(s) of the other (non-cathode-reactive) species at the cathode exit.

In other aspects, a fuel cell array can be operated to improve or maximize the energy output of the fuel cell, such as the total energy output, the electric energy output, the syngas chemical energy output, or a combination thereof. For example, molten carbonate fuel cells can be operated with an excess of reformable fuel in a variety of situations, such as for generation of a syngas stream for use in chemical synthesis plant and/or for generation of a high purity hydrogen stream. The syngas stream and/or hydrogen stream can be used as a syngas source, a hydrogen source, as a clean fuel source, and/or for any other convenient application. In such aspects, the amount of $CO_2$ in the cathode exhaust can be related to the amount of $CO_2$ in the cathode input stream and the $CO_2$ utilization at the desired operating conditions for improving or maximizing the fuel cell energy output.

Additionally or alternately, depending on the operating conditions, an MCFC can lower the $CO_2$ content of a cathode exhaust stream to about 5.0 vol % or less, e.g., about 4.0 vol % or less, or about 2.0 vol % or less, or about 1.5 vol % or less, or about 1.2 vol % or less. Additionally or alternately, the $CO_2$ content of the cathode exhaust stream can be at least about 0.9 vol %, such as at least about 1.0 vol %, or at least about 1.2 vol %, or at least about 1.5 vol %.

Molten Carbonate Fuel Cell Operation

In some aspects, a fuel cell may be operated in a single pass or once-through mode. In single pass mode, reformed products in the anode exhaust are not returned to the anode inlet. Thus, recycling syngas, hydrogen, or some other product from the anode output directly to the anode inlet is not done in single pass operation. More generally, in single pass operation, reformed products in the anode exhaust are also not returned indirectly to the anode inlet, such as by using reformed products to process a fuel stream subsequently introduced into the anode inlet. Optionally, $CO_2$ from the anode outlet can be recycled to the cathode inlet during operation of an MCFC in single pass mode. More generally, in some alternative aspects, recycling from the anode outlet to the cathode inlet may occur for an MCFC operating in single pass mode. Heat from the anode exhaust or output may additionally or alternately be recycled in a single pass mode. For example, the anode output flow may pass through a heat exchanger that cools the anode output and warms another stream, such as an input stream for the anode and/or the cathode. Recycling heat from anode to the fuel cell is consistent with use in single pass or once-through operation. Optionally but not preferably, constituents of the anode output may be burned to provide heat to the fuel cell during single pass mode.

Figure 3:
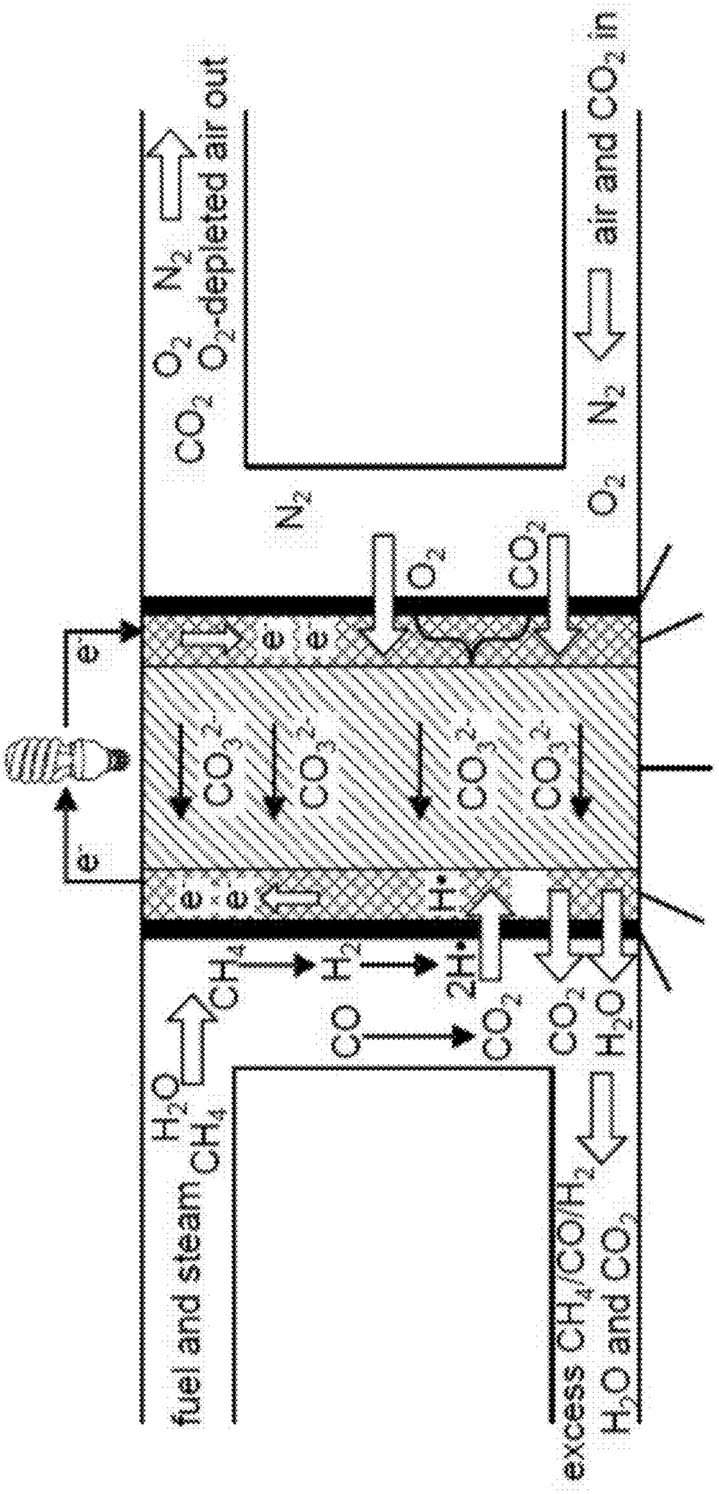
FIG. 3 schematically shows an example of the operation of a molten carbonate fuel cell.

FIG. 3 shows a schematic example of the operation of an MCFC for generation of electrical power. In FIG. 3, the anode portion of the fuel cell can receive fuel and steam ($H_2O$) as inputs, with outputs of water, $CO_2$, and optionally excess $H_2$, $CH_4$ (or other hydrocarbons), and/or CO. The cathode portion of the fuel cell can receive $CO_2$ and some oxidant (e.g., air/$O_2$) as inputs, with an output corresponding to a reduced amount of $CO_2$ in $O_2$-depleted oxidant (air). Within the fuel cell, $CO_3^{2-}$ ions formed in the cathode side can be transported across the electrolyte to provide the carbonate ions needed for the reactions occurring at the anode.

Several reactions can occur within a molten carbonate fuel cell such as the example fuel cell shown in FIG. 3. The reforming reactions can be optional, and can be reduced or eliminated if sufficient $H_2$ is provided directly to the anode. The following reactions are based on $CH_4$, but similar reactions can occur when other fuels are used in the fuel cell.

<anode reforming> $CH_4+H_2O=>3H_2+CO$ (1)

<water gas shift> $CO+H_2O=>H_2+CO_2$ (2)

<reforming and water gas shift combined> $CH_4+2H_2O=>4H_2+CO_2$ (3)

<anode $H_2$ oxidation> $H_2+CO_3^{2-}=>H_2O+CO_2+2e^-$ (4)

<cathode> $\frac{1}{2}O_2+CO_2+2e^-=>CO_3^{2-}$ (5)

Reaction (1) represents the basic hydrocarbon reforming reaction to generate $H_2$ for use in the anode of the fuel cell. The CO formed in reaction (1) can be converted to $H_2$ by the water-gas shift reaction (2). The combination of reactions (1) and (2) is shown as reaction (3). Reactions (1) and (2) can occur external to the fuel cell, and/or the reforming can be performed internal to the anode.

Reactions (4) and (5), at the anode and cathode respectively, represent the reactions that can result in electrical power generation within the fuel cell. Reaction (4) combines $H_2$, either present in the feed or optionally generated by reactions (1) and/or (2), with carbonate ions to form $H_2O$, $CO_2$, and electrons to the circuit. Reaction (5) combines $O_2$, $CO_2$, and electrons from the circuit to form carbonate ions. The carbonate ions generated by reaction (5) can be transported across the electrolyte of the fuel cell to provide the carbonate ions needed for reaction (4). In combination with the transport of carbonate ions across the electrolyte, a closed current loop can then be formed by providing an electrical connection between the anode and cathode.

In various embodiments, a goal of operating the fuel cell can be to improve the total efficiency of the fuel cell and/or the total efficiency of the fuel cell plus an integrated chemical synthesis process. This is typically in contrast to conventional operation of a fuel cell, where the goal can be to operate the fuel cell with high electrical efficiency for using the fuel provided to the cell for generation of electrical power. As defined above, total fuel cell efficiency may be determined by dividing the electric output of the fuel cell plus the lower heating value of the fuel cell outputs by the lower heating value of the input components for the fuel cell. In other words, TFCE=(LHV(el)+LHV(sg out))/LHV(in), where LHV(in) and LHV(sg out) refer to the LHV of the fuel components (such as $H_2$, $CH_4$, and/or CO) delivered to the fuel cell and syngas ($H_2$, CO and/or $CO_2$) in the anode outlet streams or flows, respectively. This can provide a measure of the electric energy plus chemical energy generated by the fuel cell and/or the integrated chemical process. It is noted that under this definition of total efficiency, heat energy used within the fuel cell and/or used within the integrated fuel cell/chemical synthesis system can contribute to total efficiency. However, any excess heat exchanged or otherwise withdrawn from the fuel cell or integrated fuel cell/chemical synthesis system is excluded from the definition. Thus, if excess heat from the fuel cell is used, for example, to generate steam for electricity generation by a steam turbine, such excess heat is excluded from the definition of total efficiency.

Several operational parameters may be manipulated to operate a fuel cell with excess reformable fuel. Some parameters can be similar to those currently recommended for fuel cell operation. In some aspects, the cathode conditions and temperature inputs to the fuel cell can be similar to those recommended in the literature. For example, the desired electrical efficiency and the desired total fuel cell efficiency may be achieved at a range of fuel cell operating temperatures typical for molten carbonate fuel cells. In typical operation, the temperature can increase across the fuel cell.

In other aspects, the operational parameters of the fuel cell can deviate from typical conditions so that the fuel cell is operated to allow a temperature decrease from the anode inlet to the anode outlet and/or from the cathode inlet to the cathode outlet. For example, the reforming reaction to convert a hydrocarbon into $H_2$ and CO is an endothermic reaction. If a sufficient amount of reforming is performed in a fuel cell anode relative to the amount of oxidation of hydrogen to generate electrical current, the net heat balance in the fuel cell can be endothermic. This can cause a temperature drop between the inlets and outlets of a fuel cell. During endothermic operation, the temperature drop in the fuel cell can be controlled so that the electrolyte in the fuel cell remains in a molten state.

Parameters that can be manipulated in a way so as to differ from those currently recommended can include the amount of fuel provided to the anode, the composition of the fuel provided to the anode, and/or the separation and capture of syngas in the anode output without significant recycling of syngas from the anode exhaust to either the anode input or the cathode input. In some aspects, no recycle of syngas or hydrogen from the anode exhaust to either the anode input or the cathode input can be allowed to occur, either directly or indirectly. In additional or alternative aspects, a limited amount of recycle can occur. In such aspects, the amount of recycle from the anode exhaust to the anode input and/or the cathode input can be less than about 10 vol % of the anode exhaust, such as less than about 5 vol %, or less than about 1 vol %.

Additionally or alternately, a goal of operating a fuel cell can be to separate $CO_2$ from the output stream of a combustion reaction or another process that produces a $CO_2$ output stream, in addition to allowing generation of electric power. In such aspects, the combustion reaction(s) can be used to power one or more generators or turbines, which can provide a majority of the power generated by the combined generator/fuel cell system. Rather than operating the fuel cell to optimize power generation by the fuel cell, the system can instead be operated to improve the capture of carbon dioxide from the combustion-powered generator while reducing or minimizing the number of fuels cells required for capturing the carbon dioxide. Selecting an appropriate configuration for the input and output flows of the fuel cell, as well as selecting appropriate operating conditions for the fuel cell, can allow for a desirable combination of total efficiency and carbon capture.

In some embodiments, the fuel cells in a fuel cell array can be arranged so that only a single stage of fuel cells (such as fuel cell stacks) can be present. In this type of embodiment, the anode fuel utilization for the single stage can represent the anode fuel utilization for the array. Another option can be that a fuel cell array can contain multiple stages of anodes and multiple stages of cathodes, with each anode stage having a fuel utilization within the same range, such as each anode stage having a fuel utilization within 10% of a specified value, for example within 5% of a specified value. Still another option can be that each anode stage can have a fuel utilization equal to a specified value or lower than the specified value by less than an amount, such as having each anode stage be not greater than a specified value by 10% or less, for example, by 5% or less. As an illustrative example, a fuel cell array with a plurality of anode stages can have each anode stage be within about 10% of 50% fuel utilization, which would correspond to each anode stage having a fuel utilization between about 40% and about 60%. As another example, a fuel cell array with a plurality of stages can have each anode stage be not greater than 60% anode fuel utilization with the maximum deviation being about 5% less, which would correspond to each anode stage having a fuel utilization between about 55% to about 60%. In still another example, one or more stages of fuel cells in a fuel cell array can be operated at a fuel utilization from about 30% to about 50%, such as operating a plurality of fuel cell stages in the array at a fuel utilization from about 30% to about 50%. More generally, any of the above types of ranges can be paired with any of the anode fuel utilization values specified herein.

Still another additional or alternate option can include specifying a fuel utilization for less than all of the anode stages. For example, in some aspects of the invention fuel cells/stacks can be arranged at least partially in one or more series arrangements such that anode fuel utilization can be specified for the first anode stage in a series, the second anode stage in a series, the final anode stage in a series, or any other convenient anode stage in a series. As used herein, the "first" stage in a series corresponds to the stage (or set of stages, if the arrangement contains parallel stages as well) to which input is directly fed from the fuel source(s), with later ("second," "third," "final," etc.) stages representing the stages to which the output from one or more previous stages is fed, instead of directly from the respective fuel source(s). In situations where both output from previous stages and input directly from the fuel source(s) are co-fed into a stage, there can be a "first" (set of) stage(s) and a "last" (set of) stage(s), but other stages ("second," "third," etc.) can be more tricky among which to establish an order (e.g., in such cases, ordinal order can be determined by concentration levels of one or more components in the composite input feed composition, such as $CO_2$ for instance, from highest concentration "first" to lowest concentration "last" with approximately similar compositional distinctions representing the same ordinal level.)

Yet another additional or alternate option can be to specify the anode fuel utilization corresponding to a particular cathode stage (again, where fuel cells/stacks can be arranged at least partially in one or more series arrangements). As noted above, based on the direction of the flows within the anodes and cathodes, the first cathode stage may not correspond to (be across the same fuel cell membrane from) the first anode stage. Thus, in some aspects of the invention, the anode fuel utilization can be specified for the first cathode stage in a series, the second cathode stage in a series, the final cathode stage in a series, or any other convenient cathode stage in a series.

Yet still another additional or alternate option can be to specify an overall average of fuel utilization over all fuel cells in a fuel cell array. In various aspects, the overall average of fuel utilization for a fuel cell array can be about 65% or less, for example, about 60% or less, about 55% or less, about 50% or less, or about 45% or less (additionally or alternately, the overall average fuel utilization for a fuel cell array can be at least about 25%, for example at least about 30%, at least about 35%, or at least about 40%). Such an average fuel utilization need not necessarily constrain the fuel utilization in any single stage, so long as the array of fuel cells meets the desired fuel utilization.

Applications for $CO_2$ Output after Capture

In various aspects of the invention, the systems and methods described above can allow for production of carbon dioxide as a pressurized fluid. For example, the $CO_2$ generated from a cryogenic separation stage can initially correspond to a pressurized $CO_2$ liquid with a purity of at least about 90%, e.g., at least about 95%, at least about 97%, at least about 98%, or at least about 99%. This pressurized $CO_2$ stream can be used, e.g., for injection into wells in order to further enhance oil or gas recovery such as in secondary oil recovery. When done in proximity to a facility that encompasses a gas turbine, the overall system may benefit from additional synergies in use of electrical/mechanical power and/or through heat integration with the overall system.

Alternatively, for systems dedicated to an enhanced oil recovery (EOR) application (i.e., not comingled in a pipeline system with tight compositional standards), the $CO_2$ separation requirements may be substantially relaxed. The EOR application can be sensitive to the presence of $O_2$, so $O_2$ can be absent, in some embodiments, from a $CO_2$ stream intended for use in EOR. However, the EOR application can tend to have a low sensitivity to dissolved CO, $H_2$, and/or $CH_4$. Also, pipelines that transport the $CO_2$ can be sensitive to these impurities. Those dissolved gases can typically have only subtle impacts on the solubilizing ability of $CO_2$ used for EOR. Injecting gases such as CO, $H_2$, and/or $CH_4$ as EOR gases can result in some loss of fuel value recovery, but such gases can be otherwise compatible with EOR applications.

Additionally or alternately, a potential use for $CO_2$ as a pressurized liquid can be as a nutrient in biological processes such as algae growth/harvesting. The use of MCFCs for $CO_2$ separation can ensure that most biologically significant pollutants could be reduced to acceptably low levels, resulting in a $CO_2$-containing stream having only minor amounts of other "contaminant" gases (such as CO, $H_2$, $N_2$, and the like, and combinations thereof) that are unlikely to substantially negatively affect the growth of photosynthetic organisms. This can be in stark contrast to the output streams generated by most industrial sources, which can often contain potentially highly toxic material such as heavy metals.

In this type of aspect of the invention, the $CO_2$ stream generated by separation of $CO_2$ in the anode loop can be used to produce biofuels and/or chemicals, as well as precursors thereof. Further additionally or alternately, $CO_2$ may be produced as a dense fluid, allowing for much easier pumping and transport across distances, e.g., to large fields of photosynthetic organisms. Conventional emission sources can emit hot gas containing modest amounts of $CO_2$ (e.g., about 4-15%) mixed with other gases and pollutants. These materials would normally need to be pumped as a dilute gas to an algae pond or biofuel "farm". By contrast, the MCFC system according to the invention can produce a concentrated $CO_2$ stream (~60-70% by volume on a dry basis) that can be concentrated further to 95%+ (for example 96%$^+$, 97%$^+$, 98%$^+$, or 99%$^+$) and easily liquefied. This stream can then be transported easily and efficiently over long distances at relatively low cost and effectively distributed over a wide area. In these embodiments, residual heat from the combustion source/MCFC may be integrated into the overall system as well.

An alternative embodiment may apply where the $CO_2$ source/MCFC and biological/chemical production sites are co-located. In that case, only minimal compression may be necessary (i.e., to provide enough $CO_2$ pressure to use in the biological production, e.g., from about 15 psig to about 150 psig). Several novel arrangements can be possible in such a case. Secondary reforming may optionally be applied to the anode exhaust to reduce $CH_4$ content, and water-gas shift may optionally additionally or alternately be present to drive any remaining CO into $CO_2$ and $H_2$.

The components from an anode output stream and/or cathode output stream can be used for a variety of purposes. One option can be to use the anode output as a source of hydrogen, as described above. For an MCFC integrated with or co-located with a refinery, the hydrogen can be used as a hydrogen source for various refinery processes, such as hydroprocessing. Another option can be to additionally or alternately use hydrogen as a fuel source where the $CO_2$ from combustion has already been "captured." Such hydrogen can be used in a refinery or other industrial setting as a fuel for a boiler, furnace, and/or fired heater, and/or the hydrogen can be used as a feed for an electric power generator, such as a turbine. Hydrogen from an MCFC fuel cell can further additionally or alternately be used as an input stream for other types of fuel cells that require hydrogen as an input, possibly including vehicles powered by fuel cells. Still another option can be to additionally or alternately use syngas generated as an output from an MCFC fuel cell as a fermentation input.

Another option can be to additionally or alternately use syngas generated from the anode output. Of course, syngas can be used as a fuel, although a syngas based fuel can still lead to some $CO_2$ production when burned as fuel. In other aspects, a syngas output stream can be used as an input for a chemical synthesis process. One option can be to additionally or alternately use syngas for a Fischer-Tropsch type process, and/or another process where larger hydrocarbon molecules are formed from the syngas input. Another option can be to additionally or alternately use syngas to form an intermediate product such as methanol. Methanol could be used as the final product, but in other aspects methanol generated from syngas can be used to generate larger compounds, such as gasoline, olefins, aromatics, and/or other products. It is noted that a small amount of $CO_2$ can be acceptable in the syngas feed to a methanol synthesis process, and/or to a Fischer-Tropsch process utilizing a shifting catalyst. Hydroformylation is an additional or alternate example of still another synthesis process that can make use of a syngas input.

It is noted that one variation on use of an MCFC to generate syngas can be to use MCFC fuel cells as part of a system for processing methane and/or natural gas withdrawn by an offshore oil platform or other production system that is a considerable distance from its ultimate market. Instead of attempting to transport the gas phase output from a well, or attempting to store the gas phase product for an extended period, the gas phase output from a well can be used as the input to an MCFC fuel cell array. This can lead to a variety of benefits. First, the electric power generated by the fuel cell array can be used as a power source for the platform. Additionally, the syngas output from the fuel cell array can be used as an input for a Fischer-Tropsch process at the production site. This can allow for formation of liquid hydrocarbon products more easily transported by pipeline, ship, or railcar from the production site to, for example, an on-shore facility or a larger terminal.

Still other integration options can additionally or alternately include using the cathode output as a source of higher purity, heated nitrogen. The cathode input can often include a large portion of air, which means a substantial portion of nitrogen can be included in the cathode input. The fuel cell can transport $CO_2$ and $O_2$ from the cathode across the electrolyte to the anode, and the cathode outlet can have lower concentrations of $CO_2$ and $O_2$, and thus a higher concentration of $N_2$ than found in air. With subsequent removal of the residual $O_2$ and $CO_2$, this nitrogen output can be used as an input for production of ammonia or other nitrogen-containing chemicals, such as urea, ammonium nitrate, and/or nitric acid. It is noted that urea synthesis could additionally or alternately use $CO_2$ separate from the anode output as an input feed.

Integration Example—Applications for Integration with Combustion Turbines

In some aspects of the invention, a combustion source for generating power and exhausting a $CO_2$-containing exhaust can be integrated with the operation of molten carbonate fuel cells. An example of a suitable combustion source is a gas turbine. Preferably, the gas turbine can combust natural gas, methane gas, or another hydrocarbon gas in a combined cycle mode integrated with steam generation and heat recovery for additional efficiency. Modern natural gas combined cycle efficiencies are about 60% for the largest and newest designs. The resulting $CO_2$-containing exhaust gas stream can be produced at an elevated temperature compatible with the MCFC operation, such as 300° C.-700° C. and preferably 500° C.-650° C. The gas source can optionally but preferably be cleaned of contaminants such as sulfur that can poison the MCFC before entering the turbine. Alternatively, the gas source can be a coal-fired generator, wherein the exhaust gas would typically be cleaned post-combustion due to the greater level of contaminants in the exhaust gas. In such an alternative, some heat exchange to/from the gas may be necessary to enable clean-up at lower temperatures. In additional or alternate embodiments, the source of the $CO_2$-containing exhaust gas can be the output from a boiler, combustor, or other heat source that burns carbon-rich fuels. In other additional or alternate embodiments, the source of the $CO_2$-containing exhaust gas can be bio-produced $CO_2$ in combination with other sources.

For integration with a combustion source, some alternative configurations for processing of a fuel cell anode can be desirable. For example, an alternative configuration can be to recycle at least a portion of the exhaust from a fuel cell anode to the input of a fuel cell anode. The output stream from an MCFC anode can include $H_2O$, $CO_2$, optionally CO, and optionally but typically unreacted fuel (such as $H_2$ or $CH_4$) as the primary output components. Instead of using this output stream as an external fuel stream and/or an input stream for integration with another process, one or more separations can be performed on the anode output stream in order to separate the $CO_2$ from the components with potential fuel value, such as $H_2$ or CO. The components with fuel value can then be recycled to the input of an anode.

This type of configuration can provide one or more benefits. First, $CO_2$ can be separated from the anode output, such as by using a cryogenic $CO_2$ separator. Several of the components of the anode output ($H_2$, CO, $CH_4$) are not easily condensable components, while $CO_2$ and $H_2O$ can be separated individually as condensed phases. Depending on the embodiment, at least about 90 vol % of the $CO_2$ in the anode output can be separated to form a relatively high purity $CO_2$ output stream. Alternatively, in some aspects less $CO_2$ can be removed from the anode output, so that about 50 vol % to about 90 vol % of the $CO_2$ in the anode output can be separated out, such as about 80 vol % or less or about 70 vol % or less. After separation, the remaining portion of the anode output can correspond primarily to components with fuel value, as well as reduced amounts of $CO_2$ and/or $H_2O$. This portion of the anode output after separation can be recycled for use as part of the anode input, along with additional fuel. In this type of configuration, even though the fuel utilization in a single pass through the MCFC(s) may be low, the unused fuel can be advantageously recycled for another pass through the anode. As a result, the single-pass fuel utilization can be at a reduced level, while avoiding loss (exhaust) of unburned fuel to the environment.

Additionally or alternatively to recycling a portion of the anode exhaust to the anode input, another configuration option can be to use a portion of the anode exhaust as an input for a combustion reaction for a turbine or other combustion device, such as a boiler, furnace, and/or fired heater. The relative amounts of anode exhaust recycled to the anode input and/or as an input to the combustion device can be any convenient or desirable amount. If the anode exhaust is recycled to only one of the anode input and the combustion device, the amount of recycle can be any convenient amount, such as up to 100% of the portion of the anode exhaust remaining after any separation to remove $CO_2$ and/or $H_2O$. When a portion of the anode exhaust is recycled to both the anode input and the combustion device, the total recycled amount by definition can be 100% or less of the remaining portion of anode exhaust. Otherwise, any convenient split of the anode exhaust can be used. In various embodiments of the invention, the amount of recycle to the anode input can be at least about 10% of the anode exhaust remaining after separations, for example at least about 25%, at least about 40%, at least about 50%, at least about 60%, at least about 75%, or at least about 90%. Additionally or alternately in those embodiments, the amount of recycle to the anode input can be about 90% or less of the anode exhaust remaining after separations, for example about 75% or less, about 60% or less, about 50% or less, about 40% or less, about 25% or less, or about 10% or less. Further additionally or alternately, in various embodiments of the invention, the amount of recycle to the combustion device can be at least about 10% of the anode exhaust remaining after separations, for example at least about 25%, at least about 40%, at least about 50%, at least about 60%, at least about 75%, or at least about 90%. Additionally or alternately in those embodiments, the amount of recycle to the combustion device can be about 90% or less of the anode exhaust remaining after separations, for example about 75% or less, about 60% or less, about 50% or less, about 40% or less, about 25% or less, or about 10% or less.

In still other alternative aspects of the invention, the fuel for a combustion device can additionally or alternately be a fuel with an elevated quantity of components that are inert and/or otherwise act as a diluent in the fuel. $CO_2$ and $N_2$ are examples of components in a natural gas feed that can be relatively inert during a combustion reaction. When the amount of inert components in a fuel feed reaches a sufficient level, the performance of a turbine or other combustion source can be impacted. The impact can be due in part to the ability of the inert components to absorb heat, which can tend to quench the combustion reaction. Examples of fuel feeds with a sufficient level of inert components can include fuel feeds containing at least about 20 vol % $CO_2$, or fuel feeds containing at least about 40 vol % $N_2$, or fuel feeds containing combinations of $CO_2$ and $N_2$ that have sufficient inert heat capacity to provide similar quenching ability. (It is noted that $CO_2$ has a greater heat capacity than $N_2$, and therefore lower concentrations of $CO_2$ can have a similar impact as higher concentrations of $N_2$. $CO_2$ can also participate in the combustion reactions more readily than $N_2$, and in doing so remove $H_2$ from the combustion. This consumption of $H_2$ can have a large impact on the combustion of the fuel, by reducing the flame speed and narrowing the flammability range of the air and fuel mixture.) More generally, for a fuel feed containing inert components that impact the flammability of the fuel feed, the inert components in the fuel feed can be at least about 20 vol %, such as at least about 40 vol %, or at least about 50 vol %, or at least about 60 vol %. Preferably, the amount of inert components in the fuel feed can be about 80 vol % or less.

When a sufficient amount of inert components are present in a fuel feed, the resulting fuel feed can be outside of the flammability window for the fuel components of the feed. In this type of situation, addition of $H_2$ from a recycled portion of the anode exhaust to the combustion zone for the generator can expand the flammability window for the combination of fuel feed and $H_2$, which can allow, for example, a fuel feed containing at least about 20 vol % $CO_2$ or at least about 40% $N_2$ (or other combinations of $CO_2$ and $N_2$) to be successfully combusted.

Relative to a total volume of fuel feed and $H_2$ delivered to a combustion zone, the amount of $H_2$ for expanding the flammability window can be at least about 5 vol % of the total volume of fuel feed plus $H_2$, such as at least about 10 vol %, and/or about 25 vol % or less. Another option for characterizing the amount of $H_2$ to add to expand the flammability window can be based on the amount of fuel components present in the fuel feed before $H_2$ addition. Fuel components can correspond to methane, natural gas, other hydrocarbons, and/or other components conventionally viewed as fuel for a combustion-powered turbine or other generator. The amount of $H_2$ added to the fuel feed can correspond to at least about one third of the volume of fuel components (1:3 ratio of $H_2$:fuel component) in the fuel feed, such as at least about half of the volume of the fuel components (1:2 ratio). Additionally or alternately, the amount of $H_2$ added to the fuel feed can be roughly equal to the volume of fuel components in the fuel feed (1:1 ratio) or less. For example, for a feed containing about 30 vol % $CH_4$, about 10% $N_2$, and about 60% $CO_2$, a sufficient amount of anode exhaust can be added to the fuel feed to achieve about a 1:2 ratio of $H_2$ to $CH_4$. For an idealized anode exhaust that contained only $H_2$, addition of $H_2$ to achieve a 1:2 ratio would result in a feed containing about 26 vol % $CH_4$, 13 vol % $H_2$, 9 vol % $N_2$, and 52 vol % $CO_2$.

Exhaust Gas Recycle

Aside from providing exhaust gas to a fuel cell array for capture and eventual separation of the $CO_2$, an additional or alternate potential use for exhaust gas can include recycle back to the combustion reaction to increase the $CO_2$ content. When hydrogen is available for addition to the combustion reaction, such as hydrogen from the anode exhaust of the fuel cell array, further benefits can be gained from using recycled exhaust gas to increase the $CO_2$ content within the combustion reaction.

In various aspects of the invention, the exhaust gas recycle loop of a power generation system can receive a first portion of the exhaust gas from combustion, while the fuel cell array can receive a second portion. The amount of exhaust gas from combustion recycled to the combustion zone of the power generation system can be any convenient amount, such as at least about 15% (by volume), for example at least about 25%, at least about 35%, at least about 45%, or at least about 50%. Additionally or alternately, the amount of combustion exhaust gas recirculated to the combustion zone can be about 65% (by volume) or less, e.g., about 60% or less, about 55% or less, about 50% or less, or about 45% or less.

In one or more aspects of the invention, a mixture of an oxidant (such as air and/or oxygen-enriched air) and fuel can be combusted and (simultaneously) mixed with a stream of recycled exhaust gas. The stream of recycled exhaust gas, which can generally include products of combustion such as $CO_2$, can be used as a diluent to control, adjust, or otherwise moderate the temperature of combustion and of the exhaust that can enter the succeeding expander. As a result of using oxygen-enriched air, the recycled exhaust gas can have an increased $CO_2$ content, thereby allowing the expander to operate at even higher expansion ratios for the same inlet and discharge temperatures, thereby enabling significantly increased power production.

A gas turbine system can represent one example of a power generation system where recycled exhaust gas can be used to enhance the performance of the system. The gas turbine system can have a first/main compressor coupled to an expander via a shaft. The shaft can be any mechanical, electrical, or other power coupling, thereby allowing a portion of the mechanical energy generated by the expander to drive the main compressor. The gas turbine system can also include a combustion chamber configured to combust a mixture of a fuel and an oxidant. In various aspects of the invention, the fuel can include any suitable hydrocarbon gas/liquid, such as syngas, natural gas, methane, ethane, propane, butane, naphtha diesel, kerosene, aviation fuel, coal derived fuel, bio-fuel, oxygenated hydrocarbon feedstock, or any combinations thereof. The oxidant can, in some embodiments, be derived from a second or inlet compressor fluidly coupled to the combustion chamber and adapted to compress a feed oxidant. In one or more embodiments of the invention, the feed oxidant can include atmospheric air and/or enriched air. When the oxidant includes enriched air alone or a mixture of atmospheric air and enriched air, the enriched air can be compressed by the inlet compressor (in the mixture, either before or after being mixed with the atmospheric air). The enriched air and/or the air-enriched air mixture can have an overall oxygen concentration of at least about 25 volume %, e.g., at least about 30 volume %, at least about 35 volume %, at least about 40 volume %, at least about 45 volume %, or at least about 50 volume %. Additionally or alternately, the enriched air and/or the air-enriched air mixture can have an overall oxygen concentration of about 80 volume % or less, such as about 70 volume % or less.

The enriched air can be derived from any one or more of several sources. For example, the enriched air can be derived from such separation technologies as membrane separation, pressure swing adsorption, temperature swing adsorption, nitrogen plant-byproduct streams, and/or combinations thereof. The enriched air can additionally or alternately be derived from an air separation unit (ASU), such as a cryogenic ASU, for producing nitrogen for pressure maintenance or other purposes. In certain embodiments of the invention, the reject stream from such an ASU can be rich in oxygen, having an overall oxygen content from about 50 volume % to about 70 volume %, can be used as at least a portion of the enriched air and subsequently diluted, if needed, with unprocessed atmospheric air to obtain the desired oxygen concentration.

In addition to the fuel and oxidant, the combustion chamber can optionally also receive a compressed recycle exhaust gas, such as an exhaust gas recirculation primarily having $CO_2$ and nitrogen components. The compressed recycle exhaust gas can be derived from the main compressor, for instance, and adapted to help facilitate combustion of the oxidant and fuel, e.g., by moderating the temperature of the combustion products. As can be appreciated, recirculating the exhaust gas can serve to increase $CO_2$ concentration.

An exhaust gas directed to the inlet of the expander can be generated as a product of combustion reaction. The exhaust gas can have a heightened $CO_2$ content based, at least in part, on the introduction of recycled exhaust gas into the combustion reaction. As the exhaust gas expands through the expander, it can generate mechanical power to drive the main compressor, to drive an electrical generator, and/or to power other facilities.

The power generation system can, in many embodiments, also include an exhaust gas recirculation (EGR) system. In one or more aspects of the invention, the EGR system can include a heat recovery steam generator (HRSG) and/or another similar device fluidly coupled to a steam gas turbine. In at least one embodiment, the combination of the HRSG and the steam gas turbine can be characterized as a power-producing closed Rankine cycle. In combination with the gas turbine system, the HRSG and the steam gas turbine can form part of a combined-cycle power generating plant, such as a natural gas combined-cycle (NGCC) plant. The gaseous exhaust can be introduced to the HRSG in order to generate steam and a cooled exhaust gas. The HRSG can include various units for separating and/or condensing water out of the exhaust stream, transferring heat to form steam, and/or modifying the pressure of streams to a desired level. In certain embodiments, the steam can be sent to the steam gas turbine to generate additional electrical power.

After passing through the HRSG and optional removal of at least some $H_2O$, the $CO_2$-containing exhaust stream can, in some embodiments, be recycled for use as an input to the combustion reaction. As noted above, the exhaust stream can be compressed (or decompressed) to match the desired reaction pressure within the vessel for the combustion reaction.

Example of Integrated System

Figure 4:
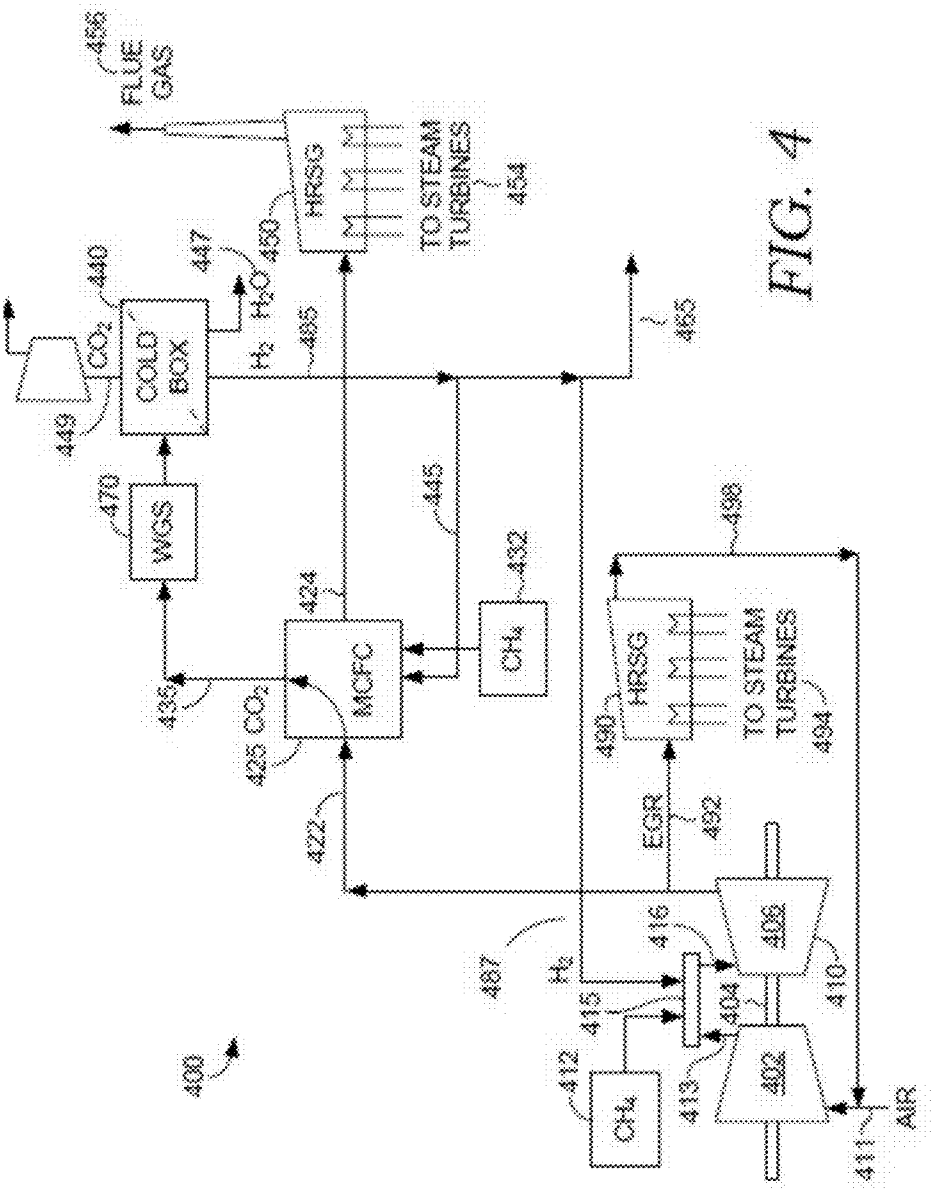
FIG. 4 schematically shows an example of a combined cycle system for generating electricity based on combustion of a carbon-based fuel.

FIG. 4 schematically shows an example of an integrated system including introduction of both $CO_2$-containing recycled exhaust gas and $H_2$ or CO from the fuel cell anode exhaust into the combustion reaction for powering a turbine. In FIG. 4, the turbine can include a compressor 402, a shaft 404, an expander 406, and a combustion zone 415. An oxygen source 411 (such as air and/or oxygen-enriched air) can be combined with recycled exhaust gas 498 and compressed in compressor 402 prior to entering combustion zone 415. A fuel 412, such as $CH_4$, and optionally a stream containing $H_2$ or CO 187 can be delivered to the combustion zone. The fuel and oxidant can be reacted in zone 415 and optionally but preferably passed through expander 406 to generate electric power. The exhaust gas from expander 106 can be used to form two streams, e.g., a $CO_2$-containing stream 422 (that can be used as an input feed for fuel cell array 425) and another $CO_2$-containing stream 492 (that can be used as the input for a heat recovery and steam generator system 490, which can, for example, enable additional electricity to be generated using steam turbines 494). After passing through heat recovery system 490, including optional removal of a portion of $H_2O$ from the $CO_2$-containing stream, the output stream 498 can be recycled for compression in compressor 402 or a second compressor that is not shown. The proportion of the exhaust from expander 406 used for $CO_2$-containing stream 492 can be determined based on the desired amount of $CO_2$ for addition to combustion zone 415.

As used herein, the EGR ratio is the flow rate for the fuel cell bound portion of the exhaust gas divided by the combined flow rate for the fuel cell bound portion and the recovery bound portion, which is sent to the heat recovery generator. For example, the EGR ratio for flows shown in FIG. 4 is the flow rate of stream 422 divided by the combined flow rate of streams 422 and 492.

The $CO_2$-containing stream 422 can be passed into a cathode portion (not shown) of a molten carbonate fuel cell array 425. Based on the reactions within fuel cell array 425, $CO_2$ can be separated from stream 422 and transported to the anode portion (not shown) of the fuel cell array 425. This can result in a cathode output stream 424 depleted in $CO_2$. The cathode output stream 424 can then be passed into a heat recovery (and optional steam generator) system 450 for generation of heat exchange and/or additional generation of electricity using steam turbines 454 (which may optionally be the same as the aforementioned steam turbines 494). After passing through heat recovery and steam generator system 450, the resulting flue gas stream 456 can be exhausted to the environment and/or passed through another type of carbon capture technology, such as an amine scrubber.

After transport of $CO_2$ from the cathode side to the anode side of fuel cell array 425, the anode output 435 can optionally be passed into a water gas shift reactor 470. Water gas shift reactor 470 can be used to generate additional $H_2$ and $CO_2$ at the expense of CO (and $H_2O$) present in the anode output 435. The output from the optional water gas shift reactor 470 can then be passed into one or more separation stages 440, such as a cold box or a cryogenic separator. This can allow for separation of an $H_2O$ stream 447 and $CO_2$ stream 449 from the remaining portion of the anode output. The remaining portion of the anode output 485 can include unreacted $H_2$ generated by reforming but not consumed in fuel cell array 425. A first portion 445 of the $H_2$-containing stream 485 can be recycled to the input for the anode(s) in fuel cell array 425. A second portion 487 of stream 485 can be used as an input for combustion zone 415. A third portion 465 can be used as is for another purpose and/or treated for subsequent further use. Although FIG. 4 and the description herein schematically details up to three portions, it is contemplated that only one of these three portions can be exploited, only two can be exploited, or all three can be exploited according to the invention.

Figure 5:
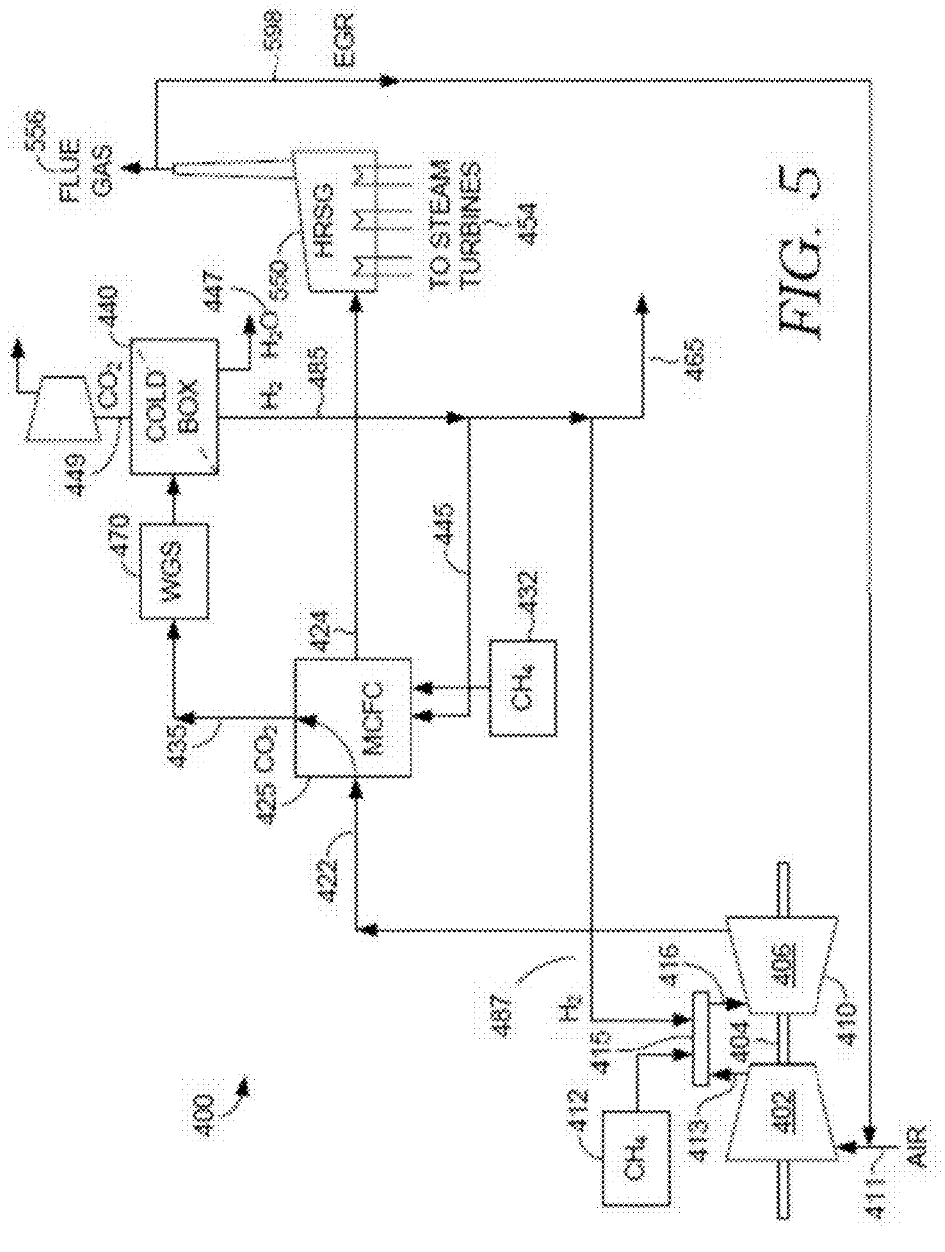
FIG. 5 schematically shows an example of a combined cycle system for generating electricity based on combustion of a carbon-based fuel.

In FIG. 4, the exhaust for the exhaust gas recycle loop is provided by a first heat recovery and steam generator system 490, while a second heat recovery and steam generator system 450 can be used to capture excess heat from the cathode output of the fuel cell array 425. FIG. 5 shows an alternative embodiment where the exhaust gas recycle loop is provided by the same heat recovery steam generator used for processing the fuel cell array output. In FIG. 5, recycled exhaust gas 598 is provided by heat recovery and steam generator system 550 as a portion of the flue gas stream 556. This can eliminate the separate heat recovery and steam generator system associated with the turbine.

In various embodiments of the invention, the process can be approached as starting with a combustion reaction for powering a turbine, an internal combustion engine, or another system where heat and/or pressure generated by a combustion reaction can be converted into another form of power. The fuel for the combustion reaction can comprise or be hydrogen, a hydrocarbon, and/or any other compound containing carbon that can be oxidized (combusted) to release energy. Except for when the fuel contains only hydrogen, the composition of the exhaust gas from the combustion reaction can have a range of $CO_2$ contents, depending on the nature of the reaction (e.g., from at least about 2 vol % to about 25 vol % or less). Thus, in certain embodiments where the fuel is carbonaceous, the $CO_2$ content of the exhaust gas can be at least about 2 vol %, for example at least about 4 vol %, at least about 5 vol %, at least about 6 vol %, at least about 8 vol %, or at least about 10 vol %. Additionally or alternately in such carbonaceous fuel embodiments, the $CO_2$ content can be about 25 vol % or less, for example about 20 vol % or less, about 15 vol % or less, about 10 vol % or less, about 7 vol % or less, or about 5 vol % or less. Exhaust gases with lower relative $CO_2$ contents (for carbonaceous fuels) can correspond to exhaust gases from combustion reactions on fuels such as natural gas with lean (excess air) combustion. Higher relative $CO_2$ content exhaust gases (for carbonaceous fuels) can correspond to optimized natural gas combustion reactions, such as those with exhaust gas recycle, and/or combustion of fuels such as coal.

In some aspects of the invention, the fuel for the combustion reaction can contain at least about 90 volume % of compounds containing five carbons or less, e.g., at least about 95 volume %. In such aspects, the $CO_2$ content of the exhaust gas can be at least about 4 vol %, for example at least about 5 vol %, at least about 6 vol %, at least about 7 vol %, or at least about 7.5 vol %. Additionally or alternately, the $CO_2$ content of the exhaust gas can be about 13 vol % or less, e.g., about 12 vol % or less, about 10 vol % or less, about 9 vol % or less, about 8 vol % or less, about 7 vol % or less, or about 6 vol % or less. The $CO_2$ content of the exhaust gas can represent a range of values depending on the configuration of the combustion-powered generator. Recycle of an exhaust gas can be beneficial for achieving a $CO_2$ content of at least about 6 vol %, while addition of hydrogen to the combustion reaction can allow for further increases in $CO_2$ content to achieve a $CO_2$ content of at least about 7.5 vol %.

Alternative Configuration—High Severity NOx Turbine

Gas turbines can be limited in their operation by several factors. One typical limitation can be that the maximum temperature in the combustion zone can be controlled below certain limits to achieve sufficiently low concentrations of nitrogen oxides (NOx) in order to satisfy regulatory emission limits. Regulatory emission limits can require a combustion exhaust to have a NOx content of about 20 vppm or less, and possible 10 vppm or less, when the combustion exhaust is allowed to exit to the environment.

NOx formation in natural gas-fired combustion turbines can be a function of temperature and residence time. Reactions that result in formation of NOx can be of reduced and/or minimal importance below a flame temperature of about 1500° F., but NOx production can increase rapidly as the temperature increases beyond this point. In a gas turbine, initial combustion products can be mixed with extra air to cool the mixture to a temperature around 1200° F., and temperature can be limited by the metallurgy of the expander blades. Early gas turbines typically executed the combustion in diffusion flames that had stoichiometric zones with temperatures well above 1500° F., resulting in higher NOx concentrations. More recently, the current generation of 'Dry Low Nox' (DLN) burners can use special pre-mixed burners to burn natural gas at cooler lean (less fuel than stoichiometric) conditions. For example, more of the dilution air can be mixed in to the initial flame, and less can be mixed in later to bring the temperature down to the 1200° F. turbine-expander inlet temperature. The disadvantages for DLN burners can include poor performance at turndown, higher maintenance, narrow ranges of operation, and poor fuel flexibility. The latter can be a concern, as DLN burners can be more difficult to apply to fuels of varying quality (or difficult to apply at all to liquid fuels). For low BTU fuels, such as fuels containing a high content of $CO_2$, DLN burners are typically not used and instead diffusion burners can be used. In addition, gas turbine efficiency can be increased by using a higher turbine-expander inlet temperature. However, because there can be a limited amount of dilution air, and this amount can decrease with increased turbine-expander inlet temperature, the DLN burner can become less effective at maintaining low NOx as the efficiency of the gas turbine improves.

In various aspects of the invention, a system integrating a gas turbine with a fuel cell for carbon capture can allow use of higher combustion zone temperatures while reducing and/or minimizing additional NOx emissions, as well as enabling DLN-like NOx savings via use of turbine fuels that are not presently compatible with DLN burners. In such aspects, the turbine can be run at higher power (i.e., higher temperature) resulting in higher NOx emissions, but also higher power output and potentially higher efficiency. In some aspects of the invention, the amount of NOx in the combustion exhaust can be at least about 20 vppm, such as at least about 30 vppm, or at least about 40 vppm. Additionally or alternately, the amount of NOx in the combustion exhaust can be about 1000 vppm or less, such as about 500 vppm or less, or about 250 vppm or less, or about 150 vppm or less, or about 100 vppm or less. In order to reduce the NOx levels to levels required by regulation, the resulting NOx can be equilibrated via thermal NOx destruction (reduction of NOx levels to equilibrium levels in the exhaust stream) through one of several mechanisms, such as simple thermal destruction in the gas phase; catalyzed destruction from the nickel cathode catalyst in the fuel cell array; and/or assisted thermal destruction prior to the fuel cell by injection of small amounts of ammonia, urea, or other reductant. This can be assisted by introduction of hydrogen derived from the anode exhaust. Further reduction of NOx in the cathode of the fuel cell can be achieved via electrochemical destruction wherein the NOx can react at the cathode surface and can be destroyed. This can result in some nitrogen transport across the membrane electrolyte to the anode, where it may form ammonia or other reduced nitrogen compounds. With respect to NOx reduction methods involving an MCFC, the expected NOx reduction from a fuel cell/fuel cell array can be about 80% or less of the NOx in the input to the fuel cell cathode, such as about 70% or less, and/or at least about 5%. It is noted that sulfidic corrosion can also limit temperatures and affect turbine blade metallurgy in conventional systems. However, the sulfur restrictions of the MCFC system can typically require reduced fuel sulfur levels that reduce or minimize concerns related to sulfidic corrosion. Operating the MCFC array at low fuel utilization can further mitigate such concerns, such as in aspects where a portion of the fuel for the combustion reaction corresponds to hydrogen from the anode exhaust.

ADDITIONAL EMBODIMENTS

This group of embodiments is Group A. References to "any of the above embodiments" are meant to refer only to other embodiments within this Group.

Embodiment 1

A method for producing electricity, and hydrogen or syngas, using a molten carbonate fuel cell comprising an anode and cathode, the method comprising: introducing a fuel stream comprising a reformable fuel into the anode of the molten carbonate fuel cell, an internal reforming element associated with the anode, or a combination thereof; introducing a cathode inlet stream comprising $CO_2$ and $O_2$ into the cathode of the molten carbonate fuel cell; generating electricity within the molten carbonate fuel cell at a fuel utilization of about 65% or less (e.g., about 60% or less, about 55% or less, about 50% or less, about 45% or less, about 40% or less, about 35% or less, about 30% or less, about 25% or less, or about 20% or less) and at a cell operating voltage, a ratio of a cell operating voltage to a cell maximum voltage being about 0.65 or less (e.g., about 0.64 or less, about 0.63 or less, about 0.62 or less, or about 0.61 or less); generating an anode exhaust from an anode outlet of the molten carbonate fuel cell; and separating from the anode exhaust a $H_2$-containing stream, a syngas-containing stream, or a combination thereof.

Embodiment 2

The method of embodiment 1, further comprising reforming the reformable fuel, wherein at least about 90% of the reformable fuel introduced into the anode of the molten carbonate fuel cell, the internal reforming element associated with the anode of the molten carbonate fuel cell, or the combination thereof, is reformed in a single pass through the anode of the molten carbonate fuel cell.

Embodiment 3

The method of embodiment 1 or 2, wherein a reformable hydrogen content of the reformable fuel introduced into the anode, the internal reforming element associated with the anode, or the combination thereof, is at least about 75% greater (e.g., at least about 100% greater) than an amount of hydrogen oxidized to generate electricity.

Embodiment 4

The method of any of the above embodiments, wherein a $CO_2$ utilization of the cathode is at least about 50% (e.g., at least about 60%).

Embodiment 5

The method of any of the above embodiments, wherein the anode fuel stream comprises at least about 10 vol % inert compounds, at least about 10 vol % $CO_2$, or a combination thereof.

Embodiment 6

The method of any of the above embodiments, wherein the anode exhaust comprises $H_2$ and CO having a molar ratio of $H_2$ to CO from about 1.5:1 to about 10.0:1 (e.g., from about 3.0:1 to about 10:1).

Embodiment 7

The method of any of the above embodiments, wherein the $H_2$-containing stream contains at least about 90% $H_2$ (e.g., about 95 vol % $H_2$, or about 98 vol % $H_2$).

Embodiment 8

The method of any of the above embodiments, wherein the cathode inlet stream comprises about 20 vol % $CO_2$ or less (e.g., about 15 vol % $CO_2$ or less, or about 12 vol % $CO_2$ or less).

Embodiment 9

The method of any of the above embodiments, further comprising recycling at least a portion of the $H_2$-containing stream to a combustion turbine.

Embodiment 10

The method of any of the above embodiments, wherein at least about 90 vol % of the reformable fuel is methane.

Embodiment 11

The method of any of the above embodiments, wherein the molten carbonate fuel cell is operated at a thermal ratio from about 0.25 to about 1.5 (e.g., from about 0.25 to about 1.25, from about 0.25 to about 1.0, from about 0.25 to about 0.9, or from about 0.25 to about 0.85)

Embodiment 12

The method of any of the above embodiments, wherein a ratio of net moles of syngas in the anode exhaust to moles of $CO_2$ in a cathode exhaust is at least about 2.0:1 (e.g., at least about 2.5:1 or at least about 3:1).

Embodiment 13

The method of any of the above embodiments, wherein a fuel utilization in the anode is about 50% or less (e.g., about 45% or less, about 40% or less, about 35% or less, about 30% or less, or about 25% or less, or about 20% or less) and a $CO_2$ utilization in the cathode is at least about 60% (e.g., at least about 65%, at least about 70%, or at least about 75%).

Embodiment 14

The method of any of the above embodiments, wherein the molten carbonate fuel cell is operated to generate electrical power at a current density of at least about 150 $mA/cm^2$ and at least about 40 $mW/cm^2$ (e.g., at least about 50 $mW/cm^2$, at least about 60 $mW/cm^2$, at least about 80 $mW/cm^2$, or at least about 100 $mW/cm^2$) of waste heat, the method further comprising performing an effective amount of an endothermic reaction to maintain a temperature differential between an anode inlet and the anode outlet of about 100° C. or less (e.g., about 80° C. or less or about 60° C. or less), optionally wherein performing the endothermic reaction consumes at least about 40% (e.g., at least about 50%, at least about 60%, or at least about 70%) of the waste heat.

Embodiment 15

The method of any of the above embodiments, wherein an electrical efficiency for the molten carbonate fuel cell is between about 10% and about 40% and a total fuel cell efficiency for the molten carbonate fuel cell is at least about 55%.

This group of embodiments is Group B. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for producing electricity, the method comprising: introducing a recycled anode exhaust fuel stream, a low energy content fuel stream, and an $O_2$-containing stream into a combustion zone, the recycled anode exhaust fuel stream comprising $H_2$, the low energy content fuel stream comprising at least about 30 vol % of one or more inert gasses; performing a combustion reaction in the combustion zone to generate a combustion exhaust; introducing an anode fuel stream comprising a reformable fuel into an anode of a molten carbonate fuel cell, an internal reforming element associated with the anode of the molten carbonate fuel cell, or a combination thereof; introducing a cathode inlet stream comprising $CO_2$ and $O_2$ into a cathode of the molten carbonate fuel cell; generating electricity within the molten carbonate fuel cell; generating an anode exhaust comprising $H_2$ from an anode outlet of the molten carbonate fuel cell; and separating at least a portion of the anode exhaust to form the recycled anode exhaust fuel stream.

Embodiment 2

The method of Embodiment 1, wherein the low energy content fuel stream comprises at least about 35 vol %.

Embodiment 3

The method of Embodiment 1 or 2, wherein the one or more inert gases in the low energy content fuel stream are $CO_2$, $N_2$, or a combination thereof.

Embodiment 4

The method of any of the above Embodiments, wherein a fuel utilization of the anode of the molten carbonate fuel cell is about 65% or less (e.g., about 60% or less).

Embodiment 5

The method of any of the above Embodiments, wherein the fuel utilization of the anode of the molten carbonate fuel cell is about 30% to about 50%.

Embodiment 6

The method of any of the above Embodiments, further comprising recycling an anode-recycle portion of the anode exhaust stream to the one or more fuel cell anodes.

Embodiment 7

The method of any of the above Embodiments, wherein the reformable fuel comprises $CH_4$.

Embodiment 8

The method of any of the above Embodiments, wherein the cathode inlet stream comprises at least a portion of the combustion exhaust.

Embodiment 9

The method of any of the above Embodiments, wherein the combustion exhaust comprises about 10 vol % or less of $CO_2$, (e.g., about 8 vol % or less of $CO_2$), the combustion exhaust optionally comprising at least about 4 vol % of $CO_2$.

Embodiment 10

The method of any of the above Embodiments, wherein the anode exhaust stream comprises at least about 5.0 vol % of $H_2$ (e.g., at least about 10 vol % or at least about 15 vol %).

Embodiment 11

The method of any of the above Embodiments, further comprising exposing the anode exhaust stream to a water gas shift catalyst prior to the separating at least a portion of the anode exhaust stream to form the recycled anode exhaust fuel stream, a $H_2$ content of the shifted anode exhaust stream being greater than a $H_2$ content of the anode exhaust stream prior to the exposure.

Embodiment 12

The method of any of the above Embodiments, wherein the recycled anode exhaust fuel stream is combined with the low energy content fuel stream prior to passing the recycled anode exhaust fuel stream into the combustion zone.

Embodiment 13

The method of any of the above Embodiments, wherein a cathode exhaust stream has a $CO_2$ content of about 2.0 vol % or less, (e.g., about 1.5 vol % or less or about 1.2 vol % or less).

This group of embodiments is Group C. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for capturing carbon dioxide from a combustion source, the method comprising: introducing a fuel stream and an $O_2$-containing stream into a combustion zone; performing a combustion reaction in the combustion zone to generate a combustion exhaust, the combustion exhaust comprising $CO_2$; processing a cathode inlet stream, the cathode inlet stream comprising at least a first portion of the combustion exhaust, with a fuel cell array of one or more molten carbonate fuel cells to form a cathode exhaust stream from at least one cathode outlet of the fuel cell array, the one or more molten carbonate fuel cells comprising one or more fuel cell anodes and one or more fuel cell cathodes, the one or more molten carbonate fuel cells being operatively connected to the combustion zone through at least one cathode inlet; reacting carbonate from the one or more fuel cell cathodes with $H_2$ within the one or more fuel cell anodes to produce electricity and an anode exhaust stream from at least one anode outlet of the fuel cell array, the anode exhaust steam comprising $CO_2$ and $H_2$; separating $CO_2$ from the anode exhaust stream in one or more separation stages to form a $CO_2$-depleted anode exhaust stream; passing at least a combustion-recycle portion of the $CO_2$-depleted anode exhaust stream to the combustion zone; and recycling at least an anode-recycle portion of the $CO_2$-depleted anode exhaust stream to the one or more fuel cell anodes.

Embodiment 2

The method of Embodiment 1, wherein a fuel utilization in the one or more fuel cell anodes is about 65% or less (e.g., about 60% or less).

Embodiment 3

The method of Embodiment 2, wherein the fuel utilization in the one or more fuel cell anodes is about 30% to about 50%.

Embodiment 4

The method of claim Embodiment 2, wherein the one or more fuel cell anodes comprise a plurality of anode stages and the one or more fuel cell cathodes comprise a plurality of cathode stages, wherein a low utilization anode stage in the plurality of anode stages has an anode fuel utilization of 65% or less (such as about 60% or less), the low utilization anode stage corresponding to high utilization cathode stage of the plurality of cathode stages, the high utilization cathode stage having a $CO_2$ content at a cathode inlet as high as or higher than a $CO_2$ at a cathode inlet of any other cathode stage of the plurality of cathode stages.

Embodiment 5

The method of Embodiment 4, wherein the fuel utilization in the low utilization anode stage is at least about 40%, (e.g., at least about 45% or at least about 50%).

Embodiment 6

The method of Embodiment 4, wherein a fuel utilization in each anode stage of the plurality of anode stages is about 65% or less (e.g., about 60% or less).

Embodiment 7

The method of any of the above embodiments, wherein the combustion-recycle portion of the $CO_2$-depleted anode exhaust stream comprises at least about 25% of the $CO_2$-depleted anode exhaust stream, and wherein the anode-recycle portion of the $CO_2$-depleted anode exhaust stream comprises at least about 25% of the $CO_2$-depleted anode exhaust stream.

Embodiment 8

The method of Embodiment 7, further comprising passing carbon-containing fuel into the one or more fuel cell anodes, the carbon-containing fuel optionally comprising $CH_4$.

Embodiment 9

The method of Embodiment 8, further comprising: reforming at least a portion of the carbon-containing fuel to generate $H_2$; and passing at least a portion of the generated $H_2$ into the one or more fuel cell anodes.

Embodiment 10

The method of Embodiment 8, wherein the carbon-containing fuel is passed into the one or more fuel cell anodes without passing the carbon-containing fuel into a reforming stage prior to entering the one or more fuel cell anodes.

Embodiment 11

The method of any of the above embodiments, wherein the combustion exhaust comprises about 10 vol % or less of $CO_2$ (e.g., 8 vol % or less of $CO_2$), the combustion exhaust optionally comprising at least about 4 vol % of $CO_2$ Embodiment 12

The method of any of the above Embodiments, further comprising recycling a second portion of the combustion exhaust to the combustion zone, the second portion of the combustion exhaust optionally comprising at least about 6 vol % $CO_2$.

Embodiment 13

The method of Embodiment 12, wherein recycling the second portion of the combustion exhaust to the combustion zone comprises: exchanging heat between a second portion of the combustion exhaust and an $H_2O$-containing stream to form steam; separating water from the second portion of the combustion exhaust to form an $H_2O$-depleted combustion exhaust stream; and passing at least a portion of the $H_2O$-depleted combustion exhaust into the combustion zone.

Embodiment 14

The method of any of the above embodiments, wherein the anode exhaust stream, prior to the separating $CO_2$ from the anode exhaust stream in one or more separation stages, comprises at least about 5.0 vol % of $H_2$ (e.g., at least about 10 vol % or at least about 15 vol %).

Embodiment 15

The method of any of the above embodiments, further comprising exposing the anode exhaust stream to a water gas shift catalyst to form a shifted anode exhaust stream prior to the separating $CO_2$ from the anode exhaust stream in one or more separation stages, a $H_2$ content of the shifted anode exhaust stream after exposure to the water gas shift catalyst being greater than a $H_2$ content of the anode exhaust stream prior to exposure to the water gas shift catalyst.

Embodiment 16

The method of any of the above Embodiments, wherein the combustion-recycle portion of the $CO_2$-depleted anode exhaust stream is combined with the fuel stream prior to passing the combustion-recycle portion of the $CO_2$-depleted anode exhaust stream to the combustion zone.

Embodiment 17

The method of any of the above embodiments, wherein a cathode exhaust stream has a $CO_2$ content of about 2.0 vol % or less (e.g., about 1.5 vol % or less or about 1.2 vol % or less).

Embodiment 18

The method of any of the above embodiments, wherein separating $CO_2$ from the anode exhaust stream in one or more separation stages comprises: optionally separating water from the anode exhaust stream to form an optionally $H_2O$-depleted anode exhaust stream; cooling the optionally $H_2O$-depleted anode exhaust stream to form a condensed phase of $CO_2$.

This group of embodiments is Group D. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for capturing carbon dioxide from a combustion source, the method comprising: introducing a combustion fuel stream and an $O_2$-containing stream into a combustion zone; performing a combustion reaction in the combustion zone to generate a combustion exhaust, the combustion exhaust comprising $CO_2$; processing a cathode inlet stream, the cathode inlet stream comprising at least a first portion of the combustion exhaust, with a fuel cell array of one or more molten carbonate fuel cells to form a cathode exhaust stream from at least one cathode outlet of the fuel cell array, the one or more molten carbonate fuel cells comprising one or more fuel cell anodes and one or more fuel cell cathodes, the one or more molten carbonate fuel cells being operatively connected to the combustion zone through at least one cathode inlet; reacting carbonate from the one or more fuel cell cathodes with $H_2$ within the one or more fuel cell anodes to produce electricity and an anode exhaust stream from at least one anode outlet of the fuel cell array, the anode exhaust steam comprising $CO_2$ and $H_2$; separating $CO_2$ from the anode exhaust stream in one or more separation stages to form a $CO_2$-depleted anode exhaust stream; and passing at least a combustion-recycle portion of the $CO_2$-depleted anode exhaust stream to the combustion zone.

Embodiment 2

The method of Embodiment 1, further comprising recycling an anode-recycle portion of the $CO_2$-depleted anode exhaust stream to the one or more fuel cell anodes.

Embodiment 3

The method of Embodiment 2, further comprising passing carbon-containing fuel into the one or more fuel cell anodes, the carbon-containing fuel optionally comprising $CH_4$.

Embodiment 4

The method of Embodiment 3, wherein passing carbon-containing fuel into the one or more fuel cell anodes comprises: reforming at least a portion of the carbon-containing fuel to generate $H_2$; and passing at least a portion of the generated $H_2$ into the one or more fuel cell anodes.

Embodiment 5

The method of Embodiment 3, wherein the carbon-containing fuel is passed into the one or more fuel cell anodes without passing the carbon-containing fuel into a reforming stage prior to entering the one or more fuel cell anodes.

Embodiment 6

The method of any of the above embodiments, wherein the combustion exhaust comprises about 10 vol % or less of $CO_2$ (e.g., 8 vol % $CO_2$), the combustion exhaust optionally comprising at least about 4 vol % of $CO_2$ Embodiment 7

The method of any of the above embodiments, further comprising recycling a second portion of the combustion exhaust to the combustion zone, the second portion of the combustion exhaust optionally comprising at least about 6 vol % $CO_2$.

Embodiment 8

The method of Embodiment 7, wherein recycling the second portion of the combustion exhaust to the combustion zone comprises: exchanging heat between the second portion of the combustion exhaust and an $H_2O$-containing stream to form steam; separating water from the second portion of the combustion exhaust to form an $H_2O$-depleted combustion exhaust stream; and passing at least a portion of the $H_2O$-depleted combustion exhaust stream into the combustion zone.

Embodiment 9

The method of any of the above embodiments, wherein the anode exhaust stream, prior to the separating $CO_2$ from the anode exhaust stream in one or more separation stages, comprises at least about 5.0 vol % of hydrogen (e.g., at least about 10 vol % or at least about 15 vol %).

Embodiment 10

The method of any of the above embodiments, further comprising exposing the anode exhaust stream to a water gas shift catalyst to form a shifted anode exhaust stream prior to the separating $CO_2$ from the anode exhaust stream in one or more separation stages, a $H_2$ content of the shifted anode exhaust stream being greater than a $H_2$ content of the anode exhaust stream prior to exposure to the water gas shift catalyst.

Embodiment 11

The method of any of the above embodiments, wherein a fuel utilization of the one or more fuel cell anodes is about 45% to about 65% (e.g., about 60% or less).

Embodiment 12

The method of any of the above embodiments, wherein the combustion-recycle portion of the $CO_2$-depleted anode exhaust stream is combined with the combustion fuel stream prior to passing the combustion-recycle portion of the $CO_2$-depleted anode exhaust stream to the combustion zone.

Embodiment 13

The method of any of the above embodiments, wherein a cathode exhaust stream has a $CO_2$ content of about 2.0 vol % or less (e.g., about 1.5 vol % or less or about 1.2 vol % or less).

Embodiment 14

The method of any of the above embodiments, wherein separating $CO_2$ from the anode exhaust stream in one or more separation stages comprises cooling the anode exhaust stream to form a condensed phase of $CO_2$.

Embodiment 15

The method of Embodiment 14, wherein separating $CO_2$ from the anode exhaust stream in one or more separation stages further comprises separating water from the anode exhaust stream prior to forming the condensed phase of $CO_2$.

Embodiment 16

Additionally or alternately to any of the above groups of embodiments, a system for power generation, comprising: a combustion turbine including a compressor, the compressor receiving an oxidant input and being in fluid communication with a combustion zone, the combustion zone further receiving at least one combustion fuel input, the combustion zone being in fluid communication with an expander having an exhaust output; an exhaust gas recirculation system providing fluid communication between a first portion of the expander exhaust output and the combustion zone; a molten carbonate fuel cell array comprising one or more fuel cell anodes and one or more fuel cell cathodes, the molten carbonate fuel cell array having at least one cathode input, at least one cathode output, at least one anode input, and at least one anode output, a second portion of the expander exhaust output being in fluid communication with the at least one cathode input; and an anode recycle loop comprising one or more carbon dioxide separation stages for separating an anode exhaust stream to form an anode recycle loop output, a first portion of an anode recycle loop output being provided to the combustion zone as a combustion fuel input.

Embodiment 17

The system of Embodiment 16, wherein a second portion of the anode recycle loop output is provided to the at least one anode input.

Embodiment 18

The system of Embodiment 16 or 17, wherein the anode recycle loop further comprises a water gas shift reaction stage, the anode exhaust stream passing through the water gas shift reaction stage prior to at least one stage of the one or more carbon dioxide separation stages.

Embodiment 19

The system of any of Embodiments 16 to 18, wherein the exhaust gas recirculation system further comprises a heat recovery steam generation system.

Embodiment 20

The system of any of Embodiments 16 to 19, wherein the exhaust gas recirculation system provides fluid communication between a first portion of the expander exhaust output and the combustion zone by passing the first portion of the expander exhaust output into the compressor.

This group of embodiments is Group E. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for capturing carbon dioxide from a combustion source, said method comprising: capturing an output stream from a combustion source, the captured output stream comprising oxygen and carbon dioxide; processing the captured output stream with a fuel cell array of one or more molten carbonate fuel cells to form a cathode exhaust stream from at least one cathode outlet of the fuel cell array, the one or more molten carbonate fuel cells comprising one or more fuel cell anodes and one or more fuel cell cathodes, the one or more molten carbonate fuel cells being operatively connected to the captured output stream from the combustion source through at least one cathode inlet; reacting carbonate from the one or more fuel cell cathodes with $H_2$ within the one or more fuel cell anodes to produce electricity and an anode exhaust stream from at least one anode outlet of the fuel cell array, the anode exhaust steam comprising $CO_2$ and $H_2$; optionally passing the anode exhaust stream through a water gas shift reaction stage to form an optionally shifted anode exhaust stream; separating carbon dioxide from the optionally shifted anode exhaust stream in one or more separation stages to form a $CO_2$-depleted anode exhaust stream; and recycling at least a portion of the $CO_2$-depleted anode exhaust stream to the one or more fuel cell anodes, at least a portion of the $H_2$ reacted with carbonate comprising $H_2$ from the recycled at least a portion of the $CO_2$-depleted anode exhaust stream.

Embodiment 2

The method of Embodiment 1, wherein a $H_2$ content of the anode exhaust stream is at least about 10 vol % (e.g., at least about 20 vol %).

Embodiment 3

The method of any of the above Embodiments, wherein a fuel utilization of the one or more fuel cell anodes is about 60% or less (e.g., about 50% or less).

Embodiment 4

The method of any of the above Embodiments, wherein the fuel utilization of the one or more fuel cell anodes is at least about 30% (e.g., at least about 40%).

Embodiment 5

The method of any of the above Embodiments, wherein a cathode exhaust has a $CO_2$ content of about 2.0 vol % or less (e.g, about 1.5 vol % or less).

Embodiment 6

The method of any of the above Embodiments, further comprising passing carbon-containing fuel into the one or more fuel cell anodes.

Embodiment 7

The method of Embodiment 6, wherein the carbon-containing fuel is reformed in at least one reforming stage internal to an assembly, the assembly comprising the at least one reforming stage and the fuel cell array.

Embodiment 8

The method of Embodiment 6 or 7, wherein the $H_2$ from the recycled at least a portion of the $CO_2$-depleted anode exhaust stream comprises at least about 5 vol % of an anode input stream.

Embodiment 9

The method of Embodiment 8, wherein the carbon-containing fuel is passed into the one or more fuel cell anodes without passing the carbon-containing fuel into a reforming stage prior to entering the one or more fuel cell anodes.

Embodiment 10

The method of any of Embodiments 6-9, wherein the carbon-containing fuel comprises methane.

Embodiment 11

The method of any of the above Embodiments, wherein the at least a portion of the $CO_2$-depleted anode exhaust stream is recycled to the one or more anodes without recycling a portion of the anode exhaust stream, directly or indirectly, to the one or more cathodes.

Embodiment 12

The method of any of the above Embodiments, wherein the captured output stream comprises at least about 4 vol % $CO_2$.

Embodiment 13

The method of any of the above claims, wherein the captured output stream comprises about 8 vol % $CO_2$ or less.

This group of embodiments is Group F. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for producing electricity, and hydrogen or syngas, using a molten carbonate fuel cell comprising an anode and a cathode, the method comprising:

introducing an anode fuel stream comprising a reformable fuel into the anode of the molten carbonate fuel cell, an internal reforming element associated with the anode of the molten carbonate fuel cell, or a combination thereof; introducing a cathode inlet stream comprising $CO_2$ and $O_2$ into the cathode of the molten carbonate fuel cell; generating electricity within the molten carbonate fuel cell; generating an anode exhaust from an anode outlet of the molten carbonate fuel cell; separating from the anode exhaust a $H_2$-containing stream, a syngas-containing stream, or a combination thereof, wherein an amount of the reformable fuel introduced into the anode of the molten carbonate fuel cell, the internal reforming element associated with the anode of the molten carbonate fuel cell, or the combination thereof, provides a reformable fuel surplus ratio of at least about 2.0 (e.g., at least about 2.5 or at least about 3.0).

Embodiment 2

Additionally or alternately to any of the above groups of embodiments, a method for producing electricity, and hydrogen or syngas, using a molten carbonate fuel cell comprising an anode and a cathode, the method comprising: introducing an anode fuel stream comprising a reformable fuel into the anode of the molten carbonate fuel cell, an internal reforming element associated with the anode of the molten carbonate fuel cell, or a combination thereof; introducing a cathode inlet stream comprising $CO_2$ and $O_2$ into the cathode of the molten carbonate fuel cell; generating electricity within the molten carbonate fuel cell; generating an anode exhaust from an anode outlet of the molten carbonate fuel cell; separating from the anode exhaust a $H_2$-containing stream, a syngas-containing stream, or a combination thereof, wherein the anode fuel stream has a reformable hydrogen content that is at least 50% greater than an amount of $H_2$ oxidized in the anode of the molten carbonate fuel cell to generate electricity.

Embodiment 3

The method of Embodiment 1 or 2, wherein a reformable hydrogen content of the reformable fuel introduced into the anode of the molten carbonate fuel cell, the internal reforming element associated with the anode of the molten carbonate fuel cell, or the combination thereof, is at least about 75% greater than the amount of $H_2$ oxidized in the anode of the molten carbonate fuel cell to generate electricity (e.g., at least about 100% greater).

Embodiment 4

The method of any of the above Embodiments, the method further comprising reforming the reformable fuel, wherein at least about 90% of the reformable fuel introduced into the anode of the molten carbonate fuel cell, the internal reforming element associated with the anode of the molten carbonate fuel cell, or the combination thereof, is reformed in a single pass through the anode of the molten carbonate fuel cell.

Embodiment 5

The method of any of the above Embodiments, wherein a $CO_2$ utilization of the cathode is at least about 50%.

Embodiment 6

The method of any of the above Embodiments, wherein the anode fuel stream comprises at least about 10 vol % inert compounds, at least about 10 vol % $CO_2$, or a combination thereof.

Embodiment 7

The method of any of the above Embodiments, wherein the syngas-containing stream has a molar ratio of $H_2$ to CO from about 3.0:1 to about 1.0:1 (e.g., from about 2.5:1 to about 1.0:1, from about 3.0:1 to about 1.5:1, or from about 2.5:1 to about 1.5:1).

Embodiment 8

The method of any of the above Embodiments, wherein the anode exhaust has a molar ratio of $H_2$ to CO of about 1.5:1 to about 10:1 (e.g., from about 3.0:1 to about 10:1).

Embodiment 9

The method of any of the above Embodiments, wherein a) less than 10 vol % of the anode exhaust b) less than 10 vol % of $H_2$ produced in the anode of the molten carbonate fuel cell in a single pass or c) less than 10 vol % of the syngas-containing stream is directly or indirectly recycled to the anode of the molten carbonate fuel cell or the cathode of the molten carbonate fuel cell.

Embodiment 10

The method of any of Embodiments 1-8, wherein no portion of the anode exhaust is directly or indirectly recycled to the anode of the molten carbonate fuel cell, directly or indirectly recycled to the cathode of the molten carbonate fuel cell, or a combination thereof.

Embodiment 11

The method of any of the above Embodiments, further comprising separating at least one of $CO_2$ and $H_2O$ from one or a combination of i) the anode exhaust, ii) the hydrogen-containing stream, and iii) the syngas-containing stream.

Embodiment 12

The method of any of the above Embodiments, wherein the hydrogen-containing stream contains at least about 90 vol % $H_2$ (e.g., about 95 vol % $H_2$, or about 98 vol % $H_2$).

Embodiment 13

The method of any of the above Embodiments, wherein the cathode inlet stream comprises about 20 vol % $CO_2$ or less (e.g., about 15 vol % $CO_2$ or less, or about 12 vol % $CO_2$ or less).

Embodiment 14

The method of any of the above Embodiments, wherein the molten carbonate fuel cell is operated at a voltage $V_A$ of about 0.67 Volts or less (e.g., about 0.65 Volts or less).

This group of embodiments is Group G. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for producing electricity, and hydrogen or syngas, using a molten carbonate fuel cell having an anode and cathode, the method comprising: introducing an anode fuel stream comprising a reformable fuel into the anode of the molten carbonate fuel cell, an internal reforming element associated with the anode of the molten carbonate fuel cell, or a combination thereof; introducing a cathode inlet stream comprising $CO_2$ and $O_2$ into the cathode of the molten carbonate fuel cell; generating electricity within the molten carbonate fuel cell; generating an anode exhaust from an anode outlet of the molten carbonate fuel cell; separating from the anode exhaust a hydrogen-containing stream, a syngas-containing stream, or a combination thereof, wherein an electrical efficiency for the molten carbonate fuel cell is between about 10% and about 40% and a total fuel cell efficiency for the fuel cell of at least about 55%.

Embodiment 2

The method of Embodiment 1, wherein the syngas-containing stream has a molar ratio of $H_2$ to CO from about 3.0:1 to about 1.0:1 (e.g., from about 2.5:1 to about 1.0:1, from about 3.0:1 to about 1.5:1, or from about 2.5:1 to about 1.5:1).

Embodiment 3

The method of any of the above Embodiments, wherein the electrical efficiency for the molten carbonate fuel cell is about 35% or less (e.g., about 30% or less, about 25% or less, or about 20% or less).

Embodiment 4

The method of any of the above Embodiments, wherein the total fuel cell efficiency for the molten carbonate fuel cell is at least about 65% (e.g., at least about 70%, at least about 75%, or at least about 80%).

Embodiment 5

The method of any of the above Embodiments, the method further comprising reforming the reformable fuel, wherein at least about 90% of the reformable fuel introduced into the anode of the molten carbonate fuel cell, the reforming stage associated with the anode of the molten carbonate fuel cell, or a combination thereof is reformed in a single pass through the anode of the molten carbonate fuel cell.

Embodiment 6

The method of any of the above Embodiments, wherein a reformable hydrogen content of the reformable fuel introduced into the anode of the molten carbonate fuel cell, the internal reforming element associated with the anode of the molten carbonate fuel cell, or the combination thereof, is at least about 75% greater (e.g., at least about 100% greater) than an amount of $H_2$ oxidized in the anode of the molten carbonate fuel cell to generate electricity.

Embodiment 7

The method of any of the above Embodiments, wherein the anode fuel stream comprises at least about 10 vol % inert compounds, at least about 10 vol % $CO_2$, or a combination thereof.

Embodiment 8

The method of any of the above Embodiments, wherein a) less than 10 vol % of the anode exhaust, b) less than 10 vol % of $H_2$ produced in the anode of the molten carbonate fuel cell in a single pass, or c) less than 10 vol % of the syngas-containing stream is directly or indirectly recycled to the anode of the molten carbonate fuel cell or the cathode of the molten carbonate fuel cell.

Embodiment 9

The method of any of Embodiments 1-7, wherein no portion of the anode exhaust is directly or indirectly recycled to the anode of the molten carbonate fuel cell, directly or indirectly recycled to the cathode of the molten carbonate fuel cell, or a combination thereof.

Embodiment 10

The method of any of the above Embodiments, further comprising separating at least one of $CO_2$ and $H_2O$ from one or a combination of i) the anode exhaust, ii) the hydrogen-containing stream, and iii) the syngas-containing stream.

Embodiment 11

The method of any of the above Embodiments, wherein the cathode inlet stream comprises about 20 vol % $CO_2$ or less (e.g., about 15 vol % or less, about 12 vol % or less, or about 10 vol % or less).

Embodiment 12

The method of any of the above Embodiments, wherein the molten carbonate fuel cell is operated at a voltage $V_A$ of less than about 0.67 Volts or less (e.g., about 0.65 Volts or less).

Embodiment 13

The method of any of the above Embodiments, wherein the anode exhaust has a molar ratio of $H_2$ to CO from about 1.5:1 to about 10:1 (e.g., from about 3.0:1 to about 10:1).

This group of embodiments is Group H. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for producing electricity, and hydrogen or syngas, using a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell to generate electricity at a thermal ratio of about 1.3 or less (e.g., about 1.15 or less or about 1.0 or less); generating an anode exhaust from an anode outlet of the molten carbonate fuel cell; and separating from the anode exhaust a hydrogen-containing stream, a syngas-containing stream, or a combination thereof.

Embodiment 2

The method of Embodiment 1, wherein a $CO_2$ utilization of the cathode is at least about 50%.

Embodiment 3

The method of any of the above Embodiments, wherein the molten carbonate fuel cell further comprises one or more integrated endothermic reaction stages.

Embodiment 4

The method of Embodiment 3, wherein at least one integrated endothermic reaction stage of the one or more integrated endothermic reaction stages comprises an integrated reforming stage, the anode fuel stream introduced into the anode inlet being passed through the integrated reforming stage prior to entering the anode inlet.

Embodiment 5

The method of any of the above Embodiments, wherein the molten carbonate fuel cell is operated at a voltage $V_A$ of about 0.67 Volts or less (e.g., about 0.65 Volts or less).

Embodiment 6

The method of any of the above Embodiments, further comprising separating at least one of $CO_2$ and $H_2O$ from one or a combination of i) the anode exhaust, ii) the hydrogen-containing stream, and iii) the syngas-containing stream.

Embodiment 7

The method of any of the above Embodiments, wherein the thermal ratio is about 0.85 or less, the method further comprising supplying heat to the molten carbonate fuel cell to maintain a temperature at the anode outlet that is less than a temperature at the anode inlet by about 5° C. to about 50° C.

Embodiment 8

The method of any of the above Embodiments, wherein the thermal ratio is at least about 0.25.

Embodiment 9

The method of any of the above Embodiments, wherein a temperature at the anode outlet is greater than a temperature at the anode inlet by about 40° C. or less.

Embodiment 10

The method of any of Embodiments 1-8, wherein a temperature at the anode inlet differs from a temperature at the anode outlet by about 20° C. or less.

Embodiment 11

The method of any of Embodiments 1-8, wherein a temperature at the anode outlet is less than a temperature at the anode inlet by about 10° C. to about 80° C.

Embodiment 12

The method of any of the above Embodiments, wherein a) less than 10 vol % of the anode exhaust b) less than 10 vol % of $H_2$ produced in the anode of the molten carbonate fuel cell in a single pass or c) less than 10 vol % of the syngas-containing stream is directly or indirectly recycled to the anode of the molten carbonate fuel cell or the cathode of the molten carbonate fuel cell.

Embodiment 13

The method of any of Embodiments 1-11, wherein no portion of the anode exhaust is directly or indirectly recycled to the anode of the molten carbonate fuel cell, directly or indirectly recycled to the cathode of the molten carbonate fuel cell, or a combination thereof.

Embodiment 14

The method of any of the above Embodiments, wherein the syngas-containing stream has a molar ratio of $H_2$ to CO from about 3.0:1 to about 1.0:1 (e.g., from about 2.5:1 to about 1.0:1, from about 3.0:1 to about 1.5:1, or from about 2.5:1 to about 1.5:1).

Embodiment 15

The method of any of the above Embodiments, wherein the anode exhaust has a molar ratio of $H_2$ to CO from about 1.5:1 to about 10:1 (e.g., from about 3.0:1 to about 10:1).

This group of embodiments is Group J. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for producing electricity using a molten carbonate fuel cell comprising an anode and a cathode, the method comprising: introducing an anode fuel stream comprising a reformable fuel into the anode of the molten carbonate fuel cell, an internal reforming element associated with the anode of the molten carbonate fuel cell, or a combination thereof; introducing a cathode inlet stream comprising $CO_2$ and $O_2$ into the cathode of the molten carbonate fuel cell; generating electricity within the molten carbonate fuel cell; and generating an anode exhaust from an anode outlet of the molten carbonate fuel cell; wherein a ratio of net moles of syngas in the anode exhaust to moles of $CO_2$ in a cathode exhaust is at least about 2.0.

Embodiment 2

Additionally or alternately to any of the above groups of embodiments, a method for producing electricity using a molten carbonate fuel cell comprising an anode and a cathode, the method comprising: introducing an anode fuel stream comprising a reformable fuel into the anode of the molten carbonate fuel cell, an internal reforming element associated with the anode of the molten carbonate fuel cell, or a combination thereof; introducing a cathode inlet stream comprising $CO_2$ and $O_2$ into the cathode of the molten carbonate fuel cell, a $CO_2$ concentration in the cathode inlet stream being about 6 vol % or less; and generating electricity within the molten carbonate fuel cell; and generating an anode exhaust from an anode outlet of the molten carbonate fuel cell, wherein a ratio of net moles of syngas in the anode exhaust to moles of $CO_2$ in a cathode exhaust is at least about 1.5.

Embodiment 3

The method of Embodiment 2, wherein the $CO_2$ concentration in the cathode inlet stream is about 5 vol % or less.

Embodiment 4

The method of any of the above Embodiments, wherein the ratio of net moles of syngas in the anode exhaust to moles of $CO_2$ in the cathode exhaust is at least about 3.0 (e.g., at least about 4.0).

Embodiment 5

The method of any of the above Embodiments, wherein the method further comprises separating from the anode exhaust a $H_2$-containing stream, a syngas-containing stream, or a combination thereof.

Embodiment 6

The method of Embodiment 5, further comprising separating the $H_2$-containing stream from the anode exhaust prior to separating the syngas-containing stream from the anode exhaust, the $H_2$-containing stream containing at least about 90 vol % $H_2$ (e.g., at least about 95 vol % $H_2$, or at least about 98 vol % $H_2$).

Embodiment 7

The method of Embodiment 5 or 6, wherein the syngas-containing stream has a molar ratio of $H_2$ to CO of about 3.0:1 (e.g., about 2.5:1 or less) to about 1.0:1 (e.g. at least about 1.5:1).

Embodiment 8

The method of any of Embodiments 5-7, further comprising separating at least one of $CO_2$ and $H_2O$ from one or a combination of i) the anode exhaust, ii) the $H_2$-containing stream, and iii) the syngas-containing stream.

Embodiment 9

The method of any of Embodiments 5-8, further comprising separating a stream containing at least about 90 vol % $H_2$ from the syngas-containing stream.

Embodiment 10

The method of any of the above claims, wherein the anode exhaust has a ratio of $H_2$ to CO of about 1.5:1 (e.g., at least about 3.0:1) to about 10:1.

Embodiment 11

The method of any of the above claims, wherein the anode fuel stream comprises at least about 10 vol % inert compounds, at least about 10 vol % $CO_2$, or a combination thereof.

Embodiment 12

The method of any of the above claims, wherein a) less than 10 vol % of the anode exhaust b) less than 10 vol % of $H_2$ produced in the anode of the molten carbonate fuel cell in a single pass or c) less than 10 vol % of the syngas-containing stream is directly or indirectly recycled to the anode of the molten carbonate fuel cell or the cathode of the molten carbonate fuel cell.

Embodiment 13

The method of any of Embodiments 1-11, wherein no portion of the anode exhaust is directly or indirectly recycled to the anode of the molten carbonate fuel cell, directly or indirectly recycled to the cathode of the molten carbonate fuel cell, or a combination thereof.

Embodiment 14

The method of any of the above Embodiments, wherein the cathode inlet stream comprises a combustion exhaust stream from a combustion-powered generator.

Embodiment 15

The method of any of the above Embodiments, wherein the molten carbonate fuel cell is operated at a voltage $V_A$ of about 0.67 Volts or less.

This group of embodiments is Group K. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for producing electricity, and hydrogen or syngas, using a molten carbonate fuel cell comprising an anode and a cathode, the method comprising: introducing an anode fuel stream comprising a reformable fuel into the anode of the molten carbonate fuel cell, an internal reforming element associated with the anode of the molten carbonate fuel cell, or a combination thereof; introducing a cathode inlet stream comprising $CO_2$ and $O_2$ into the cathode of the molten carbonate fuel cell; generating electricity within the molten carbonate fuel cell; generating an anode exhaust from an anode outlet of the molten carbonate fuel cell; separating from the anode exhaust a $H_2$-containing stream, a syngas-containing stream, or a combination thereof, wherein a fuel utilization of the anode is about 50% or less and a $CO_2$ utilization of the cathode is at least about 60%.

Embodiment 2

The method of Embodiment 1, wherein a reformable hydrogen content of the reformable fuel introduced into the anode of the molten carbonate fuel cell, the internal reforming element associated with the anode of the molten carbonate fuel cell, or the combination thereof, is at least about 75% greater than the amount of $H_2$ oxidized in the anode of the molten carbonate fuel cell to generate electricity.

Embodiment 3

The method of any of the above Embodiments, wherein the cathode inlet stream comprises about 20 vol % $CO_2$ or less (e.g., about 15 vol % $CO_2$ or less, or about 12 vol % $CO_2$ or less).

Embodiment 4

The method of any of the above Embodiments, wherein the fuel utilization of the anode of the molten carbonate fuel cell is about 40% or less (e.g., about 30% or less).

Embodiment 5

The method of any of the above Embodiments, wherein the $CO_2$ utilization of the cathode of the molten carbonate fuel cell is at least about 65% (e.g., at least about 70%).

Embodiment 6

The method of any of the above Embodiments, wherein the anode fuel stream comprises at least about 10 vol % inert compounds, at least about 10 vol % $CO_2$, or a combination thereof.

Embodiment 7

The method of any of the above Embodiments, wherein the syngas-containing stream has a molar ratio of $H_2$ to CO of about 3.0:1 (e.g., about 2.5:1 or less) to about 1.0:1 (e.g., at least about 1.5:1).

Embodiment 8

The method of any of the above Embodiments, wherein the anode exhaust has a molar ratio of $H_2$ to CO of about 1.5:1 (e.g., at least about 3.0:1) to about 10:1.

Embodiment 9

The method of any of the above Embodiments, wherein a) less than 10 vol % of the anode exhaust b) less than 10 vol % of $H_2$ produced in the anode of the molten carbonate fuel cell in a single pass or c) less than 10 vol % of the syngas-containing stream is directly or indirectly recycled to the anode of the molten carbonate fuel cell or the cathode of the molten carbonate fuel cell.

Embodiment 10

The method of any of Embodiments 1-8, wherein no portion of the anode exhaust is directly or indirectly recycled to the anode of the molten carbonate fuel cell, directly or indirectly recycled to the cathode of the molten carbonate fuel cell, or a combination thereof.

Embodiment 11

The method of any of the above Embodiments, further comprising separating at least one of $CO_2$ and $H_2O$ from one or a combination of i) the anode exhaust, ii) the $H_2$-containing stream, and iii) the syngas-containing stream.

Embodiment 12

The method of any of the above Embodiments, wherein the $H_2$-containing stream contains at least about 90 vol % $H_2$ (e.g., at least about 95 vol %, or at least about 98 vol %).

Embodiment 13

The method of any of the above Embodiments, wherein the cathode inlet stream comprises a combustion exhaust stream from a combustion-powered generator.

Embodiment 14

The method of any of the above Embodiments, wherein the molten carbonate fuel cell is operated at a voltage $V_A$ of about 0.67 Volts or less (e.g, about 0.65 Volts or less).

This group of embodiments is Group L. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for operating a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell at a first operating condition to generate electrical power and at least 30 mW/cm$^2$ of waste heat, the first operating condition providing a current density of at least about 150 mA/cm$^2$; generating an anode exhaust from an anode outlet of the molten carbonate fuel cell; and performing an effective amount of an endothermic reaction to maintain a temperature differential between the anode inlet and the anode outlet of about 100° C. or less.

Embodiment 2

Additionally or alternately to any of the above groups of embodiments, a method for operating a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell at a first operating condition to generate electricity, the first operating condition providing a current density of at least about 150 mA/cm$^2$, the first operating condition having a corresponding baseline operating condition; generating an anode exhaust from an anode outlet of the molten carbonate fuel cell; and performing an effective amount of an endothermic reaction to maintain a temperature differential between the anode inlet and the anode outlet of about 80° C. or less, wherein operating the molten carbonate fuel cell at the baseline operating condition would result in a temperature increase of at least about 100° C. between the anode inlet and the anode outlet, the baseline operating condition for the molten carbonate fuel cell being defined as an operating condition that is the same as the first operating condition except that the baseline operating condition comprises a fuel utilization of the anode of the molten carbonate fuel cell of about 75% and the anode fuel stream in the baseline operating condition comprises at least about 80 vol % of methane.

Embodiment 3

Additionally or alternately to any of the above groups of embodiments, a method for operating a molten carbonate fuel cell, the method comprising: introducing an anode fuel stream comprising reformable fuel into an anode inlet of an anode of a molten carbonate fuel cell; introducing a cathode inlet stream comprising $CO_2$ and $O_2$ into a cathode inlet of a cathode of the molten carbonate fuel cell; operating the molten carbonate fuel cell at a first operating condition to generate electrical power at a first power density and waste heat, the first operating condition comprising a first anode inlet temperature, a first anode inlet flow rate, a first anode fuel partial pressure, a first anode water partial pressure, a first cathode inlet flow rate, a first cathode inlet $CO_2$ partial pressure, and a first cathode inlet $O_2$ partial pressure, the first operating condition having a corresponding maximum power operating condition; generating an anode exhaust from an anode outlet of the molten carbonate fuel cell; and performing an effective amount of an endothermic reaction to maintain a temperature differential between the anode inlet and the anode outlet of about 80° C. or less, wherein operating the fuel cell assembly at the maximum power operating condition would result in a power density that differs from the first power density by less than about 20%, the maximum power operating condition corresponding to an operating condition that generates the maximum power density for an operating condition that comprises the first anode inlet temperature, the first anode inlet flow rate, the first anode fuel partial pressure, the first anode water partial pressure, the first cathode inlet flow rate, the first cathode inlet $CO_2$ partial pressure, and the first cathode inlet $O_2$ partial pressure.

Embodiment 4

The method of Embodiment 3, wherein the power density at the maximum power operating condition differs from the first power density by less than about 15%.

Embodiment 5

The method of any of the above Embodiments, further comprising withdrawing a product stream from the molten carbonate fuel cell comprising one or more reaction products generated by performing the effective amount of the endothermic reaction.

Embodiment 6

The method of Embodiment 5, wherein the product stream is withdrawn from the molten carbonate fuel cell without passing through an anode of the molten carbonate fuel cell.

Embodiment 7

The method of any of the above Embodiments, wherein the molten carbonate fuel cell further comprises one or more integrated endothermic reaction stages.

Embodiment 8

The method of Embodiment 7, wherein at least one integrated endothermic reaction stage of the one or more integrated endothermic reaction stages comprises an integrated reforming stage, the anode fuel stream being passed through the integrated reforming stage prior to being introduced into the anode inlet of the anode of the molten carbonate fuel cell.

Embodiment 9

The method of Embodiment 7 or 8, wherein performing an effective amount of an endothermic reaction comprises reforming a reformable fuel.

Embodiment 10

The method of any of the above Embodiments, wherein performing an effective amount of an endothermic reaction comprises performing an endothermic reaction that consumes at least about 40% of the waste heat generated by operating the molten carbonate fuel cell at the first operating condition.

Embodiment 11

The method of any of the above Embodiments, wherein a temperature at the anode outlet is less than 50° C. greater than a temperature at the anode inlet.

Embodiment 12

The method of the above Embodiments, wherein the molten carbonate fuel cell is operated to generate waste heat of at least about 40 $mW/cm^2$ (e.g., at least about 50 $mW/cm^2$, or at least about 60 $mW/cm^2$).

Embodiment 13

The method of any of the above Embodiments, wherein the first operating condition provides a current density of at least about 200 $mA/cm^2$.

Embodiment 14

The method of any of the above Embodiments, wherein the molten carbonate fuel cell is operated at a voltage $V_A$ of less than about 0.7 Volts (e.g., about 0.67 Volts or less, or about 0.65 Volts or less).

Embodiment 15

The method of any of the above Embodiments, wherein no portion of the anode exhaust is directly or indirectly recycled to the anode, directly or indirectly recycled to the cathode, or a combination thereof.

Embodiment 16

The method of any of the above Embodiments, wherein less than 10 vol % of the anode exhaust is directly or indirectly recycled to the anode of the molten carbonate fuel cell or the cathode of the molten carbonate fuel cell.

Embodiment 17

The method of any of the above Embodiments, further comprising separating from the anode exhaust a $H_2$-containing stream, a syngas-containing stream, or a combination thereof.

Embodiment 18

The method of Embodiment 17, wherein less than 10 vol % of $H_2$ produced in the anode of the molten carbonate fuel cell in a single pass is directly or indirectly recycled to the anode of the molten carbonate fuel cell or the cathode of the molten carbonate fuel cell.

Embodiment 19

The method of Embodiment 17, wherein less than 10 vol % of the syngas-containing stream is directly or indirectly recycled to the anode of the molten carbonate fuel cell or the cathode of the molten carbonate fuel cell.

This group of embodiments is Group M. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for producing electricity using a molten carbonate fuel having an anode and a cathode, the method comprising: introducing a combustion fuel stream and an $O_2$-containing stream into a combustion zone; performing a combustion reaction in the combustion zone to generate a combustion exhaust, the combustion exhaust comprising at least about 20 vppm of NOx; introducing an anode fuel stream comprising a reformable fuel into the anode of the molten carbonate fuel cell, an internal reforming element associated with the anode of the molten carbonate fuel cell, or a combination thereof; introducing a cathode inlet stream comprising at least a portion of the combustion exhaust into the cathode of the molten carbonate fuel cell, the cathode inlet stream comprising $CO_2$, $O_2$, and at least about 20 vppm of a nitrogen oxide; generating a) electricity within the molten carbonate fuel cell, b) an anode exhaust comprising $H_2$ and $CO_2$, and c) a cathode exhaust comprising less than about half of the $NO_x$ content of the cathode inlet stream; and separating at least a portion of the anode exhaust to form a $CO_2$-enriched anode exhaust stream having a higher $CO_2$ content than the anode exhaust and a $CO_2$-depleted anode exhaust stream having a lower $CO_2$ content than the anode exhaust.

Embodiment 2

The method of embodiment 1, wherein the cathode exhaust comprises about 15 vppm or less of NOx.

Embodiment 3

The method of embodiment 1 or 2, wherein the cathode inlet stream comprises about 500 vppm or less of NOx.

Embodiment 4

The method of any of the above embodiments, wherein the combustion exhaust comprises about 10 vol % or less of $CO_2$ (e.g., about 8 vol % or less).

Embodiment 5

The method of any of the above embodiments, wherein the combustion zone is operated at a temperature of at least about 1200° F.

Embodiment 6

The method of any of the above embodiments, further comprising recycling at least a portion of the $CO_2$-depleted anode exhaust stream to the combustion zone, to the anode of the molten carbonate fuel cell, or a combination thereof.

Embodiment 7

The method of any of the above embodiments, further comprising exposing the anode exhaust stream to a water gas shift catalyst prior to separating $CO_2$ from the anode exhaust stream, a $H_2$ content of the shifted anode exhaust stream being less than a $H_2$ content of the anode exhaust stream prior to the exposure.

Embodiment 8

The method of any of the above embodiments, further comprising recycling a combustion exhaust recycle portion from the combustion exhaust to the combustion zone.

Embodiment 9

The method of any of the above embodiments, wherein the cathode exhaust stream has a $CO_2$ content of about 2.0 vol. % or less (e.g., about 1.5 vol % or less, or about 1.2 vol % or less).

Embodiment 10

The method of any of the above embodiments, wherein the anode fuel stream comprises at least about 10 vol % inert compounds, at least about 10 vol % $CO_2$, or a combination thereof.

Embodiment 11

The method of any of the above embodiments, wherein the anode exhaust stream comprises $H_2$ and CO at a molar ratio of about 3.0:1 to about 10.0:1.

Embodiment 12

The method of any of the above embodiments, wherein the combustion fuel stream to the combustion zone is hydrocarbonaceous, a ratio of $CO_2$ in the cathode inlet stream to NOx in the cathode inlet stream being about 100 to about 10,000.

Embodiment 13

Additionally or alternately to any of the above groups of embodiments, a method for producing electricity, the method comprising: introducing one or more fuel streams and an $O_2$-containing stream into a reaction zone; performing a combustion reaction in the combustion zone to generate a combustion exhaust, the combustion exhaust comprising at least about 20 vppm of NOx; introducing an anode fuel stream comprising a reformable fuel into an anode of the molten carbonate fuel cell, an internal reforming element associated with the anode, or a combination thereof; introducing a cathode inlet stream comprising at least a portion of the combustion exhaust into a cathode of the molten carbonate fuel cell, the cathode inlet stream comprising a nitrogen oxide content of about 20 vppm to about 500 vppm of a nitrogen oxide; generating electricity within the molten carbonate fuel cell; and generating an anode exhaust having a nitrogen oxide content that is less than half of the nitrogen oxide content of the cathode inlet stream.

Embodiment 14

The method of embodiment 13, wherein the fuel stream to the combustion zone is hydrocarbonaceous, a ratio of $CO_2$ in the cathode inlet stream to NOx in the cathode inlet stream being about 100 to about 10,000.

This group of embodiments is Group N. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for producing electricity, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the molten carbonate fuel cell; generating electricity within the molten carbonate fuel cell, the molten carbonate fuel cell being operated at a fuel utilization of about 60% or less; generating an anode exhaust comprising $H_2$, CO, and $CO_2$; separating, from at least a portion of the anode exhaust, a first $H_2$-rich gas stream comprising at least about 80 vol % (e.g., at least about 90%) $H_2$; and combusting at least a portion of the first $H_2$-rich gas stream to produce electricity.

Embodiment 2

The method of embodiment 1, further comprising (i) performing a water gas shift process on the anode exhaust, the at least a portion of the anode exhaust, or a combination thereof; (ii) separating $CO_2$ and/or $H_2O$ from the anode exhaust, the at least a portion of the anode exhaust, or a combination thereof; or (iii) both (i) and (ii).

Embodiment 3

The method of embodiment 1 or 2, wherein the separating step comprises: performing a water gas shift process on the anode exhaust or at least a portion of the anode exhaust to form a shifted anode exhaust portion; and separating $H_2O$ and $CO_2$ from the shifted anode exhaust portion to form the first $H_2$-rich gas stream.

Embodiment 4

The method of any of the above embodiments, wherein combusting step comprises generating steam from heat generated by the combustion, and producing electricity from at least a portion of the generated steam.

Embodiment 5

The method of any of the above embodiments, wherein the combusting step comprises combusting the at least a portion of the first $H_2$-rich gas stream in a turbine.

Embodiment 6

The method of any of the above embodiments, wherein the cathode inlet stream comprises exhaust from combustion of a carbon-containing fuel in a combustion turbine.

Embodiment 7

The method of embodiment 6, wherein the carbon-containing fuel comprises one or more of: at least 5 vol % of inert gases; at least about 10 vol % $CO_2$; and at least about 10 vol % $N_2$.

Embodiment 8

The method of any of the above embodiments, wherein the anode exhaust has a ratio of $H_2$:CO of at least about 2.5:1 (e.g., at least about 3.0:1, at least about 4.0:1, or at least about 5.0:1).

Embodiment 9

The method of any of the above embodiments, further comprising forming a second $H_2$-containing stream from the anode exhaust, the at least a portion of the anode exhaust, the first $H_2$-rich gas stream, or a combination thereof; and recycling at least a portion of the second $H_2$-containing stream to the combustion turbine.

Embodiment 10

The method of any of the above embodiments, wherein at least about 90 vol % of the reformable fuel is methane.

Embodiment 11

The method of any of the above embodiments, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, from about 0.25 to about 0.8, or from about 0.25 to about 0.75).

Embodiment 12

The method of any of the above embodiments, wherein an amount of the reformable fuel introduced into the anode, the internal reforming element associated with the anode, or the combination thereof, is at least about 50% greater (e.g., at least about 75% greater or at least about 100% greater) than an amount of hydrogen reacted in the molten carbonate fuel cell to generate electricity.

Embodiment 13

The method of any of the above embodiments, wherein a ratio of net moles of syngas in the anode exhaust to moles of $CO_2$ in a cathode exhaust is at least about 2.0:1 (e.g., at least about 3.0, at least about 4.0, at least about 5.0, at least about 10.0, or at least about 20.0), and optionally about 40.0 or less (e.g., about 30.0 or less or about 20.0 or less).

Embodiment 14

The method of any of the above embodiments, wherein a fuel utilization in the anode is about 50% or less (e.g., about 30% or less, about 25% or less, or about 20% or less) and a $CO_2$ utilization in the cathode is at least about 60% (e.g., at least about 65%, at least about 70%, or at least about 75%).

Embodiment 15

The method of any of the above embodiments, wherein the molten carbonate fuel cell is operated to generate electrical power at a current density of at least about 150 $mA/cm^2$ and at least about 40 $mW/cm^2$ (e.g., at least about 50 $mW/cm^2$, at least about 60 $mW/cm^2$, at least about 80 $mW/cm^2$, or at least 100 $mW/cm^2$) of waste heat, the method further comprising performing an effective amount of an endothermic reaction to maintain a temperature differential between an anode inlet and an anode outlet of about 100° C. or less (e.g., about 80° C. or less or about 60° C. or less), and optionally wherein performing the endothermic reaction consumes at least about 40% (e.g., at least about 50%, at least about 60%, or at least about 75%) of the waste heat.

Embodiment 16

The method of any of the above embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

This group of embodiments is Group P. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for synthesizing hydrocarbonaceous compounds, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode inlet of the molten carbonate fuel cell; generating electricity within the molten carbonate fuel cell; generating an anode exhaust comprising $H_2$, CO, $H_2O$, and at least about 20 vol % $CO_2$; reacting at least a portion of the anode exhaust under effective Fischer-Tropsch conditions in the presence of a shifting Fischer-Tropsch catalyst (e.g., comprising Fe) to produce at least one gaseous product and at least one non-gaseous product, wherein a $CO_2$ concentration in the at least a portion of the anode exhaust is at least 80% of a $CO_2$ concentration in the anode exhaust; and recycling at least a portion of the at least one gaseous product to the cathode inlet.

Embodiment 2

Additionally or alternately to any of the above groups of embodiments, a method for synthesizing hydrocarbonaceous compounds, the method comprising: introducing a fuel stream comprising a reformable fuel into the anode of a molten carbonate fuel cell, an internal reforming element associated with a anode, or a combination thereof; introducing a cathode inlet stream comprising $CO_2$ and $O_2$ into a cathode inlet of the molten carbonate fuel cell; generating electricity within the molten carbonate fuel cell; generating an anode exhaust comprising $H_2$, CO, $H_2O$, and at least about 20 vol % $CO_2$; and reacting at least a portion of the anode exhaust under effective Fischer-Tropsch conditions in the presence of a shifting Fischer-Tropsch catalyst (e.g., comprising Fe) to produce at least one gaseous product and at least one non-gaseous product, wherein a $CO_2$ concentration in the at least a portion of the anode exhaust is at least 80% of a $CO_2$ concentration in the anode exhaust, wherein an amount of the reformable fuel introduced into the anode, the internal reforming element associated with the anode, or the combination thereof, provides a reformable fuel surplus ratio of at least about 1.5.

Embodiment 3

The method of embodiment 2, further comprising recycling at least a portion of the gaseous product to the anode inlet, the cathode inlet, or a combination thereof.

Embodiment 4

The method of any of the above embodiments, wherein a ratio of $H_2$ to CO in the anode exhaust is at least about 2.5:1 (e.g., at least about 3.0:1, at least about 4.0:1, or at least about 5.0:1).

Embodiment 5

The method of any of embodiments 1 and 3-4, wherein the recycling step comprises: removing $CO_2$ from the at least one gaseous product to produce a $CO_2$-containing stream and a separated syngas effluent comprising $CO_2$, CO, and $H_2$, such that the $CO_2$-containing stream has a $CO_2$ content greater than a $CO_2$ content in the at least one gaseous product; optionally oxidizing the at least a portion of the separated syngas effluent; and then recycling at least a portion of the separated syngas effluent, optionally oxidized, to the cathode inlet.

Embodiment 6

The method of any of the above embodiments, further comprising compressing the anode exhaust, the at least a portion of the anode exhaust, or a combination thereof prior to the reacting of the at least a portion of the anode exhaust under effective Fischer-Tropsch conditions.

Embodiment 7

The method of any of the above embodiments, further comprising exposing at least a portion of the anode exhaust stream to a water gas shift catalyst to form a shifted anode exhaust, and then removing water and $CO_2$ from at least a portion of the shifted anode exhaust.

Embodiment 8

The method of any of the above embodiments, wherein the cathode inlet stream comprises exhaust from a combustion turbine.

Embodiment 9

The method of any of the above embodiments, wherein an amount of the reformable fuel introduced into the anode, the internal reforming element associated with the anode, or the combination thereof, is at least about 50% greater (e.g., at least about 75% greater or at least about 100% greater) than an amount of hydrogen reacted in the molten carbonate fuel cell to generate electricity.

Embodiment 10

The method of any of the above embodiments, wherein a ratio of net moles of syngas in the anode exhaust to moles of $CO_2$ in a cathode exhaust is at least about 2.0:1 (e.g., at least about 3.0, at least about 4.0, at least about 5.0, at least about 10.0, or at least about 20.0), and optionally about 40.0 or less (e.g., about 30.0 or less or about 20.0 or less).

Embodiment 11

The method of any of the above embodiments, wherein a fuel utilization in the anode is about 50% or less (e.g., about 30% or less, about 25% or less, or about 20% or less) and a $CO_2$ utilization in a cathode is at least about 60% (e.g., at least about 65%, at least about 70%, or at least about 75%).

Embodiment 12

The method of any of the above embodiments, wherein the molten carbonate fuel cell is operated to generate electrical power at a current density of at least about 150 $mA/cm^2$ and at least about 40 $mW/cm^2$ (e.g., at least about 50 $mW/cm^2$, at least about 60 $mW/cm^2$, at least about 80 $mW/cm^2$, or at least 100 $mW/cm^2$) of waste heat, the method further comprising performing an effective amount of an endothermic reaction to maintain a temperature differential between an anode inlet and an anode outlet of about 100° C. or less (e.g., about 80° C. or less or about 60° C. or less), and optionally wherein performing the endothermic reaction consumes at least about 40% (e.g., at least about 50%, at least about 60%, or at least about 75%) of the waste heat.

Embodiment 13

The method of any of the above embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

Embodiment 14

The method of any of the above embodiments, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, from about 0.25 to about 0.8, or from about 0.25 to about 0.75).

Embodiment 15

The method of any of the above embodiments, wherein the at least one gaseous product comprises a tail gas stream comprising one or more of (i) unreacted $H_2$, (ii) unreacted CO, and (iii) C4-hydrocarbonaceous and/or C4-oxygenate compounds.

This group of embodiments is Group Q. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for synthesizing hydrocarbonaceous compounds, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode inlet of the molten carbonate fuel cell; generating electricity within the molten carbonate fuel cell; generating an anode exhaust comprising $H_2$, CO, $CO_2$, and $H_2O$, and having a ratio of $H_2$ to CO of at least about 2.5:1 (e.g., at least about 3.0:1, at least about 4.0:1, or at least about 5.0:1); reducing the ratio of $H_2$ to CO in at least a portion of the anode exhaust to a ratio of about 1.7:1 to about 2.3:1 to form a classic syngas stream, which also has a $CO_2$ concentration that is at least 60% of a $CO_2$ concentration in the anode exhaust; reacting the classic syngas stream under effective Fischer-Tropsch conditions in the presence of a non-shifting Fischer-Tropsch catalyst (e.g., comprising Co, Rh, Ru, Ni, Zr, or a combination thereof) to produce at least one gaseous product and at least one non-gaseous product; and recycling at least a portion of the at least one gaseous product to the cathode inlet.

Embodiment 2

Additionally or alternately to any of the above groups of embodiments, a method for synthesizing hydrocarbonaceous compounds, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode inlet of the molten carbonate fuel cell; generating electricity within the molten carbonate fuel cell; generating an anode exhaust comprising $H_2$, CO, $CO_2$, and $H_2O$, and having a ratio of $H_2$ to CO of at least about 2.5:1 (e.g., at least about 3.0:1, at least about 4.0:1, or at least about 5.0:1); reducing the ratio of $H_2$ to CO in at least a portion of the anode exhaust to a ratio of about 1.7:1 to about 2.3:1 to form a classic syngas stream, which also has a $CO_2$ concentration that is at least 60% of a $CO_2$ concentration in the anode exhaust; and reacting the classic syngas stream under effective Fischer-Tropsch conditions in the presence of a non-shifting Fischer-Tropsch catalyst (e.g., comprising Co, Rh, Ru, Ni, Zr, or a combination thereof) to produce at least one gaseous product and at least one non-gaseous product, wherein an amount of the reformable fuel introduced into the anode, the internal reforming element associated with the anode, or the combination thereof, provides a reformable fuel surplus ratio of at least about 1.5.

Embodiment 3

The method of embodiment 2, further comprising recycling at least a portion of the at least one gaseous product to the cathode inlet.

Embodiment 4

The method of any of the above embodiments, wherein reducing the ratio of $H_2$ to CO in the classic syngas stream comprises (i) performing a reverse water gas shift on the classic syngas stream, (ii) withdrawing a gas stream comprising $H_2$ from the anode exhaust, from the classic syngas stream, or from a combination thereof, or (iii) both (i) and (ii).

Embodiment 5

The method of any of embodiments 1 and 3-4, wherein the recycling step comprises: removing $CO_2$ from the at least one gaseous product to produce a $CO_2$-containing stream and a separated syngas effluent comprising $CO_2$, CO, and $H_2$; optionally oxidizing the at least a portion of the separated syngas effluent; and then recycling at least a portion of the separated syngas effluent, optionally oxidized, to the cathode inlet.

Embodiment 6

The method of any of the above embodiments, further comprising compressing the anode exhaust, the classic syngas stream, or a combination thereof prior to the reacting of the classic syngas stream under effective Fischer-Tropsch conditions.

Embodiment 7

The method of any one of the above embodiments, wherein the cathode inlet stream comprises exhaust from a combustion turbine.

Embodiment 8

The method of any of the above embodiments, wherein an amount of the reformable fuel introduced into the anode, the internal reforming element associated with the anode, or the combination thereof, is at least about 50% greater (e.g., at least about 75% greater or at least about 100% greater) than an amount of hydrogen reacted in the molten carbonate fuel cell to generate electricity.

Embodiment 9

The method of any of the above embodiments, wherein a ratio of net moles of syngas in the anode exhaust to moles of $CO_2$ in a cathode exhaust is at least about 2.0 (e.g., at least about 3.0, at least about 4.0, at least about 5.0, at least about 10.0, or at least about 20.0), and optionally about 40.0 or less (e.g., about 30.0 or less or about 20.0 or less).

Embodiment 10

The method of any of the above embodiments, wherein a fuel utilization in the anode is about 50% or less (e.g., about 30% or less, about 25% or less, or about 20% or less) and a $CO_2$ utilization in a cathode is at least about 60% (e.g., at least about 65%, at least about 70%, or at least about 75%).

Embodiment 11

The method of any of the above embodiments, wherein the molten carbonate fuel cell is operated to generate electrical power at a current density of at least about 150 $mA/cm^2$ and at least about 40 $mW/cm^2$ (e.g., at least about 50 $mW/cm^2$, at least about 60 $mW/cm^2$, at least about 80 $mW/cm^2$, or at least 100 $mW/cm^2$) of waste heat, the method further comprising performing an effective amount of an endothermic reaction to maintain a temperature differential between an anode inlet and an anode outlet of about 100° C. or less (e.g., about 80° C. or less or about 60° C. or less).

Embodiment 12

The method of embodiment 11, wherein performing the endothermic reaction consumes at least about 40% (e.g., at least about 50%, at least about 60%, or at least about 75%) of the waste heat.

Embodiment 13

The method of any of the above embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

Embodiment 14

The method of any of the above embodiments, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, from about 0.25 to about 0.8, or from about 0.25 to about 0.75).

Embodiment 15

The method of any of the above embodiments, wherein the at least one gaseous product comprises a tail gas stream comprising one or more of (i) unreacted $H_2$, (ii) unreacted CO, and (iii) C4-hydrocarbonaceous and/or C4-oxygenate compounds.

This group of embodiments is Group R. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for synthesizing hydrocarbonaceous compounds, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the molten carbonate fuel cell; generating electricity within the molten carbonate fuel cell; generating an anode exhaust: comprising $H_2$, CO, and $CO_2$, having a ratio of $H_2$ to CO of at least about 2.5:1, and having a $CO_2$ content of at least about 20 vol %; removing water and $CO_2$ from at least a portion of the anode exhaust to produce an anode effluent gas stream, the anode effluent gas stream having a concentration of water that is less than half of a concentration of water in the anode exhaust, having a concentration of $CO_2$ that is less than half of a concentration of $CO_2$ in the anode exhaust, or a combination thereof, the anode effluent gas stream also having a ratio of $H_2$ to CO of about 2.3:1 or less; reacting at least a portion of the anode effluent gas stream over a non-shifting Fischer-Tropsch catalyst (e.g., comprising Co, Rh, Ru, Ni, Zr, or a combination thereof) to produce at least one gaseous product and at least one non-gaseous product; and optionally recycling at least a portion of the gaseous product to an anode inlet, to a cathode inlet, or to a combination thereof.

Embodiment 2

The method of embodiment 1, wherein the recycling step comprises: removing $CO_2$ from the gaseous product to produce a $CO_2$-concentrated stream and a separated syngas product comprising $CO_2$, CO, and $H_2$; optionally oxidizing at least a portion of the separated syngas product; and then recycling at least a portion of the separated syngas product to the anode inlet, the cathode inlet, or a combination thereof.

Embodiment 3

The method of embodiment 1 or 2, wherein the gaseous product comprises a tail gas stream comprising one or more of (i) unreacted $H_2$, (ii) unreacted CO, and (iii) C4-hydrocarbonaceous or C4-oxygenate compounds.

Embodiment 4

The method of any of the above embodiments, further comprising exposing at least a portion of the anode exhaust to a water gas shift catalyst to form a shifted anode exhaust (which can optionally have a molar ratio of $H_2$ to CO that is less than a molar ratio of $H_2$ to CO in the anode exhaust), and then removing water and $CO_2$ from at least a portion of the shifted anode exhaust to form a purified $H_2$ stream.

Embodiment 5

The method of any of the above embodiments, further comprising exposing at least a portion of the anode effluent gas stream to a water gas shift catalyst to form a shifted anode effluent (which can optionally have a molar ratio of $H_2$ to CO that is less than a molar ratio of $H_2$ to CO in the anode effluent gas stream).

Embodiment 6

The method of any of the above embodiments, wherein the cathode inlet stream comprises exhaust from a combustion turbine.

Embodiment 7

The method of any of the above embodiments, wherein the anode exhaust has a ratio of $H_2$:CO of at least about 3.0:1 (e.g., at least about 4.0:1, from about 3.0:1 to about 10:1, or from about 4.0:1 to about 10:1).

Embodiment 8

The method of any of the above embodiments, wherein an amount of the reformable fuel introduced into the anode, the internal reforming element associated with the anode, or the combination thereof, at least about 50% greater (e.g., at least about 75% greater or at least about 100% greater) than an amount of hydrogen reacted in the molten carbonate fuel cell to generate electricity.

Embodiment 9

The method of any of the above embodiments, wherein a ratio of net moles of syngas in a fuel cell anode exhaust to moles of $CO_2$ in a fuel cell cathode exhaust is at least about 2.0 (e.g., at least about 3.0, at least about 4.0, at least about 5.0, at least about 10.0, or at least about 20.0), and optionally about 40.0 or less (e.g., about 30.0 or less or about 20.0 or less).

Embodiment 10

The method of any of the above embodiments, wherein a fuel utilization in the anode is about 50% or less (e.g., about 30% or less, about 25% or less, or about 20% or less) and a $CO_2$ utilization in the cathode is at least about 60% (e.g., at least about 65%, at least about 70%, or at least about 75%).

Embodiment 11

The method of any of the above embodiments, wherein the molten carbonate fuel cell is operated to generate electrical power at a current density of at least about 150 $mA/cm^2$ and at least about 40 $mW/cm^2$ (e.g., at least about 50 $mW/cm^2$, at least about 60 $mW/cm^2$, at least about 80 $mW/cm^2$, or at least 100 $mW/cm^2$) of waste heat, the method further comprising performing an effective amount of an endothermic reaction to maintain a temperature differential between an anode inlet and an anode outlet of about 100° C. or less (e.g., about 80° C. or less or about 60° C. or less).

Embodiment 12

The method of embodiment 11, wherein performing the endothermic reaction consumes at least about 40% (e.g., at least about 50%, at least about 60%, or at least about 75%) of the waste heat.

Embodiment 13

The method of any of the above embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

Embodiment 14

The method of any of the above embodiments, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, from about 0.25 to about 0.8, or from about 0.25 to about 0.75).

Embodiment 15

The method of any of the above embodiments, wherein an amount of the reformable fuel introduced into the anode, the internal reforming element associated with the anode, or the combination thereof, provides a reformable fuel surplus ratio of at least about 1.5 (e.g., at least about 2.0, at least about 2.5, or at least about 3.0).

This group of embodiments is Group S. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for synthesizing hydrocarbonaceous compounds, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the fuel cell, the cathode inlet stream optionally comprising exhaust from a combustion turbine; generating electricity within the molten carbonate fuel cell; generating an anode exhaust comprising $H_2$, CO, and $CO_2$; separating $CO_2$ from at least a portion of the anode exhaust to produce an anode effluent gas stream; reacting at least a portion of the anode effluent gas stream in the presence of a methanol synthesis catalyst under effective conditions for forming methanol to produce at least one methanol-containing stream and one or more streams comprising gaseous or liquid products; and recycling at least a portion of the one or more streams comprising gaseous or liquid products to form at least a portion of a cathode inlet stream.

Embodiment 2

The method of embodiment 1, further comprising adjusting a composition of the anode exhaust, the anode effluent gas stream, or a combination thereof (e.g., by removal of $CO_2$ therefrom, by performing a reverse water gas shift process, or a combination thereof) to achieve a Module value M for the anode effluent gas stream of about 1.7 to about 2.3 (e.g., about 1.8 to about 2.3, about 1.9 to about 2.3, about 1.7 to about 2.2, about 1.8 to about 2.2, about 1.9 to about 2.2, about 1.7 to about 2.1, about 1.8 to about 2.1, or about 1.9 to about 2.1), where M is defined as $M=[H_2-CO_2]/[CO+CO_2]$.

Embodiment 3

The method of embodiment 2, wherein the adjusting step comprises: dividing the anode exhaust or the anode effluent gas stream to form a first divided stream and a second divided stream; performing a reverse water gas shift on the first divided stream to form a first shifted stream; and combining at least a portion of the first shifted stream with at least a portion of the second divided stream to form an adjusted anode exhaust or an adjusted anode effluent gas stream.

Embodiment 4

The method of any of the above embodiments, wherein the anode exhaust has a molar ratio of $H_2$:CO of at least about 3.0:1 (e.g., at least about 4.0:1 or at least about 5.0:1) and optionally of about 10:1 or less.

Embodiment 5

The method of any of the above embodiments, further comprising compressing the at least a portion of the anode effluent gas stream prior to the reacting in the presence of the methanol synthesis catalyst.

Embodiment 6

The method of any of the above embodiments, wherein the one or more streams comprising gaseous or liquid products include: (i) at least one stream comprising C2+ alcohols; (ii) at least one stream comprising $H_2$, CO, the reformable fuel, or a combination thereof; or (iii) both (i) and (ii).

Embodiment 7

The method of any of the above embodiments, wherein the reacting step further produces at least one stream comprising syngas that is recycled for reacting in the presence of the methanol synthesis catalyst.

Embodiment 8

The method of any of the above embodiments, wherein at least about 90 vol % of the reformable fuel is methane.

Embodiment 9

The method of any of the above embodiments, wherein the fuel stream further comprises at least 5 vol % (e.g., at least about 10 vol %, at least about 20 vol %, at least about 30 vol %, at least about 35 vol %, or at least about 40 vol %) of inert gases (e.g., comprising $CO_2$ and/or $N_2$).

Embodiment 10

The method of any of the above embodiments, wherein the effective methanol synthesis conditions comprise a pressure from about 5 MPag to about 10 MPag and a temperature from about 250° C. to about 300° C.

Embodiment 11

The method of any of the above embodiments, further comprising separating $H_2O$ from the anode exhaust, the anode effluent gas stream, or a combination thereof.

Embodiment 12

The method of any of the above embodiments, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, from about 0.25 to about 0.8, or from about 0.25 to about 0.75).

Embodiment 13

The method of any of the above embodiments, wherein an amount of the reformable fuel introduced into the anode, the internal reforming element associated with the anode, or the combination thereof, provides a reformable fuel surplus ratio of at least about 1.5 (e.g., at least about 2.0, at least about 2.5, or at least about 3.0).

Embodiment 14

The method of any of the above embodiments, wherein a ratio of net moles of syngas in the anode exhaust to moles of $CO_2$ in a cathode exhaust is at least about 2.0 (e.g., at least about 3.0, at least about 4.0, at least about 5.0, at least about 10.0, or at least about 20.0), and optionally about 40.0 or less (e.g., about 30.0 or less or about 20.0 or less).

Embodiment 15

The method of any of the above embodiments, wherein a fuel utilization in the anode is about 50% or less (e.g., about 30% or less, about 25% or less, or about 20% or less) and a $CO_2$ utilization in the cathode is at least about 60% (e.g., at least about 65%, at least about 70%, or at least about 75%).

Embodiment 16

The method of any of the above embodiments, wherein the molten carbonate fuel cell is operated to generate electrical power at a current density of at least about 150 $mA/cm^2$ and at least about 40 $mW/cm^2$ (e.g., at least about 50 $mW/cm^2$, at least about 60 $mW/cm^2$, at least about 80 $mW/cm^2$, or at least 100 $mW/cm^2$) of waste heat, the method further comprising performing an effective amount of an endothermic reaction to maintain a temperature differential between an anode inlet and an anode outlet of about 100° C. or less, wherein performing the endothermic reaction optionally consumes at least about 40% of the waste heat.

Embodiment 17

The method of any of the above embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

This group of embodiments is Group T. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for generating hydrogen in a refinery, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the molten carbonate fuel cell; generating electricity within the molten carbonate fuel cell; generating an anode exhaust comprising $H_2$ and $CO_2$; performing a separation (e.g., using a membrane) on the anode exhaust to form a $CO_2$-rich gas stream having a $CO_2$ content greater than a $CO_2$ content of the anode exhaust, and a $CO_2$-depleted gas stream having a $CO_2$ content less than the $CO_2$ content of the anode exhaust, which $CO_2$-depleted gas stream optionally comprises an $H_2$-rich gas stream and a syngas stream; and delivering the $CO_2$-depleted gas stream to one or more second refinery processes.

Embodiment 2

The method of embodiment 1, wherein the cathode inlet stream comprises one or more $CO_2$-containing streams derived directly or indirectly from one or more first refinery processes.

Embodiment 3

The method of embodiment 1 or 2, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, or from about 0.25 to about 0.75).

Embodiment 4

The method of any of the above embodiments, further comprising separating $H_2O$ from at least one of the anode exhaust, the $CO_2$-depleted stream, and the $CO_2$-rich stream in one or more separation stages.

Embodiment 5

The method of any of the above embodiments, wherein an amount of the reformable fuel introduced into the anode, the internal reforming element associated with the anode, or the combination thereof, provides a reformable fuel surplus ratio of at least about 1.5 (e.g., at least about 2.0, at least about 2.5 or at least about 3.0).

Embodiment 6

The method of any of the above embodiments, wherein a ratio of net moles of syngas in the anode exhaust to moles of $CO_2$ in a cathode exhaust is at least about 2.0 (e.g., at least about 3.0, at least about 4.0, at least about 5.0, at least about 10.0, or at least about 20.0), and optionally is about 40.0 or less (e.g., about 30.0 or less or about 20.0 or less).

Embodiment 7

The method of any of the above embodiments, wherein a fuel utilization in the anode is about 50% or less (e.g., about 45% or less, about 40% or less, about 35% or less, about 30% or less, about 25% or less, or about 20% or less) and a $CO_2$ utilization in the cathode is at least about 60% (e.g., at least about 65%, at least about 70%, or at least about 75%).

Embodiment 8

The method of any of the above embodiments, wherein the molten carbonate fuel cell is operated at a first operating condition to generate electrical power and at least about 50 $mW/cm^2$ (e.g., at least about 80 $mW/cm^2$ or at least 100 $mW/cm^2$) of waste heat, the first operating condition providing a current density of at least about 150 $mA/cm^2$, and wherein an effective amount of an endothermic reaction is performed to maintain a temperature differential between an anode inlet and an anode outlet of about 100° C. or less (e.g., about 80° C. or less or about 60° C. or less).

Embodiment 9

The method of embodiment 8, wherein performing the endothermic reaction consumes at least about 40% (e.g., at least about 50%, at least about 60%, or at least about 75%) of the waste heat.

Embodiment 10

The method of any of the above embodiments, wherein an electrical efficiency for the molten carbonate fuel cell is between about 10% and about 40% (e.g., between about 10% and about 35%, between about 10% and about 30%, between about 10% and about 25%, or between about 10% and about 20%) and a total fuel cell efficiency for the molten carbonate fuel cell is at least about 55% (e.g., at least about 60%, at least about 65%, at least about 70%, at least about 75%, or at least about 80%).

Embodiment 11

The method of any of the above embodiments, wherein one or more of the following are satisfied: at least one process in the one or more first refinery processes is a process in the one or more second refinery processes; the fuel stream is derived from one or more third refinery processes; and the anode exhaust has a molar ratio of $H_2$ to CO of at least about 3.0:1, and has a $CO_2$ content of at least about 10 vol %.

Embodiment 12

The method of any of the above embodiments, wherein at least a portion of the fuel stream passes through a pre-reforming stage prior to being introduced into the anode.

Embodiment 13

The method of any of the above embodiments, wherein at least a portion of the fuel stream passes through a desulfurization stage prior to being introduced into the anode.

Embodiment 14

The method of any of the above embodiments, further comprising modifying an $H_2$ content of one or more of the anode exhaust, the $CO_2$-rich gas stream, and the a $CO_2$-depleted gas stream using a water gas shift process.

Embodiment 15

The method of any of the above embodiments, wherein the $CO_2$-depleted gas stream is further separated into a first $H_2$-rich stream having a first $H_2$ purity and a second $H_2$-rich stream having a second $H_2$ purity, wherein the second $H_2$-rich stream is compressed to a pressure greater than the first $H_2$-rich stream.

This group of embodiments is Group U. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for synthesizing nitrogen-containing compounds, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the fuel cell; generating electricity within the molten carbonate fuel cell; generating an anode exhaust comprising $H_2$ and $CO_2$; separating $CO_2$ from at least a portion of the anode exhaust to produce a $CO_2$-rich stream having a $CO_2$ content greater than a $CO_2$ content of the anode exhaust and a $CO_2$-depleted gas stream having an $H_2$ content greater than an $H_2$ content of the anode exhaust; and using at least a portion of the $CO_2$-depleted gas stream in an ammonia synthesis process and/or using at least a portion of the $CO_2$-rich stream in a second synthesis process for forming an organic nitrogen-containing compound (e.g., urea).

Embodiment 2

The method of Embodiment 1, wherein using at least a portion of the $CO_2$-depleted gas stream comprises exposing the at least a portion of the $CO_2$-depleted gas stream to a catalyst under effective ammonia synthesis conditions so as to form at least one ammonia-containing stream and one or more streams comprising gaseous or liquid products (which can include one or more streams comprising gaseous or liquid products include at least one stream comprising $H_2$ and/or $CH_4$), and optionally recycling at least a portion of the one or more streams comprising gaseous or liquid products to form at least a portion of a cathode inlet stream.

Embodiment 3

The method of any of the above embodiments, further comprising adjusting a composition of the anode exhaust, the at least a portion of the anode exhaust before $CO_2$ is separated, the $CO_2$-depleted gas stream, the at least a portion of the $CO_2$-depleted gas stream before being used in the ammonia synthesis process, or a combination thereof.

Embodiment 4

The method of Embodiment 3, wherein adjusting the composition comprises one or more of (i) performing a water gas shift process, (ii) performing a reverse water gas shift process, (iii) performing a separation to reduce a water content of the composition, and (iv) performing a separation to reduce a $CO_2$ content of the composition.

Embodiment 5

The method of any of the above embodiments, wherein the at least a portion of the $CO_2$-depleted gas stream is formed by separating a $H_2$-concentrated stream from the $CO_2$-depleted gas stream, the separated $H_2$-concentrated stream comprising at least about 90 vol % $H_2$ (e.g., at least about 95 vol % $H_2$, at least about 98 vol % $H_2$, or at least about 99 vol % $H_2$).

Embodiment 6

The method of any of the above embodiments, wherein the anode exhaust has a molar ratio of $H_2$:CO of at least about 3.0:1 (e.g., at least about 4.0:1), and optionally also about 10:1 or less.

Embodiment 7

The method of any of the above embodiments, further comprising: withdrawing, from a cathode exhaust, a gas stream comprising $N_2$; and using at least a portion of the withdrawn gas stream comprising $N_2$ as a source of $N_2$ in an ammonia synthesis process.

Embodiment 8

The method of any of the above embodiments, wherein the second synthesis process further comprises using ammonia from the ammonia synthesis process to form the organic nitrogen-containing compound.

Embodiment 9

The method of any of the above embodiments, wherein at least about 90 vol % of the reformable fuel is methane.

Embodiment 10

The method of any of the above embodiments, wherein the effective ammonia synthesis conditions comprise a pressure from about 6 MPag to about 18 MPag and a temperature from about 350° C. to about 500° C.

Embodiment 11

The method of any of the above claims, wherein a cathode inlet stream comprises exhaust from a combustion turbine.

Embodiment 12

The method of any of the above embodiments, wherein at least a portion of the $O_2$ in the cathode inlet stream is derived from an air separation step in which air is passed through a PSA apparatus to generate a nitrogen-rich product stream and an oxygen-rich off-gas stream, such that at least a portion of said oxygen-rich off-gas stream is sent to the cathode inlet, and such that at least a portion of said nitrogen-rich product stream is sent to the ammonia synthesis process.

Embodiment 13

The method of any of the above embodiments, further comprising withdrawing, from a cathode exhaust, an $N_2$-rich gas stream comprising $N_2$; and using at least a portion of the $N_2$-rich gas stream as a source of $N_2$ in the ammonia synthesis process (e.g., by exposing the at least a portion of the $N_2$-rich gas stream to a synthesis catalyst under effective synthesis conditions).

Embodiment 14

The method of Embodiment 13, wherein using at least a portion of the cathode exhaust stream as a source of $N_2$ in an ammonia synthesis process comprises performing at least one of a separation process and a purification process on the $N_2$-rich gas stream to increase the concentration of $N_2$, and then passing at least a portion of the $N_2$-rich gas stream into the ammonia synthesis process with the increased $N_2$ concentration.

Embodiment 15

The method of any of the above Embodiments, further comprising separating $H_2O$ from at least one of the anode exhaust, the $CO_2$-rich gas stream, the $CO_2$-depleted gas stream, and a cathode exhaust.

Embodiment 16

The method of any of the above Embodiments, further comprising exposing one or more of the $CO_2$-rich stream, the $CO_2$-depleted stream, and at least a portion of the anode exhaust stream to a water gas shift catalyst.

Embodiment 17

The method of any of the above Embodiments, wherein the cathode inlet stream comprises exhaust from a combustion turbine.

Embodiment 18

The method of any of the above Embodiments, wherein less than 10 vol % of an anode exhaust is directly or indirectly recycled to the anode or to the cathode.

Embodiment 19

The method of any of the above Embodiments, wherein no portion of the anode exhaust is directly or indirectly recycled to the anode.

Embodiment 20

The method of any of the above Embodiments, wherein no portion of the anode exhaust is directly or indirectly recycled to the cathode.

Embodiment 21

The method of any of the above Embodiments, wherein less than 10 vol % of $H_2$ produced in the anode in a single pass is directly or indirectly recycled to the anode or to the cathode.

Embodiment 22

The method of any of the above Embodiments, the method further comprising reforming the reformable fuel, wherein at least about 90% of the reformable fuel introduced into the anode, the reforming stage associated with the anode, or a combination thereof is reformed in a single pass through the anode.

Embodiment 23

The method of any of the above Embodiments, wherein a reformable hydrogen content of the reformable fuel introduced into the anode, into the reforming stage associated with the anode, or into a combination thereof is at least about 50% (e.g., at least about 75% or at least about 100%) greater than an amount of hydrogen reacted to generate electricity.

Embodiment 24

The method of any of the above Embodiments, wherein a reformable fuel surplus ratio is at least about 2.0 (e.g., at least about 2.5 or at least about 3.0).

Embodiment 25

The method of any of the above Embodiments, wherein a $CO_2$ utilization in the cathode is at least about 50% (e.g., at least about 60%).

Embodiment 26

The method of any of the above Embodiments, wherein an electrical efficiency for the molten carbonate fuel cell is between about 10% and about 40% (e.g., between about 10% and about 35%, between about 10% and about 30%, between about 10% and about 25%, or between about 10% and about 20%) and a total fuel cell efficiency for the molten carbonate fuel cell is at least about 55% (e.g., at least about 60%, at least about 65%, at least about 70%, at least about 75%, or at least about 80%).

Embodiment 27

The method of any of the above Embodiments, wherein the molten carbonate fuel cell is operated at a thermal ratio from about 0.25 to about 1.5 (e.g., from about 0.25 to about 1.3, from about 0.25 to about 1.15, from about 0.25 to about 1.0, from about 0.25 to about 0.85, or from about 0.25 to about 0.75).

Embodiment 28

The method of any of the above Embodiments, wherein a ratio of net moles of syngas in the anode exhaust to moles of $CO_2$ in a cathode exhaust is at least about 2.0 (e.g., at least about 3.0, at least about 4.0, at least about 5.0, at least about 10.0, or at least about 20.0), and optionally is about 40.0 or less (e.g., about 30.0 or less or about 20.0 or less).

Embodiment 29

The method of any of the above Embodiments, wherein a fuel utilization in the anode is about 50% or less (e.g., about 45% or less, about 40% or less, about 35% or less, about 30% or less, about 25% or less, or about 20% or less) and a $CO_2$ utilization in the cathode is at least about 60% (e.g., at least about 65%, at least about 70%, or at least about 75%).

Embodiment 30

The method of any of the above Embodiments, wherein the molten carbonate fuel cell is operated at a first operating condition to generate electrical power and at least about 50 $mW/cm^2$ (e.g., at least 100 $mW/cm^2$) of waste heat, the first operating condition providing a current density of at least about 150 $mA/cm^2$, and wherein an effective amount of an endothermic reaction is performed to maintain a temperature differential between an anode inlet and an anode outlet of about 100° C. or less (e.g., about 80° C. or less or about 60° C. or less).

Embodiment 31

The method of embodiment 30, wherein performing the endothermic reaction consumes at least about 40% (e.g., at least about 50%, at least about 60%, or at least about 75%) of the waste heat.

This group of embodiments is Group V. References to “any of the above embodiments” are meant to refer only to other embodiments within this Group, whereas references to “any of the above groups of embodiments” are meant to refer to any individual or combination of embodiments from one or more other Groups.

Embodiment 1

Additionally or alternately to any of the above groups of embodiments, a method for producing iron and/or steel, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the molten carbonate fuel cell; generating electricity within the molten carbonate fuel cell; withdrawing, from an anode exhaust, a first gas stream comprising CO, the anode exhaust having a pressure of about 500 kPag or less; and introducing the first gas stream withdrawn from the anode exhaust into a process for production of iron and/or steel.

Embodiment 2

The method of Embodiment 1, further comprising using the electricity generated to provide heat to the process for production of iron and/or steel.

Embodiment 3

The method of any of the above embodiments, further comprising withdrawing a second gas stream comprising $H_2$ from the anode exhaust, and using the second gas stream as fuel for heating the process for production of iron and/or steel.

Embodiment 4

The method of any of the above embodiments, further comprising separating water from the anode exhaust, the first gas stream withdrawn from the anode exhaust, or a combination thereof, and washing a process slag using the separated water.

Embodiment 5

The method of any of the above embodiments, wherein the cathode inlet stream comprises at least a portion of a $CO_2$-containing exhaust produced by the process for production of iron and/or steel.

Embodiment 6

The method of Embodiment 5, further comprising separating $CO_2$ from the $CO_2$-containing exhaust produced by the process for production of iron and/or steel.

Embodiment 7

The method of any of the above embodiments, further comprising exposing the first withdrawn gas stream to a water gas shift catalyst under effective water gas shift conditions prior to introducing the withdrawn first gas stream into the process for production of iron and/or steel.

Embodiment 8

The method of any of the above embodiments, wherein the molten carbonate fuel cell is operated to generate electricity at a thermal ratio of about 1.0 or less, the method further comprising transferring heat from the process for production of iron and/or steel (e.g., from a furnace) to the molten carbonate fuel cell, wherein a temperature of the anode exhaust is greater than a temperature at an anode inlet.

Embodiment 9

The method of Embodiment 8, wherein transferring heat comprises performing heat exchange between the anode inlet stream and at least one of an iron and/or steel production process furnace and an iron and/or steel production process exhaust, wherein performing the heat exchange optionally comprises increasing a temperature of the anode inlet stream by at least about 100° C. (e.g., by at least about 150° C.

Embodiment 10

The method of any of the above Embodiments, further comprising exposing the withdrawn gas stream to a water gas shift catalyst under effective water gas shift conditions prior to introducing the gas stream into the process for production of iron and/or steel.

Embodiment 11

The method of any of the above embodiments, further comprising separating water from the anode exhaust, the withdrawn first gas stream, or a combination thereof, and washing a process slag using the separated water.

Embodiment 12

The method of any of the previous embodiments, wherein an amount of the reformable fuel introduced into the anode, into the internal reforming element associated with the anode, or into the combination thereof, provides a reformable fuel surplus ratio of at least about 1.5 (e.g., at least about 2.0, at least about 2.5, or at least about 3.0).

Embodiment 13

The method of any of the above Embodiments, the method further comprising reforming the reformable fuel, wherein at least about 90% of the reformable fuel introduced into the anode, the reforming stage associated with the anode, or a combination thereof is reformed in a single pass through the anode.

Embodiment 14

The method of any of the above embodiments, wherein a ratio of net moles of syngas in a fuel cell anode exhaust to moles of $CO_2$ in a fuel cell cathode exhaust is at least about 2.0 (e.g., at least about 3.0, at least about 4.0, at least about 5.0, at least about 10.0, or at least about 20.0), and optionally about 40.0 or less (e.g., about 30.0 or less or about 20.0 or less).

Embodiment 15

The method of any of the above Embodiments, wherein a fuel utilization in the anode is about 65% or less (e.g., about 60% or less, about 50% or less, about 40% or less, about 30% or less, about 25% or less, or about 20% or less) and a $CO_2$ utilization in the cathode is at least about 50% (e.g., at least about 60%, at least about 65%, at least about 70%, or at least about 75%).

Embodiment 16

The method of any of the above Embodiments, wherein an electrical efficiency for the molten carbonate fuel cell is between about 10% and about 40% (e.g., between about 10% and about 35%, between about 10% and about 30%, between about 10% and about 25%, between about 10% and about 20%) and a total fuel cell efficiency for the fuel cell of at least about 50% (e.g., at least about 55%, at least about 60%, at least about 65%, at least about 70%, at least about 75%, or at least about 80%).

Embodiment 17

The method of any of the above embodiments, wherein the anode exhaust has a molar ratio of $H_2$:CO of at least about 3.0:1 (e.g., at least about 4.0:1, from about 3.0:1 to about 10:1, or from about 4.0:1 to about 10:1).

Embodiment 18

The method of any of the above embodiments, wherein at least about 90 vol % of the reformable fuel is methane.

Embodiment 19

The method of any of the above Embodiments, wherein less than 10 vol % of $H_2$ produced in the anode in a single pass is directly or indirectly recycled to the anode or to the cathode.

Embodiment 20

The method of any of the above Embodiments, wherein a reformable hydrogen content of the reformable fuel introduced into the anode, a reforming stage associated with the anode, or a combination thereof is at least about 50% greater (e.g., at least about 75% greater or at least about 100% greater) than an amount of hydrogen reacted to generate electricity.

Embodiment 21

The method of any of the above embodiments, wherein the molten carbonate fuel cell further comprises one or more integrated endothermic reaction stages.

Embodiment 22

The method of Embodiment 21, wherein at least one of the integrated endothermic reaction stages comprises an integrated reforming stage, the fuel stream introduced into the anode optionally being passed through at least one of the integrated reforming stages prior to entering the anode.

Embodiment 23

The method of any of the above Embodiments, wherein the molten carbonate fuel cell is operated at a first operating condition to generate electrical power and at least about 30 $mW/cm^2$ (e.g., at least about 40 $mW/cm^2$, at least about 50 $mW/cm^2$, or at least 100 $mW/cm^2$) of waste heat, the first operating condition providing a current density of at least about 150 $mA/cm^2$, and wherein an effective amount of an endothermic reaction is performed to maintain a temperature differential between an anode inlet and an anode outlet of about 100° C. or less (e.g., about 80° C. or less or about 60° C. or less).

Embodiment 24

The method of embodiment 23, wherein performing the endothermic reaction consumes at least about 40% (e.g., at least about 50%, at least about 60%, or at least about 75%) of the waste heat.

Embodiment 25

The method of any of the above embodiments, wherein the molten carbonate fuel cell is operated at a voltage $V_A$ of less than about 0.68V (e.g., less than about 0.67V, less than about 0.66V, or about 0.65V or less), and optionally of at least about 0.60V (e.g., at least about 0.61V, at least about 0.62V, or at least about 0.63V).

Embodiment 26

The method of any of the above Embodiments, further comprising reforming the reformable fuel, wherein at least about 90% of the reformable fuel introduced into the anode, the reforming stage associated with the anode, or a combination thereof is reformed in a single pass through the anode.

This group of embodiments is Group W. References to "any of the above embodiments" are meant to refer only to other embodiments within this Group, whereas references to "any of the above groups of embodiments" are meant to refer to any individual or combination of embodiments from one or more other Groups.

Embodiment 1

Additionally or alternately to any of the above groups of embodiments, a method for producing a fermented product, the method comprising: introducing a fuel stream comprising a reformable fuel into an anode of a molten carbonate fuel cell, an internal reforming element associated with the anode, or a combination thereof; introducing a cathode inlet stream comprising $CO_2$ and $O_2$ into a cathode of the fuel cell; generating electricity within the molten carbonate fuel cell; separating from the anode exhaust an $H_2$-containing stream, a syngas-containing stream, or a combination thereof; processing biomass to produce at least one fermentation product and a fermentation exhaust; and distilling the at least one fermentation product, at least some heat for distillation being provided by heat exchange with the anode exhaust, combustion of the syngas-containing stream, combustion of the $H_2$-containing stream, electric heating using the electricity generated within the molten carbonate fuel cell, or a combination thereof, wherein the method further comprises one or more of the following: a) the cathode inlet stream comprises at least a portion of the fermentation exhaust; b) the processing step is done in the presence of $H_2O$ separated from the anode exhaust, $H_2O$ separated from the syngas-containing stream, $H_2O$ separated from the $H_2$-containing stream, or a combination thereof; c) the reformable fuel comprises a portion of the fermentation product, the reformable fuel optionally containing at least 50 vol % of the fermentation product (e.g., at least 60 vol % or at least 70 vol %), the portion of the fermentation product optionally being a distilled portion of the fermentation product having a water to carbon ratio of about 1.5:1 to about 3.0:1 (e.g., about 1.5:1 to about 2.5:1); d) the processing step comprises separating a substantially fermentable biomass portion from a substantially non-fermentable biomass portion, the substantially non-fermentable biomass portion being processed in one or more thermal, chemical, and/or thermochemical processes in the presence of at least a portion of the $H_2$-containing gas stream, at least a portion of the syngas-containing stream, or a combination thereof; e) an amount of the reformable fuel introduced into the anode of the molten carbonate fuel cell, the internal reforming element associated with the anode of the molten carbonate fuel cell, or the combination thereof, provides a reformable fuel surplus ratio of at least about 2.0; f) a reformable hydrogen content of reformable fuel introduced into the anode of the molten carbonate fuel cell, the internal reforming element associated with the anode of the molten carbonate fuel cell, or the combination thereof, is at least about 50% greater than an amount of hydrogen oxidized to generate electricity (e.g., at least about 75% greater or at least about 100% greater); g) an electrical efficiency for the molten carbonate fuel cell is between about 10% and about 40% (e.g., from about 10% to about 35%, from about 10% to about 30%, or from about 10% to about 25%), and a total fuel cell efficiency for the fuel cell is at least about 55% (e.g., at least about 65%, at least about 70%, at least about 75%, or at least about 80%); h) the molten carbonate fuel cell is operated at a thermal ratio of about 0.25 to about 1.5 (e.g., from about 0.25 to about 1.3, from about 0.25 to about 1.15, from about 0.25 to about 1.0, from about 0.25 to about 0.85, or from about 0.25 to about 0.75); i) a ratio of net moles of syngas in the anode exhaust to moles of $CO_2$ in a cathode exhaust is at least about 2.0 (e.g., at least about 3.0, at least about 4.0, at least about 5.0, at least about 10.0, or at least about 20.0), and optionally about 40.0 or less (e.g., about 30.0 or less or about 20.0 or less); j) a fuel utilization in the anode of the molten carbonate fuel cell is about 50% or less (e.g., about 40% or less, about 30% or less, about 25% or less, or about 20% or less) and a $CO_2$ utilization in the cathode is at least about 60% (e.g., at least about 65%, at least about 70%, or at least about 75%); k) the molten carbonate fuel cell is operated at a first operating condition to generate electrical power and at least 100 $mW/cm^2$ of waste heat, the first operating condition providing a current density of at least about 150 $mA/cm^2$, and an effective amount of an endothermic reaction is performed to maintain a temperature differential between the anode inlet and an anode outlet of about 80° C. or less (e.g., about 60° C. or less); l) the molten carbonate fuel cell is operated at a voltage $V_A$ of about 0.60 Volts to about 0.67 Volts (e.g., about 0.60 Volts to about 0.65 Volts, about 0.62 Volts to about 0.67 Volts, or about 0.62 Volts to about 0.65 Volts), the molten carbonate fuel cell optionally being operated at a fuel utilization of about 65% or less; m) the cathode inlet stream comprises at least a portion of a combustion turbine exhaust, at least a portion of the anode exhaust being recycled into the anode; n) the cathode inlet stream comprises at least a portion of a combustion turbine exhaust, at least a portion of the anode exhaust being used as an anode recycle fuel for a combustion zone of the combustion turbine, an optional second fuel stream for the combustion zone of the combustion turbine optionally comprising at least about 30 vol % $CO_2$ and/or at least about 35 vol % of a combination of $CO_2$ and inerts (e.g., at least about 40 vol % of a combination of $CO_2$ and inerts, at least about 45 vol % of a combination of $CO_2$ and inerts, or at least about 50 vol % of a combination of $CO_2$ and inerts); o) the cathode inlet stream comprises at least a portion of a combustion turbine exhaust, at least a first portion of the anode exhaust being used as an anode recycle fuel for a combustion zone of the combustion turbine, and at least a second portion of the anode exhaust being recycled into the anode of the molten carbonate fuel cell; p) the cathode inlet stream comprises at least a portion of a combustion turbine exhaust, the cathode inlet stream comprising at least about 20 vppm of NOx, and a cathode exhaust comprising less than about half of the NOx content of the cathode inlet stream; q) the method further comprises combusting at least a portion of the $H_2$-containing gas stream to produce electricity, the combusting optionally being done in a combustion zone of a second turbine, and the cathode inlet stream optionally comprising at least a portion of a combustion turbine exhaust generated by combustion of a carbon-containing fuel; r) the method further comprises reacting at least a portion of the syngas-containing stream in the presence of a methanol synthesis catalyst under effective conditions for forming methanol to produce at least one methanol-containing stream and one or more streams comprising gaseous or liquid products, and optionally recycling at least a portion of the one or more streams comprising gaseous or liquid products to form at least a portion of the cathode inlet stream; s) the method further comprises optionally sending one or more $CO_2$-containing streams derived from one or more first refinery processes to the cathode inlet, separating $CO_2$ from at least a portion of the anode exhaust to form a $CO_2$-rich gas stream having a $CO_2$ content greater than a $CO_2$ content of the anode exhaust, and a $CO_2$-depleted gas stream having a $CO_2$ content less than the $CO_2$ content of the anode exhaust, and delivering the $CO_2$-depleted gas stream to one or more second refinery processes; t) the method further comprises separating $CO_2$ from at least a portion of the anode exhaust to produce a $CO_2$-rich stream having a $CO_2$ content greater than a $CO_2$ content of the anode exhaust and a $CO_2$-depleted gas stream having an $H_2$ content greater than an $H_2$ content of the anode exhaust, and using at least a portion of the $CO_2$-depleted gas stream in an ammonia synthesis process, in a process for synthesis of an organic nitrogen-containing compound, or in both; u) the method further comprises withdrawing, from an anode exhaust, a first gas stream comprising CO, the anode exhaust having a pressure of about 500 kPag or less, introducing the first gas stream withdrawn from the anode exhaust into a process for production of iron and/or steel, and optionally withdrawing a second gas stream comprising $H_2$ from the anode exhaust and, if withdrawn, using the second gas stream as fuel for heating in the process for production of iron and/or steel; v) the method further comprises generating an anode exhaust comprising $H_2$, CO, $H_2O$, and at least about 20 vol % $CO_2$, reacting at least a portion of the anode exhaust under effective Fischer-Tropsch conditions in the presence of a shifting Fischer-Tropsch catalyst to produce at least one gaseous product and at least one non-gaseous product, wherein a $CO_2$ concentration in the at least a portion of the anode exhaust is at least 80% of a $CO_2$ concentration in the anode exhaust, and recycling at least a portion of the at least one gaseous product to the cathode inlet; w) the method further comprises generating an anode exhaust comprising $H_2$, CO, $CO_2$, and $H_2O$, and having a ratio of $H_2$ to CO of at least about 2.5:1, reducing the ratio of $H_2$ to CO in at least a portion of the anode exhaust to a ratio of about 1.7:1 to about 2.3:1 to form a classic syngas stream, which also has a $CO_2$ concentration that is at least 60% of a $CO_2$ concentration in the anode exhaust, reacting the classic syngas stream under effective Fischer-Tropsch conditions in the presence of a non-shifting Fischer-Tropsch catalyst to produce at least one gaseous product and at least one non-gaseous product, and optionally recycling at least a portion of the at least one gaseous product to the cathode inlet; and x) the method further comprises generating an anode exhaust: comprising $H_2$, CO, and $CO_2$, having a ratio of $H_2$ to CO of at least about 2.5:1, and having a $CO_2$ content of at least about 20 vol %, removing water and $CO_2$ from at least a portion of the anode exhaust to produce an anode effluent gas stream, the anode effluent gas stream having a concentration of water that is less than half of a concentration of water in the anode exhaust, having a concentration of $CO_2$ that is less than half of a concentration of $CO_2$ in the anode exhaust, or a combination thereof, the anode effluent gas stream also having a ratio of $H_2$ to CO of about 2.3:1 or less, and reacting at least a portion of the anode effluent gas stream over a non-shifting Fischer-Tropsch catalyst to produce at least one gaseous product and at least one non-gaseous product.

Embodiment 2

The method of embodiment 1, wherein the cathode inlet stream comprises at least a portion of the anode exhaust, at least a portion of any gas stream withdrawn from the anode exhaust, or a combination thereof.

Embodiment 3

The method of embodiment 1 or 2, wherein the cathode inlet stream comprises at least a portion of an exhaust from a combustion reaction, an exhaust from a combustion turbine, or a combination thereof.

Embodiment 4

The method of any of the above embodiments, wherein $CO_2$ is separated from the anode exhaust, from any gas stream withdrawn from the anode exhaust, or a combination thereof, at least a portion of the separated $CO_2$ optionally being combined with a at least a portion of the fermentation exhaust.

Embodiment 5

The method of any of the above embodiments, wherein $H_2O$ is separated from the anode exhaust, from any gas stream withdrawn from the anode exhaust, or a combination thereof.

Embodiment 6

The method of any of the above embodiments, further comprising separating $H_2O$ from the anode exhaust, and using the separated $H_2O$ during the processing of the biomass to produce the at least one fermentation product.

Embodiment 7

The method of any of the above embodiments, wherein generating electricity within the molten carbonate fuel cell comprises operating the fuel cell at a fuel utilization, the fuel utilization being selected based on at least one of an electrical demand of the processing of the biomass, a heat demand of the processing of the biomass, and a heat demand of the distillation of the fermentation product.

Embodiment 8

The method of any of the above embodiments, wherein the reformable fuel is derived from biomass by anaerobic digestion of biomass residue produced by the processing of the biomass.

Embodiment 9

The method of embodiment 8, wherein at least some of the reformable fuel is derived from biomass by partial oxidation and/or gasification of biomass residue produced by the processing of the biomass.

Embodiment 10

The method of any of the above embodiments, wherein the at least one fermentation product comprises ethanol.

Embodiment 11

The method of any of the above embodiments, further comprising separating from an anode exhaust a $CO_2$-rich stream, and using the $CO_2$-rich stream as part of a photosynthetic algae growth process.

Embodiment 12

The method of any of the above embodiments, wherein the reformable fuel is derived from algae biomass generated in an algae growth pond.

Embodiment 13

The method of any of the above embodiments, further comprising separating from an anode exhaust a $CO_2$-rich stream, and sending at least a portion of the $CO_2$-rich stream to the cathode inlet.

Embodiment 14

The method of any of the above embodiments, wherein at least some of the heat for distillation is provided based on combustion of a fermentation product.

Embodiment 15

The method of any of the above embodiments, wherein the anode exhaust has a molar ratio of $H_2$:CO of at least about 3.0:1.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications that fall within the true spirit/scope of the invention.

What is claimed is:

1. A method for producing electricity, and hydrogen or syngas, using a molten carbonate fuel cell comprising an anode and cathode, the method comprising:

introducing a fuel stream comprising a reformable fuel into the anode of the molten carbonate fuel cell, an internal reforming element associated with the anode, or a combination thereof;

introducing a cathode inlet stream comprising $CO_2$ and $O_2$ into the cathode of the molten carbonate fuel cell;

generating electricity within the molten carbonate fuel cell at a fuel utilization of about 65% or less and at a cell operating voltage, a ratio of a cell operating voltage to a cell maximum voltage being about 0.65 or less; and generating an anode exhaust from an anode outlet of the molten carbonate fuel cell; and separating from the anode exhaust a $H_2$-containing stream, a syngas-containing stream, or a combination thereof, wherein a reformable hydrogen content of the reformable fuel introduced into the anode, the internal reforming element associated with the anode, or the combination thereof, is at least about 75% greater than an amount of hydrogen oxidized to generate electricity.

2. The method of claim 1, further comprising reforming the reformable fuel, wherein at least about 90% of the reformable fuel introduced into the anode of the molten carbonate fuel cell, the internal reforming element associated with the anode of the molten carbonate fuel cell, or the combination thereof, is reformed in a single pass through the anode of the molten carbonate fuel cell.

3. A method for producing electricity, and hydrogen or syngas, using a molten carbonate fuel cell comprising an anode and cathode, the method comprising:

introducing a fuel stream comprising a reformable fuel into the anode of the molten carbonate fuel cell, an internal reforming element associated with the anode, or a combination thereof;

introducing a cathode inlet stream comprising $CO_2$ and $O_2$ into the cathode of the molten carbonate fuel cell;

generating electricity within the molten carbonate fuel cell at a fuel utilization of about 65% or less and at a cell operating voltage, a ratio of a cell operating voltage to a cell maximum voltage being about 0.65 or less; and generating an anode exhaust from an anode outlet of the molten carbonate fuel cell; and separating from the anode exhaust a $H_2$-containing stream, a syngas-containing stream, or a combination thereof, wherein the molten carbonate fuel cell is operated to generate electrical power at a current density of at least about 150 $mA/cm^2$ and at least about 40 $mW/cm^2$ of waste heat, the method further comprising performing an effective amount of an endothermic reaction to maintain a temperature differential between an anode inlet and the anode outlet of about 100° C. or less.

4. The method of claim 1, wherein a $CO_2$ utilization of the cathode is at least about 50%.

5. The method of claim 1, wherein the anode fuel stream comprises at least about 10 vol % inert compounds, at least about 10 vol % $CO_2$, or a combination thereof.

6. The method of claim 1, wherein the anode exhaust comprises $H_2$ and CO having a molar ratio of $H_2$ to CO from about 1.5:1 to about 10.0:1.

7. The method of claim 6, wherein the anode exhaust has a molar ratio of $H_2$:CO from about 3.0:1 to about 10:1.

8. The method of claim 1, wherein the $H_2$-containing stream contains at least about 90% $H_2$.

9. The method of claim 1, wherein the cathode inlet stream comprises about 20 vol % $CO_2$ or less.

10. The method of claim 1, further comprising recycling at least a portion of the $H_2$-containing stream to a combustion turbine.

11. The method of claim 1, wherein at least about 90 vol % of the reformable fuel is methane.

12. The method of claim 1, wherein the molten carbonate fuel cell is operated at a thermal ratio from about 0.25 to about 1.0.

13. The method of claim 1, wherein a ratio of net moles of syngas in the anode exhaust to moles of $CO_2$ in a cathode exhaust is at least about 2.0:1.

14. The method of claim 1, wherein a fuel utilization in the anode is about 50% or less and a $CO_2$ utilization in the cathode is at least about 60%.

15. The method of claim 1, wherein the molten carbonate fuel cell is operated to generate electrical power at a current density of at least about 150 $mA/cm^2$ and at least about 40 $mW/cm^2$ of waste heat, the method further comprising performing an effective amount of an endothermic reaction to maintain a temperature differential between an anode inlet and the anode outlet of about 100° C. or less.

16. The method of claim 15, wherein performing the endothermic reaction consumes at least about 40% of the waste heat.

17. The method of claim 1, wherein an electrical efficiency for the molten carbonate fuel cell is between about 10% and about 40% and a total fuel cell efficiency for the molten carbonate fuel cell is at least about 55%.

18. The method of claim 3, wherein a reformable hydrogen content of the reformable fuel introduced into the anode, the internal reforming element associated with the anode, or the combination thereof, is at least about 75% greater than an amount of hydrogen oxidized to generate electricity.

19. The method of claim 3, wherein performing the endothermic reaction consumes at least about 40% of the waste heat.

* * * * *